United States Patent
Lee et al.

(10) Patent No.: US 12,356,851 B2
(45) Date of Patent: Jul. 8, 2025

(54) ORGANIC COMPOUND AND ORGANIC ELECTROLUMINESCENT DEVICE INCLUDING THE SAME

(71) Applicant: MATERIAL SCIENCE CO., LTD., Seoul (KR)

(72) Inventors: Tae Wan Lee, Seoul (KR); Jeong Hoe Heo, Seoul (KR); Dong hun Lee, Seoul (KR); Seong min Park, Seoul (KR); Sun Jae Kim, Goyang-si (KR); Sung Hoon Kim, Gwangmyeong-si (KR)

(73) Assignee: MATERIAL SCIENCE CO., LTD., Gyeonggi-Do (KR)

( * ) Notice: Subject to any disclaimer, the term of this patent is extended or adjusted under 35 U.S.C. 154(b) by 256 days.

(21) Appl. No.: 16/838,353

(22) Filed: Apr. 2, 2020

(65) Prior Publication Data
US 2020/0321525 A1 Oct. 8, 2020

(30) Foreign Application Priority Data
Apr. 2, 2019 (KR) .......... 10-2019-0038302

(51) Int. Cl.
| | | |
|---|---|---|
| *H01L 51/00* | (2006.01) | |
| *C07C 211/61* | (2006.01) | |
| *C07D 307/91* | (2006.01) | |
| *H10K 85/60* | (2023.01) | |
| *H10K 50/15* | (2023.01) | |

(52) U.S. Cl.
CPC .......... *H10K 85/633* (2023.02); *C07C 211/61* (2013.01); *C07D 307/91* (2013.01); *H10K 85/636* (2023.02); *H10K 50/15* (2023.02); *H10K 85/626* (2023.02); *H10K 85/6574* (2023.02)

(58) Field of Classification Search
CPC .............. H01L 51/006; H01L 51/0061; H01L 51/0058; H01L 51/0073; H01L 51/5056; C07C 211/61; C07C 211/60; C07D 307/91; H10K 85/633; H10K 85/636
See application file for complete search history.

(56) References Cited

U.S. PATENT DOCUMENTS

| | | | | |
|---|---|---|---|---|
| 11,744,145 B2 * | 8/2023 | Song | ................... | H10K 85/626 |
| 2015/0207075 A1 * | 7/2015 | Mujica-Fernaud | ... | H01L 51/006 |
| | | | | 252/500 |
| 2016/0028014 A1 * | 1/2016 | Kim | ...................... | H01L 51/006 |
| | | | | 257/40 |
| 2016/0111653 A1 * | 4/2016 | Itoi | ....................... | H10K 85/636 |
| | | | | 257/40 |
| 2016/0126471 A1 * | 5/2016 | Lui | ....................... | H10K 85/654 |
| | | | | 257/40 |
| 2016/0126477 A1 * | 5/2016 | Kim | ..................... | H01L 51/0067 |
| | | | | 548/440 |
| 2017/0271624 A1 * | 9/2017 | Hua | ..................... | H10K 50/858 |
| 2019/0016666 A1 * | 1/2019 | Jeong | ................... | H01L 51/0073 |

FOREIGN PATENT DOCUMENTS

| | | | | |
|---|---|---|---|---|
| CN | 103108859 A | 5/2013 | | |
| CN | 105980518 A | 9/2016 | | |
| CN | 108003038 A | 5/2018 | | |
| CN | 108129332 A | 6/2018 | | |
| CN | 108774141 A | 11/2018 | | |
| CN | 108864013 A | 11/2018 | | |
| CN | 108976196 A | 12/2018 | | |
| CN | 110903276 A * | 3/2020 | ........... | C07C 211/61 |
| KR | 2010015029 A * | 2/2010 | ........ | H01L 51/5024 |
| KR | 1020140133572 A | 11/2014 | | |
| KR | 2016040826 A * | 4/2016 | | |
| KR | 20170094708 A | 8/2017 | | |
| KR | 2017111802 A * | 10/2017 | ........... | C07C 211/54 |
| KR | 2017136391 A * | 12/2017 | ........... | C07C 211/54 |
| WO | WO2009139501 A1 | 11/2009 | | |
| WO | WO-2017116167 A1 * | 7/2017 | ........... | C07C 13/615 |
| WO | WO2018083053 A1 | 5/2018 | | |
| WO | WO2019013487 A1 | 1/2019 | | |

OTHER PUBLICATIONS

CAS Abstract and Indexed Compounds, M. Kim et al., US 2016/0028014 (2016) (Year: 2016).*
M. Lin et al., 22 Journal of Materials Chemistry, 16114-16120 (2012) (Year: 2012).*
C.W. Tang and S.A. Vanslyke, Organic electroluminescent diodes, Applied Physics, Sep. 21, 1987, pp. 913-915, vol. 51, No. 12, American Institute of Physics, College Park, USA.
Machine Translation of portion of Chinese Office Action for application No. 202010671137.5, Mar. 31, 2023, 12 pages.

* cited by examiner

*Primary Examiner* — Alexander R Pagano
(74) *Attorney, Agent, or Firm* — Carter, DeLuca & Farrell LLP; Jeffrey S. Steen

(57) ABSTRACT

The present invention relates to a novel organic compound and an organic light emitting device including the same, and more specifically provides an organic electroluminescent device with remarkably improved light emitting efficiency and service life.

2 Claims, No Drawings

ORGANIC COMPOUND AND ORGANIC ELECTROLUMINESCENT DEVICE INCLUDING THE SAME

CROSS-REFERENCE TO RELATED APPLICATIONS

This application claims priority to and the benefit of Korean Patent Application No. 10-2019-0038302 filed in the Korean Intellectual Property Office on Apr. 2, 2019, the entire contents of which are incorporated herein by reference.

TECHNICAL FIELD

The present invention relates to a novel organic compound and an organic electroluminescent device including the same, and more particularly, to an organic compound for a hole transport auxiliary layer of an organic electroluminescent device and an organic electroluminescent device including the same.

BACKGROUND ART

Since an organic electroluminescent device (OLED) has a simple structure, various advantages in the manufacturing process, high brightness and excellent viewing angle characteristics, and a high response speed and a low driving voltage, as compared to other flat panel display devices such as an existing liquid crystal display (LCD), a plasma display panel (PDP), and a field emission display (FED), the organic electroluminescent device has been actively developed and commercialized as for use in a light source for a flat panel display such as a wall-mounted TV or a backlight of a display, a lighting, and a billboard.

For the organic electroluminescent device, a first organic EL diode was reported by C. W. Tang et al., from Eastman Kodak Co. (C. W. Tang, S. A. VanSlyke, Applied Physics Letters, vol. 51, p. 913, 1987), and the light emission principle thereof is based on a principle in which in general, when a voltage is applied to the organic electroluminescent diode, holes injected from a positive electrode are recombined with electron injection from a negative electrode to form excitons as electron-hole pairs, and energy of the excitons is transmitted to a light emitting material and converted into light.

More specifically, the organic electroluminescent element has a structure including a negative electrode (electron injection electrode), a positive electrode (hole injection electrode), and one or more organic layers between the two electrodes. In this case, in the organic electroluminescent device, from a positive electrode, a hole injection layer (HIL), a hole transport layer (HTL), a light emitting layer (EML), and an electron transport layer (ETL) or an electron injection layer (EIL) are stacked in this order, and in order to increase the efficiency of the light emitting layer, a hole transport auxiliary layer or a hole blocking layer (HBL) may be additionally included before and behind the light emitting layer.

The reason that the organic electroluminescent device is manufactured as a multilayer thin film structure as described above is to stabilize the interface between the electrode and the organic material, and the structure may increase the light emitting efficiency.

In particular, in the case of organic compounds used as materials for a multilayer thin film, the difference in transfer speed of holes and electrons is large depending on the characteristics of the respective organic compounds. Thus, only when a hole transport layer and an electron transport layer containing appropriate compounds are used, holes and electrons may be effectively transferred to a light emitting layer, and the densities of holes and electrons may be balanced, thereby significantly improving the light emitting efficiency.

For this reason, characteristics of the organic compound components included in each layer of the organic multilayer thin film have a great effect not only on the driving voltage, light emitting efficiency, luminance, and service life of the device, but also on the efficiency or service life of a display finally produced. Thus, it is considered important to use a specific organic material suitable for a multilayer structure in an organic electroluminescent device.

Therefore, studies on components included in each layer of the organic multilayer thin film have been actively conducted.

PRIOR ART DOCUMENT

Patent Document (Patent Document 1) (Patent Document 1) KR 10-2014-0133572 A1

SUMMARY OF THE INVENTION

The present invention has been made in an effort to provide a novel organic compound and an organic electroluminescent device including the same.

The present invention has been made in an effort to provide a novel compound which has an HOMO energy level that facilitates the transport of holes and thus may be used as a material for a hole transport auxiliary layer of an organic electroluminescent device having excellent hole transport characteristics to a light emitting layer.

The present invention has been made in an effort to provide an organic electroluminescent device with remarkably improved light emitting efficiency and service life characteristics as a hole transport auxiliary layer including a novel organic compound is used.

The present invention has been made in an effort to provide an organic electroluminescent device suitable for AM-OLED by using the organic compound.

An exemplary embodiment of the present invention provides a compound represented by the following Formula 1:

[Formula 1]

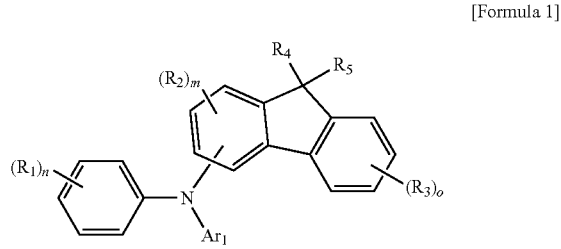

here,
n is an integer from 1 to 5,
m is an integer from 0 to 3,
is an integer from 0 to 4.
$Ar_1$ is selected from the group consisting of hydrogen, a substituted or unsubstituted aryl group having 6 to 30 carbon atoms, and a substituted or unsubstituted heteroaryl group having 3 to 30 carbon atoms, $R_1$ to $R_5$ are the same as or different from each other, are each independently selected from the group consisting of hydrogen, deuterium, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 6 to 30 carbon atoms, a substituted or unsubstituted aryl group having 5 to 30 carbon atoms, a substituted or unsubstituted heteroaryl group having 2 to 30 carbon atoms, a substituted or unsubstituted heteroarylalkyl group having 3 to 30 carbon atoms, a substituted or unsubstituted cycloalkyl group having 3 to 20 carbon atoms, a substituted or unsubstituted heterocycloalkyl group having 3 to 20 carbon atoms, a substituted or unsubstituted cycloalkenyl group having 3 to 20 carbon atoms, a substituted or unsubstituted heteroaralkyl group having 3 to 30 carbon atoms, and a substituted or unsubstituted heteroalkenyl group having 1 to 20 carbon atoms, and may be bonded to an adjacent group to form a substituted or unsubstituted ring, and the substituents of $Ar_1$ and $R_1$ to $R_5$ are substituted with a substituent selected from the group consisting of hydrogen, deuterium, a cyano group, a nitro group, a halogen group, a hydroxyl group, an alkyl group having 1 to 30 carbon atoms, an alkenyl group having 2 to 30 carbon atoms, an alkynyl group having 2 to 24 carbon atoms, a heteroalkyl group having 2 to 30 carbon atoms, an aralkyl group having 6 to 30 carbon atoms, a cycloalkyl group having 3 to 20 carbon atoms, a heterocycloalkyl group having 3 to 20 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylsilyl group having 1 to 30 carbon atoms, an arylsilyl group having 6 to 30 carbon atoms, and an aryloxy group having 6 to 30 carbon atoms, and when the substituents are substituted with a plurality of substituents, the substituted substituents are the same as or different from each other.

The present invention provides an organic electroluminescent device including: a first electrode; a second electrode provided to face the first electrode; and one or more organic material layers provided between the first electrode and the second electrode, in which at least one of the one or more organic material layers includes the aforementioned compound represented by Formula 1.

For example, the organic electroluminescent device may have a structure including a hole injection layer, a hole transport layer, a hole transport auxiliary layer, a light emitting layer, a hole blocking layer, an electron transport layer, an electron injection layer, a capping layer, and the like. However, the structure of the organic electroluminescent device is not limited thereto, and may include a fewer number of organic material layers.

According to a preferred embodiment of the present invention, the organic material layer is a hole transport auxiliary layer, and the hole transport auxiliary layer may be characterized by including the compound represented by Formula 1.

In the present specification, the "halogen group" is fluorine, chlorine, bromine, or iodine.

In the present invention, "alkyl" means a monovalent substituent derived from a linear or branched saturated hydrocarbon having 1 to 40 carbon atoms. Examples thereof include methyl, ethyl, propyl, isobutyl, sec-butyl, pentyl, iso-amyl hexyl, and the like, but are not limited thereto.

In the present invention, "alkenyl" means a monovalent substituent derived from a linear or branched unsaturated hydrocarbon having 2 to 40 carbon atoms and having one or more carbon-carbon double bonds. Examples thereof include vinyl, allyl, isopropenyl, 2-butenyl, and the like, but are not limited thereto.

In the present invention, "alkynyl" means a monovalent substituent derived from a linear or branched unsaturated hydrocarbon having 2 to 40 carbon atoms and having one or more carbon-carbon triple bonds. Examples thereof include ethynyl, 2-propynyl, and the like, but are not limited thereto.

In the present invention, "alkylthio" means the above-described alkyl group which is bonded through a sulfur linkage (—S—).

In the present invention, "aryl" means a monovalent substituent derived from an aromatic hydrocarbon having 6 to 60 carbon atoms and having a single ring or a combination of two or more rings. Further, the aryl may also include a form in which two or more rings are simply pendant to or fused with each other. Examples of the aryl include phenyl, naphthyl, phenanthryl, anthryl, fluonyl, dimethylfluorenyl, and the like, but are not limited thereto.

In the present invention, "heteroaryl" means a monovalent substituent derived from a monoheterocyclic or polyheterocyclic aromatic hydrocarbon having 6 to 30 carbon atoms. In this case, one or more carbons, preferably 1 to 3 carbons in the ring are substituted with a heteroatom such as N, O, S, or Se. Further, the heteroaryl may also include a form in which two or more rings are simply pendant to or fused with each other, and may also include a form in which two or more rings are fused with an aryl group. Examples of the heteroaryl include: a 6-membered monocyclic ring, such as pyridyl, pyrazinyl, pyrimidinyl, pyridazinyl, and triazinyl, a polycyclic ring, such as phenoxathienyl, indolizinyl, indolyl, purinyl, quinolyl, benzothiazole, and carbazolyl, 2-furanyl, N-imidazolyl, 2-isoxazolyl, 2-pyridinyl, 2-pyrimidinyl, and the like, but are not limited thereto.

In the present invention, "aryloxy" means a monovalent substituent represented by RO—, in which R is an aryl having 6 to 60 carbon atoms. Examples of the aryloxy include phenyloxy, naphthyloxy, diphenyloxy, and the like, but are not limited thereto.

In the present invention, "alkyloxy" means a monovalent substituent represented by R'O—, in which R' is an alkyl having 1 to 40 carbon atoms, and may include a linear, branched, or cyclic structure. Examples of the alkyloxy include methoxy, ethoxy, n-propoxy, 1-propoxy, t-butoxy, n-butoxy, pentoxy, and the like, but are not limited thereto.

In the present invention, "alkoxy" may be linear, branched, or cyclic. The number of carbon atoms of the alkoxy is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present invention, "aralkyl" means an aryl-alkyl group in which aryl and alkyl are as described above. A preferred aralkyl includes a lower alkyl group. Non-limiting examples of a suitable aralkyl group include benzyl, 2-pentenyl, and naphthalenylmethyl. Binding to the parent moiety is achieved through alkyl.

In the present invention, "arylamino group" means an amine substituted with an aryl group having 6 to 30 carbon atoms.

In the present invention, "alkylamino group" means an amine substituted with an alkyl group having 1 to 30 carbon atoms.

In the present invention, "aralkylamino group" means an amine substituted with an aryl-alkyl group having 6 to 30 carbon atoms.

In the present invention, "heteroarylamino group" means an amine group substituted with an aryl group having 6 to 30 carbon atoms and a heterocyclic group.

In the present invention, "heteroaralkyl group" means an aryl-alkyl group substituted with a heterocyclic group.

In the present invention, "cycloalkyl" means a monovalent substituent derived from a monocyclic or polycyclic non-aromatic hydrocarbon having 3 to 40 carbon atoms. Examples of the cycloalkyl include cyclopropyl, cyclobutyl, cyclopentyl, cyclohexyl, norbornyl, adamantine, and the like, but are not limited thereto.

In the present invention, "heterocycloalkyl" means a monovalent substituent derived from a non-aromatic hydrocarbon having 3 to 40 carbon atoms, and one or more carbons, preferably 1 to 3 carbons in a ring are substituted with a hetero atom such as N, O, S, or Se.

Examples of the heterocycloalkyl include morpholine, piperazine, and the like, but are not limited thereto.

In the present invention, "alkylsilyl" means a silyl substituted with an alkyl having 1 to 40 carbon atoms, and "arylsilyl" means a silyl substituted with an aryl having 6 to 60 carbon atoms.

In the present invention, the "arylene group" means that there are two bonding positions in an aryl group, that is, a divalent group. The above-described description on the aryl group may be applied to the arylene group, except for a divalent arylene group. As an example, the arylene group may be phenylene, biphenylene, naphthylene, anthracenylene, or fluorenylene.

In the present invention, "fused ring" means a fused aliphatic ring, a fused aromatic ring, a fused heteroaliphatic ring, a fused heteroaromatic ring, or a combined form thereof.

In the present invention, "being bonded to an adjacent group to form a ring" means being bonded to an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a fused ring thereof.

In the present specification, "alicyclic compound" has the same meaning as "aliphatic hydrocarbon ring", and means a ring composed only of carbon and hydrogen atoms as a ring which is not an aromatic group.

In the present specification, "hetero alicyclic compound" means an alicyclic compound in which one or more carbon atoms of the "aliphatic hydrocarbon ring" is substituted with a heteroatom, and includes at least one heteroatom.

In the present specification, examples of "aromatic hydrocarbon ring" include a phenyl group, a naphthyl group, an anthracenyl group, and the like, but are not limited thereto.

In the present specification, "aliphatic hetero ring" means an aliphatic ring including one or more heteroatoms.

In the present specification, "aromatic hetero ring" means an aromatic ring including one or more heteroatoms.

In the present specification, the aliphatic hydrocarbon ring, the aromatic hydrocarbon ring, the aliphatic hetero ring, and the aromatic hetero ring may be monocyclic or polycyclic.

In the present specification, "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more substituents are substituted, the two or more substituents may be the same as or different from each other. The substituent may be substituted with one or more substituents selected from the group consisting of hydrogen, deuterium, a cyano group, a nitro group, a halogen group, a hydroxyl group, an alkyl group having 1 to 30 carbon atoms, an alkenyl group having 2 to 30 carbon atoms, an alkynyl group having 2 to 24 carbon atoms, a heteroalkyl group having 2 to 30 carbon atoms, an aralkyl group having 6 to 30 carbon atoms, an aryl group having 5 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, and a heteroarylamino group having 2 to 24 carbon atoms, but is not limited to the examples.

The present invention relates to a novel organic compound, and the novel organic compound has a HOMO energy level that facilitates the transport of holes, and thus may be utilized as a material for a hole transport auxiliary layer of an organic electroluminescent device having excellent hole transport characteristics to a light emitting layer.

As a hole transport auxiliary layer including the novel organic compound is used, it is possible to provide an organic electroluminescent device in which most of the device characteristics such as light emitting efficiency and service life characteristics are remarkably improved.

DETAILED DESCRIPTION

Hereinafter, the Examples of the present invention will be described in detail such that a person skilled in the art to which the present invention pertains can easily carry out the present invention. However, the present invention can be implemented in various different forms, and is not limited to the Examples described herein.

The distribution of excitons formed by the combination of electrons and holes in the light emitting layer in an OLED is a major factor that directly and indirectly affects the voltage, efficiency, and service life of the device. The distribution of excitons is affected by the characteristics of a material for a light emitting layer and the mobility or energy level of holes and electrons injected into the light emitting layer.

The compound of the present invention may be used as a material for a hole transport auxiliary layer between a light emitting layer and a hole transport layer, and when the compound of the present invention is used as a material for a hole transport auxiliary layer, excellent device characteristics may be exhibited by adjusting the injection rate and the amount of holes into the light emitting layer to improve the efficiency and service life.

Materials used for a hole transport layer in an actual OLED panel are used in common between the light emitting layers together with the hole injection layer, and it is difficult for the materials to optimize all the characteristics of the materials used for each of the red, green, and blue light emitting layers. Thus, a hole transport auxiliary layer suitable for each light emitting layer is used.

In the present compound, a fluorenyl group is a main substituent that determines the intermolecular packing property with the highest occupied molecular orbital (HOMO) during the formation of a thin film.

An aryl group including a substituent at the ortho position enables fine adjustment of the structure caused by the HOMO level and stereoscopic property due to the substituent substituted at the ortho position.

More specifically, when the aryl group is compared with a biphenyl group showing a structure similar to a fluorenyl group, the HOMO level of the aryl group is increased with a considerable energy difference of approximately 0.1 eV, and due to this difference, when an auxiliary layer in which the present compound is included is inserted between a hole transport layer and a light emitting layer, the auxiliary layer serves as a step between the hole transport layer and the light emitting layer to facilitate the injection of holes into the light emitting layer.

When an aryl group including a substituent at the ortho position is compared with an aryl group which including no substituent at the ortho position, the aryl group including a substituent at the ortho position may lower the HOMO to 0.01 to 0.04 eV, and adjust the hole mobility for the electron mobility of $10^{-4}$ to $10^{-6}$ depending on the substituent thereof. That is, when a phenyl group is introduced into the ortho position, the mobility will become faster 5 to 20 times depending on the structure thereof.

By finely adjusting an increase in HOMO with a considerable difference due to the substitution of the fluorenyl group through an aryl group including a substituent at the ortho position, the hole mobility may be optimally adjusted according to the mobility of electrons injected into the light emitting layer, thereby improving the light emitting efficiency and service life.

Specifically, a compound represented by the following Formula 1 is as follows:

[Formula 1]

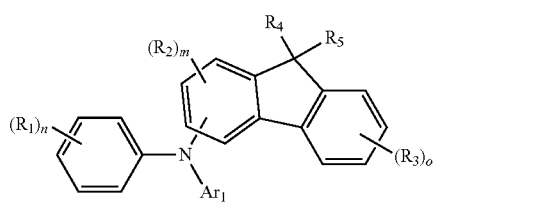

here, n is an integer from 1 to 5, m is an integer from 0 to 3, is an integer from 0 to 4.

$Ar_1$ is selected from the group consisting of hydrogen, a substituted or unsubstituted aryl group having 6 to 30 carbon atoms, and a substituted or unsubstituted heteroaryl group having 3 to 30 carbon atoms, $R_1$ to $R_5$ are the same as or different from each other, are each independently selected from the group consisting of hydrogen, deuterium, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 6 to 30 carbon atoms, a substituted or unsubstituted aryl group having 5 to 30 carbon atoms, a substituted or unsubstituted heteroaryl group having 2 to 30 carbon atoms, a substituted or unsubstituted heteroarylalkyl group having 3 to 30 carbon atoms, a substituted or unsubstituted cycloalkyl group having 3 to 20 carbon atoms, a substituted or unsubstituted heterocycloalkyl group having 3 to 20 carbon atoms, a substituted or unsubstituted cycloalkenyl group having 3 to 20 carbon atoms, a substituted or unsubstituted heteroaralkyl group having 3 to 30 carbon atoms, and a substituted or unsubstituted heteroalkenyl group having 1 to 20 carbon atoms, and may be bonded to an adjacent group to form a substituted or unsubstituted ring, and the substituents of $Ar_1$ and $R_1$ to $R_5$ are substituted with a substituent selected from the group consisting of hydrogen, deuterium, a cyano group, a nitro group, a halogen group, a hydroxyl group, an alkyl group having 1 to 30 carbon atoms, an alkenyl group having 2 to 30 carbon atoms, an alkynyl group having 2 to 24 carbon atoms, a heteroalkyl group having 2 to 30 carbon atoms, an aralkyl group having 6 to 30 carbon atoms, a cycloalkyl group having 3 to 20 carbon atoms, a heterocycloalkyl group having 3 to 20 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylsilyl group having 1 to 30 carbon atoms, an arylsilyl group having 6 to 30 carbon atoms, and an aryloxy group having 6 to 30 carbon atoms, and when the substituents are substituted with a plurality of substituents, the substituted substituents are the same as or different from each other.

The compound represented by Formula 1 may be a compound represented by the following Formula 2:

[Formula 2]

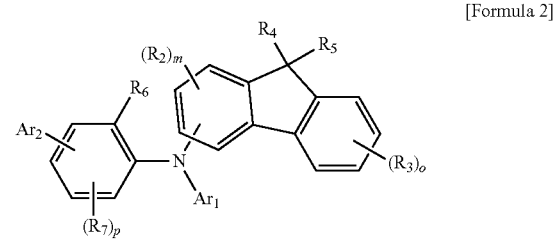

here, m, o, $Ar_1$ and $R_2$ to $R_5$ are the same as those defined in Formula 1, p is an integer from 0 to 4, $Ar_2$ is selected from the group consisting of hydrogen, a substituted or unsubstituted aryl group having 6 to 30 carbon atoms, and a substituted or unsubstituted heteroaryl group having 3 to 30 carbon atoms, $R_6$ and $R_7$ are the same as or different from each other, and are each independently selected from the group consisting of hydrogen, deuterium, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 6 to 30 carbon atoms, a substituted or unsubstituted aryl group having 5 to 30 carbon atoms, a substituted or unsubstituted heteroaryl group having 2 to 30 carbon atoms, a substituted or unsubstituted heteroarylalkyl group having 3 to 30 carbon atoms, a substituted or unsubstituted cycloalkyl group having 3 to 20 carbon atoms, a substituted or unsubstituted heterocycloalkyl group having 3 to 20 carbon atoms, a substituted or unsubstituted cycloalkenyl group having 3 to 20 carbon atoms, a substituted or unsubstituted heteroaralkyl group having 3 to 30 carbon atoms, and a substituted or unsubstituted heteroalkenyl group having 1 to 20 carbon atoms, and the substituents of $Ar_2$, $R_6$, and $R_7$ are substituted with a substituent selected from the group consisting of hydrogen, deuterium, a cyano group, a nitro group, a halogen group, a hydroxyl group, an alkyl group having 1 to 30 carbon atoms, an alkenyl group having 2 to 30 carbon atoms, an alkynyl group having 2 to 24 carbon atoms, a heteroalkyl group having 2 to 30 carbon atoms, an aralkyl group having 6 to 30 carbon atoms, a cycloalkyl group having 3 to 20 carbon atoms, a heterocycloalkyl group having 3 to 20 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylsilyl group having 1 to 30 carbon atoms, an arylsilyl group having 6 to 30 carbon atoms, and an aryloxy group having 6 to 30 carbon atoms, and when the substituents are substituted with a plurality of substituents, the substituted substituents are the same as or different from each other.

The compound represented by Formula 2 may be a compound represented by the following Formula 3:

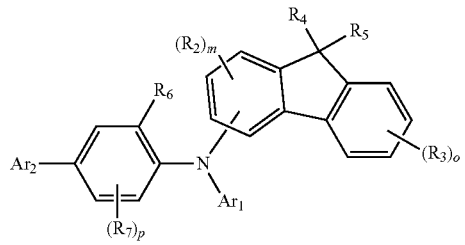

[Formula 3]

here, m, o, p, $Ar_1$, $Ar_2$, and $R_2$ to $R_7$ are the same as those defined in Formula 2.

$Ar_2$ may be selected from the group consisting of the substituents represented by the following Formulae 4 to 7:

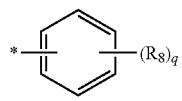

[Formula 4]

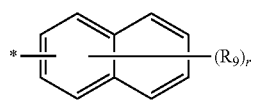

[Formula 5]

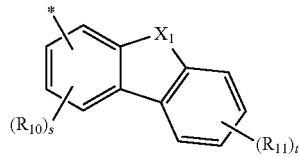

[Formula 6]

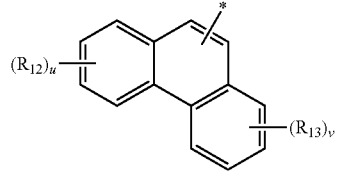

[Formula 7]

here,

* means a portion to be bonded,
q is an integer from 0 to 5,
r is an integer from 0 to 7,
s is an integer from 0 to 3,
t, u, and v are the same as or different from each other, and are each independently an integer from 0 to 4,
$X_1$ is selected from the group consisting of O, S, $N(R_{14})$, and $C(R_{15})(R_{16})$,
$R_8$ to $R_{16}$ are the same as or different from each other, and are each independently selected from the group consisting of hydrogen, deuterium, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 6 to 30 carbon atoms, a substituted or unsubstituted aryl group having 5 to 30 carbon atoms, a substituted or unsubstituted heteroaryl group having 2 to 30 carbon atoms, a substituted or unsubstituted heteroarylalkyl group having 3 to 30 carbon atoms, a substituted or unsubstituted cycloalkyl group having 3 to 20 carbon atoms, a substituted or unsubstituted heterocycloalkyl group having 3 to 20 carbon atoms, a substituted or unsubstituted cycloalkenyl group having 3 to 20 carbon atoms, a substituted or unsubstituted heteroaralkyl group having 3 to 30 carbon atoms, and a substituted or unsubstituted heteroalkenyl group having 1 to 20 carbon atoms, and the substituents of $R_8$ to $R_{16}$ are substituted with a substituent selected from the group consisting of hydrogen, deuterium, a cyano group, a nitro group, a halogen group, a hydroxyl group, an alkyl group having 1 to 30 carbon atoms, an alkenyl group having 2 to 30 carbon atoms, an alkynyl group having 2 to 24 carbon atoms, a heteroalkyl group having 2 to 30 carbon atoms, an aralkyl group having 6 to 30 carbon atoms, a cycloalkyl group having 3 to 20 carbon atoms, a heterocycloalkyl group having 3 to 20 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylsilyl group having 1 to 30 carbon atoms, an arylsilyl group having 6 to 30 carbon atoms, and an aryloxy group having 6 to 30 carbon atoms, and when the substituents are substituted with a plurality of substituents, the substituted substituents are the same as or different from each other.

Ar₁ is characterized by being a substituted or unsubstituted aryl group having 6 to 15 carbon atoms, preferably a substituted or unsubstituted phenyl group, a substituted or unsubstituted naphthyl group, a substituted or unsubstituted phenanthrenyl group, a substituted or unsubstituted fluorenyl group, and more preferably a substituted or unsubstituted fluorenyl group.

The substituent of $Ar_1$ may be selected from the group consisting of deuterium, an alkyl group having 1 to 4 carbon atoms, a cycloalkyl group having 3 to 10 carbon atoms, and an aryl group having 6 to 15 carbon atoms.

$R_4$ and $R_5$ are the same as or different from each other, and may be each independently a substituted or unsubstituted alkyl group having 1 to 30 carbon atoms or a substituted or unsubstituted aryl group having 5 to 30 carbon atoms.

The compound according to another exemplary embodiment of the present invention may be a compound represented by the following Formula 8:

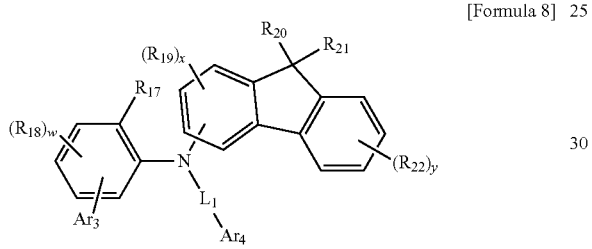

[Formula 8]

here, w is an integer from 1 to 3, x is an integer from 0 to 3, y is an integer from 0 to 4, $Ar_3$ and $Ar_4$ are the same as or different from each other, and are each independently selected from the group consisting of hydrogen, a substituted or unsubstituted aryl group having 6 to 30 carbon atoms, and a substituted or unsubstituted heteroaryl group having 3 to 30 carbon atoms, $R_{17}$ is selected from the group consisting of a substituted or unsubstituted alkyl group having 1 to 10 carbon atoms, a substituted or unsubstituted cycloalkyl group having 3 to 10 carbon atoms, and a substituted or unsubstituted aryl group having 6 to 30 carbon atoms, at least one of $Ar_3$, $Ar_4$, and $R_{17}$ is a substituted or unsubstituted aryl group having 7 to 30 carbon atoms, $L_1$ is a single bond or a substituted or unsubstituted aryl group having 6 to 30 carbon atoms, $R_{18}$ to $R_{22}$ are the same as or different from each other, and are each independently selected from the group consisting of hydrogen, deuterium, a substituted or unsubstituted alkyl group having 1 to 20 carbon atoms, a substituted or unsubstituted cycloalkyl group having 3 to 30 carbon atoms, a substituted or unsubstituted alkenyl group having 2 to 20 carbon atoms, a substituted or unsubstituted alkynyl group having 2 to 20 carbon atoms, a substituted or unsubstituted heteroalkyl group having 1 to 20 carbon atoms, a substituted or unsubstituted aralkyl group having 6 to 20 carbon atoms, a substituted or unsubstituted aryl group having 6 to 30 carbon atoms, a substituted or unsubstituted heteroaryl group having 3 to 30 carbon atoms, and a substituted or unsubstituted heteroaralkyl group having 3 to 20 carbon atoms, $R_{17}$ to $R_{22}$ may be each linked to an adjacent substituent to form a saturated or unsaturated ring, and the formed alicyclic or aromatic monocyclic or polycyclic ring includes or does not include at least one heteroatom selected from the group consisting of N, O, S, and Si in addition to a carbon atom, and the substituents of $Ar_3$, $Ar_4$, $L_1$, and $R_{17}$ to $R_{22}$ are each substituted with a substituent selected from the group consisting of hydrogen, deuterium, a cyano group, a nitro group, a halogen group, a hydroxyl group, an alkyl group having 1 to 30 carbon atoms, an alkenyl group having 2 to 30 carbon atoms, an alkynyl group having 2 to 24 carbon atoms, a heteroalkyl group having 2 to 30 carbon atoms, an aralkyl group having 6 to 30 carbon atoms, a cycloalkyl group having 3 to 20 carbon atoms, a heterocycloalkyl group having 3 to 20 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylsilyl group having 1 to 30 carbon atoms, an arylsilyl group having 6 to 30 carbon atoms, and an aryloxy group having 6 to 30 carbon atoms, and when the substituents are each substituted with a plurality of substituents, the substituted substituents are the same as or different from each other.

$L_1$ may be a single bond or a substituted or unsubstituted aryl group having 6 to 10 carbon atoms.

At least one of $Ar_3$, $Ar_4$, and $R_{17}$ may be selected from the group consisting of a phenyl substituted with an alkyl having 1 to 5 carbon atoms, a substituted or unsubstituted naphthyl group, and a substituted or unsubstituted phenanthrenyl group.

The compound represented by Formula 1 may be selected from the group consisting of the following compounds:

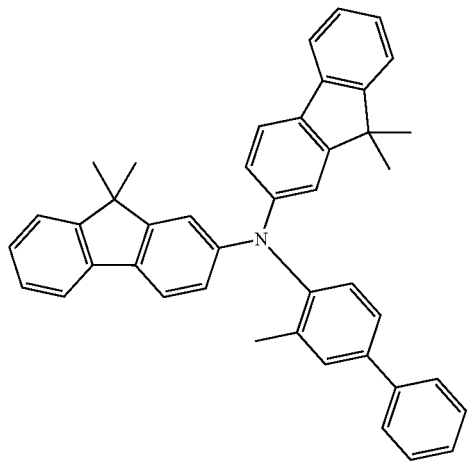

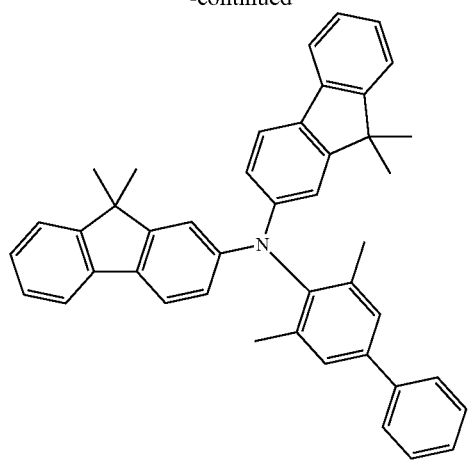
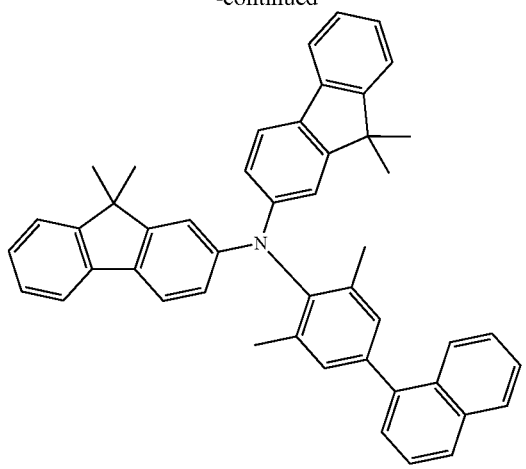
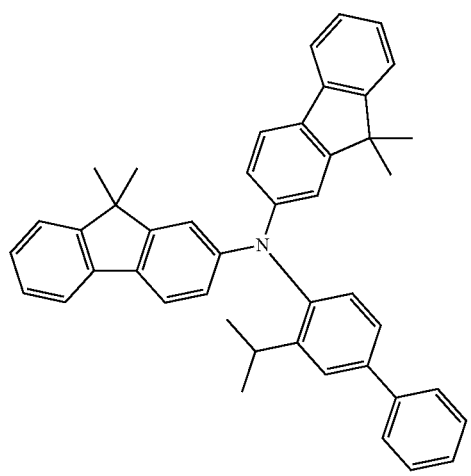
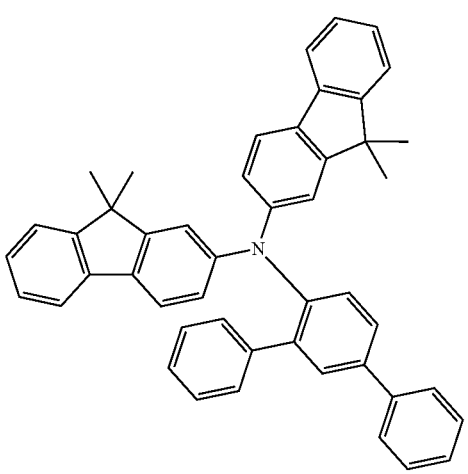
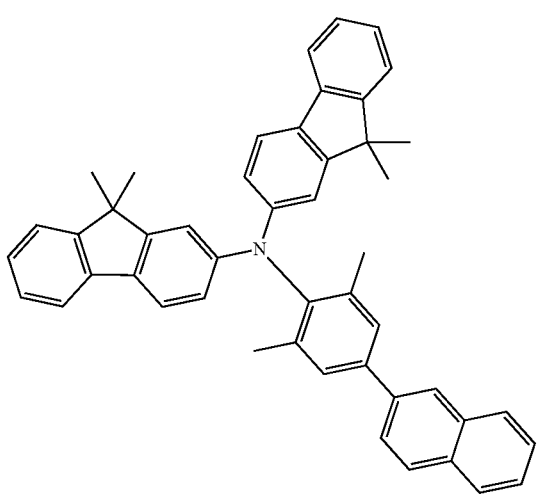
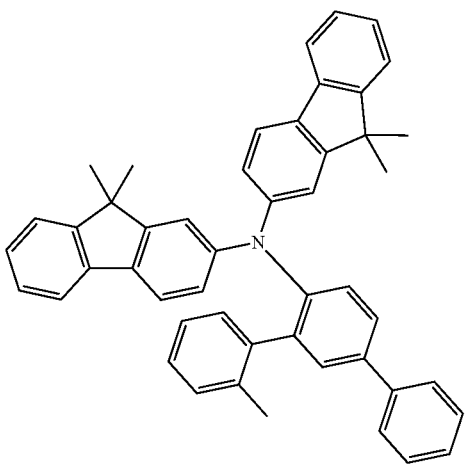

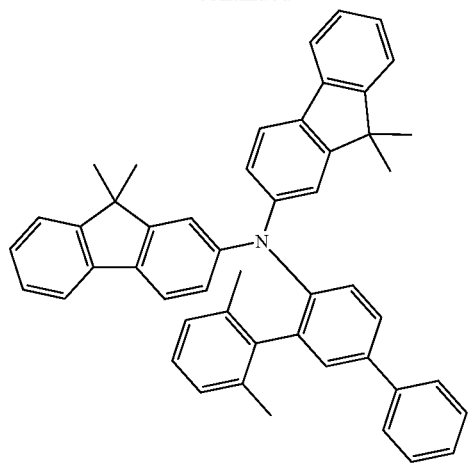
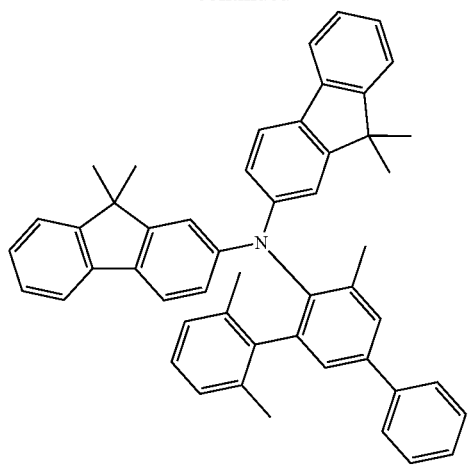
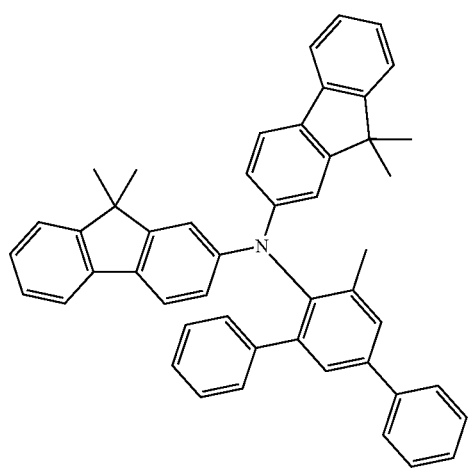
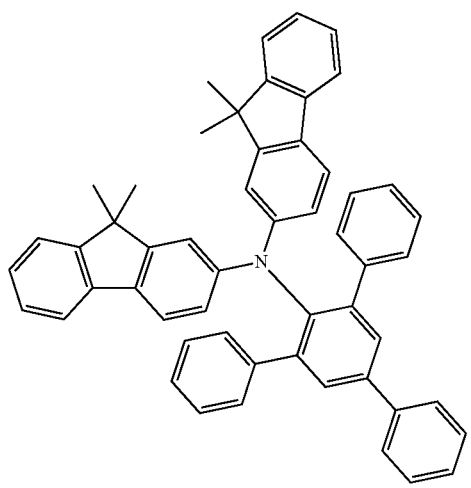
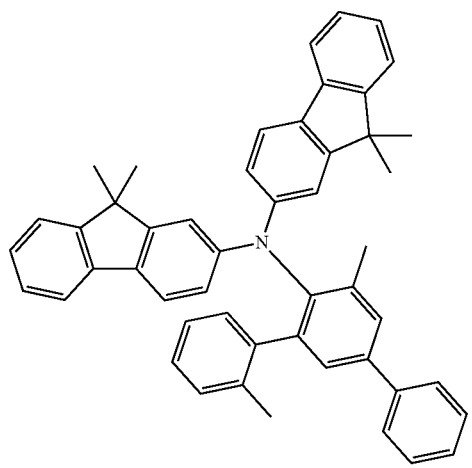
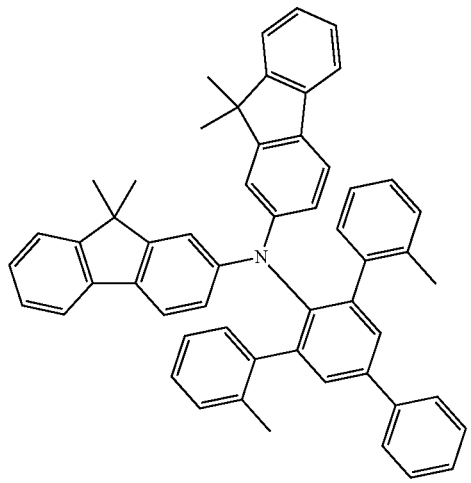

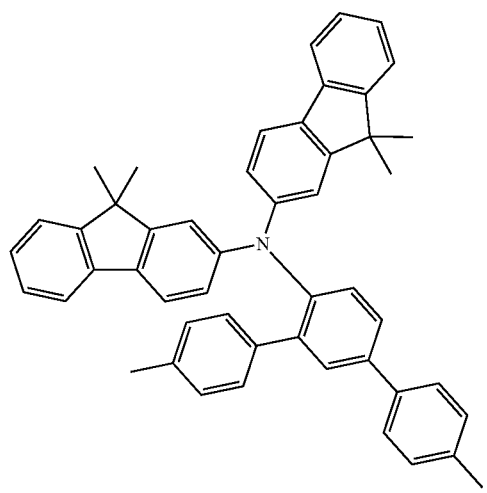
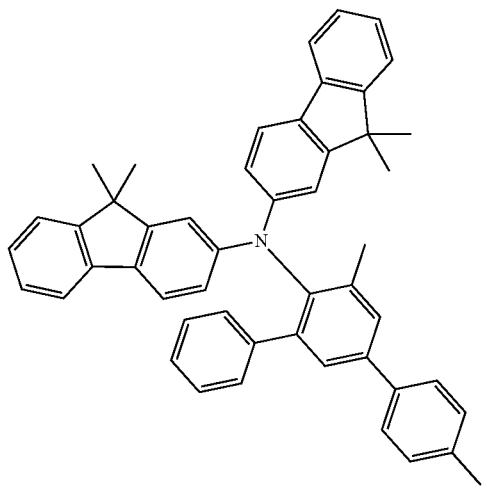
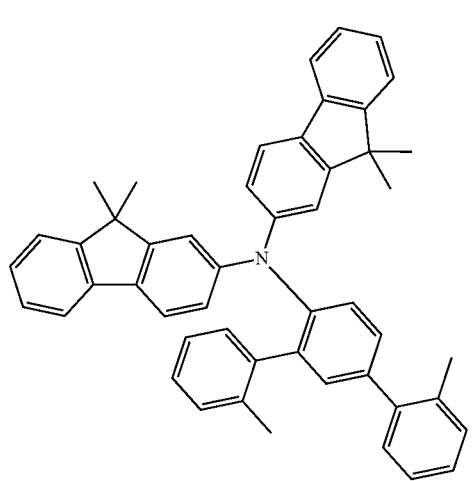
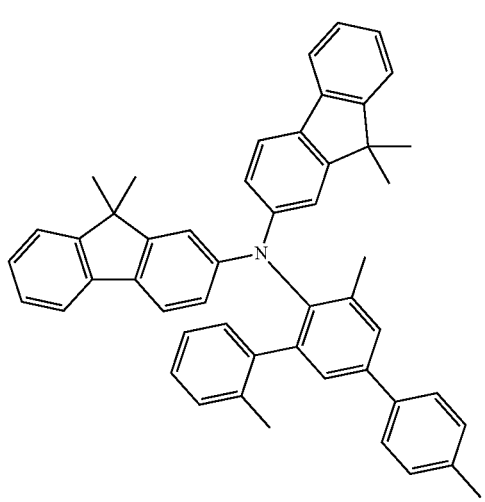
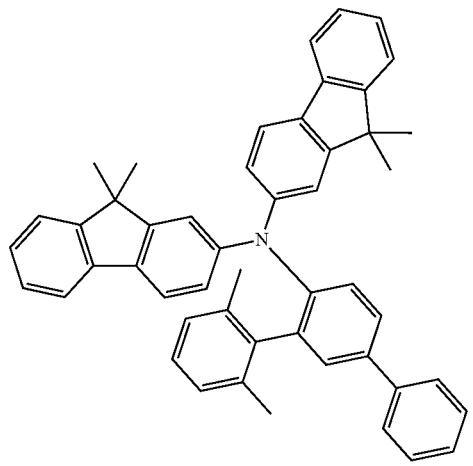
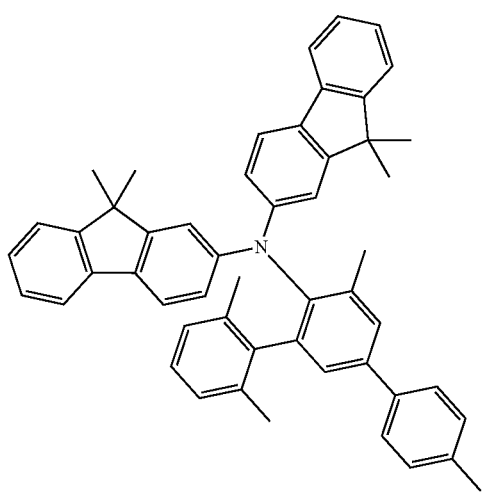

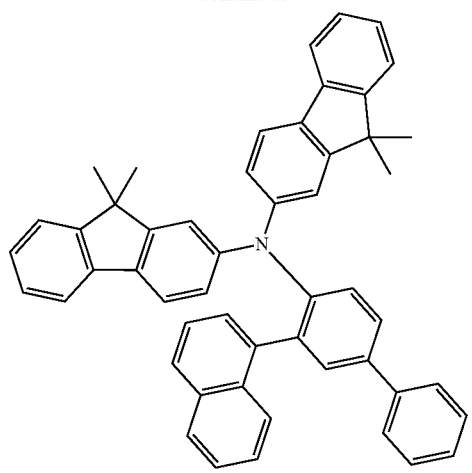
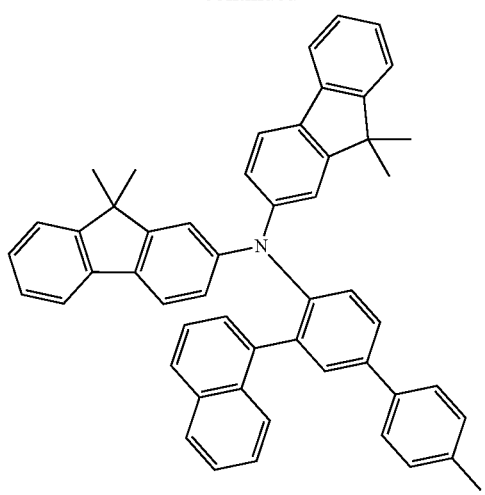
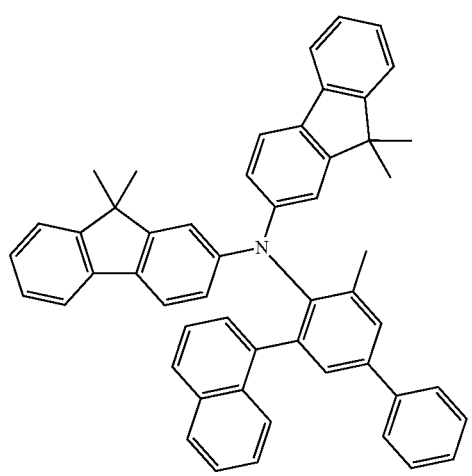
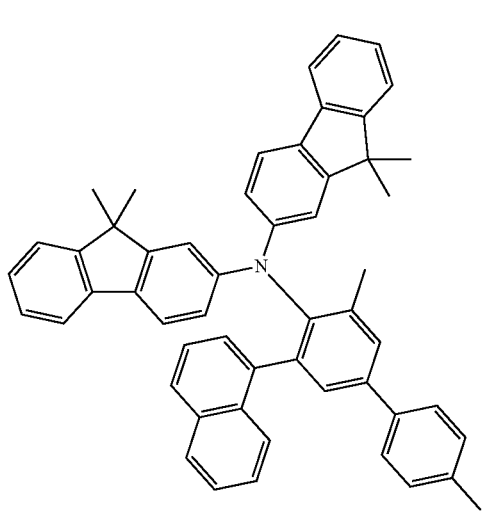
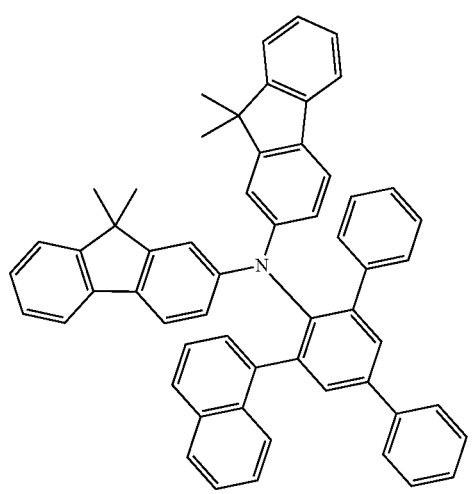
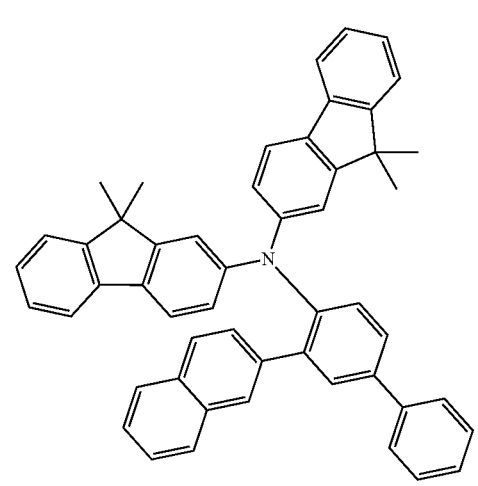

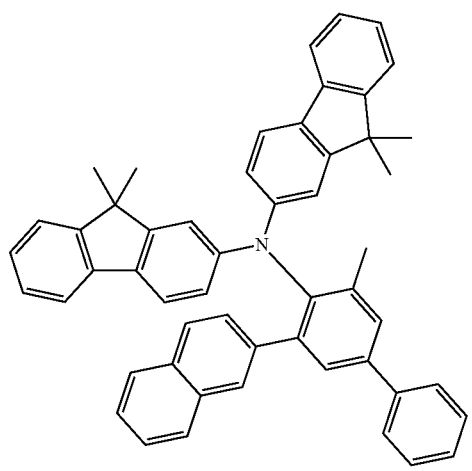
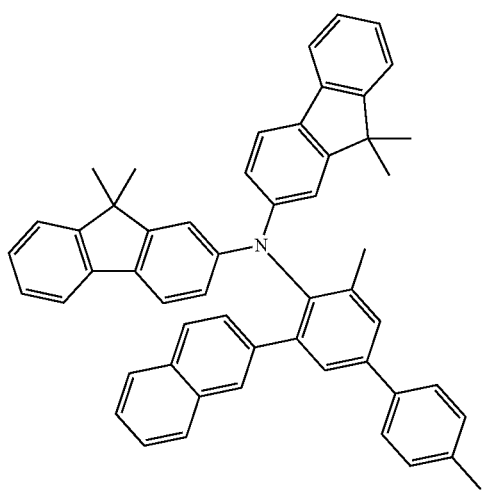
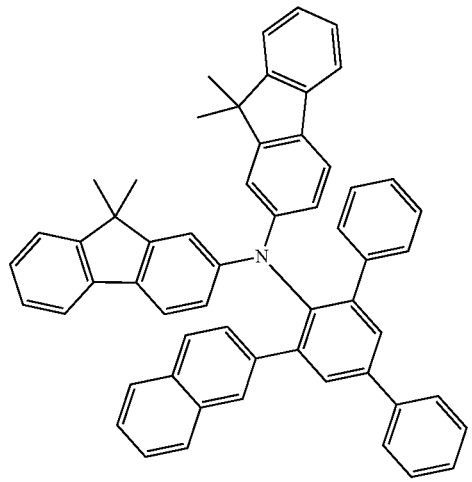
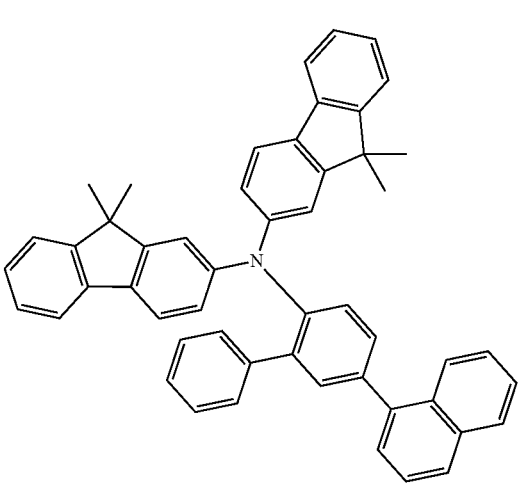
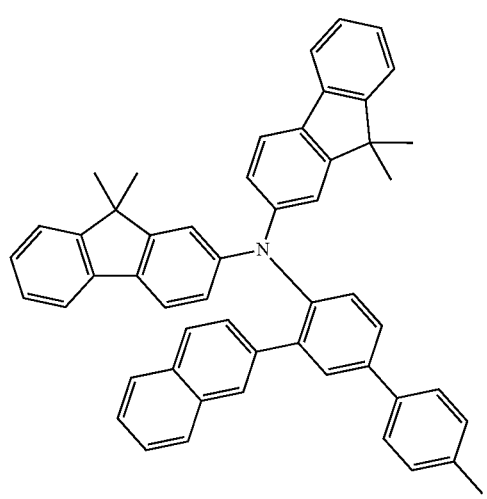
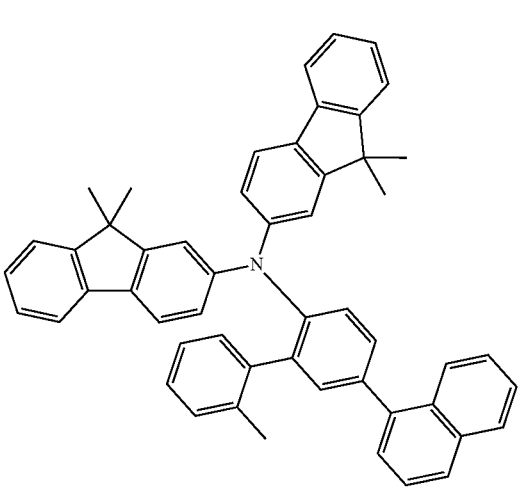

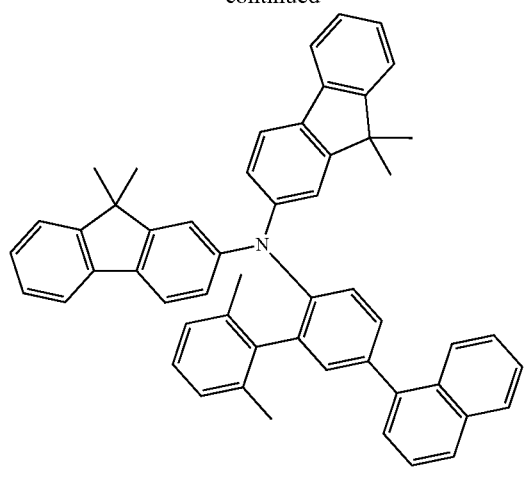
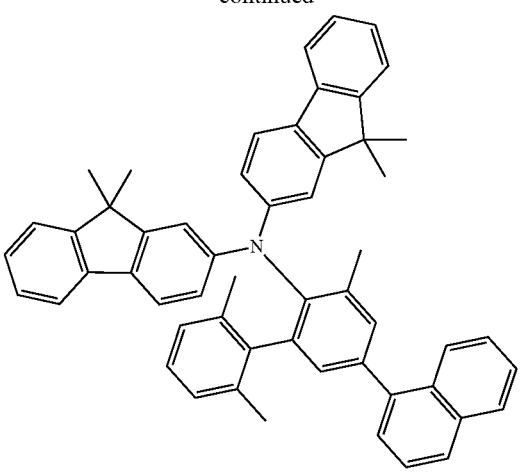
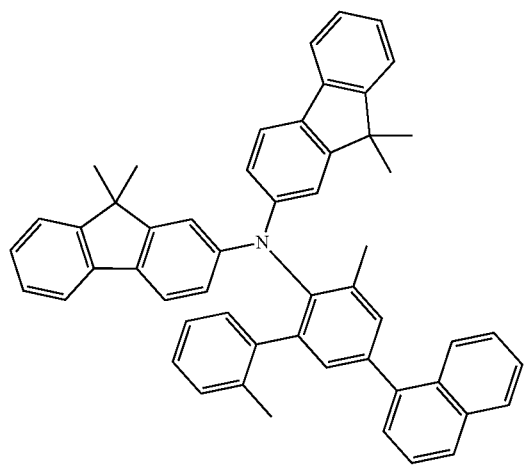

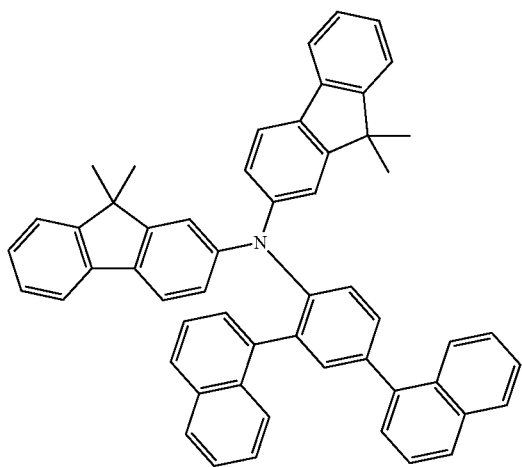
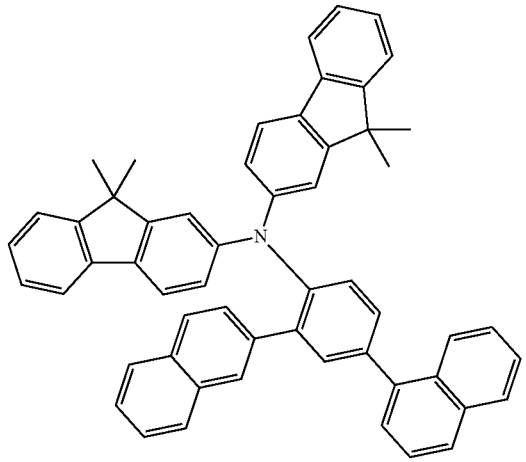
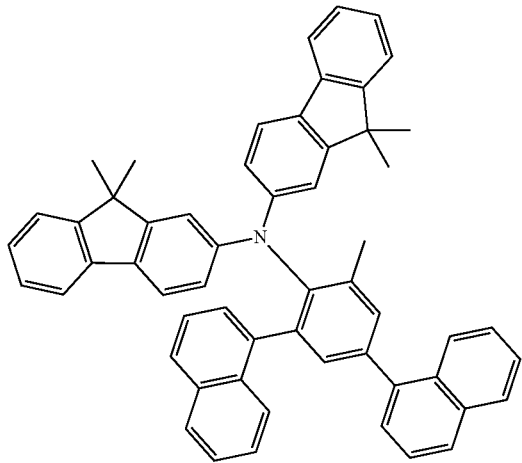
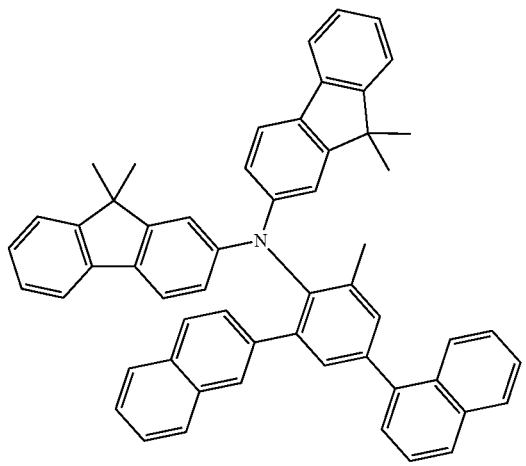
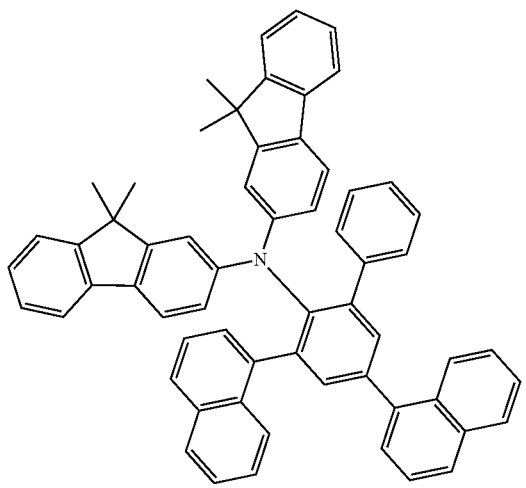
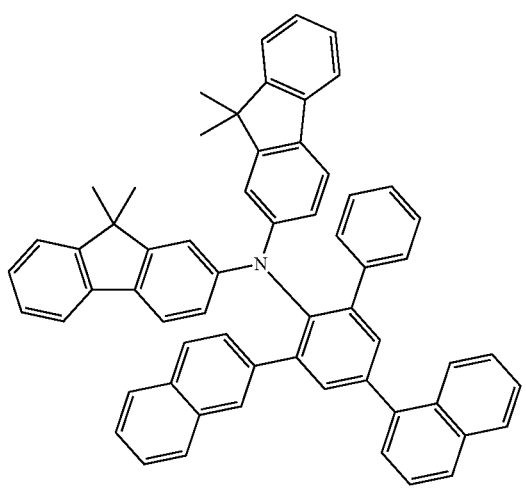

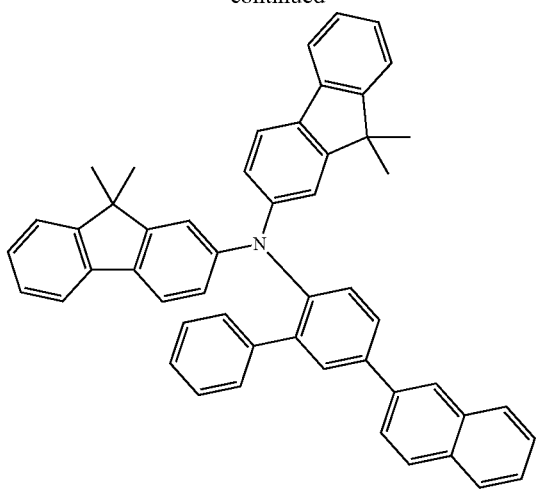
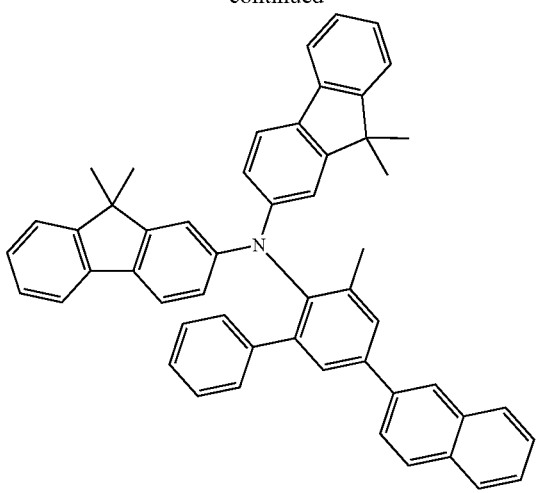
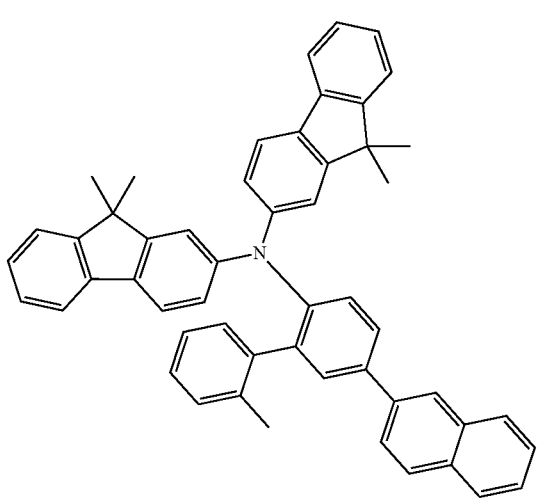
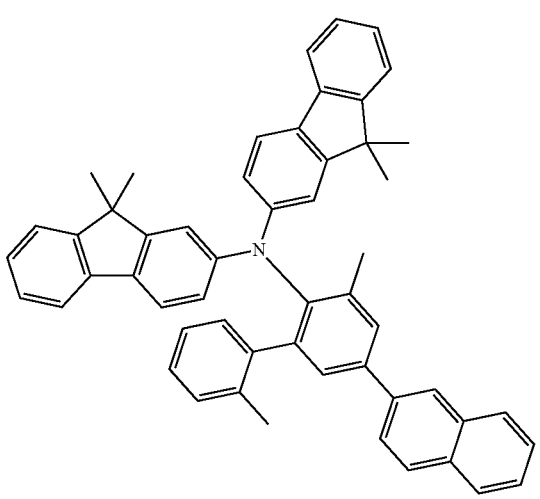
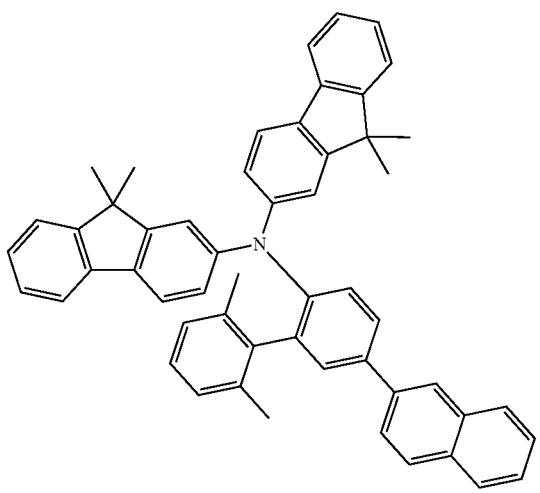

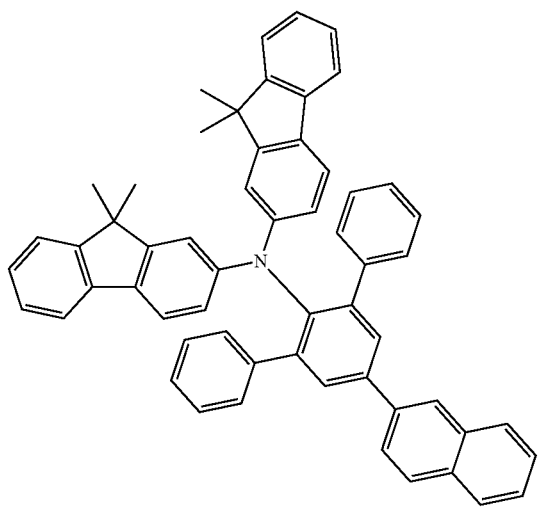
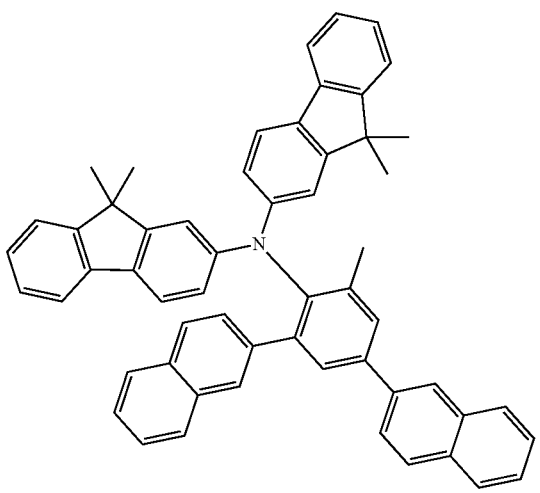
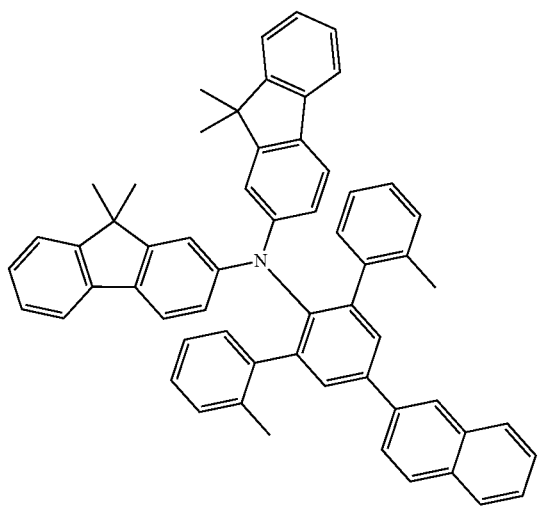
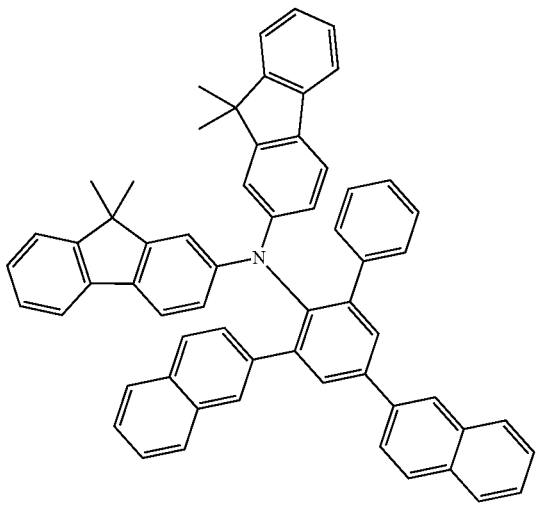
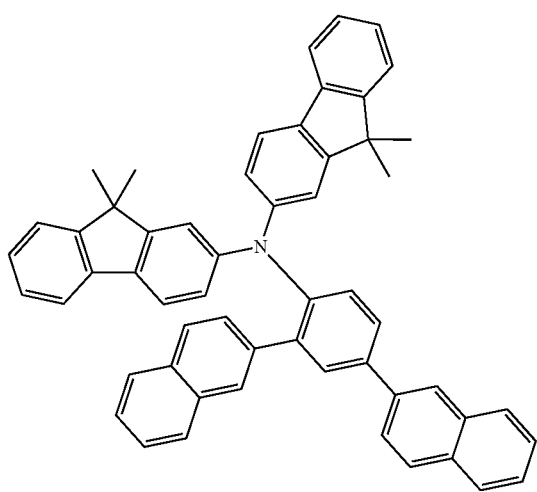
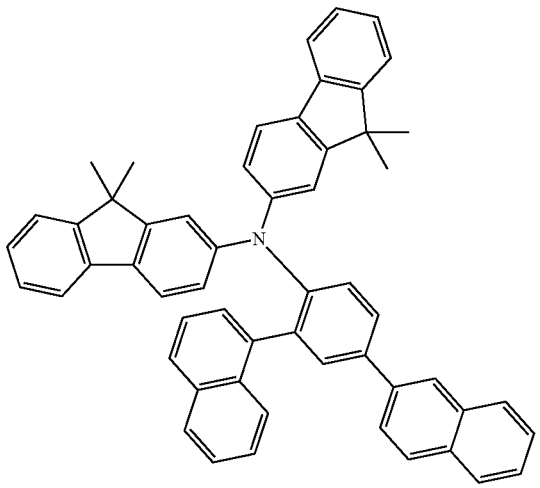

31
-continued
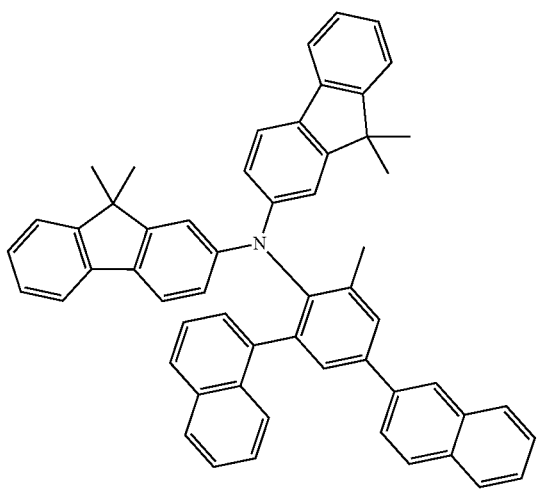
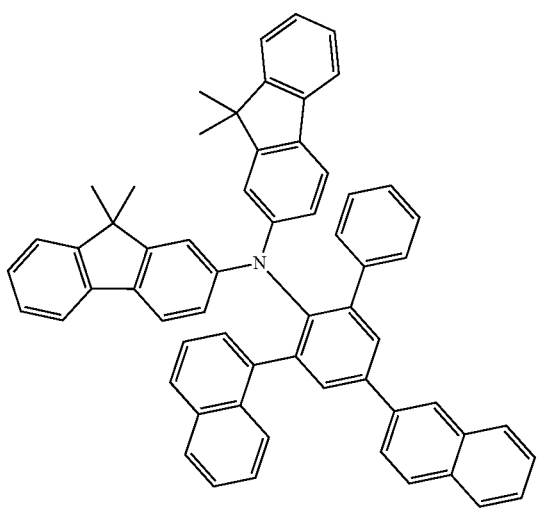
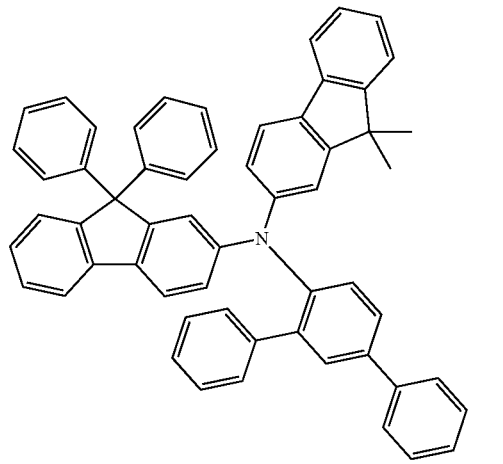
32
-continued
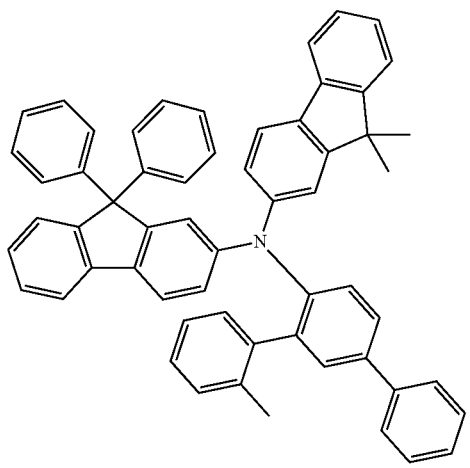
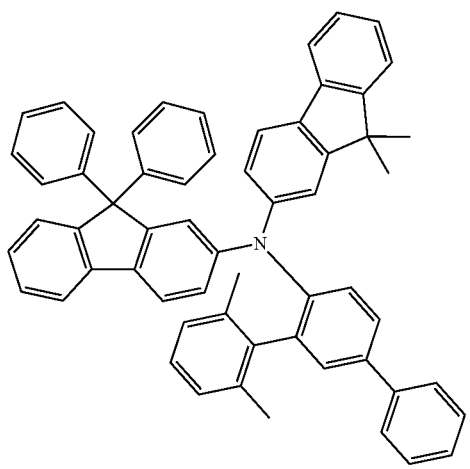
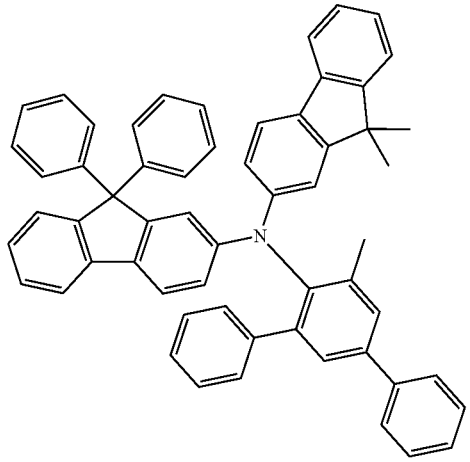

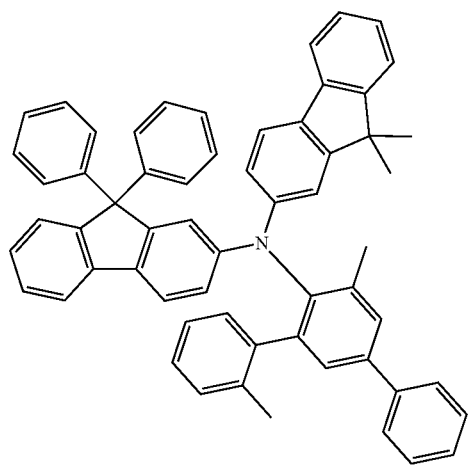
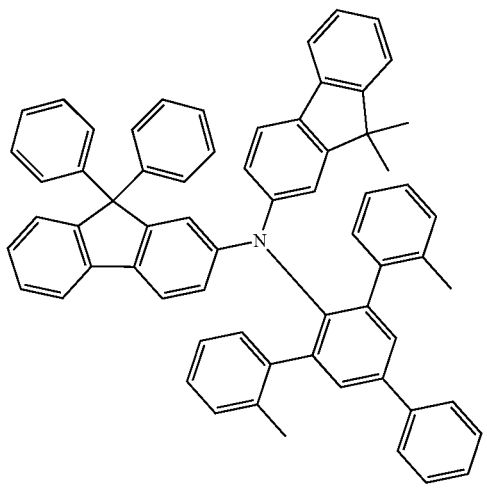
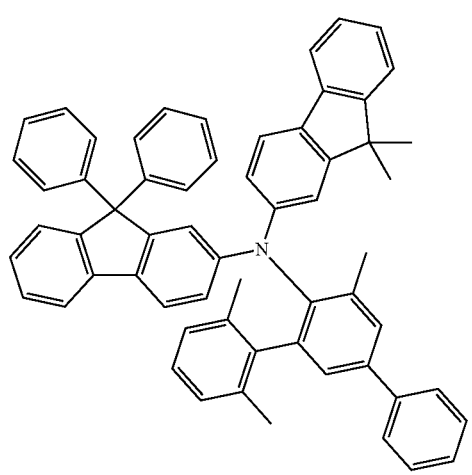
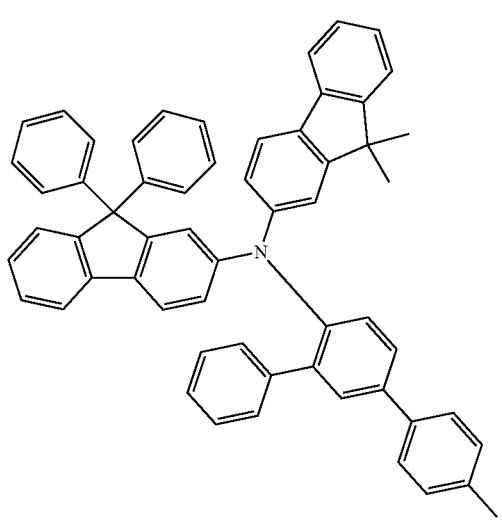
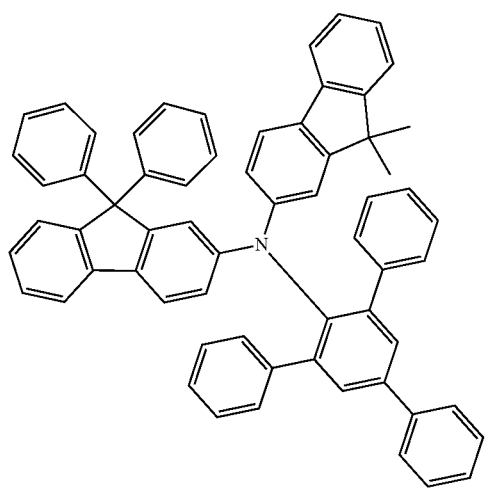
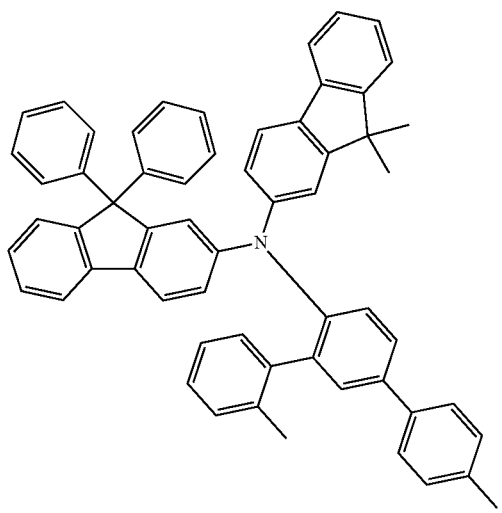

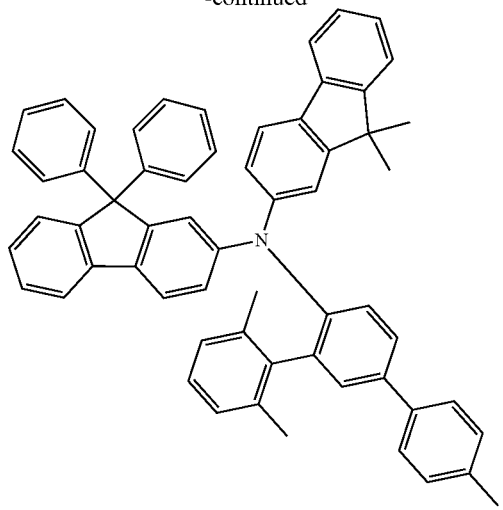
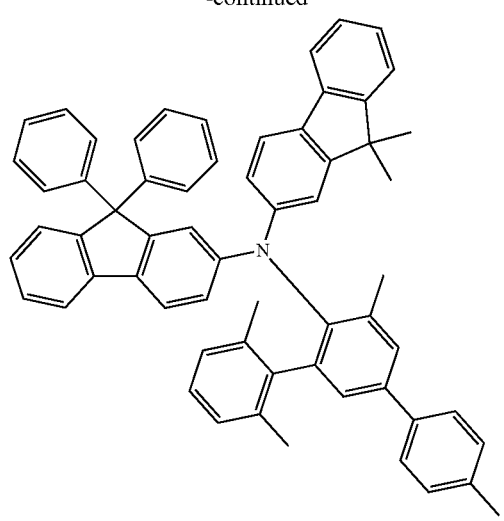
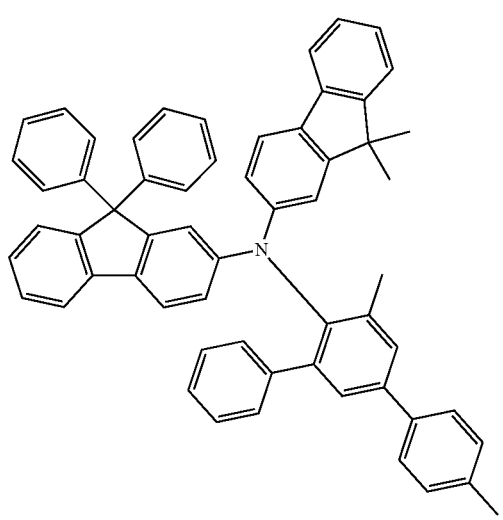
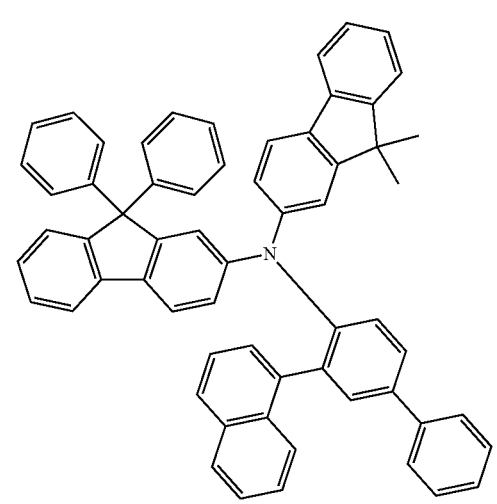
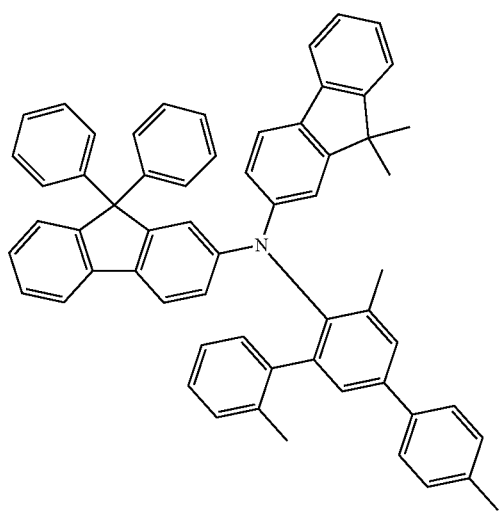
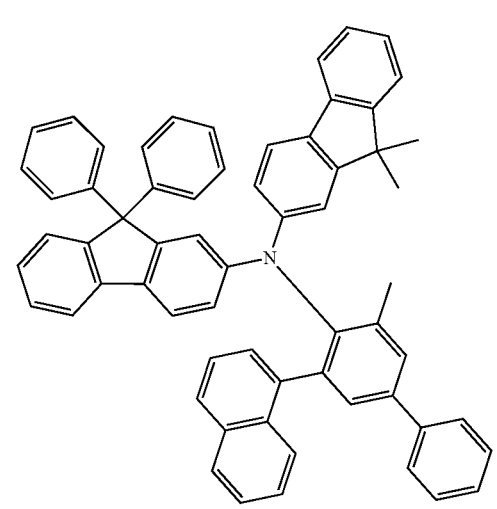

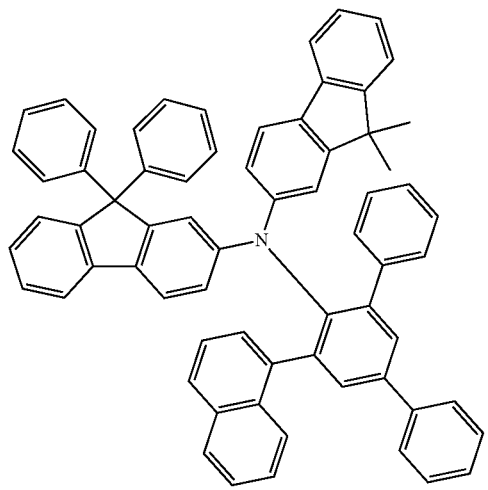
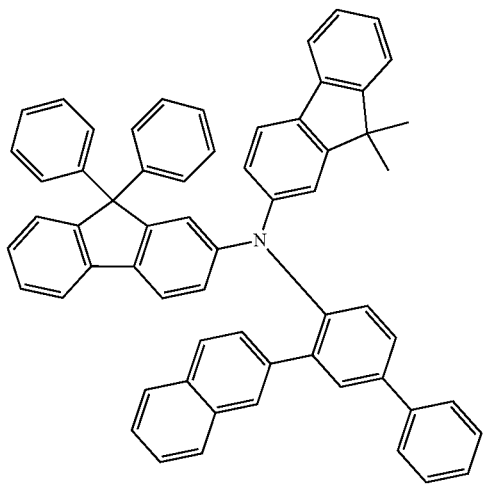
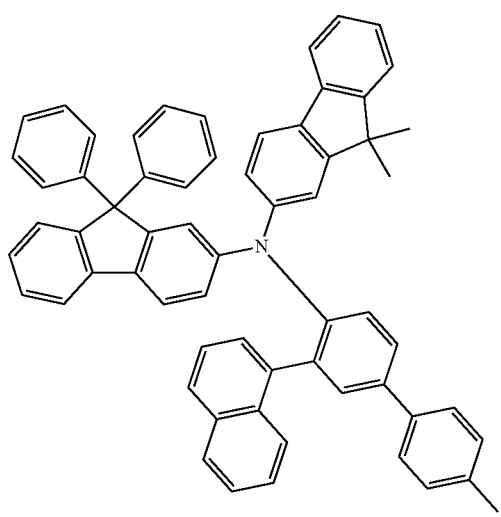
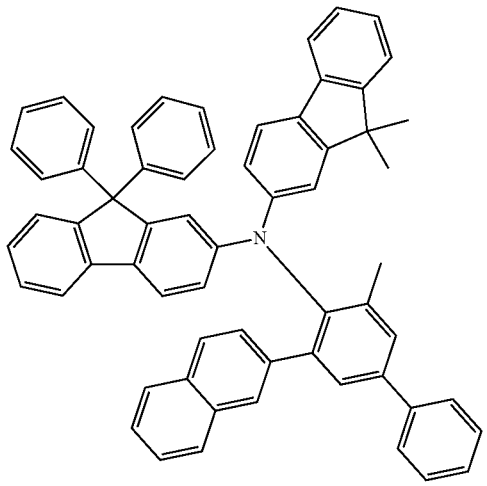
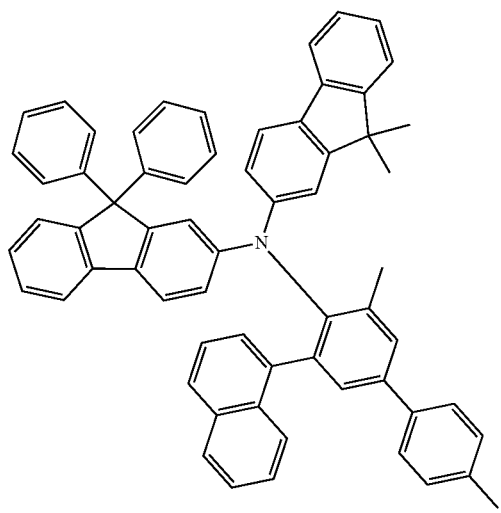

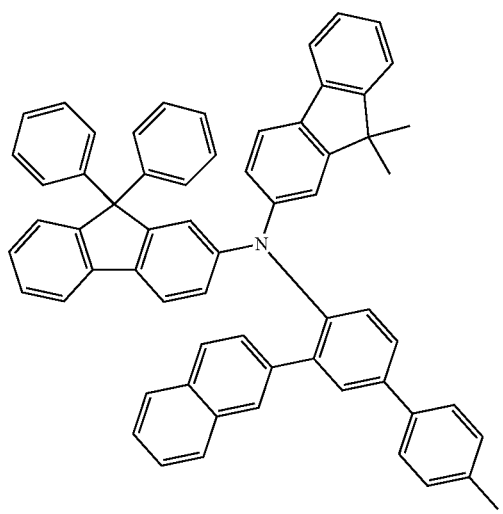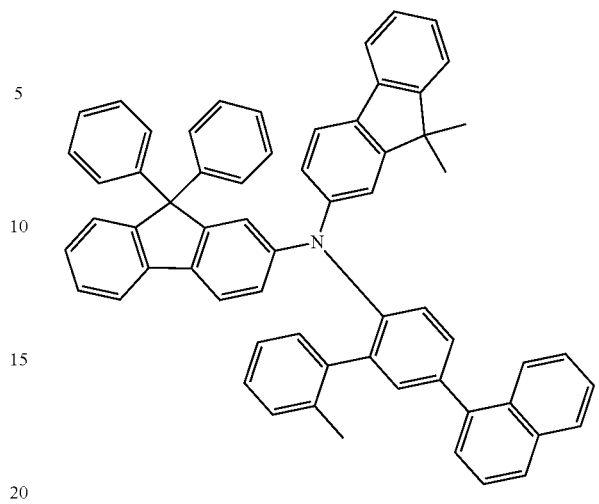

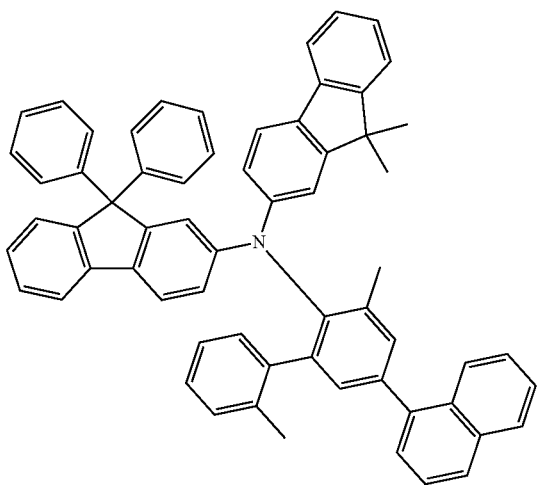
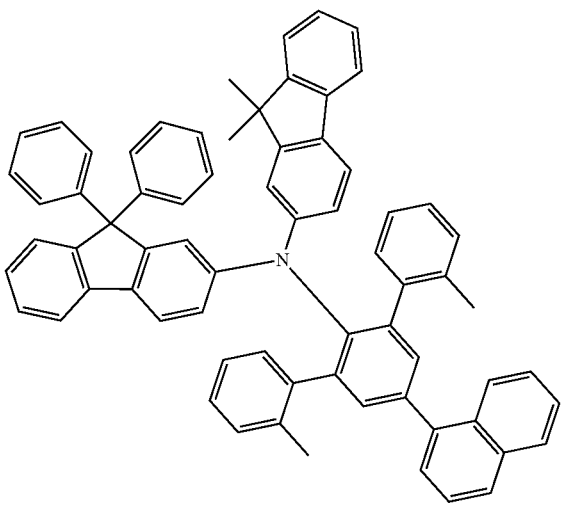
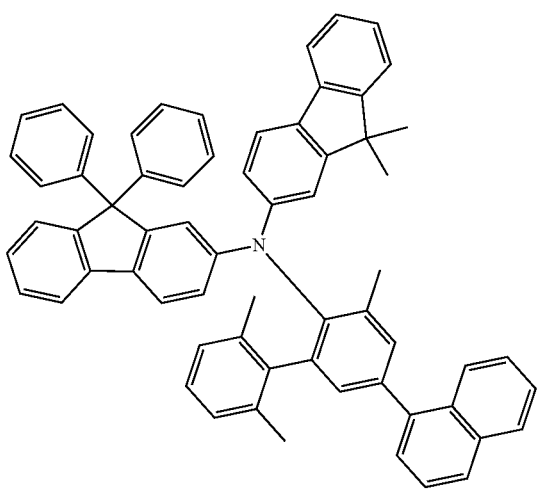
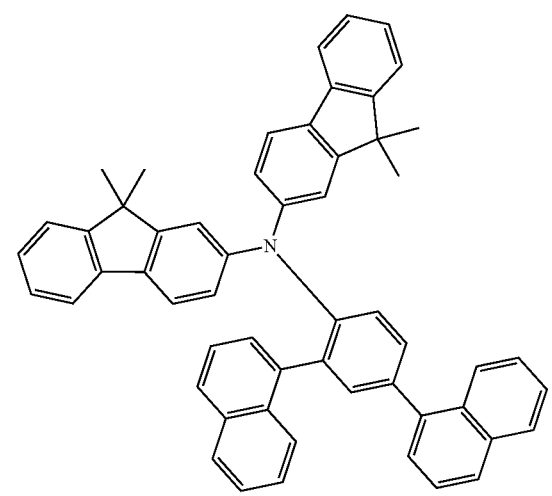
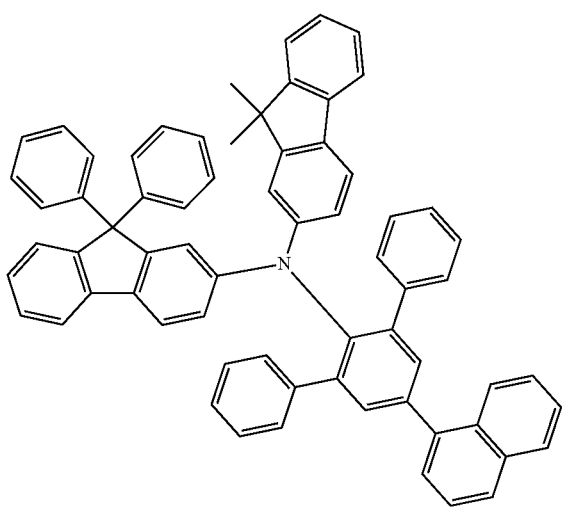
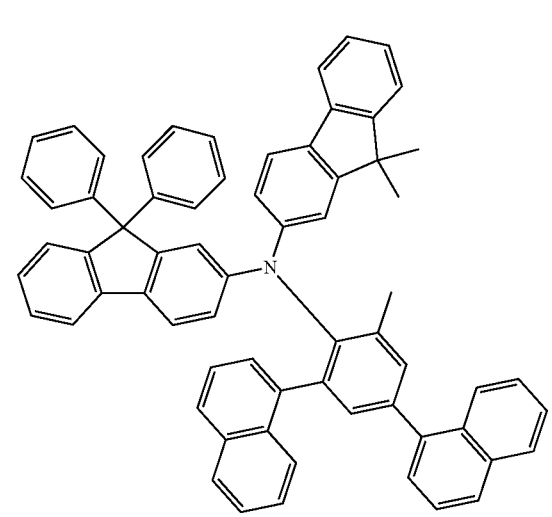

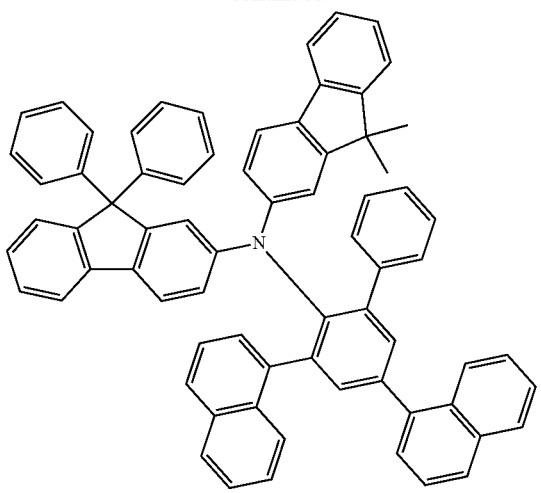
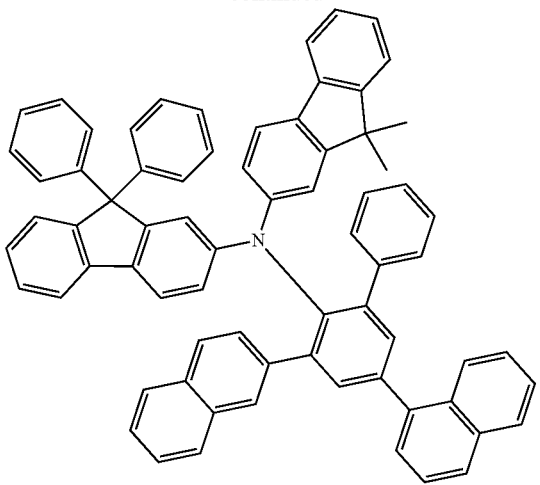
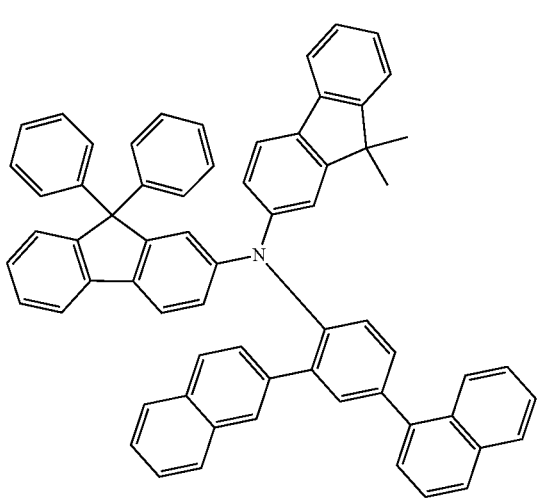
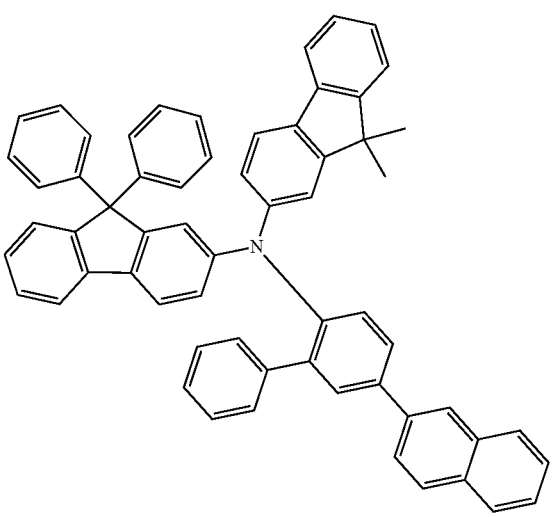
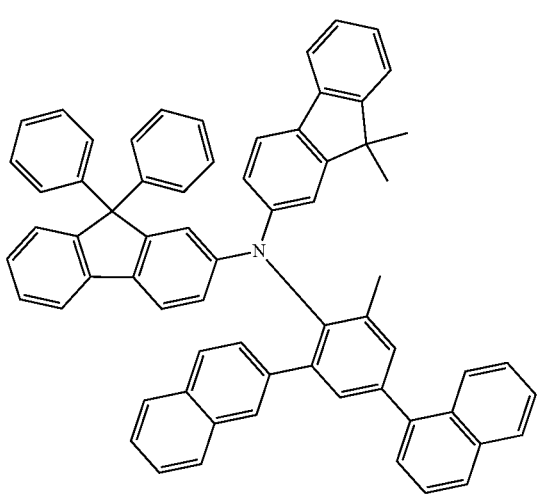

| 45 -continued | 46 -continued |
|---|---|
| 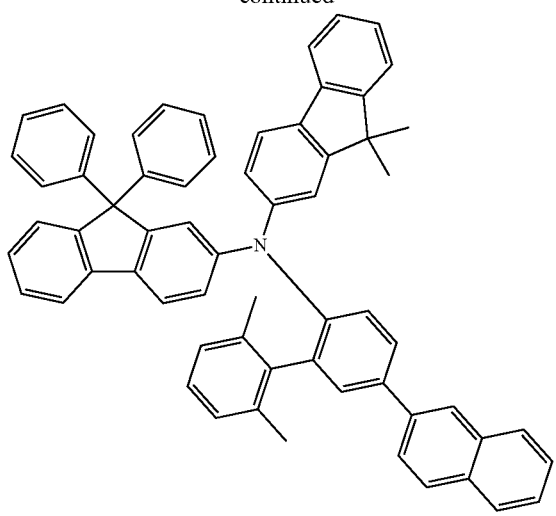 | 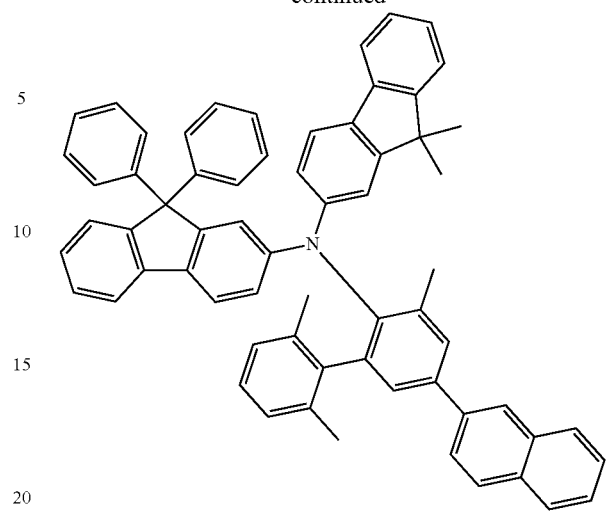 |
| 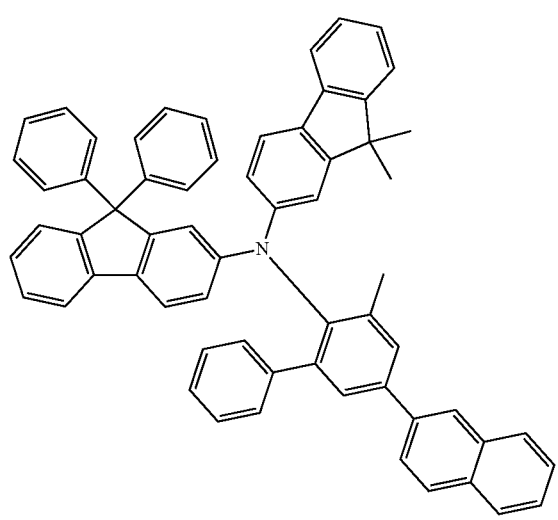 | 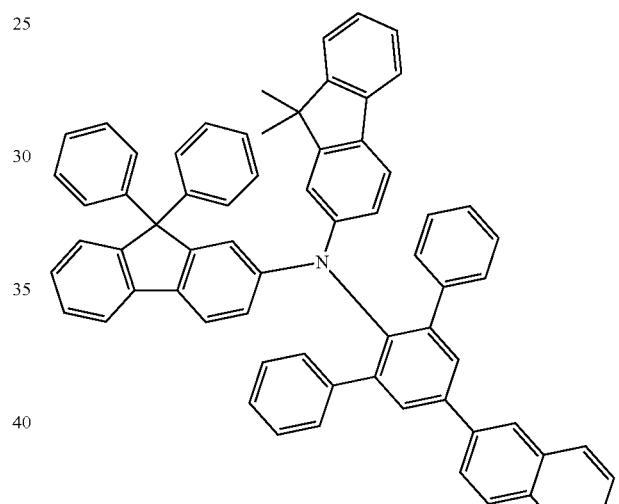 |
| 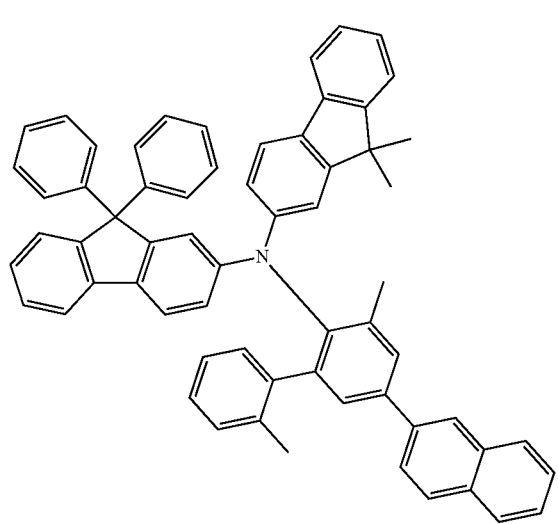 | 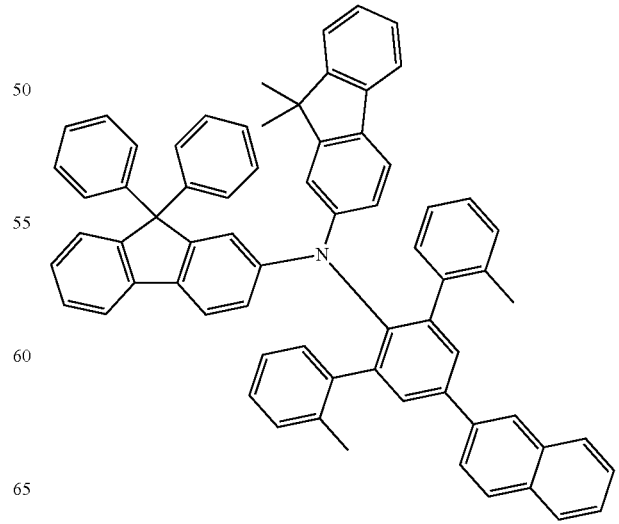 |

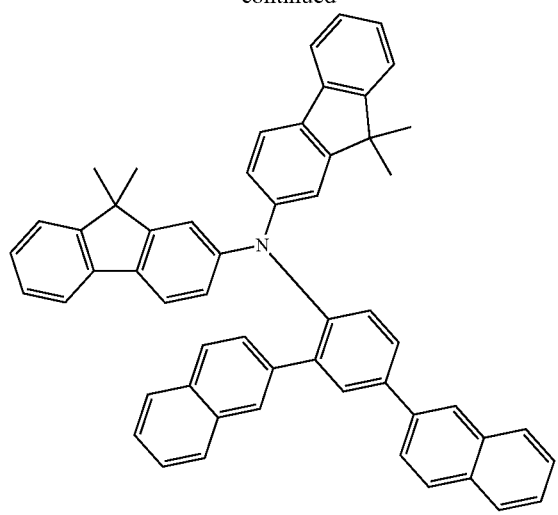
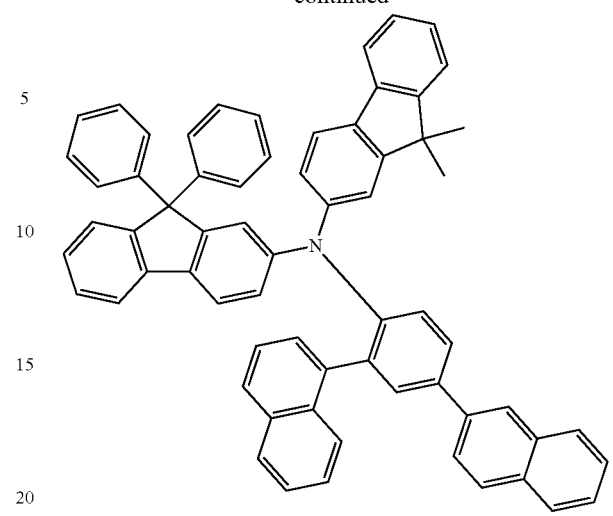
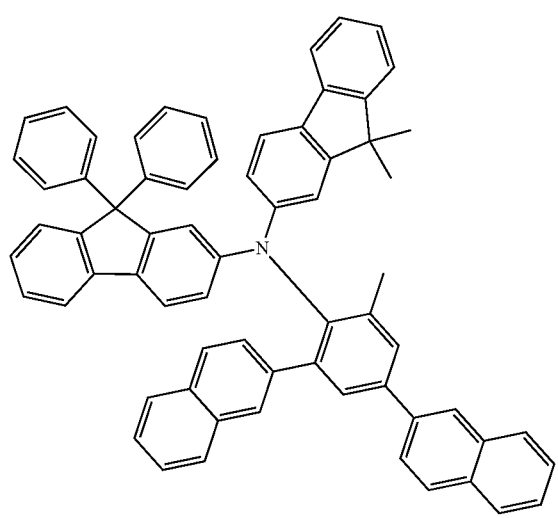
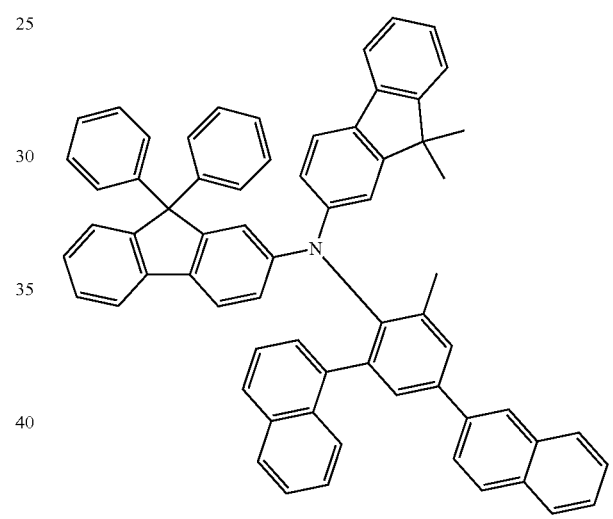
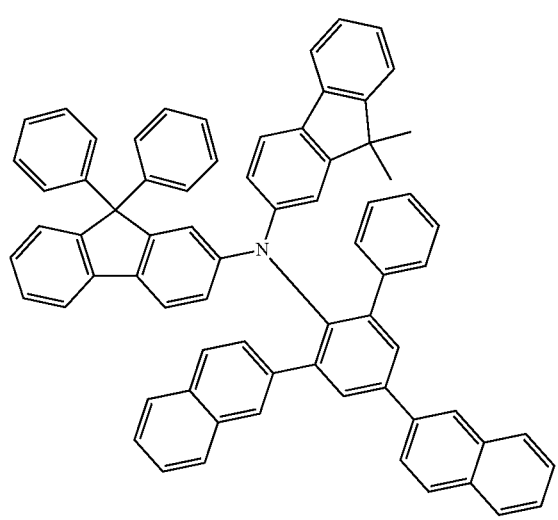
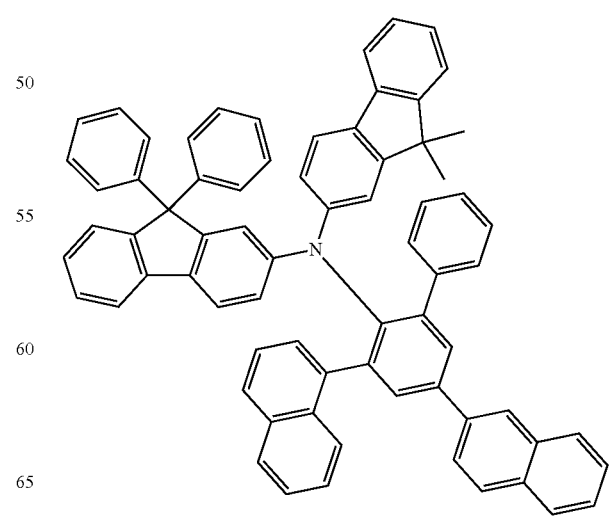

-continued
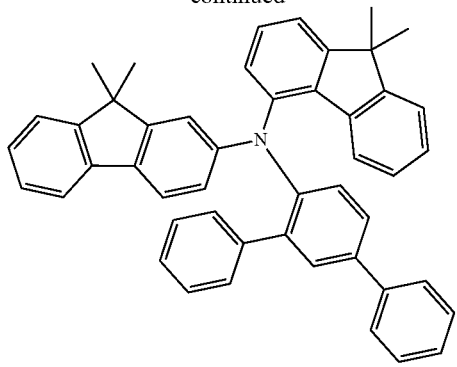
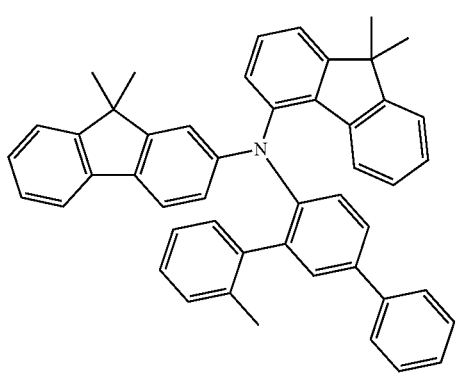
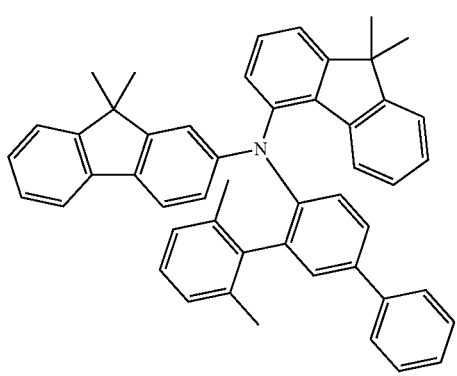
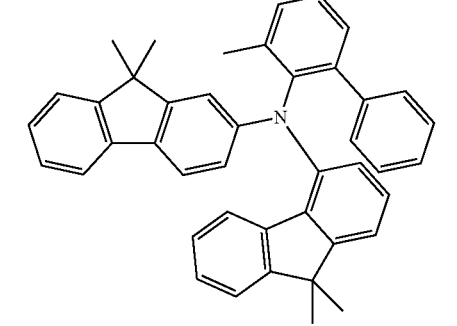
-continued
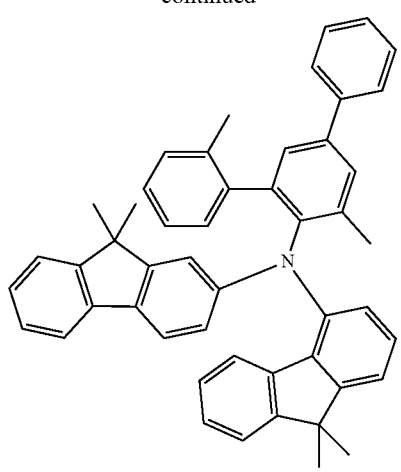
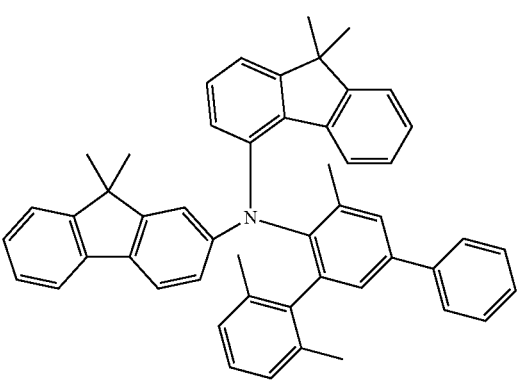
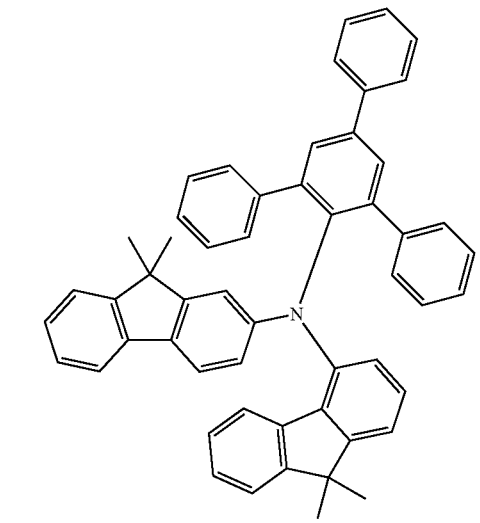

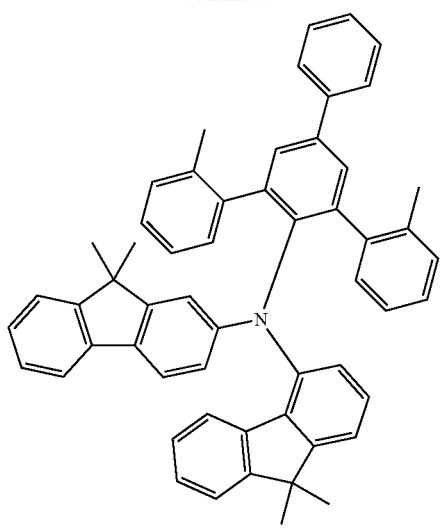
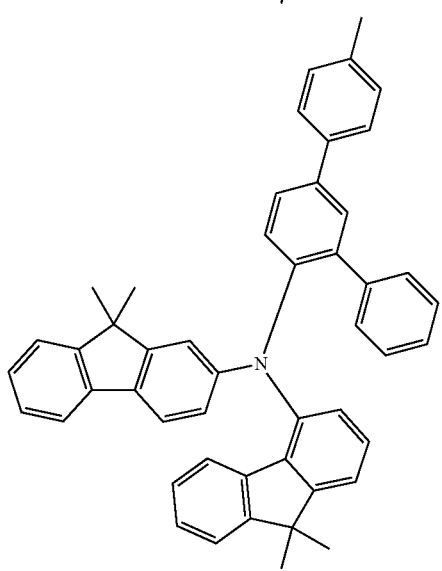
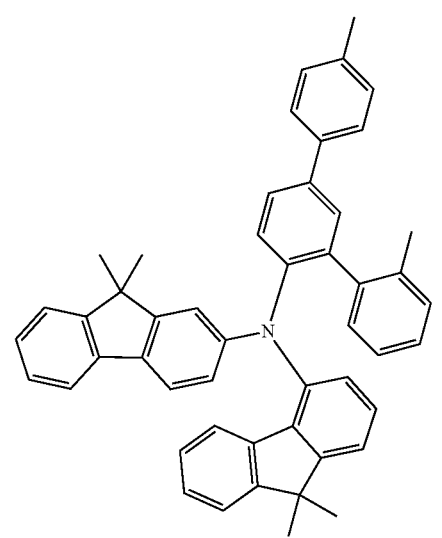
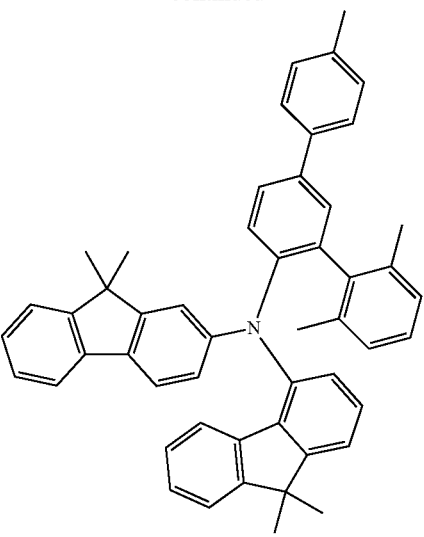
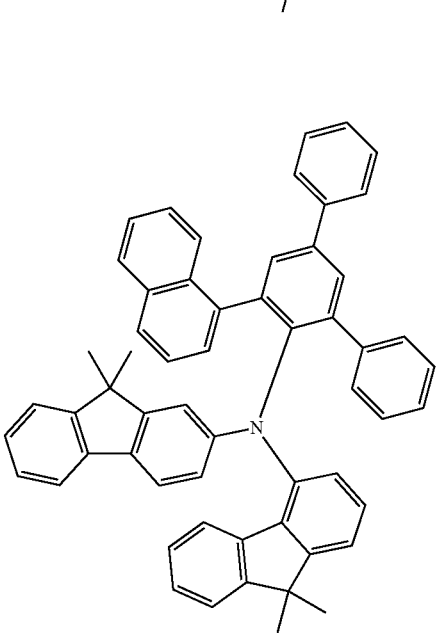
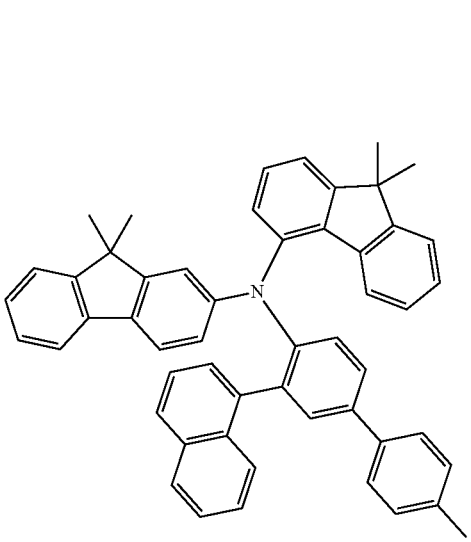

53
-continued
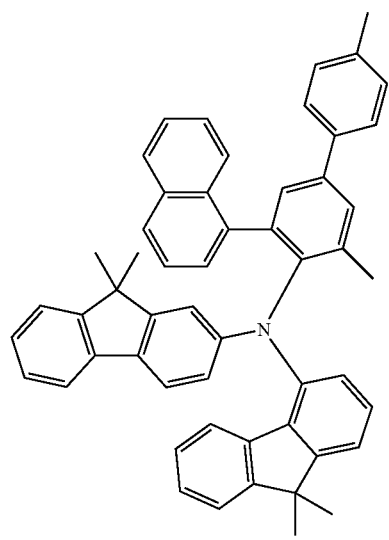
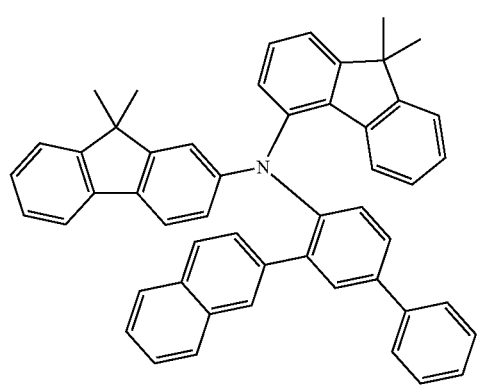
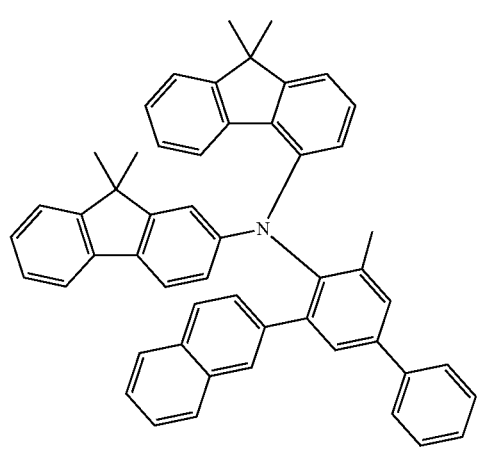
54
-continued
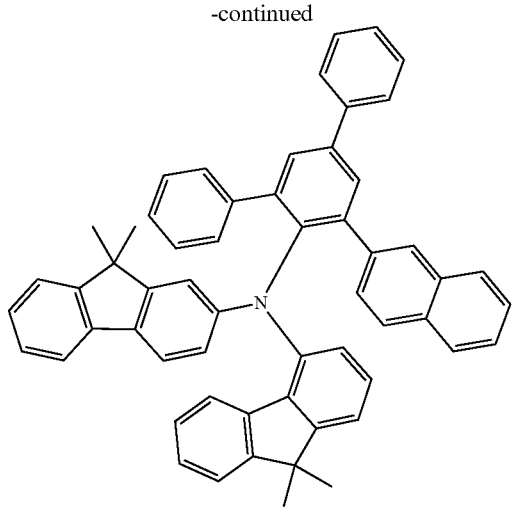
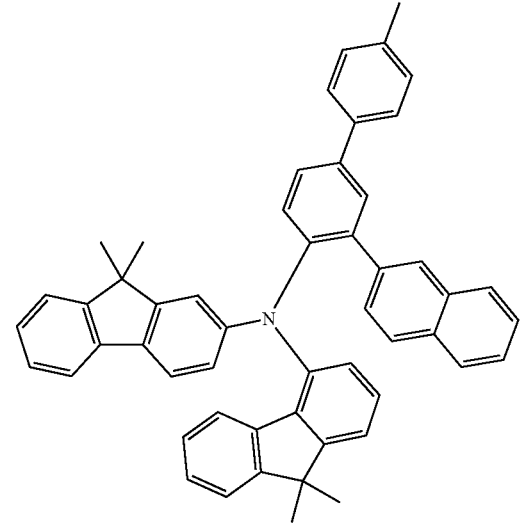
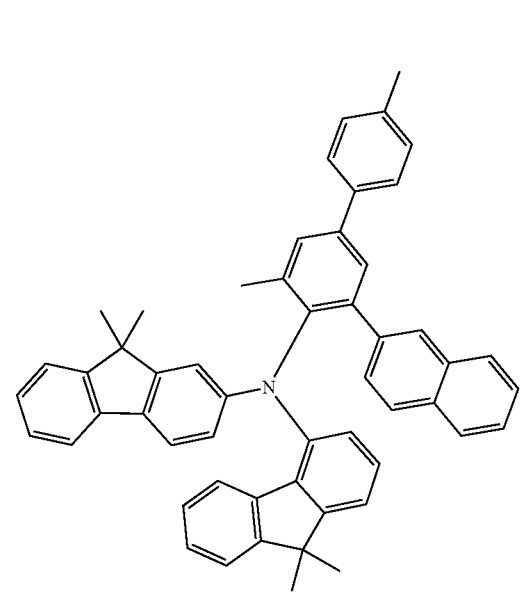

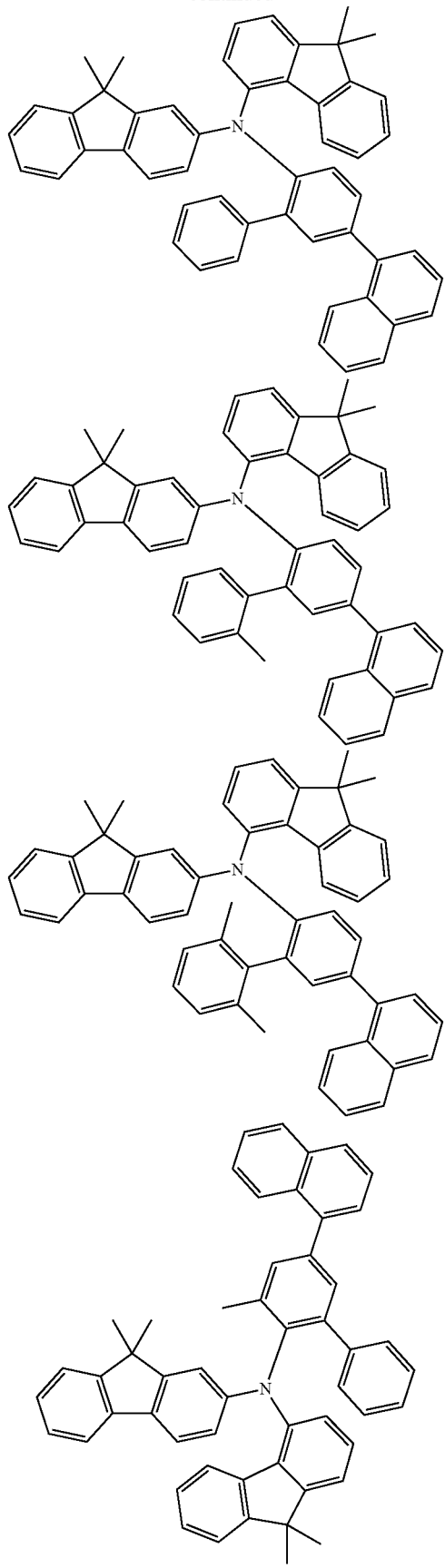
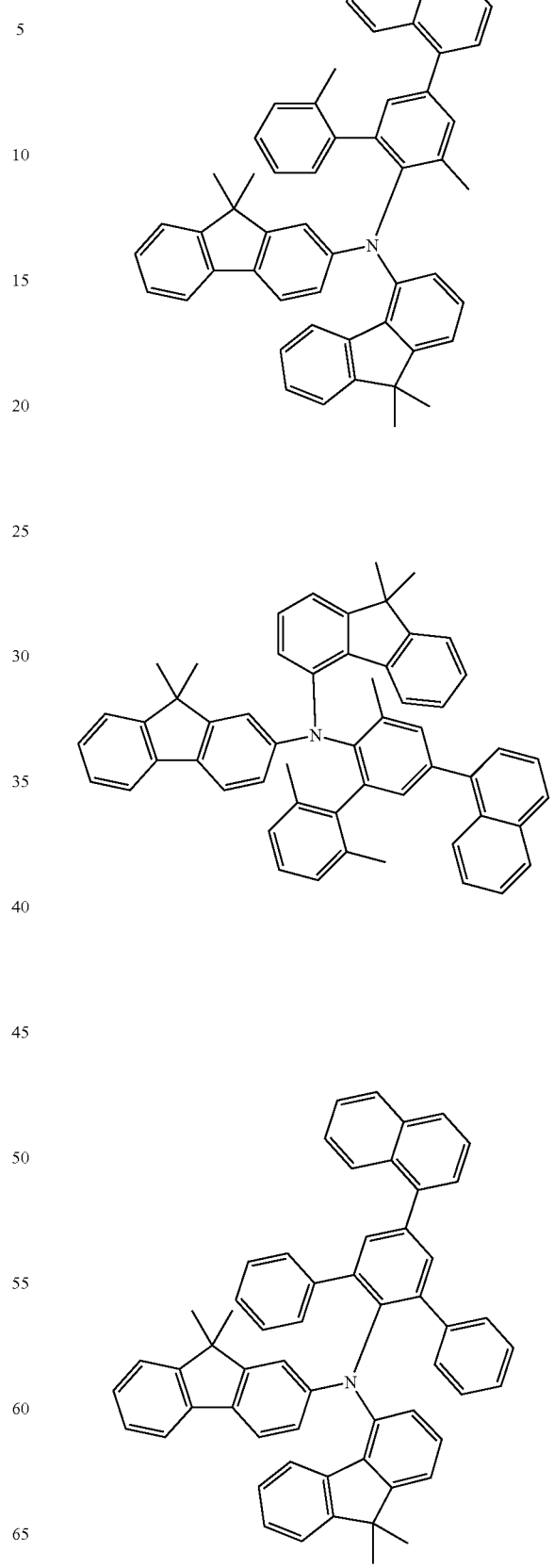

57
-continued
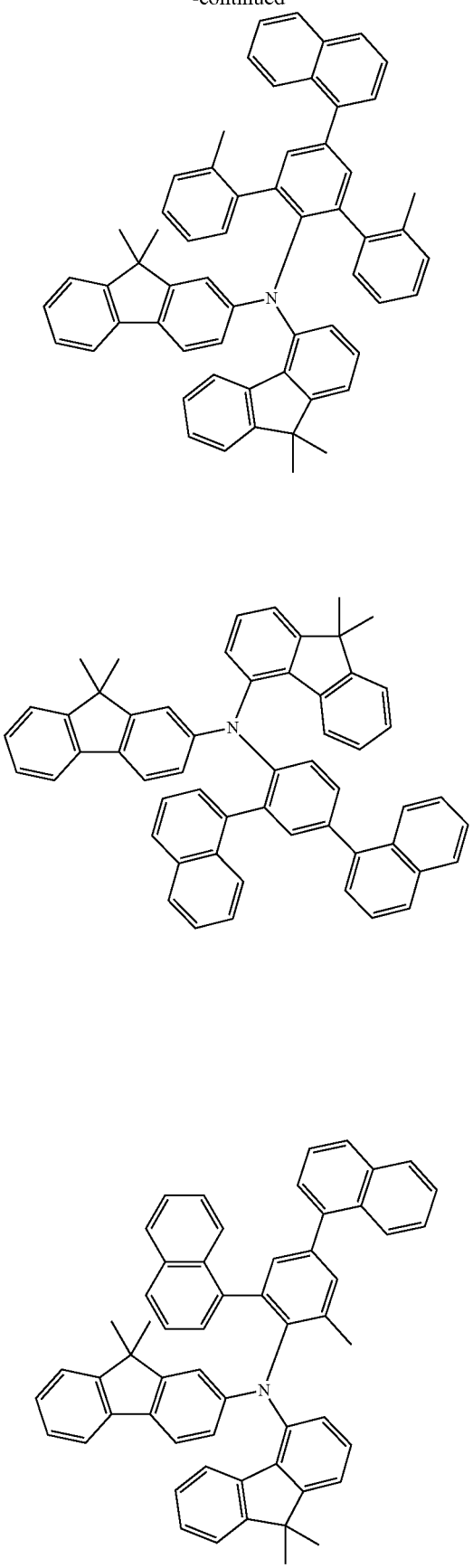
58
-continued
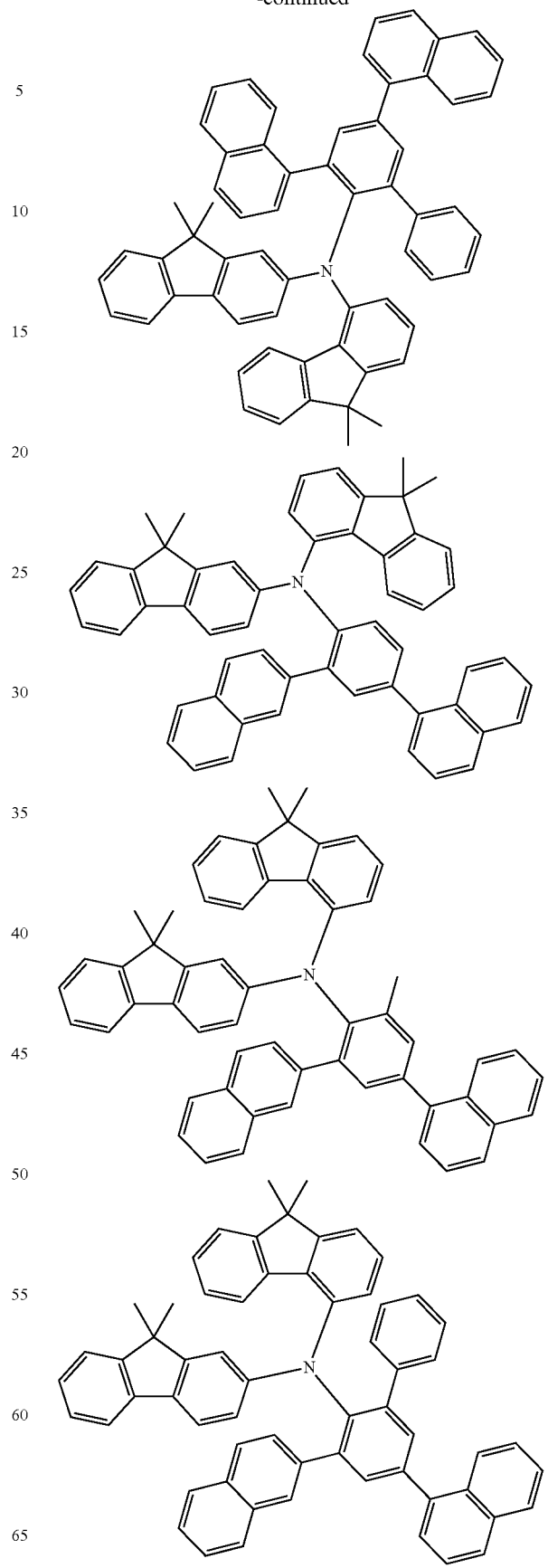

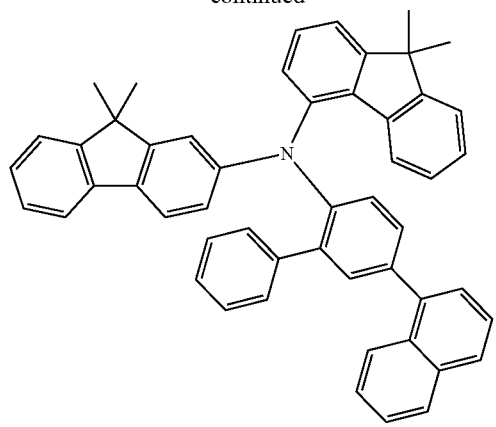
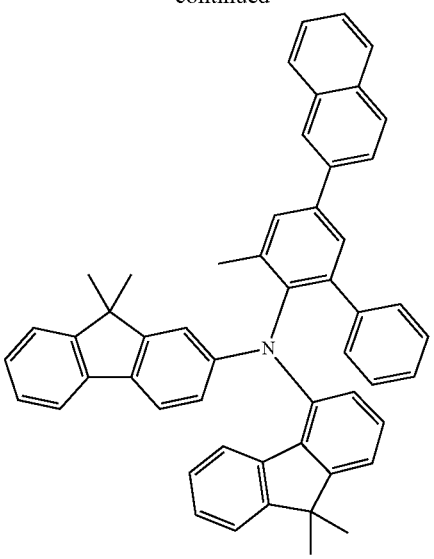
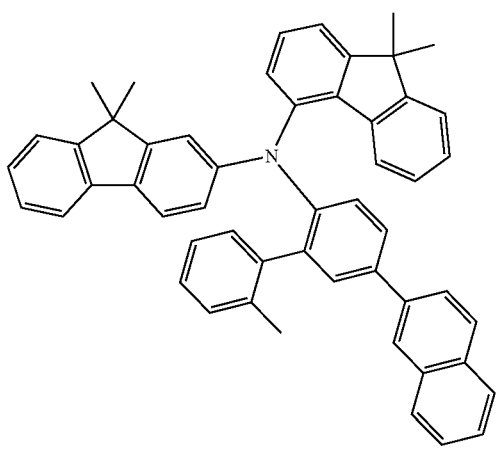
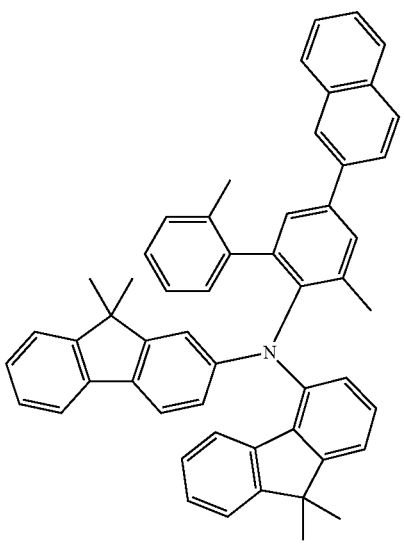
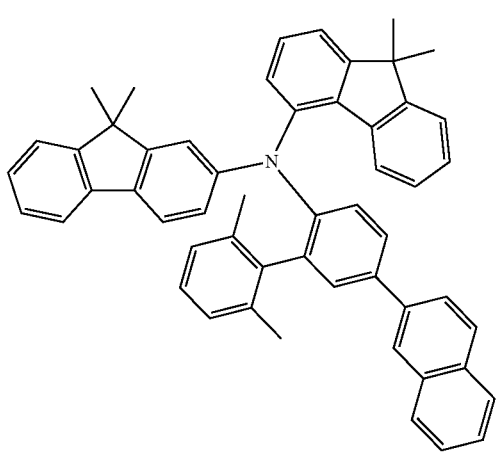
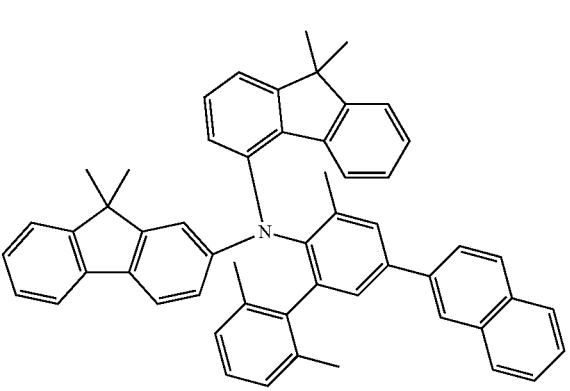

61
-continued
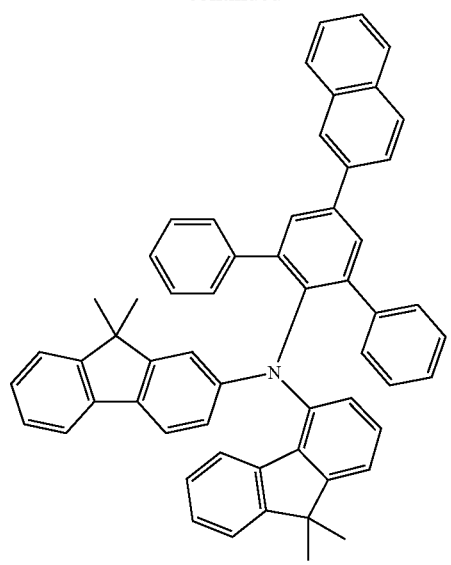
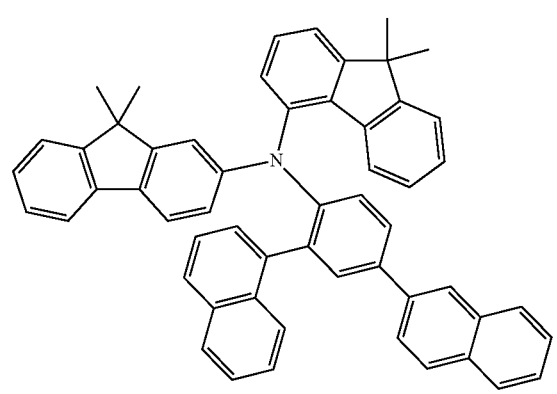
62
-continued
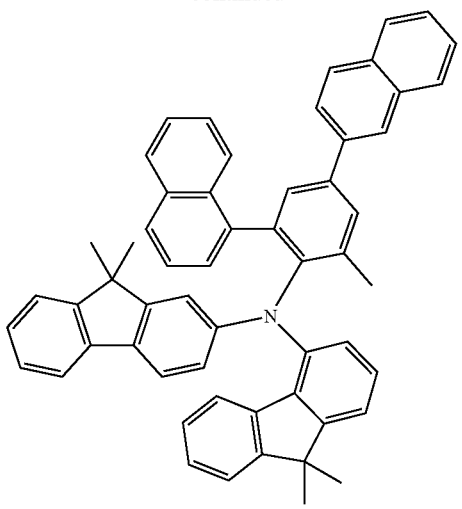
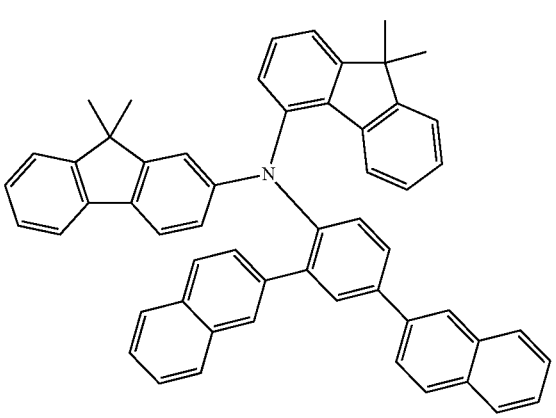

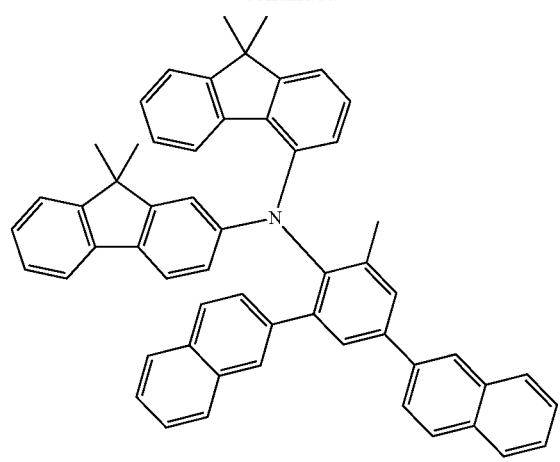
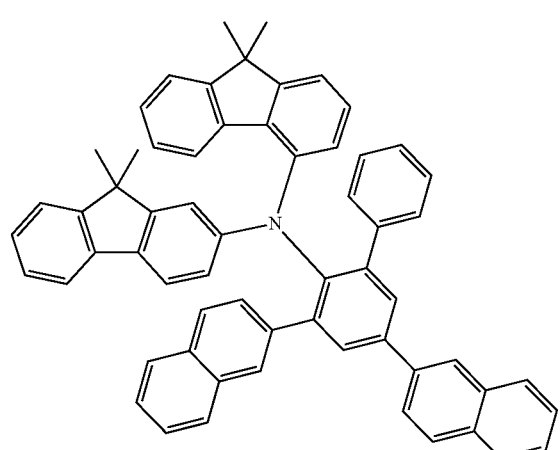
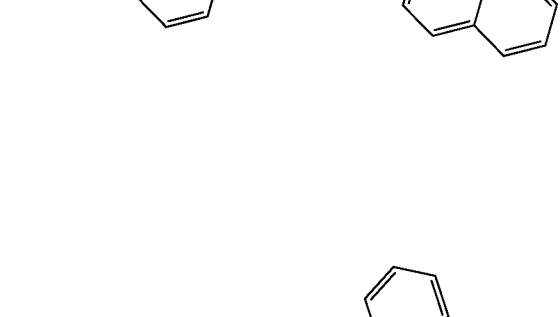
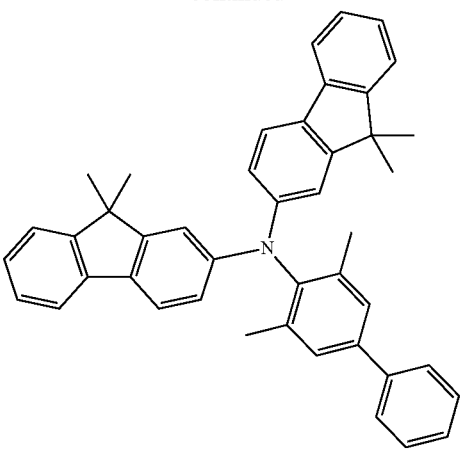
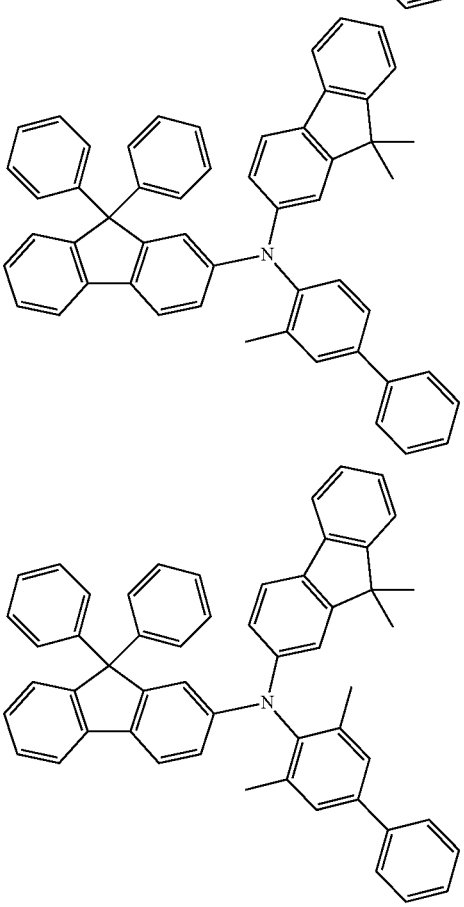
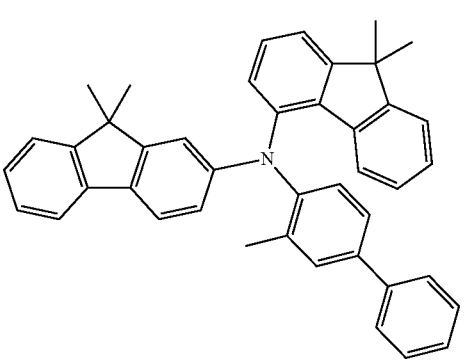

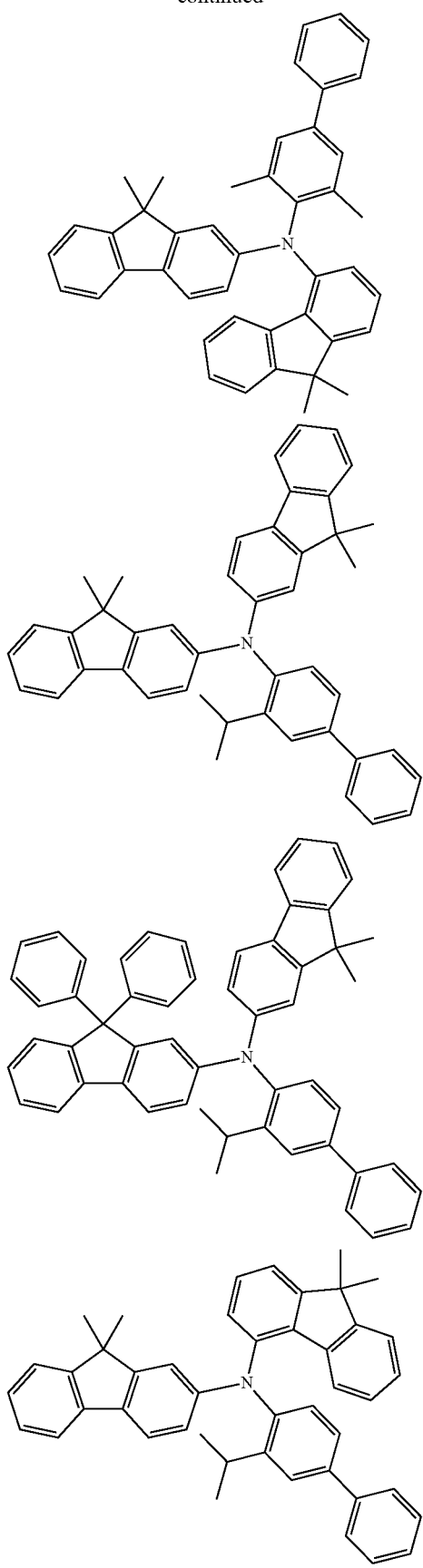
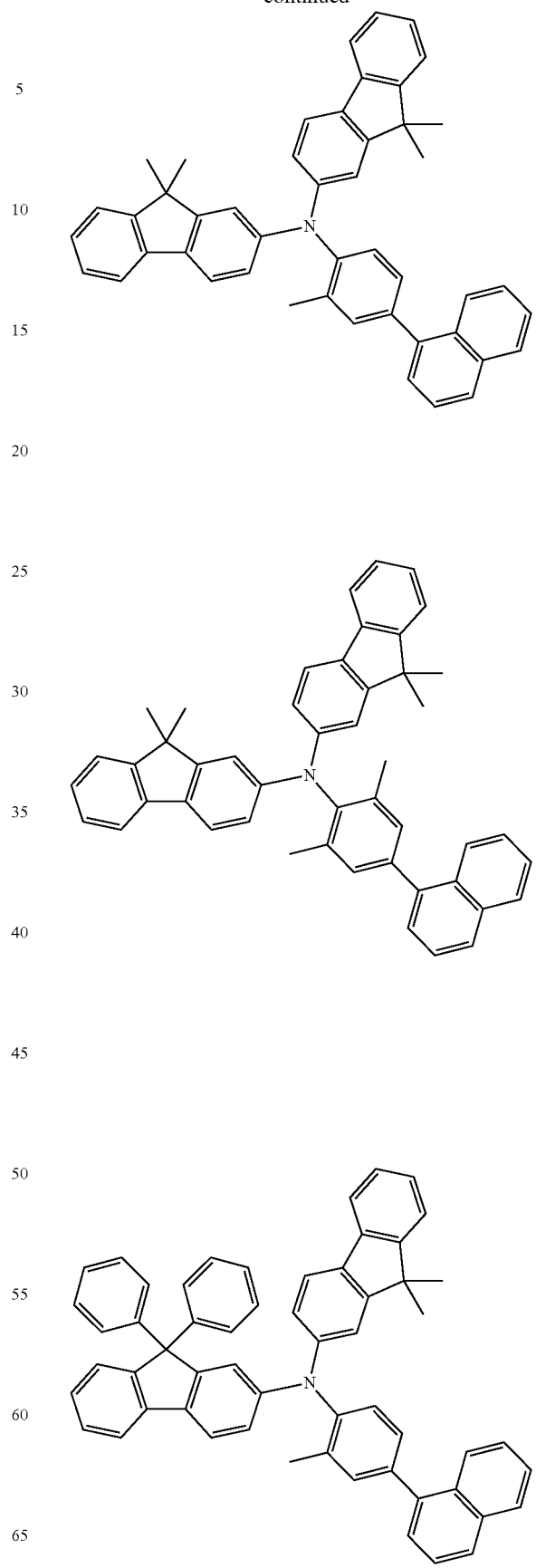

-continued
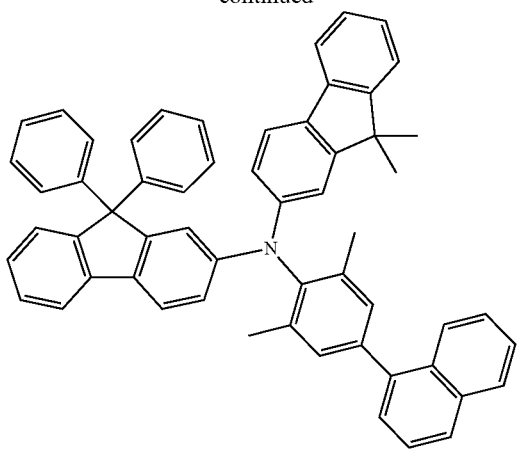
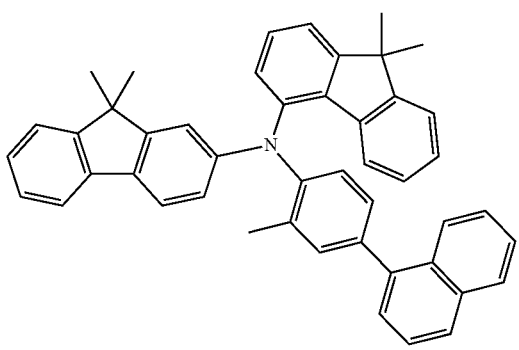 [SMILES: Cc1cc(-c2cccc3ccccc23)ccc1N(c1ccc2c(c1)C(C)(C)c1ccccc1-2)c1cccc2c1-c1ccccc1C2(C)C]
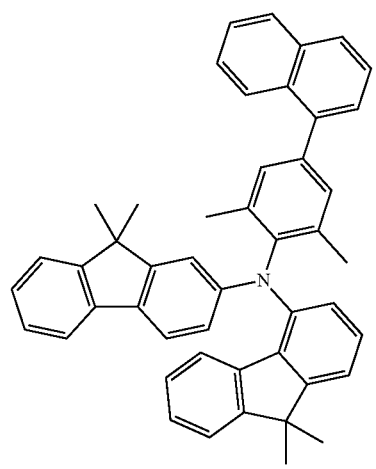
-continued
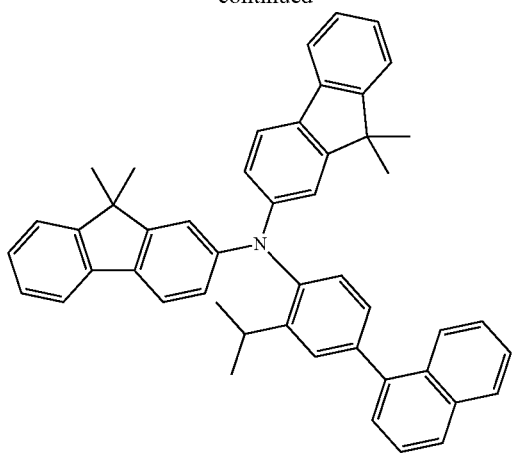
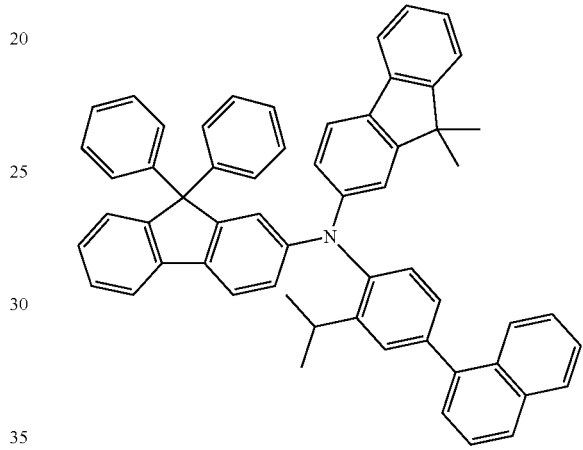
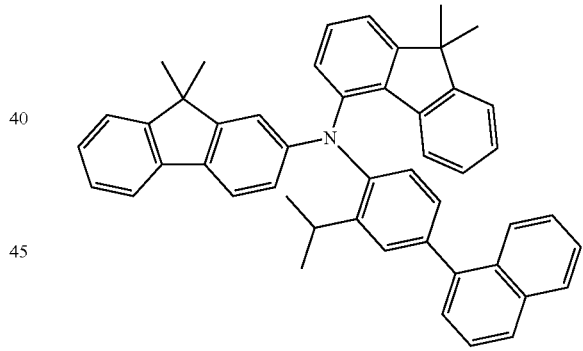
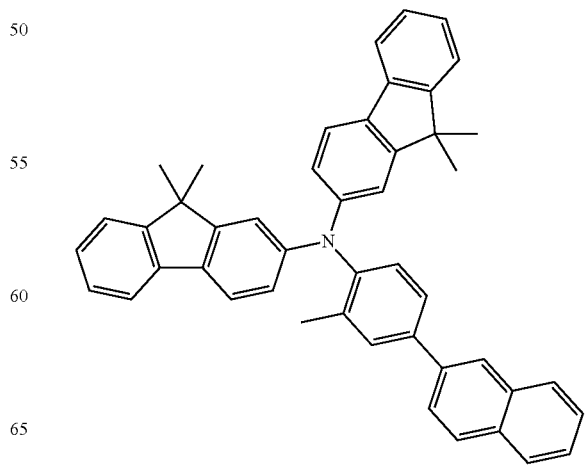

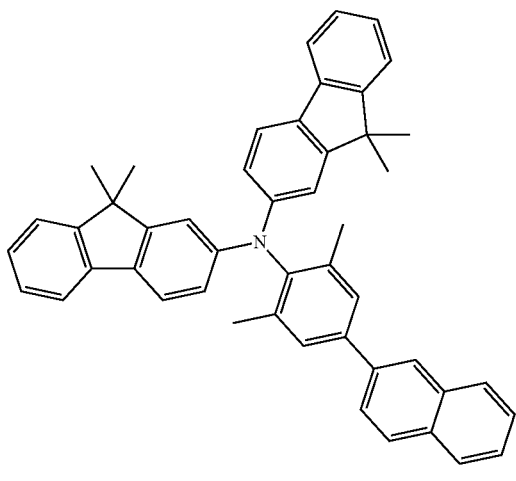
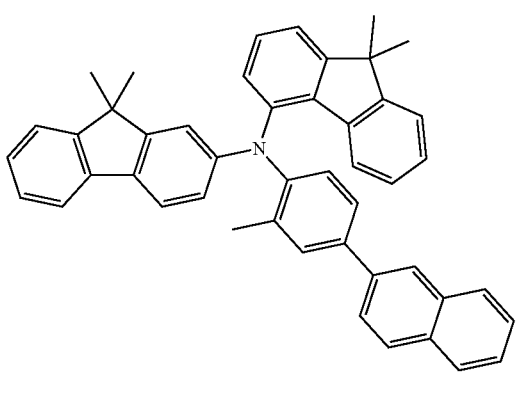
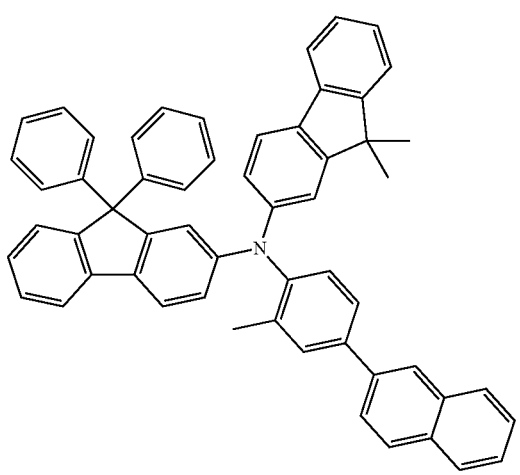
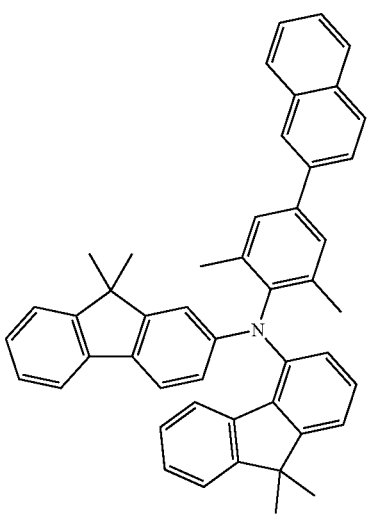
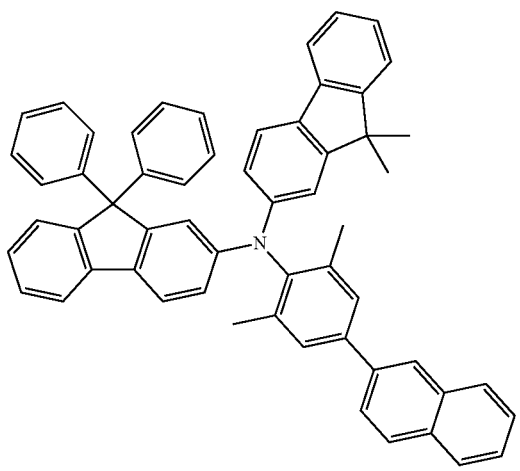
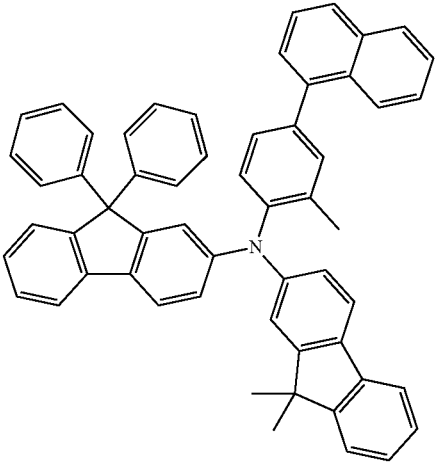

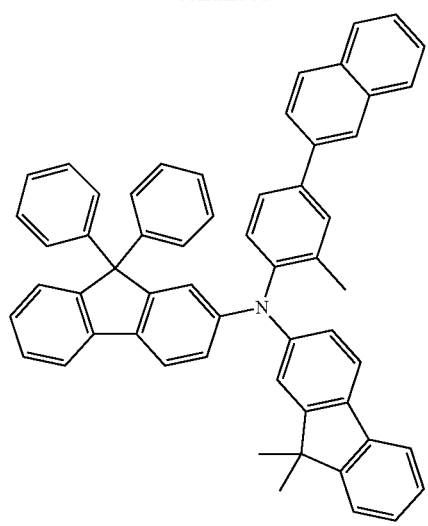
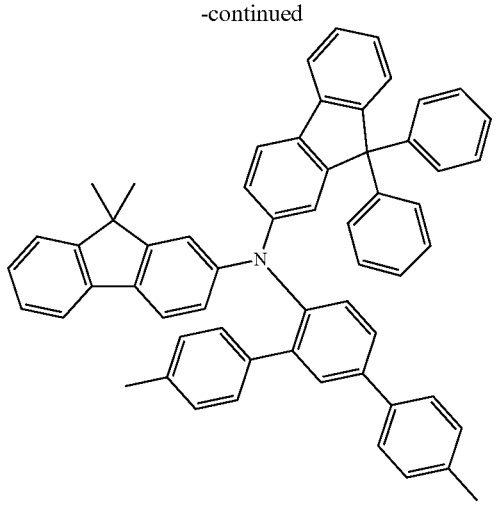
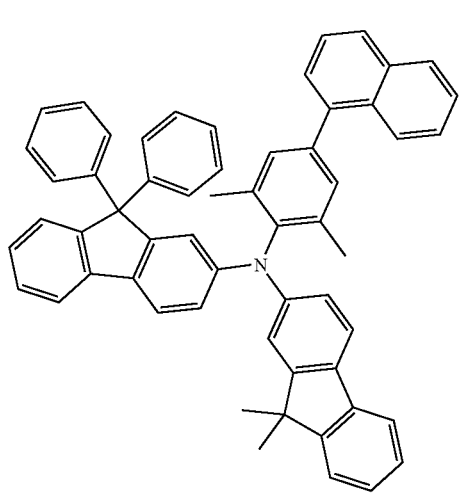
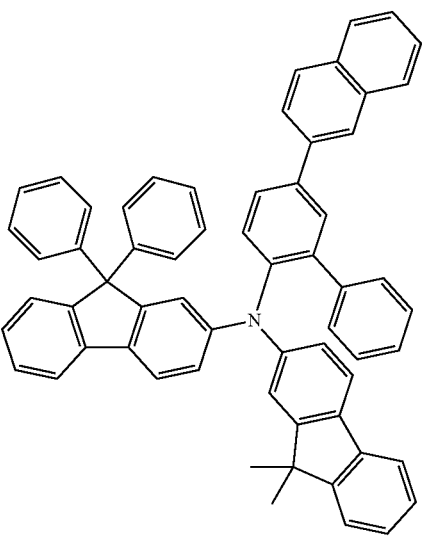

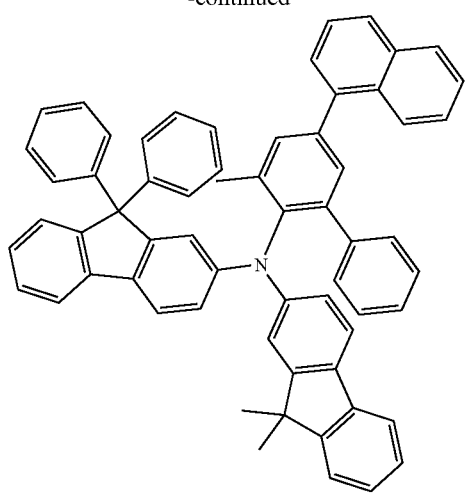
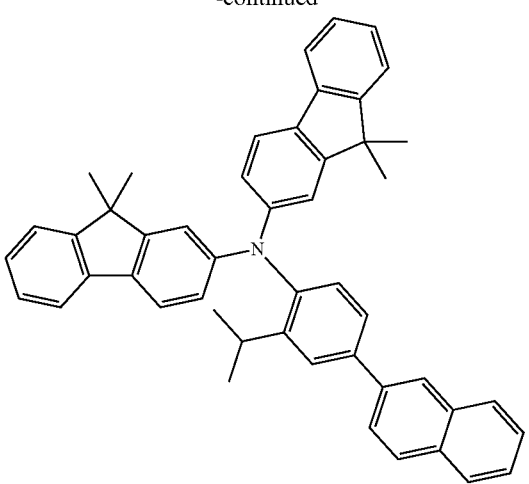
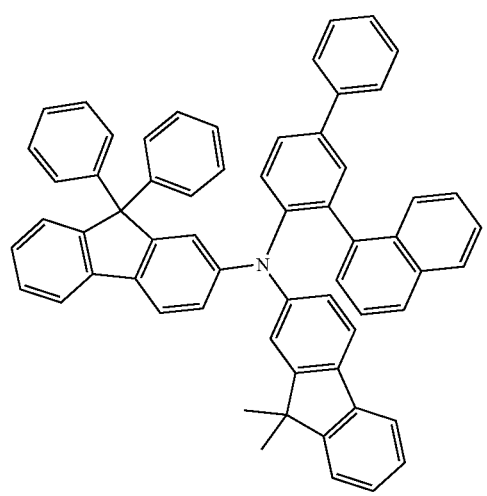
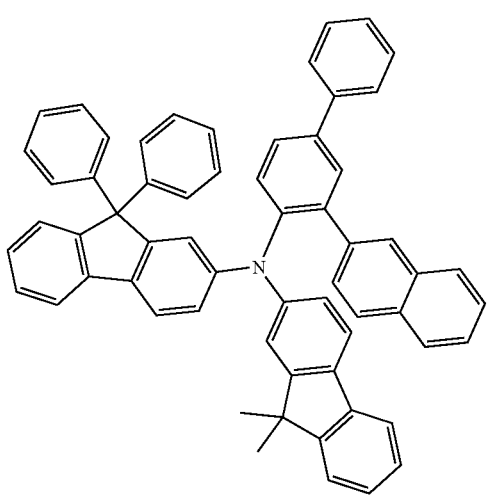

75
-continued
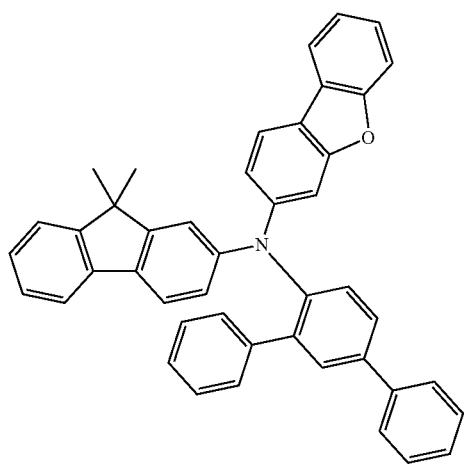
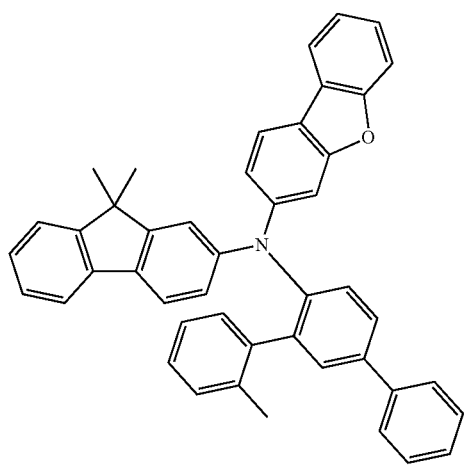
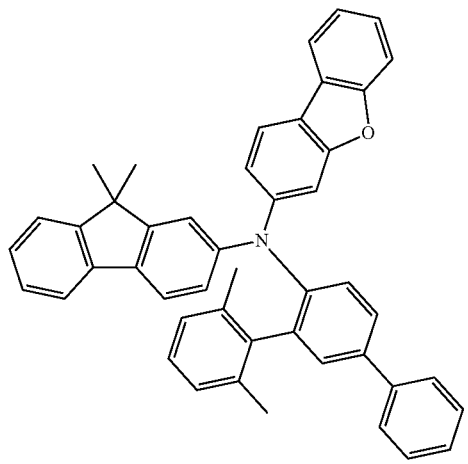
76
-continued
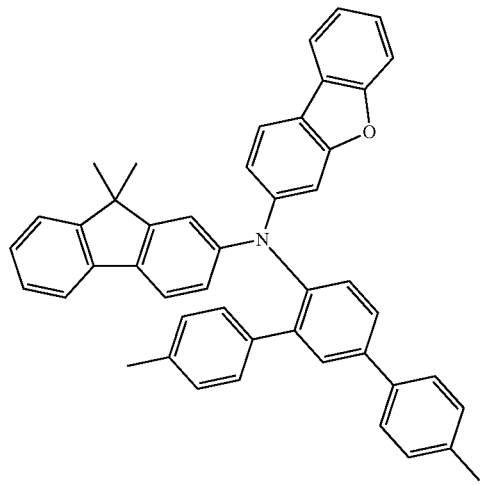
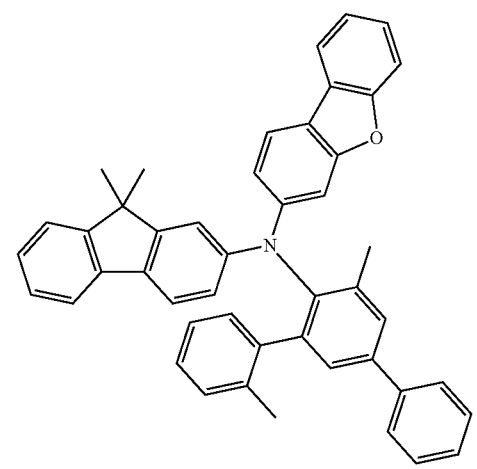
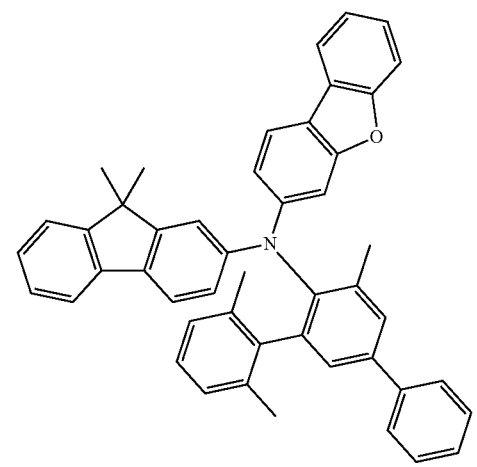

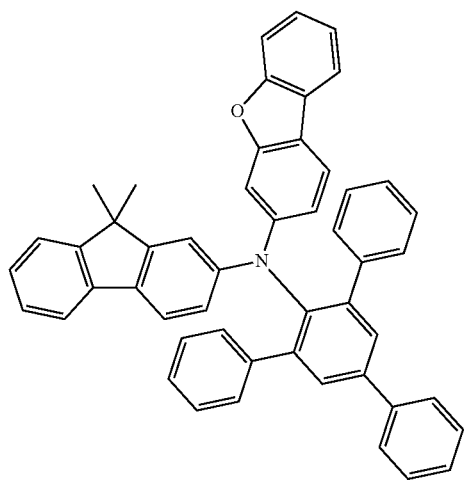
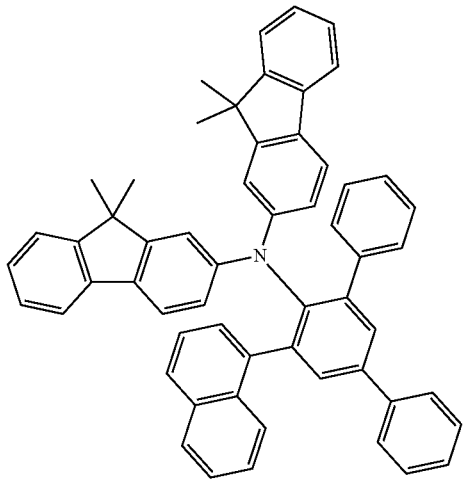
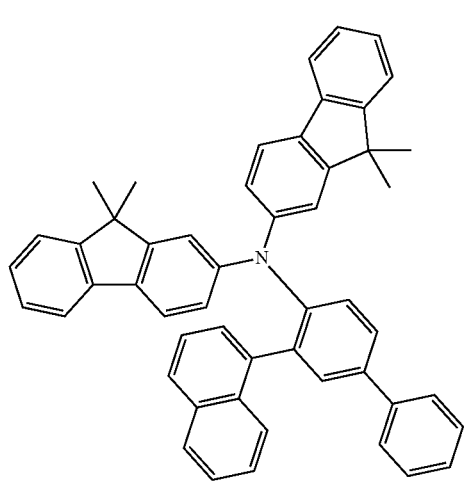
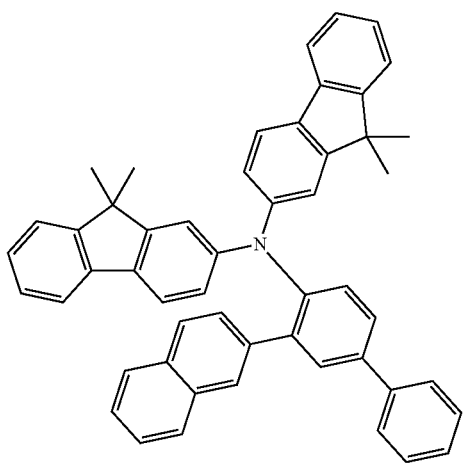
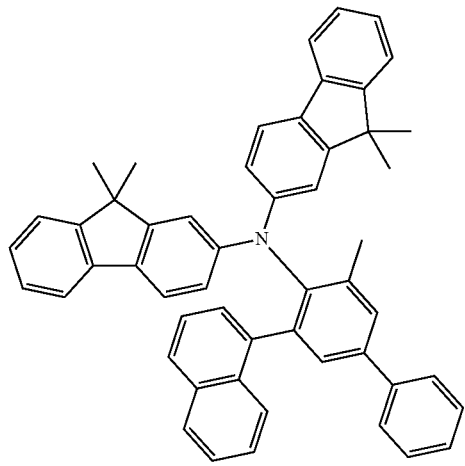
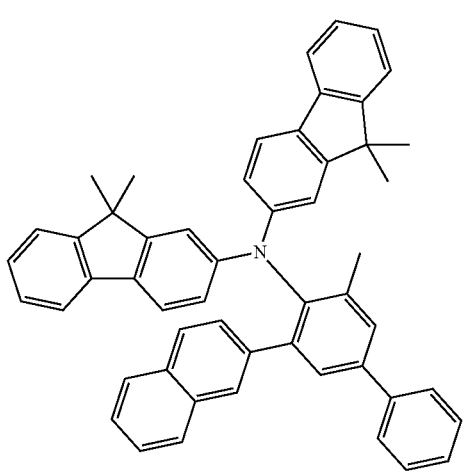

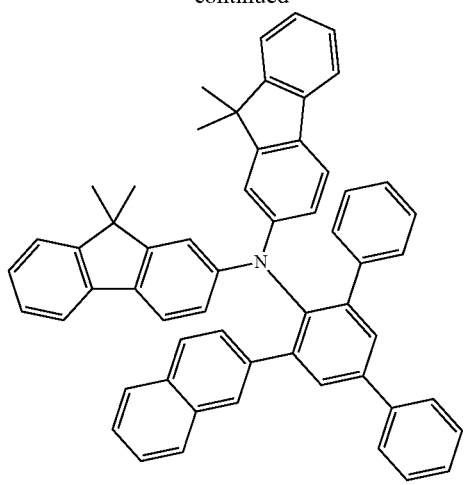
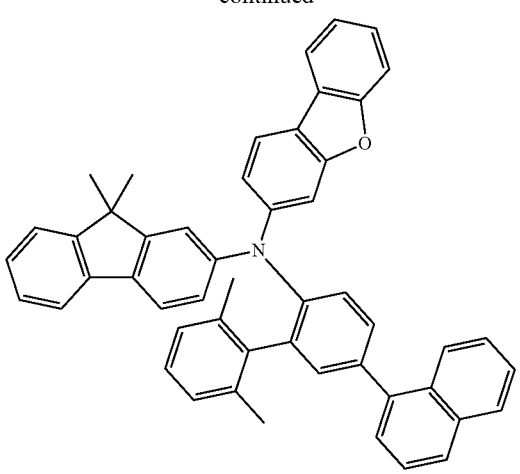
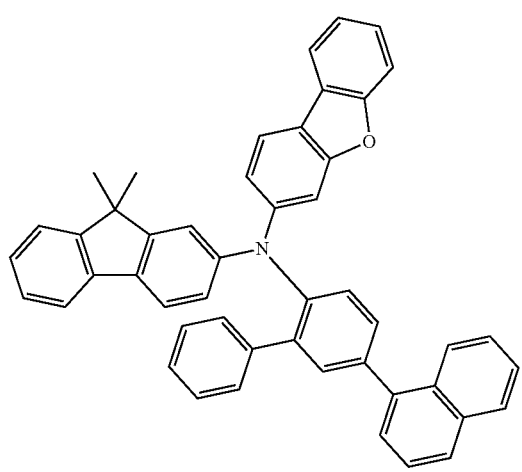
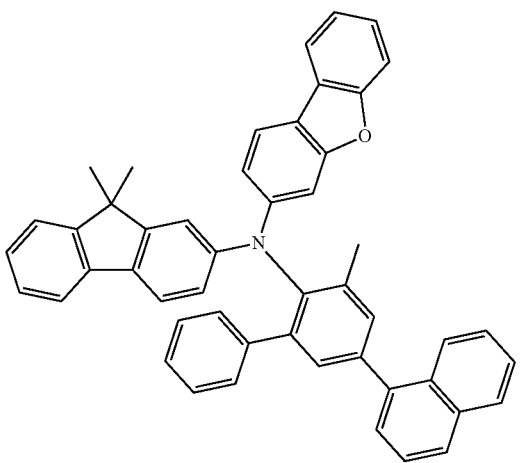
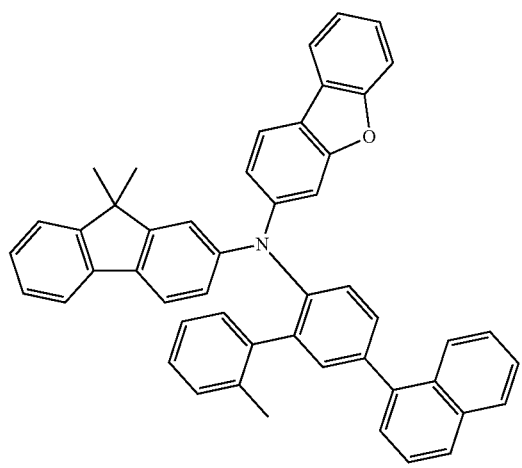
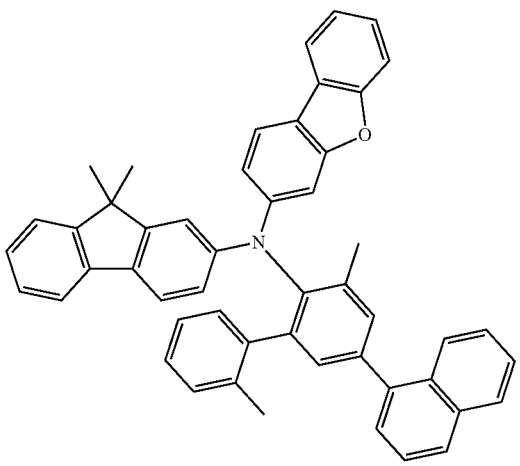

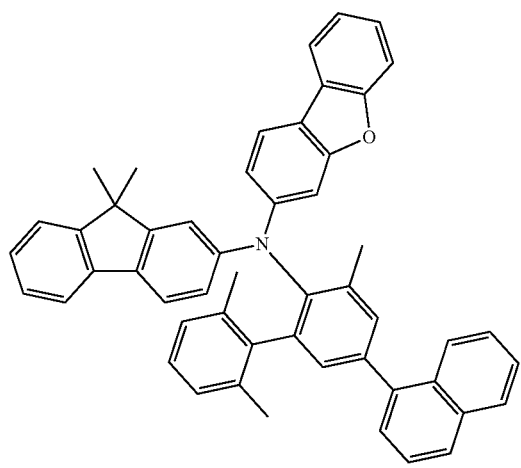
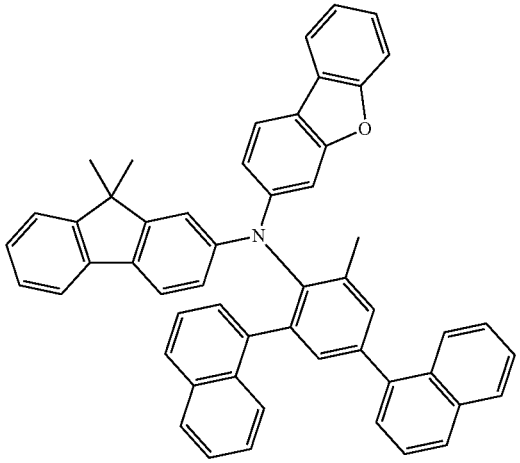

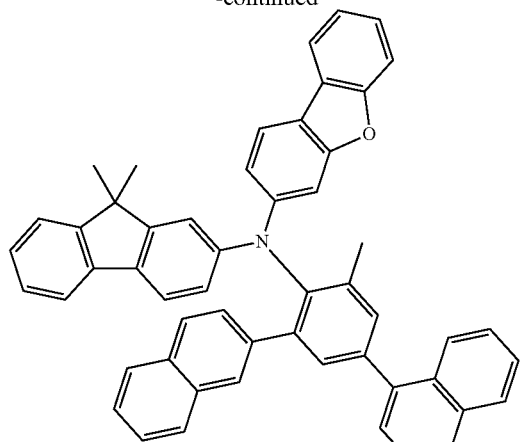
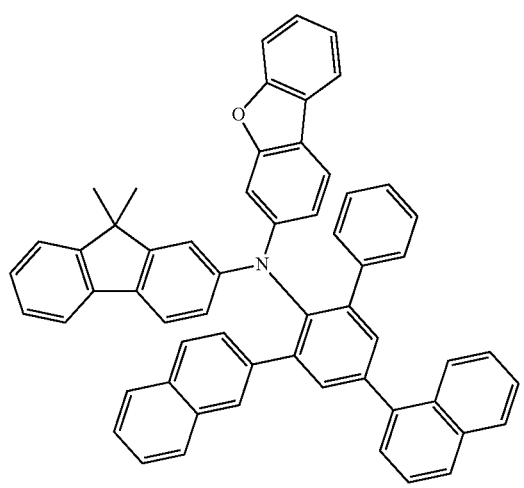
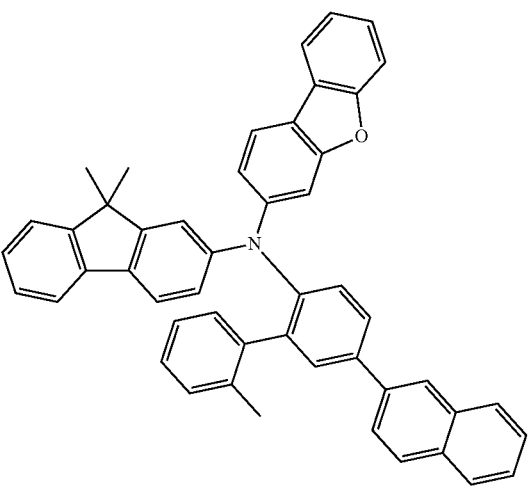
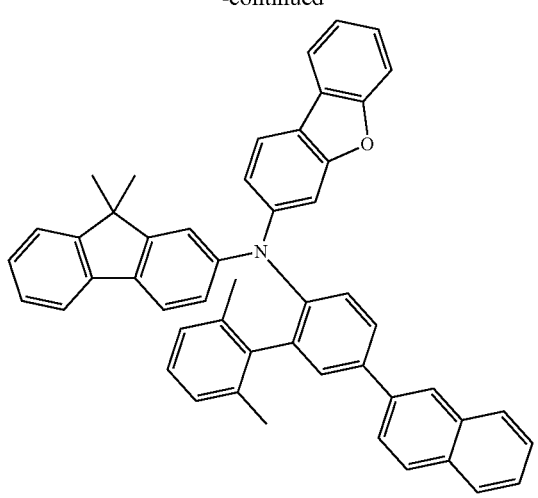
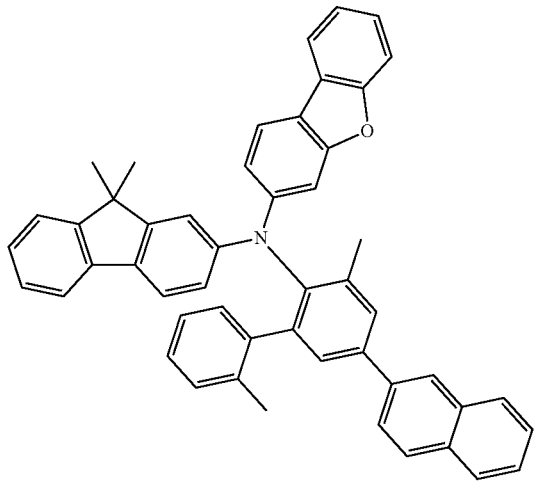

85
-continued
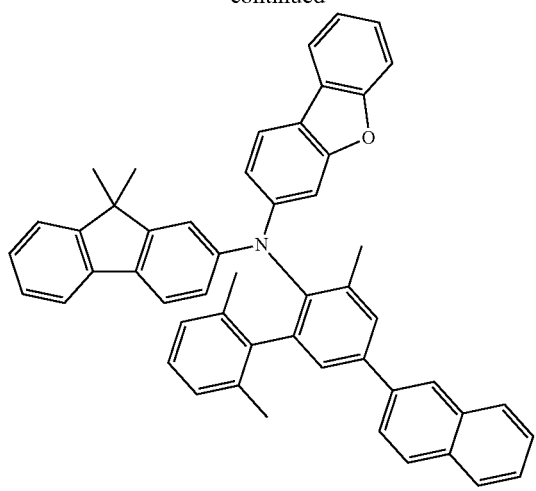
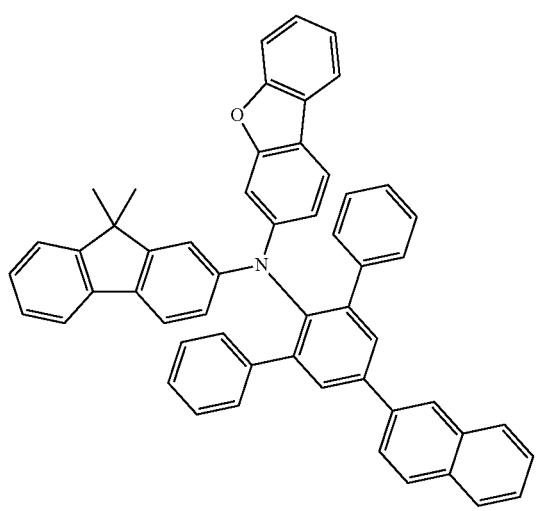
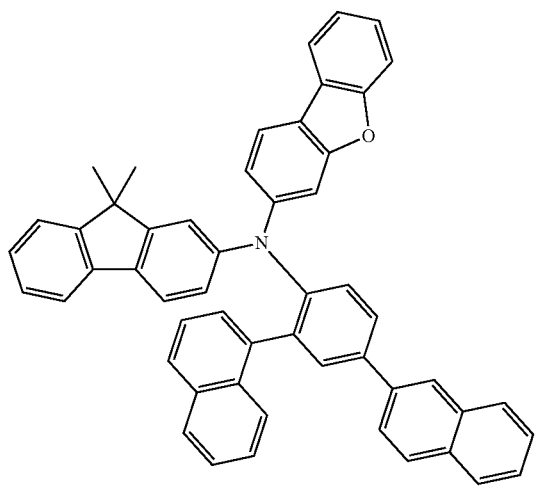
86
-continued
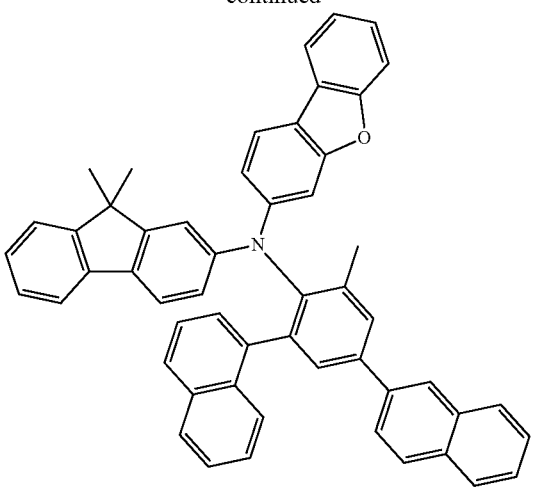
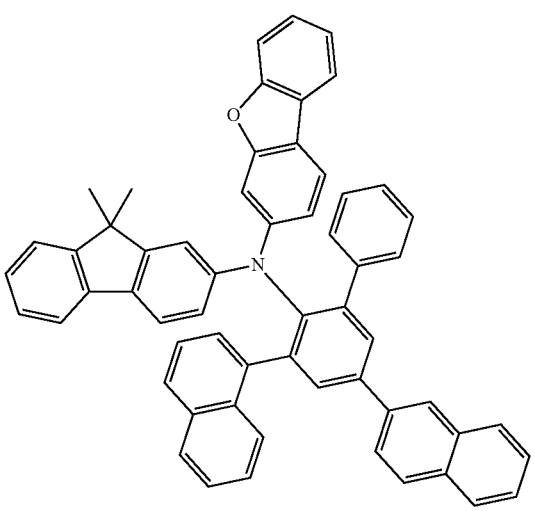
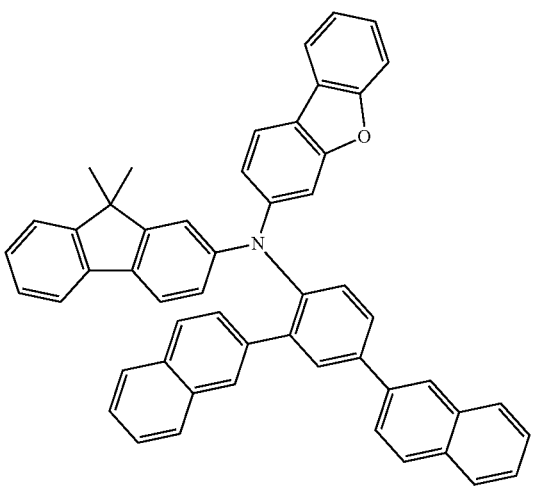

-continued
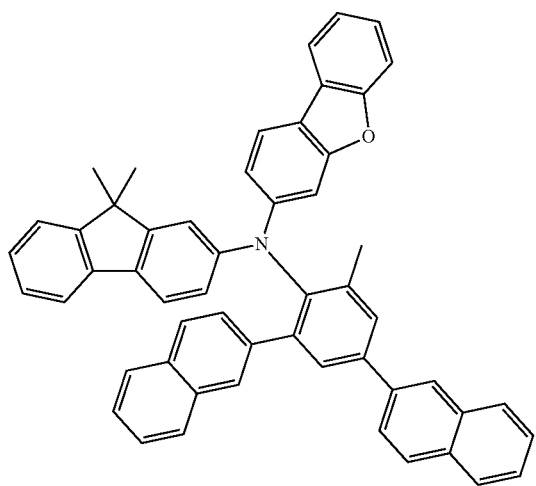
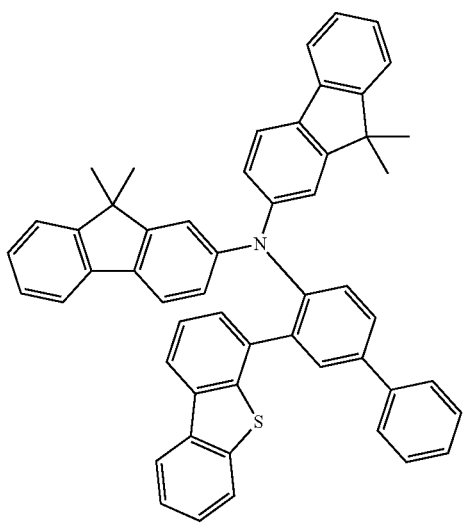
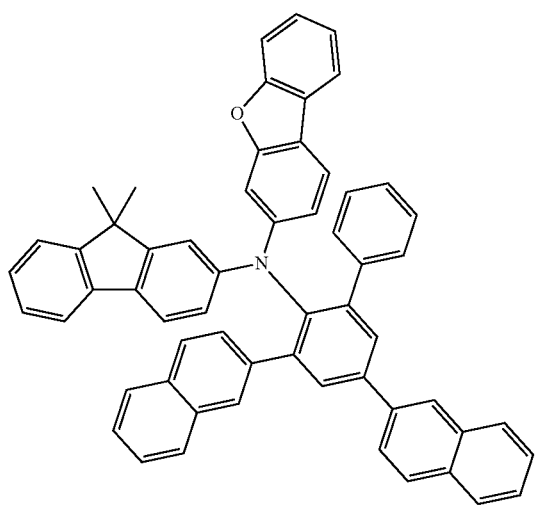
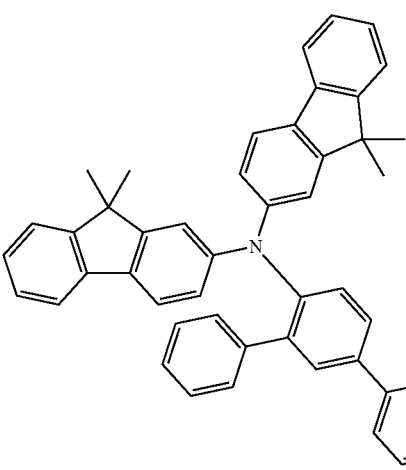
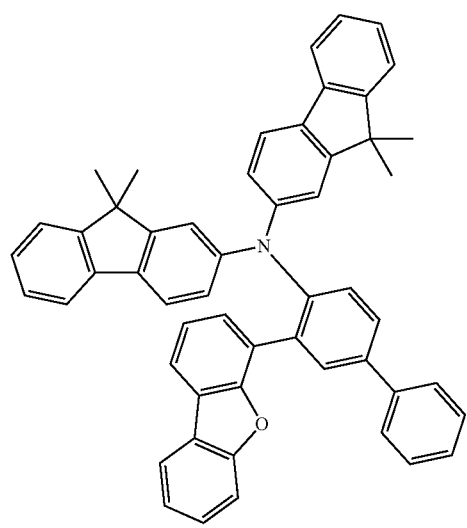
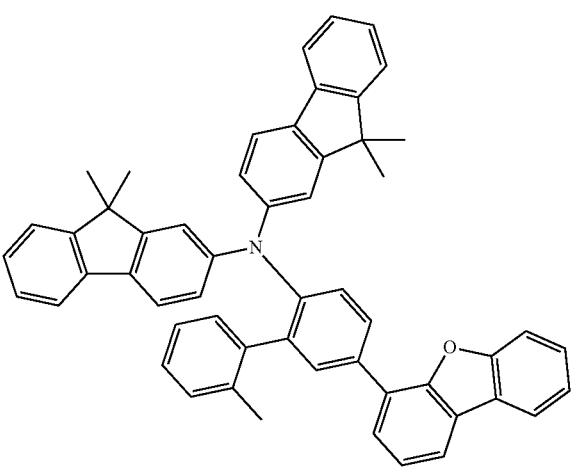

89
-continued
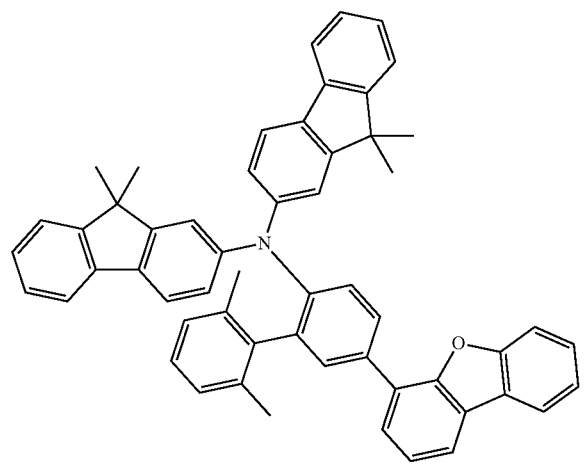
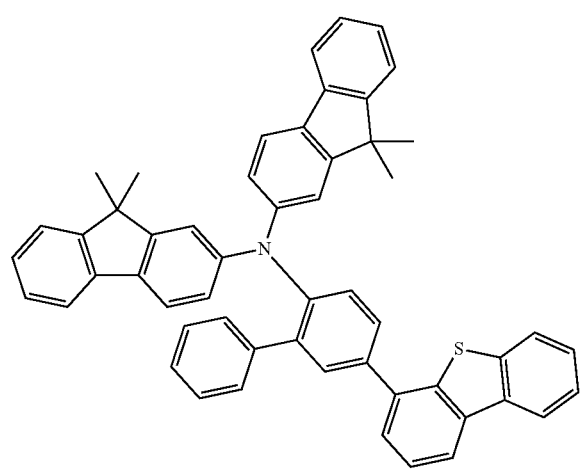
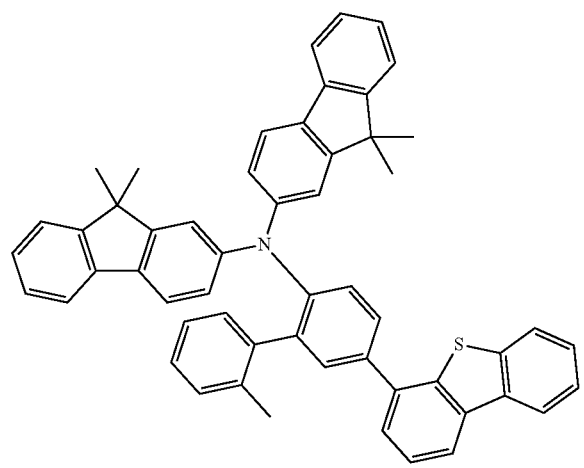
90
-continued
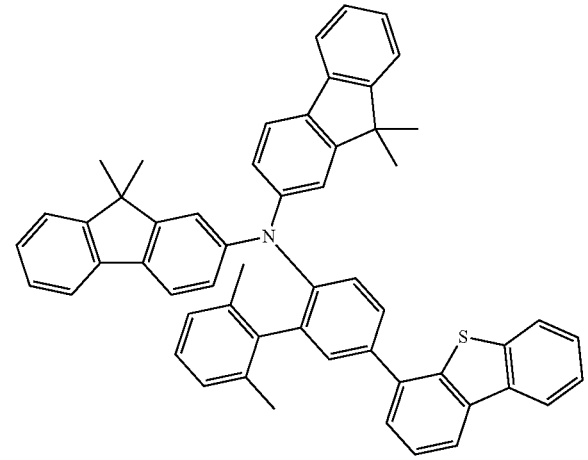
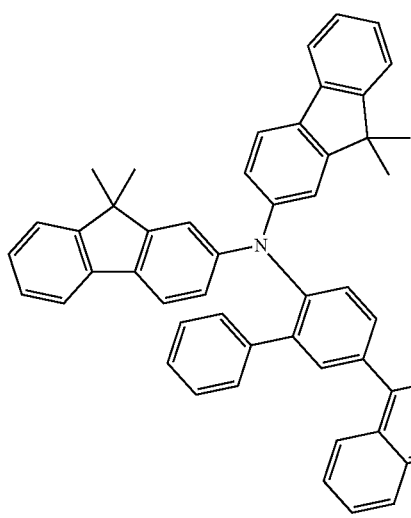
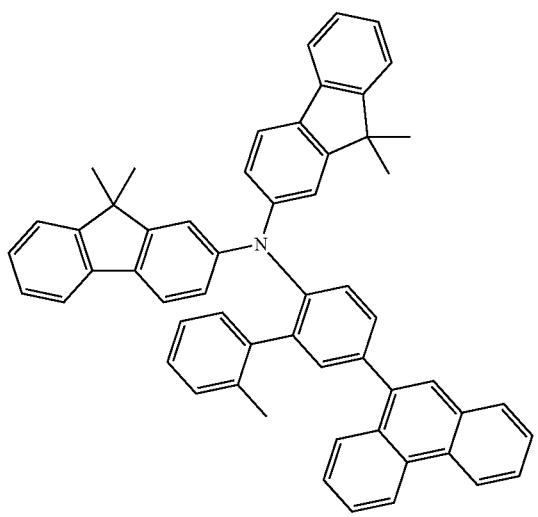

-continued
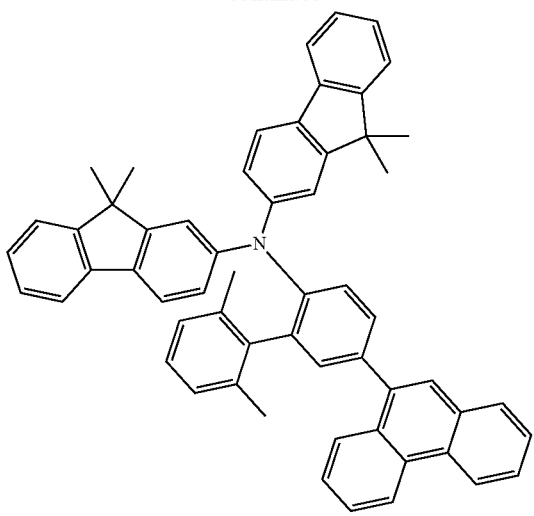
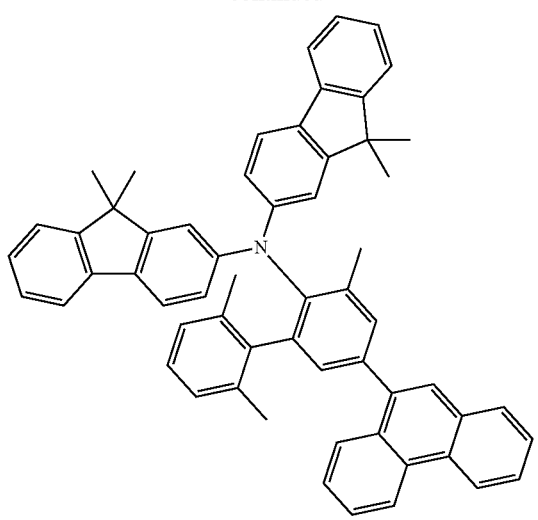
-continued
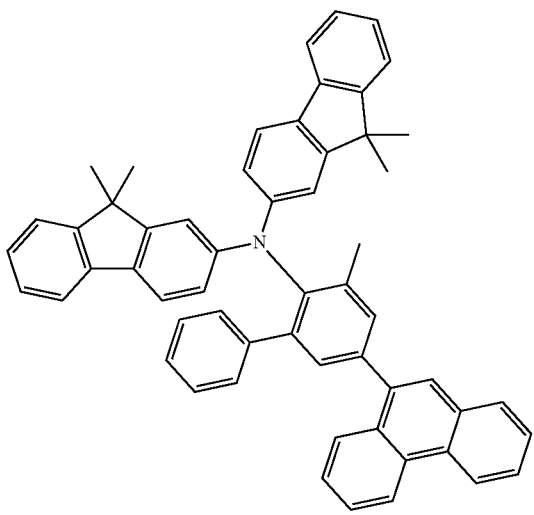
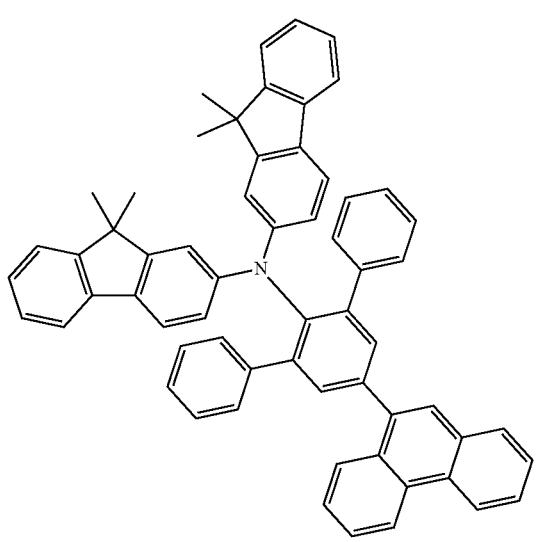
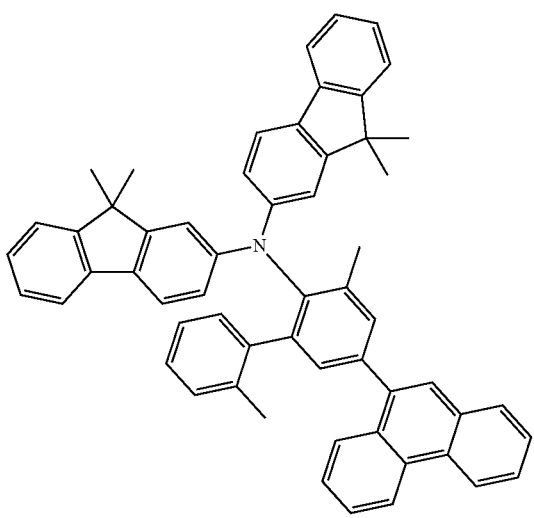
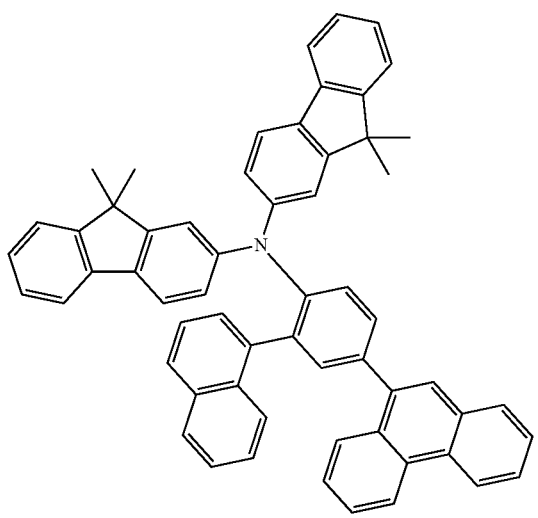

-continued
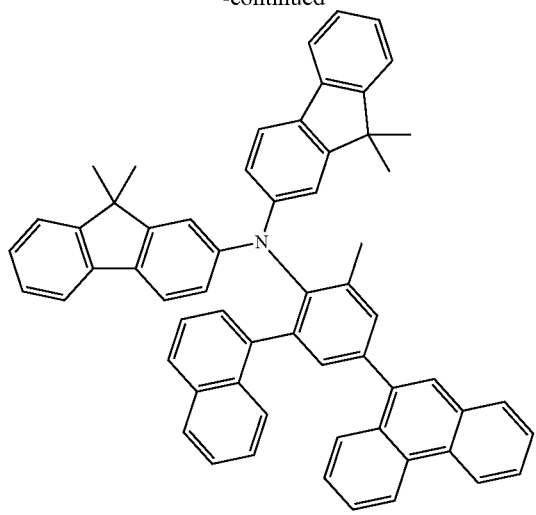
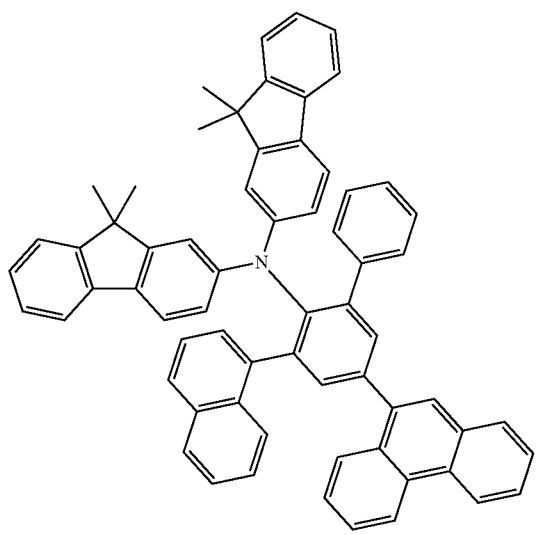
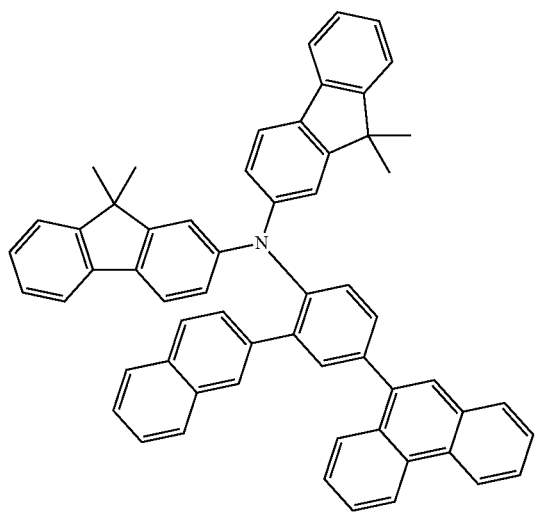
-continued
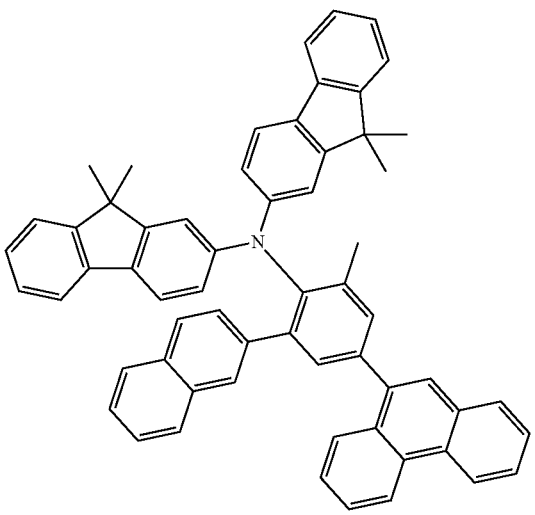
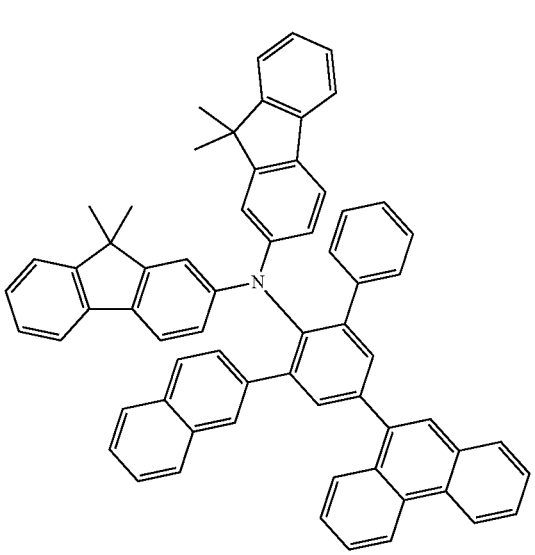
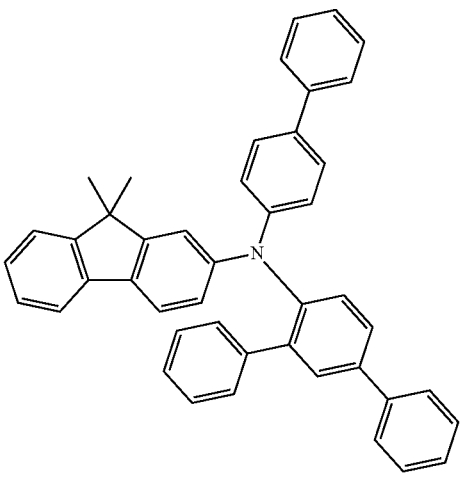

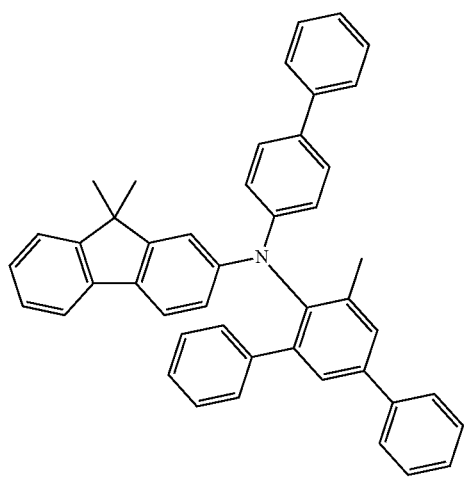
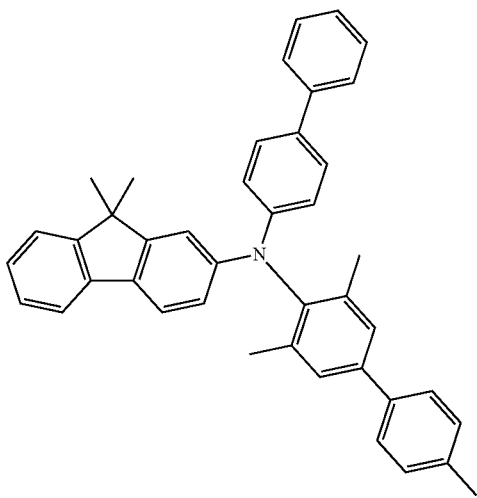
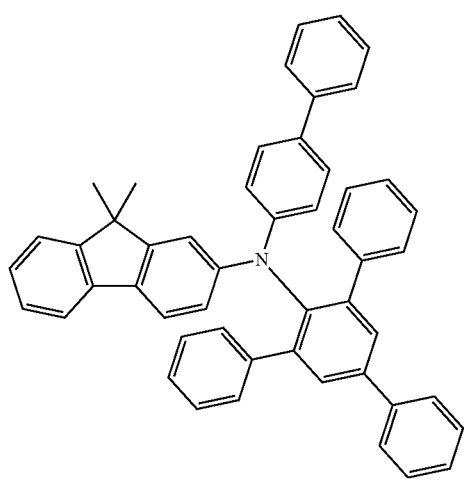
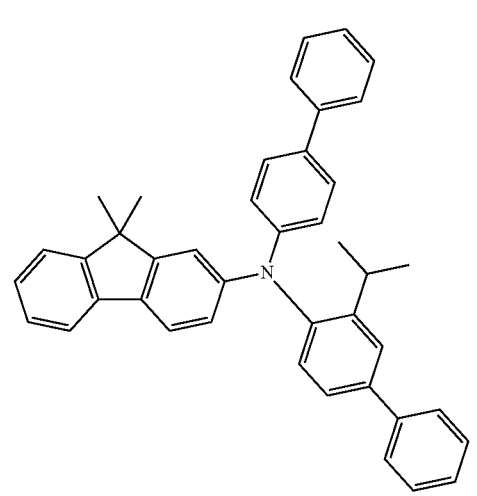
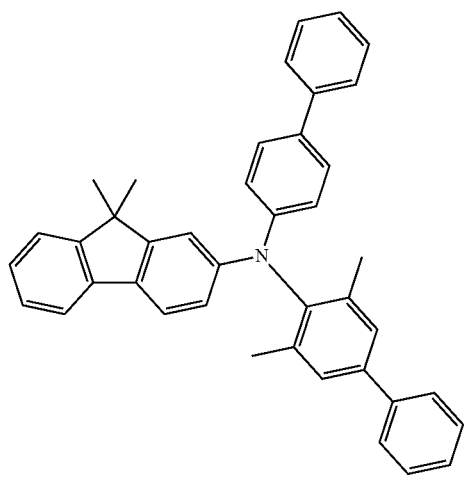
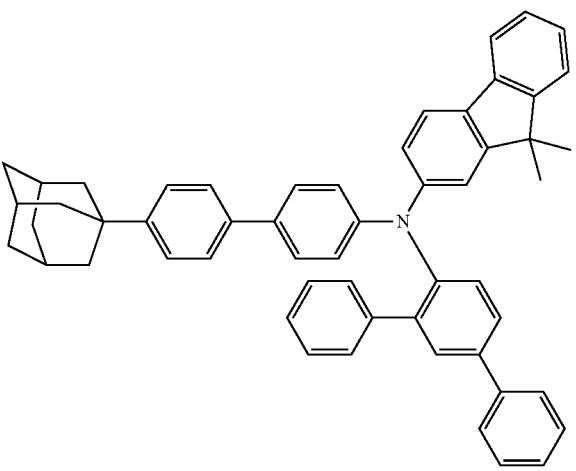

97
-continued
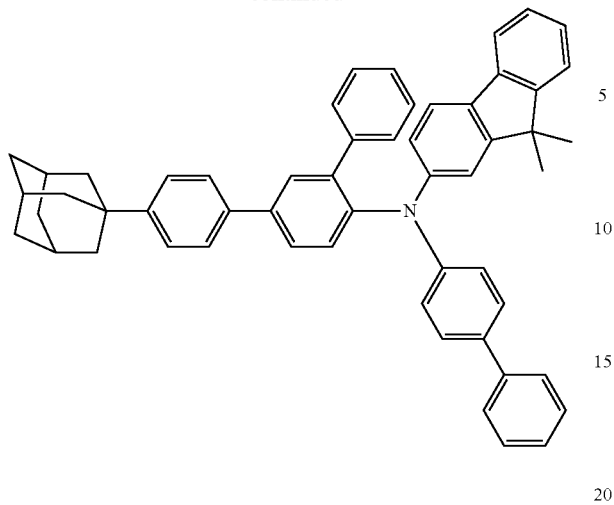
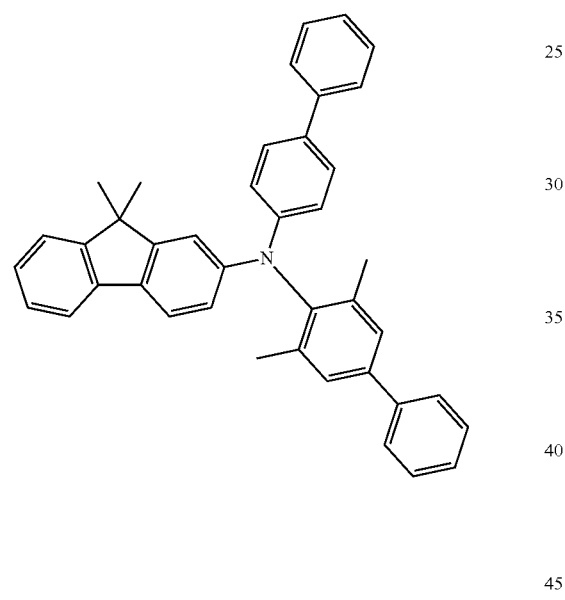
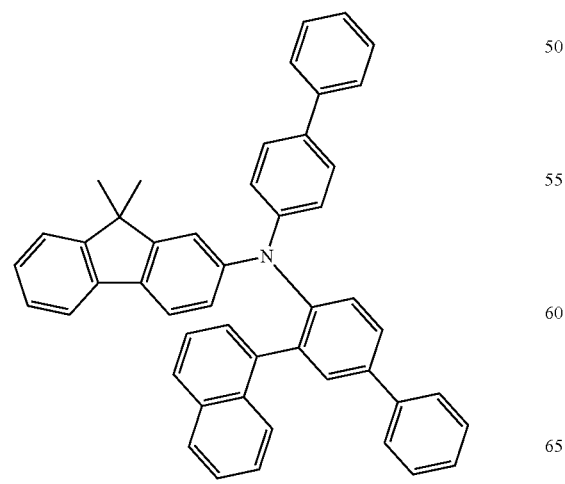
98
-continued
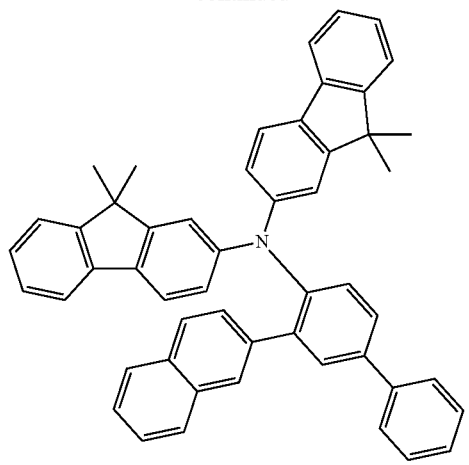
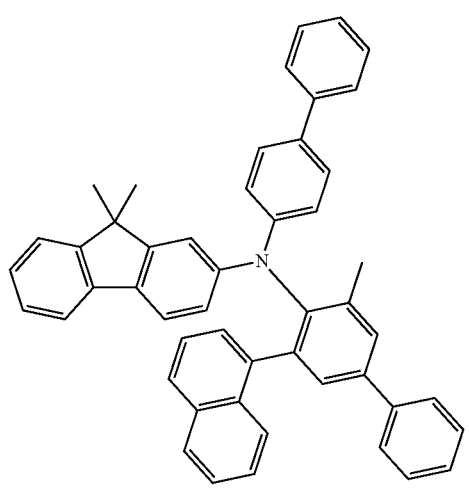
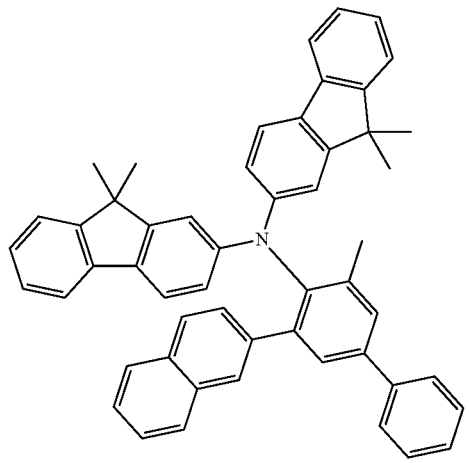

99
-continued
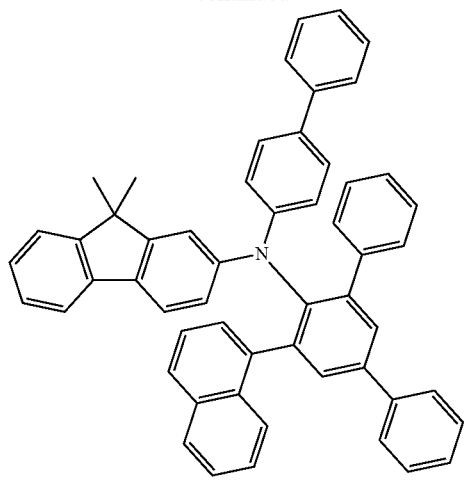
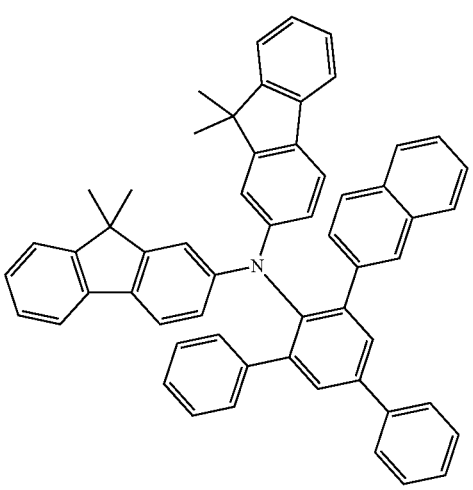
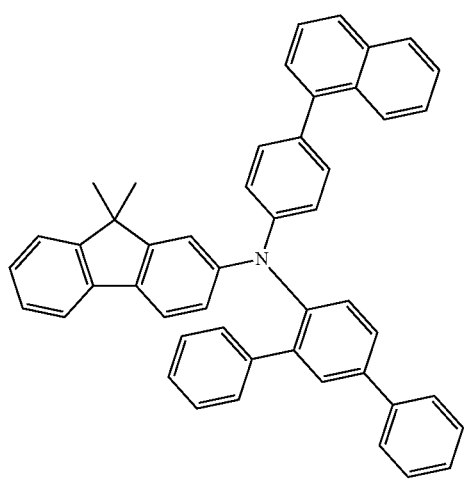
100
-continued
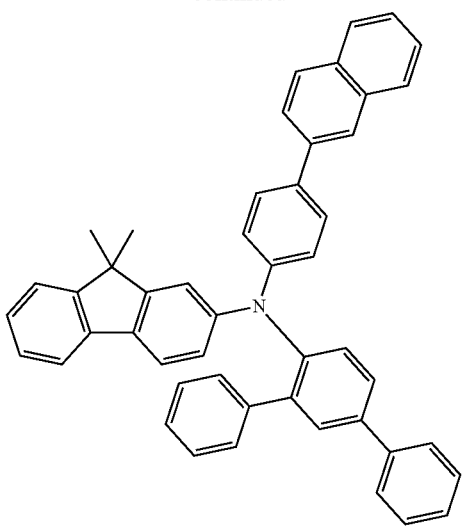
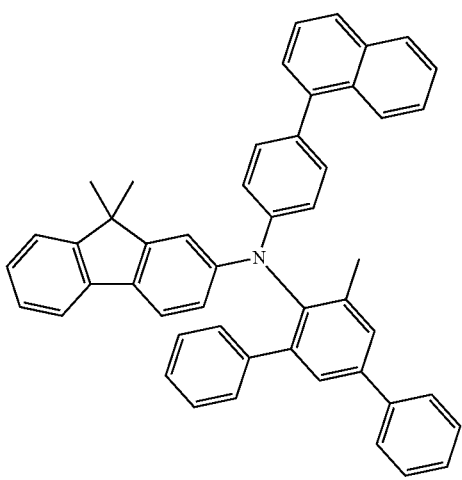
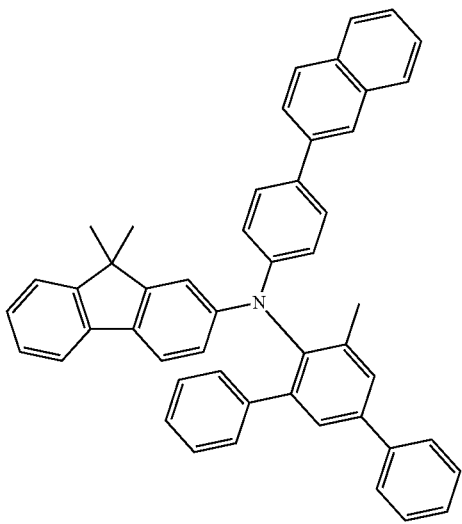

101
-continued
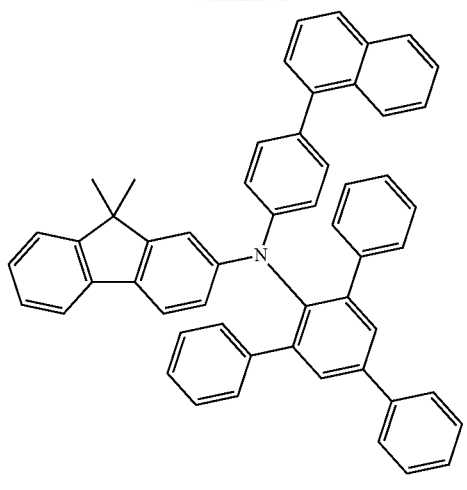
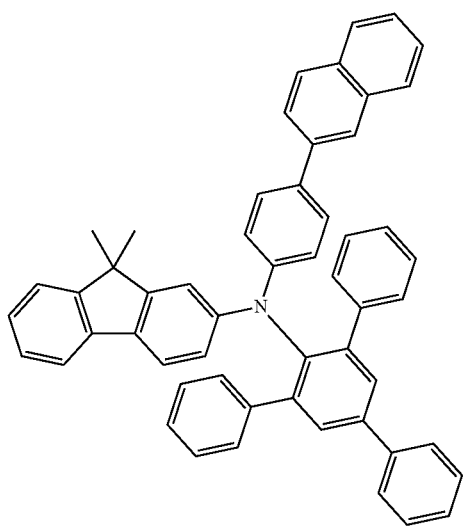
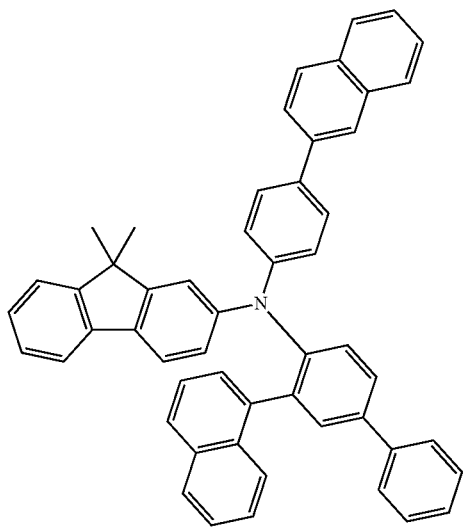
102
-continued
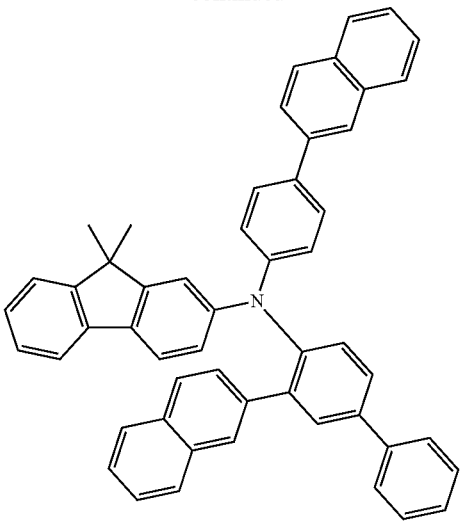
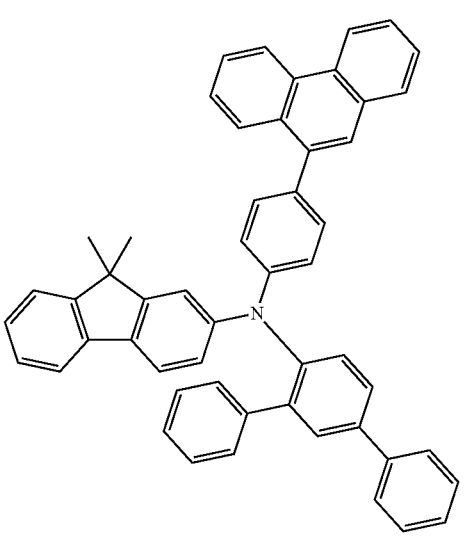
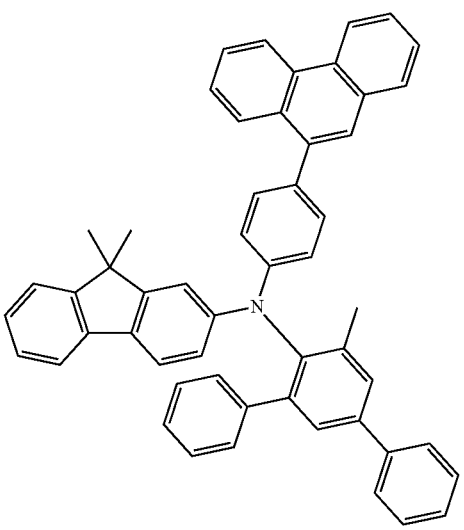

103
-continued
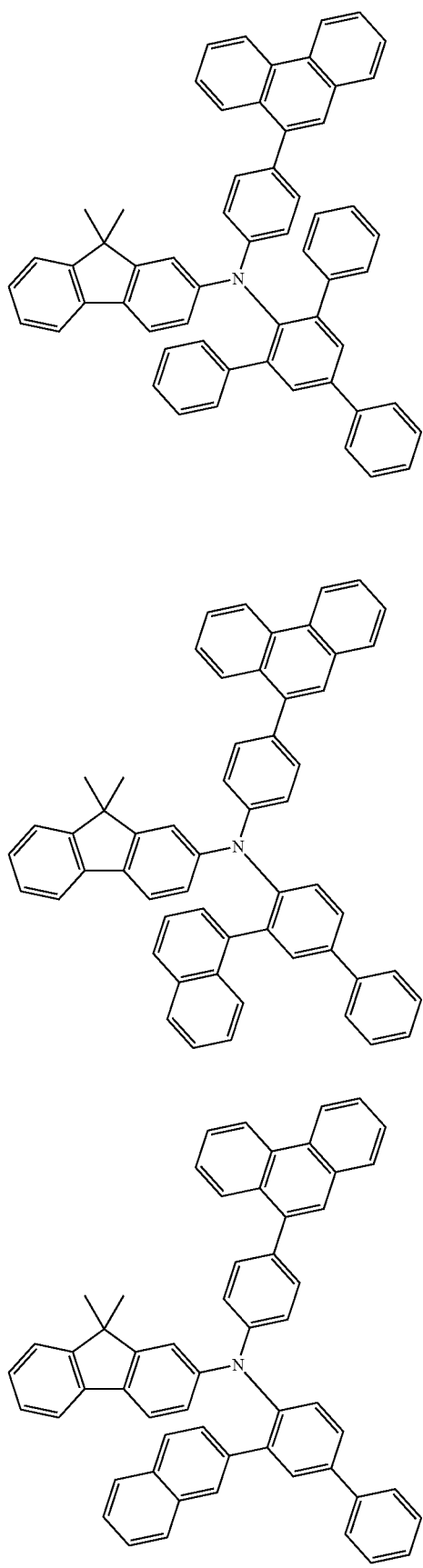
104
-continued
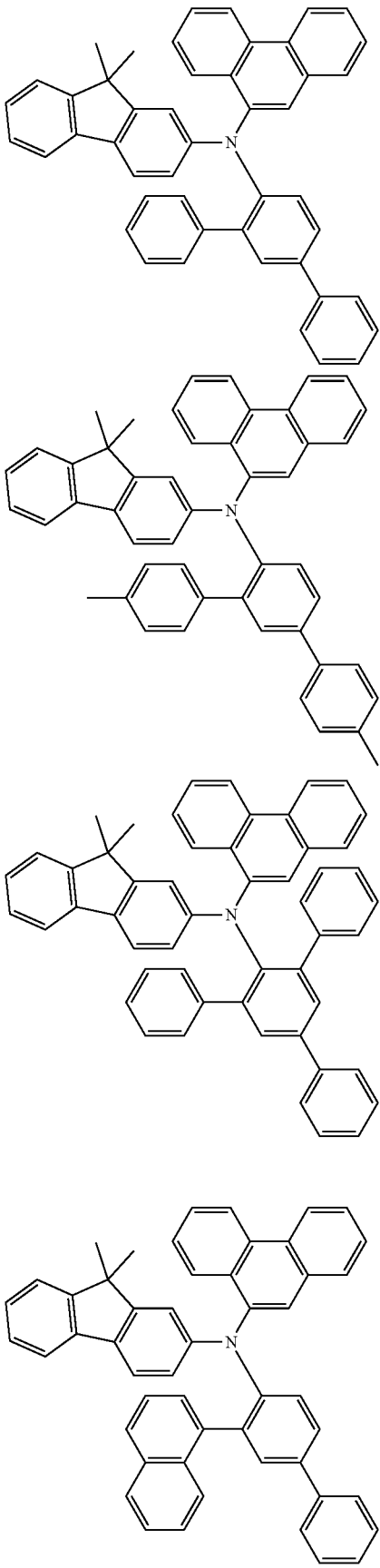

105
-continued
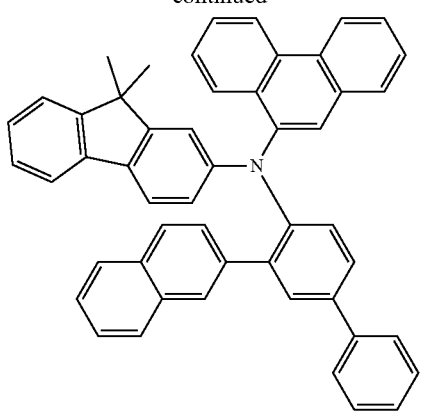
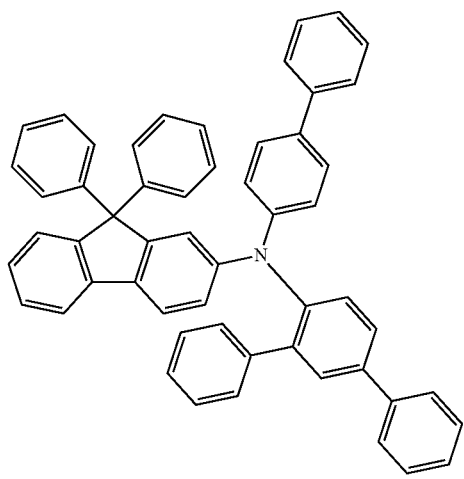
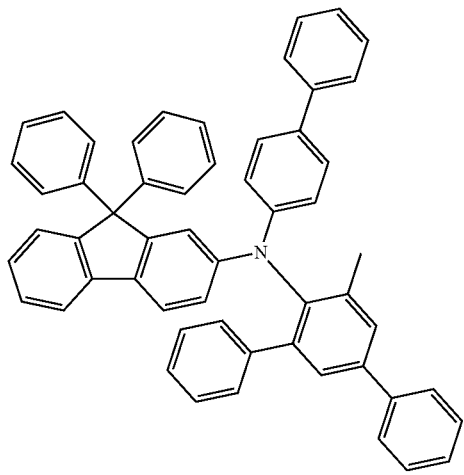
106
-continued
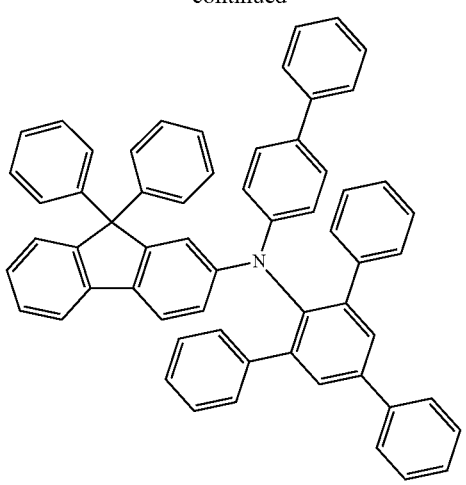
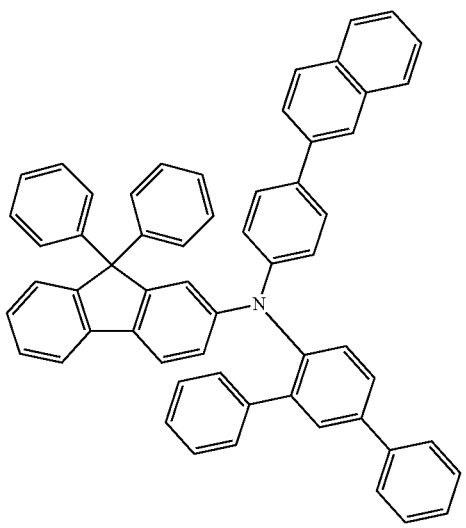
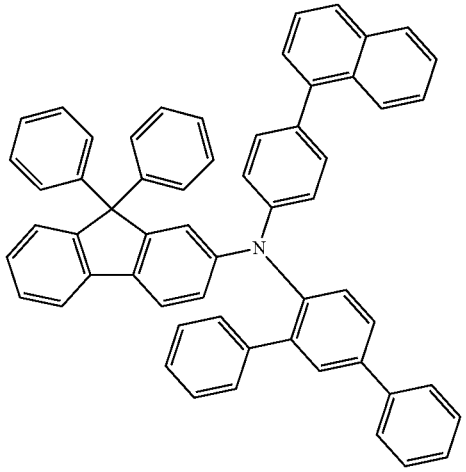

107
-continued
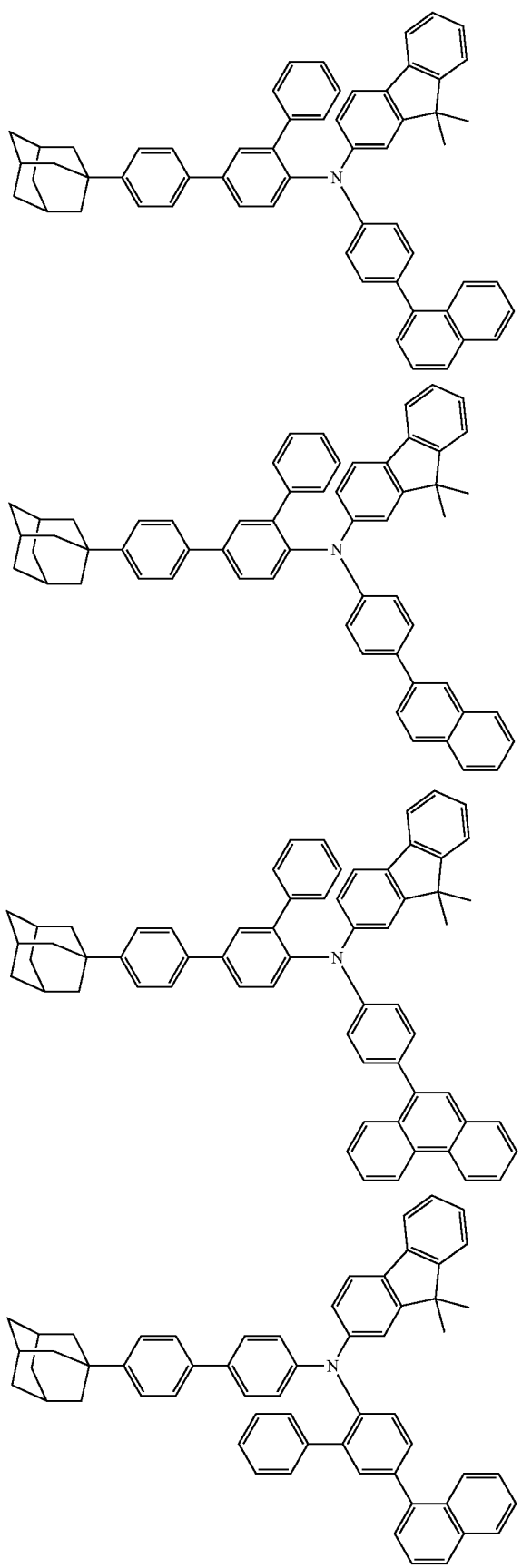
108
-continued
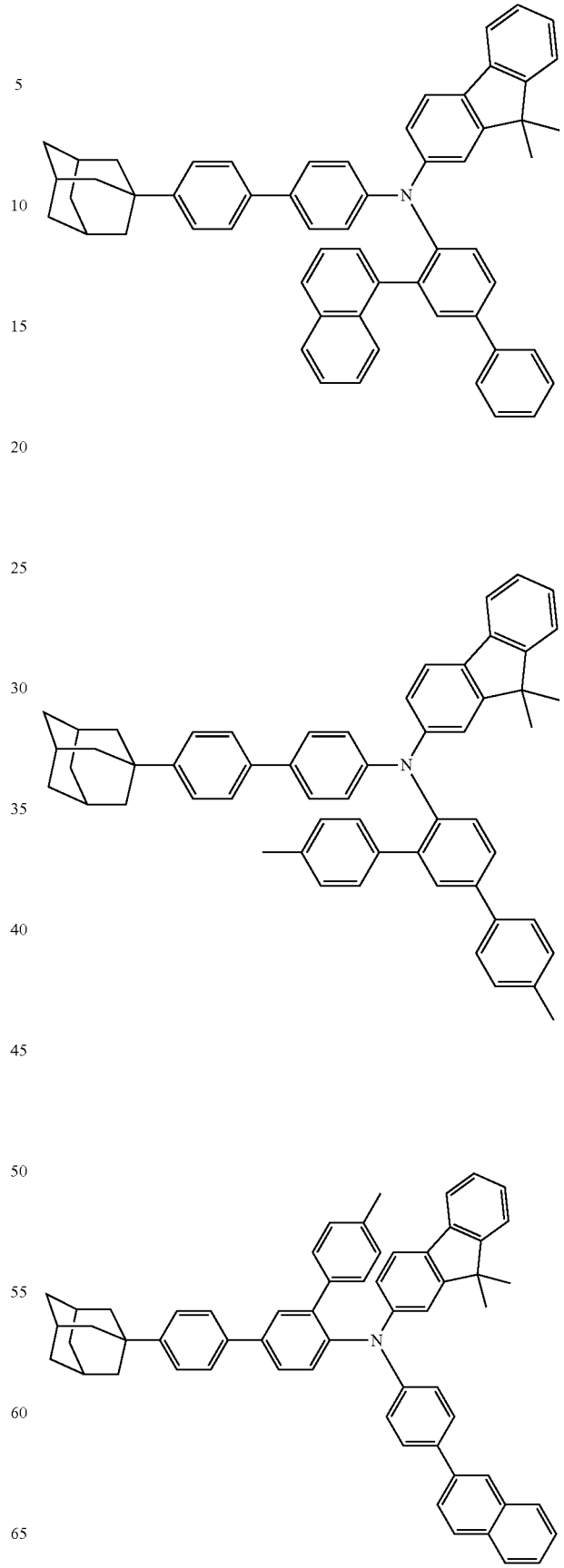

109
-continued
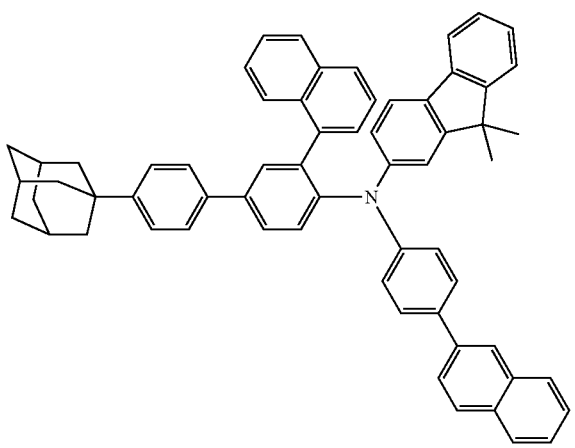
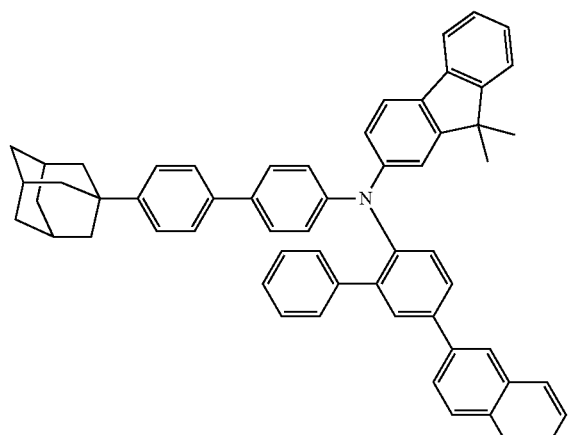
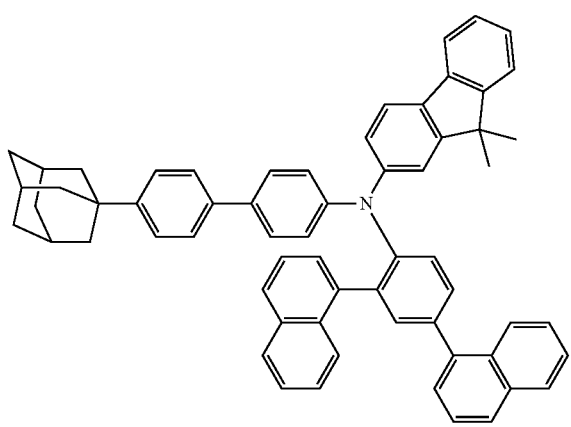
110
-continued
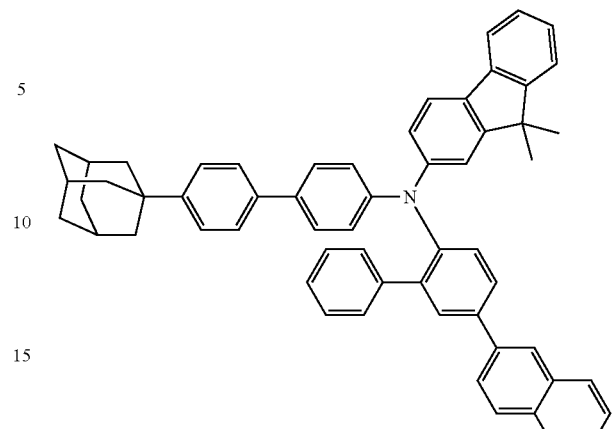
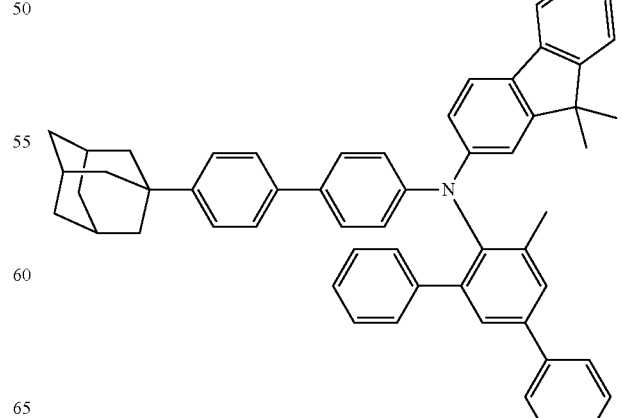

111
-continued
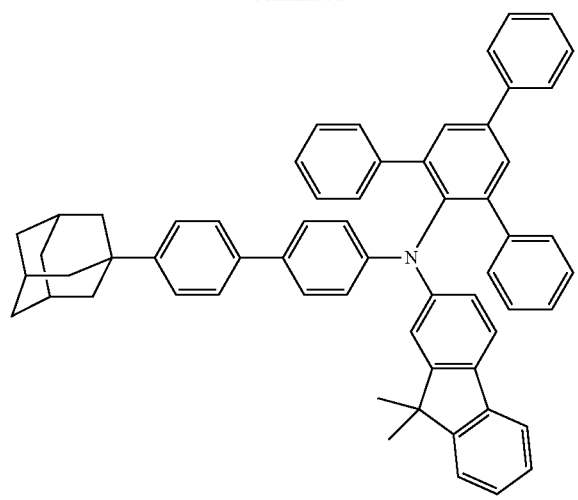
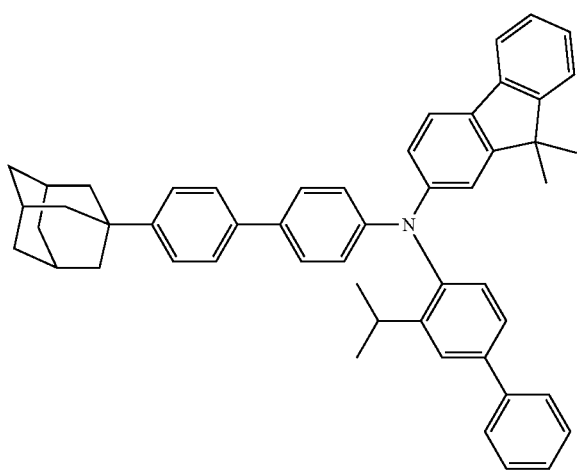
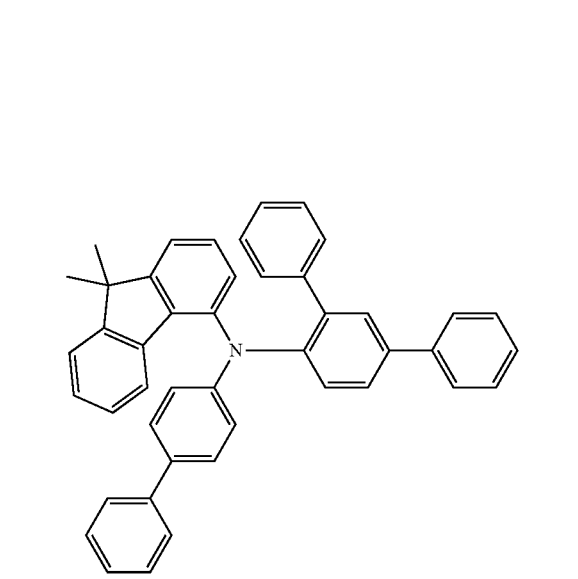
112
-continued
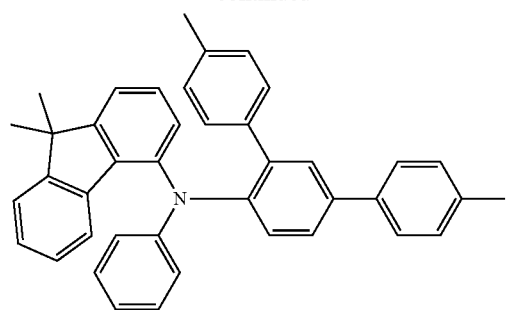
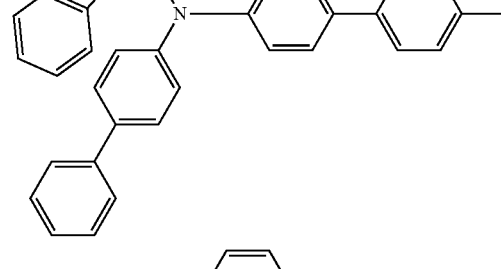
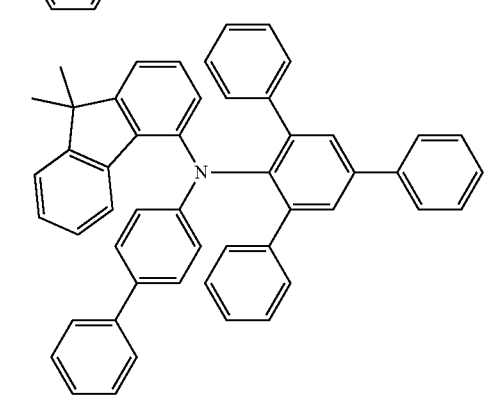
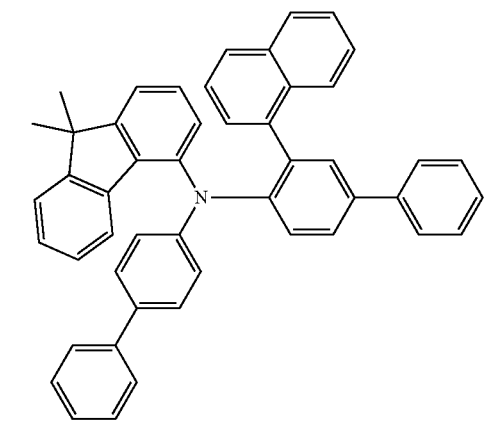
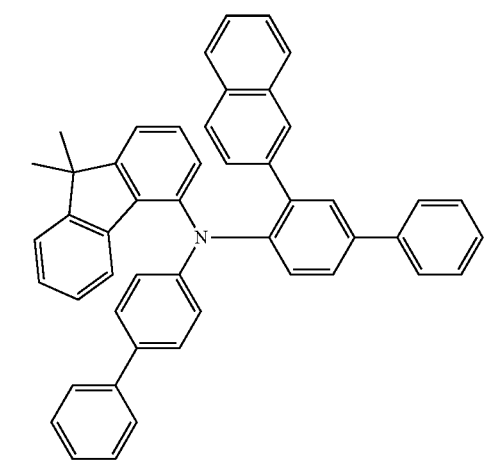

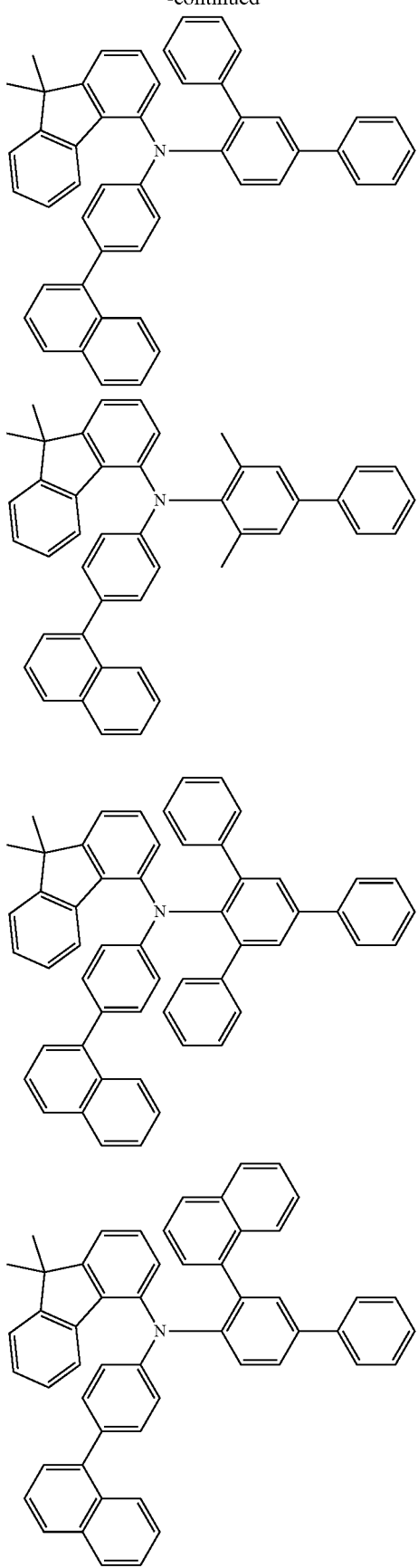

115
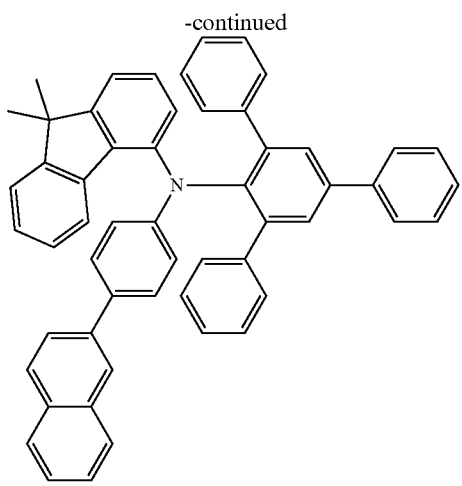
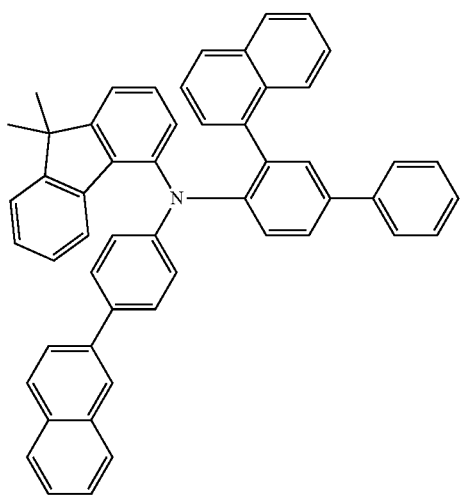
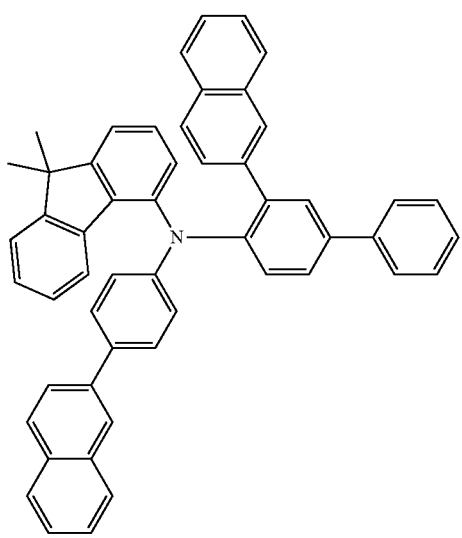
116
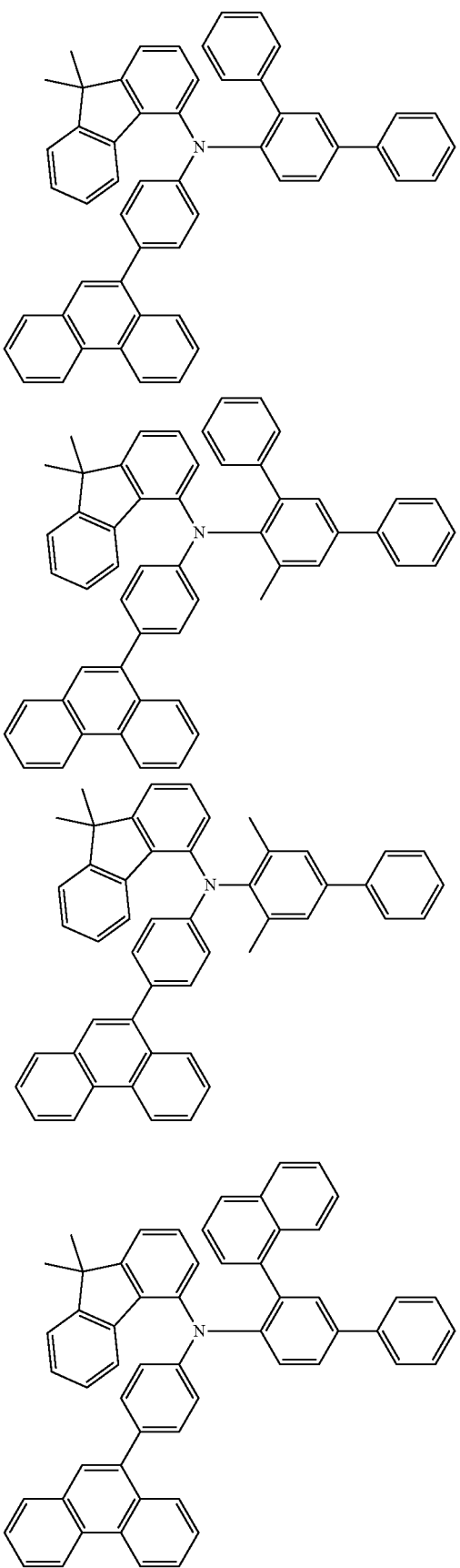

117
-continued
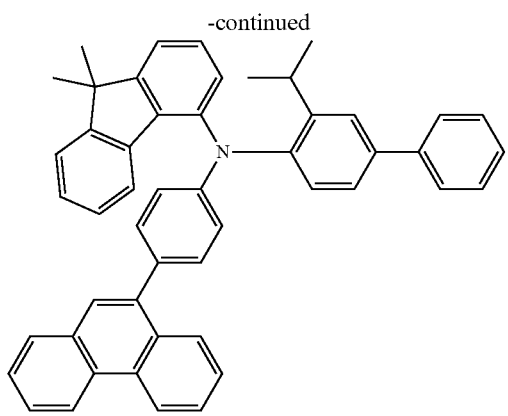
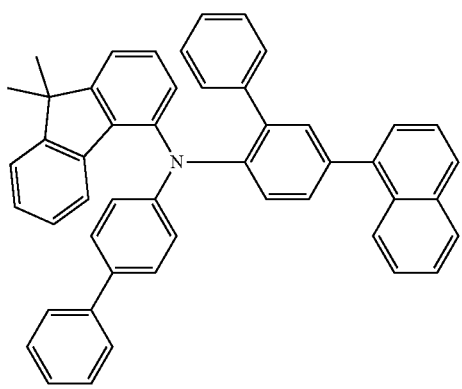
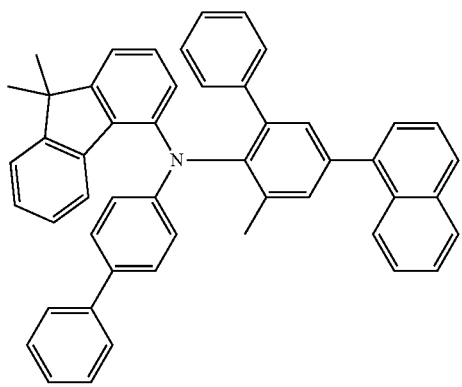
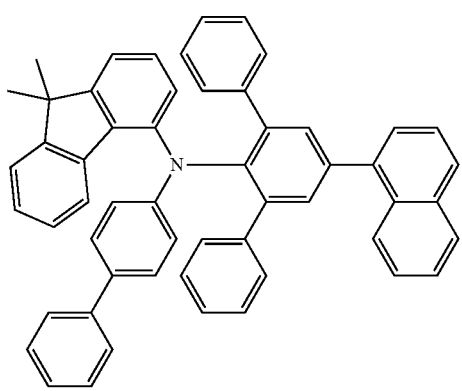
118
-continued
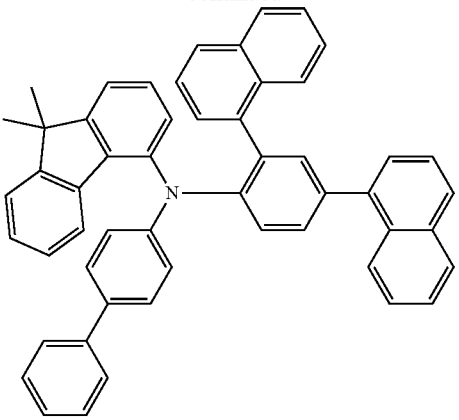
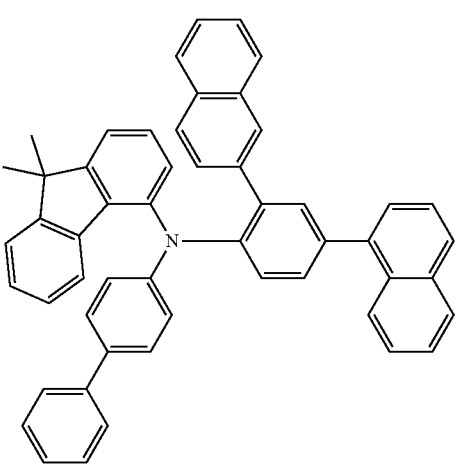
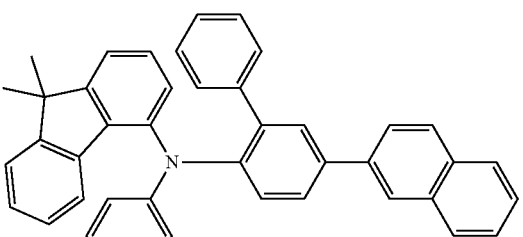
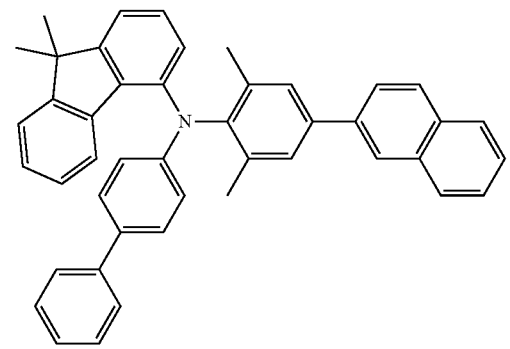

119
-continued
120
-continued
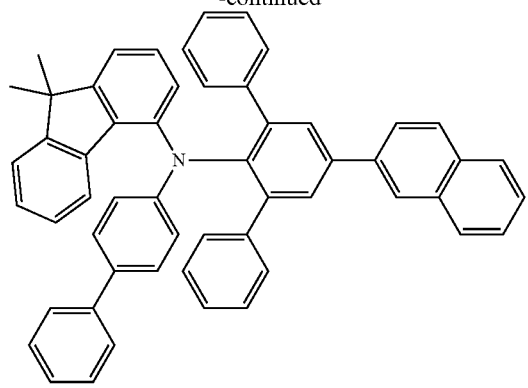
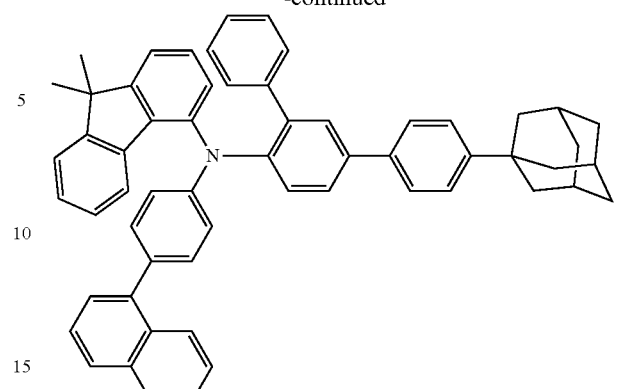
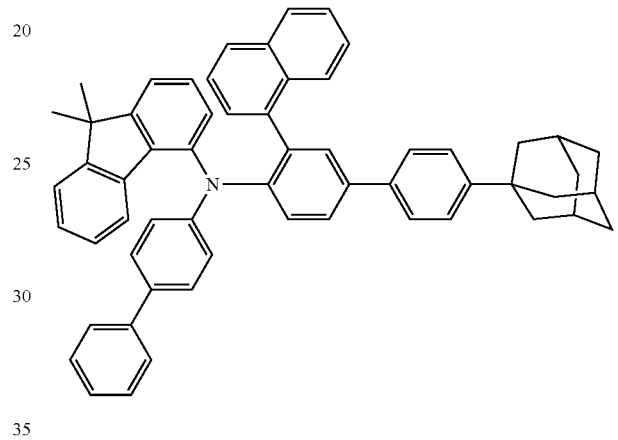
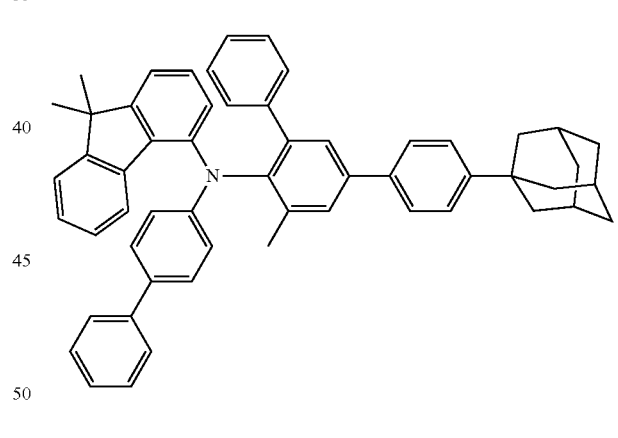
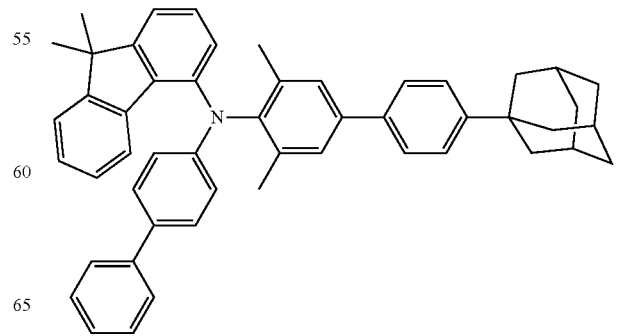

121
-continued
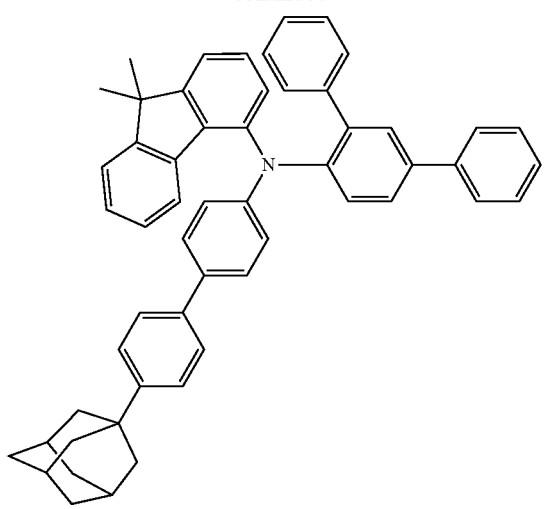
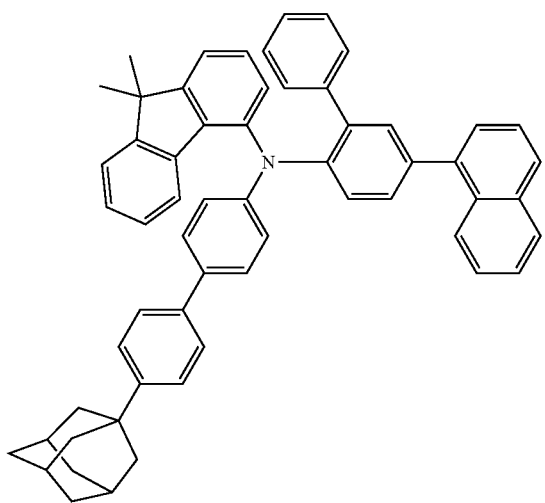
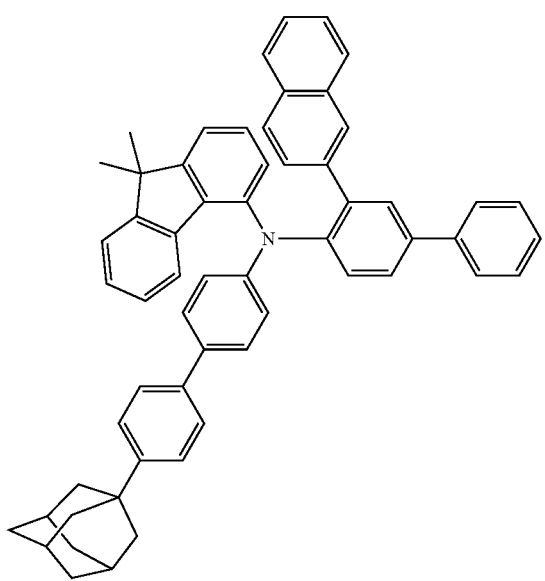
122
-continued
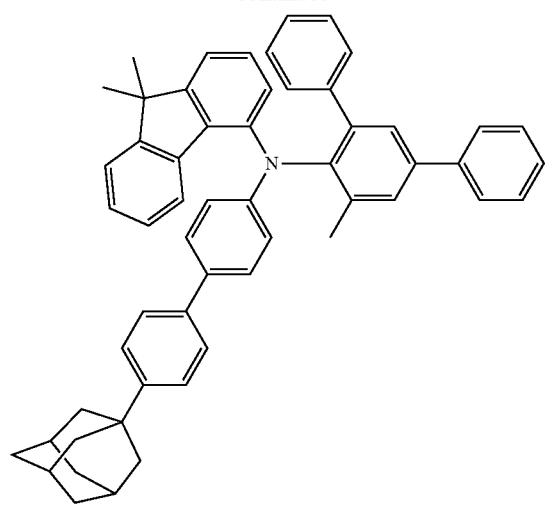
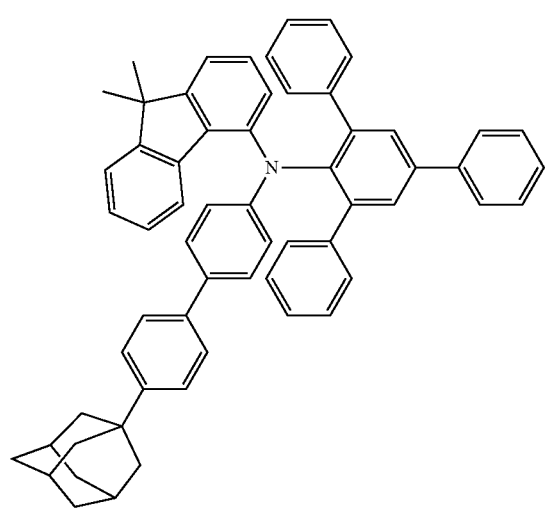
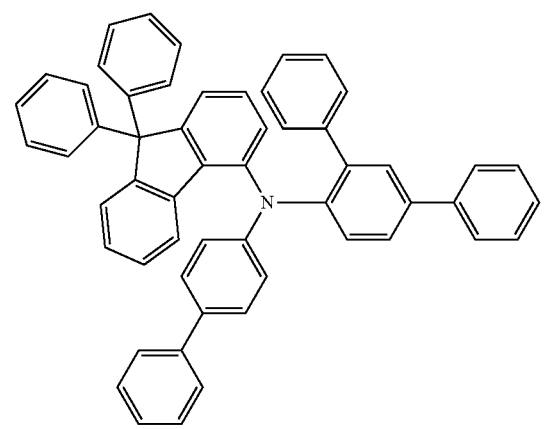

123
-continued
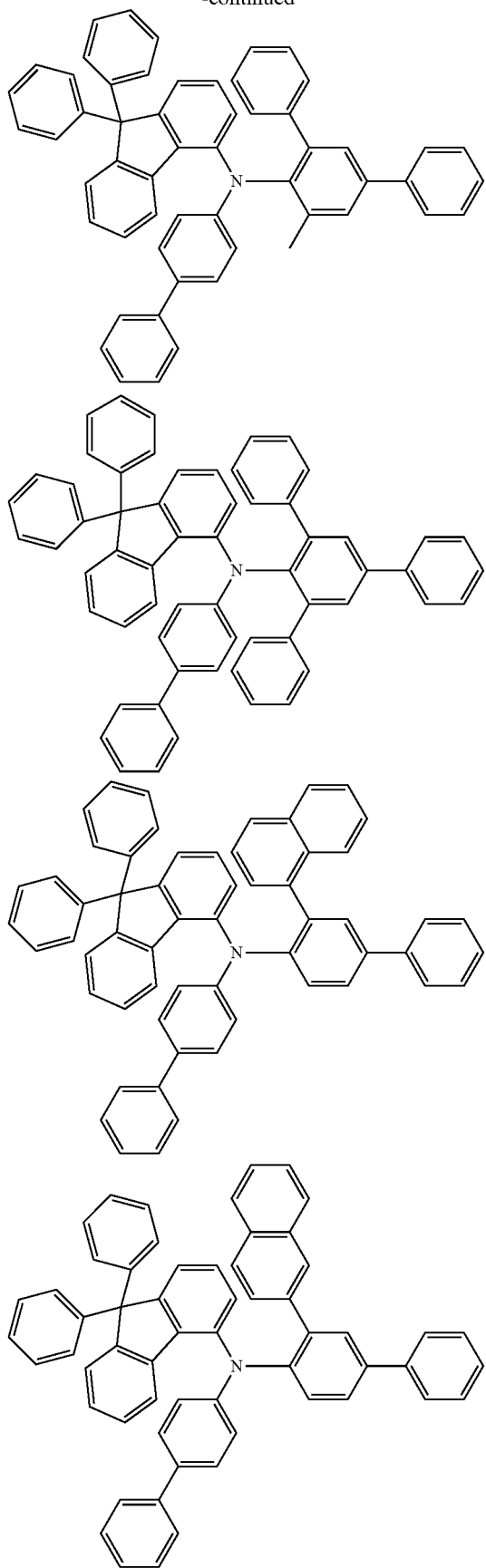
124
-continued
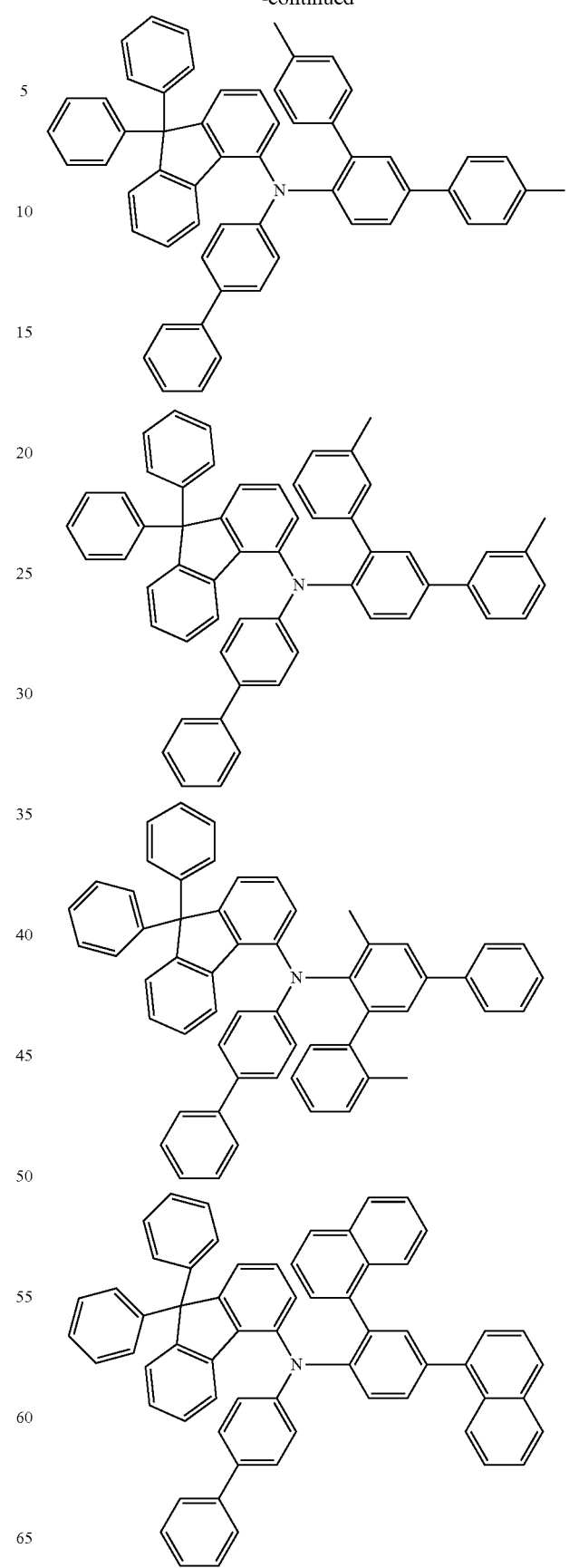

125
-continued
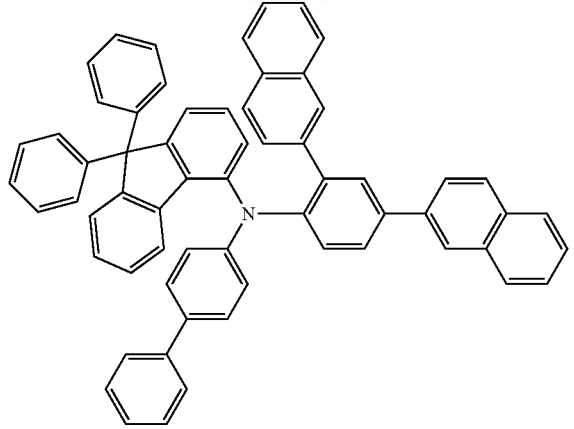
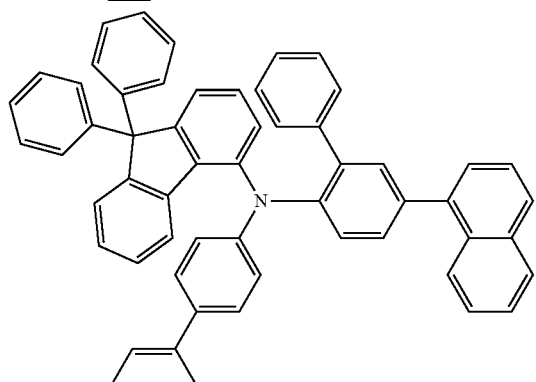
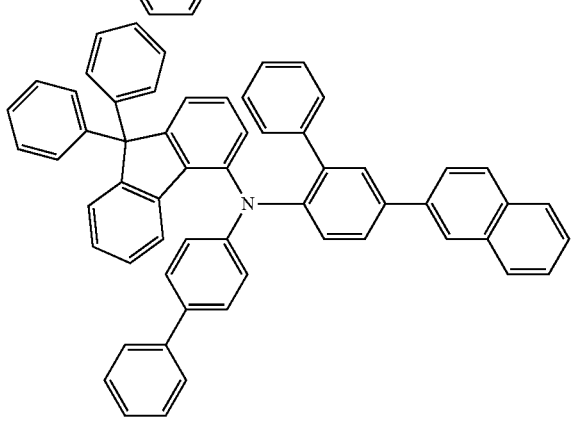
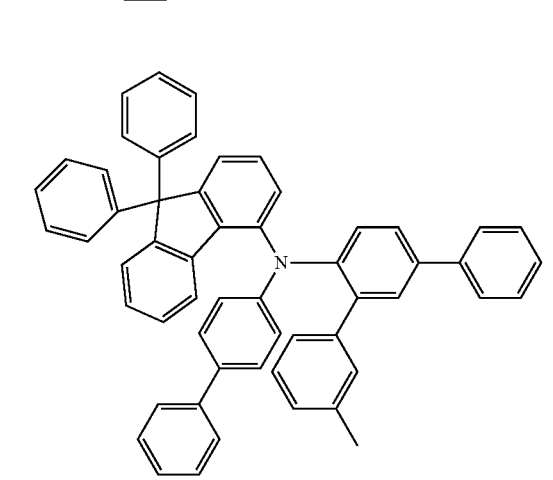
126
-continued
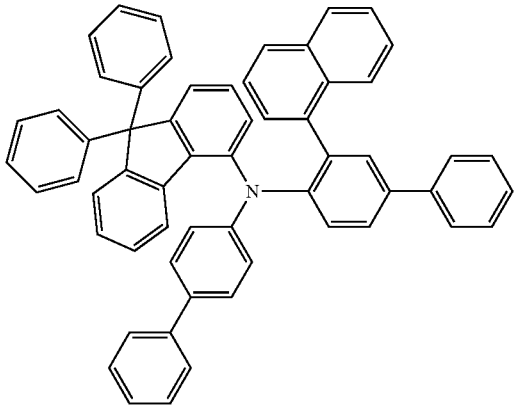
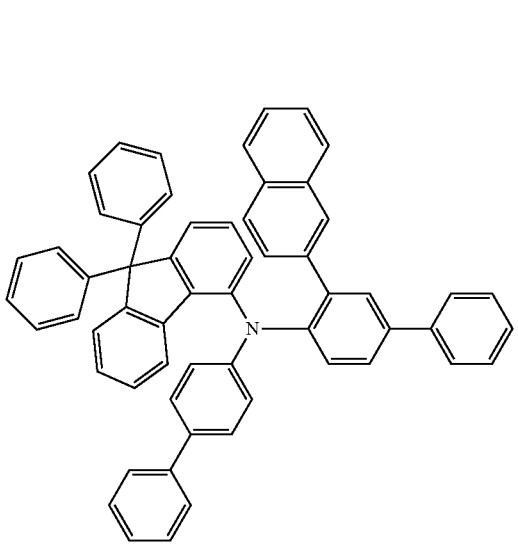
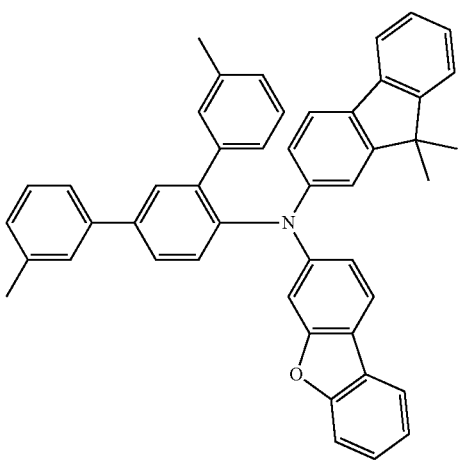

127
-continued

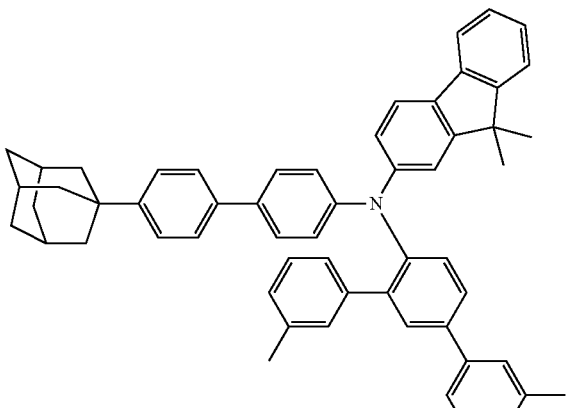

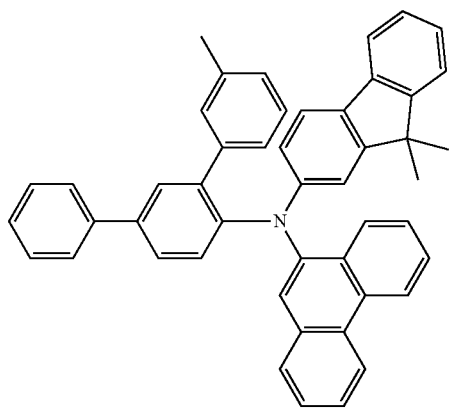

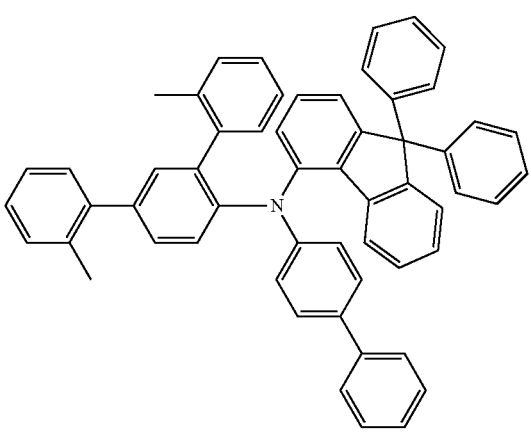

128
-continued

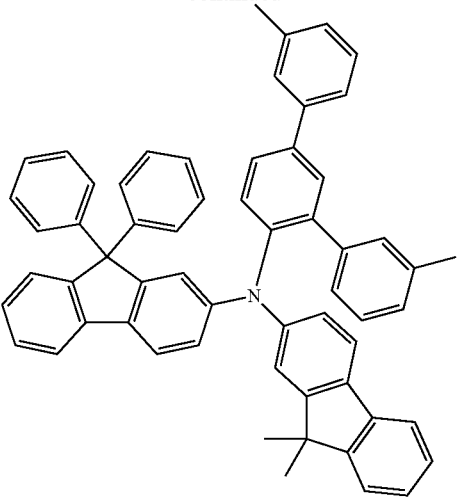

The compound of Formula 1 of the present invention may be usefully used as a material for a hole transport auxiliary layer.

As the compound of the present invention is used as a material for a hole transport auxiliary layer in an organic electroluminescent device, the compound of the present invention includes a substituent, which increases the HOMO in the compound and enables fine adjustment, such that the hole mobility may be optimally adjusted according to the mobility of electrons injected into the light emitting layer.

Due to these characteristics, when the organic compound is used as a material for an organic electroluminescent device, it is possible to exhibit almost the same or excellent characteristics in most of the device characteristics such as light emitting efficiency and service life.

The present invention provides an organic electroluminescent device including the compound represented by Formula 1.

The organic compound of the present invention may be usefully used as a material for a hole transport auxiliary layer.

The present invention is an organic electroluminescent device in which organic thin film layers composed of a single layer or a plurality of layers at least including a light emitting layer are stacked between a negative electrode and a positive electrode, in which the organic thin film layers are a hole transport layer and a hole transport auxiliary layer between the first electrode and the light emitting layer.

The organic electroluminescent device may have a structure in which a positive electrode, a hole injection layer, a hole transport layer, a hole transport auxiliary layer, a light emitting layer, an electron transport layer, an electron injection layer, and a negative electrode are stacked, and a hole blocking layer may be further stacked, if necessary.

Hereinafter, the organic electroluminescent device of the present invention will be described with reference to examples. However, the content exemplified below does not limit the organic electroluminescent device of the present invention.

The organic electroluminescent device of the present invention may have a structure in which a positive electrode (hole injection electrode), a hole injection layer (HIL), a hole transport layer (HTL), a hole transport auxiliary layer, a light emitting layer (EML), and a negative electrode (electron injection electrode) are sequentially stacked, and preferably, may additionally include an electron blocking layer (EBL) between the positive electrode and the light emitting layer and an electron transport layer (ETL) and an electron injection layer (EIL) between the negative electrode and the light emitting layer. Further, the organic electroluminescent device of the present invention may further include a hole blocking layer (HBL) between the negative electrode and the light emitting layer.

In a method for manufacturing an organic electroluminescent device according to the present invention, first, the surface of a substrate is coated with a material for a positive electrode by a typical method, thereby forming a positive electrode. In this case, the substrate to be used is preferably a glass substrate or a transparent plastic substrate, which is excellent in transparency, surface smoothness, ease of handling and waterproofness. Further, as the material for a positive electrode, it is possible to use indium tin oxide (ITO), indium zinc oxide (IZO), tin oxide (SnO2), zinc oxide (ZnO), and the like, which are transparent and excellent in conductivity.

Next, a hole injection layer (HIL) material is thermally vacuum-deposited onto the surface of the positive electrode or the surface of the positive electrode is spin-coated with the hole injection layer (HIL) material, by a typical method, thereby forming a hole injection layer. Examples of the hole injection layer material include copper phthalocyanine (CuPc), 4,4',4''-tris(3-methylphenylamino)triphenylamine (m-MTDATA), 4,4',4''-tris(3-methylphenylamino)phenoxybenzene (m-MTDAPB), starburst amines 4,4',4''-tri(N-carbazolyl)triphenylamine (TCTA) and 4,4',4''-tris(N-(2-napthyl)-N-phenylamino)-triphenylamine (2-TNATA), or IDE406 commercially available from Idemitsu Inc.

A hole injection layer material is thermally vacuum-deposited onto the surface of the hole injection layer or the surface of the hole injection layer is spin-coated with the hole transport layer material, by a typical method, thereby forming a hole transport layer.

As the hole transport layer material, the compound of the present invention or a material that may be purchased by those skilled in the art may be used.

The compound of the present invention is thermally vacuum-deposited onto the surface of the hole transport layer or the surface of the hole transport layer is spin-coated with the compound of the present invention, thereby forming a hole transport auxiliary layer.

A light emitting layer (EML) material is thermally vacuum-deposited onto the surface of the hole transport auxiliary layer or the surface of the hole transport auxiliary layer is spin-coated with the light emitting layer (EML) material, by a typical method, thereby forming a light emitting layer. In this case, among the light emitting layer materials used, as a single light emitting material or light emitting host material, tris(8-hydroxyquinolinolato)aluminum (Alq$_3$) and the like may be used in the case of the green color, and Alq$_3$, 4,4'-N,N'-dicabazole-biphenyl (CBP), poly (n-vinylcarbazole)(PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, distyrylarylene (DSA) or a mixture of two or more thereof may be used in the case of the blue color, but the materials are not limited thereto.

As a dopant which may be used along with a light emitting host among the light emitting layer materials, it is possible to use IDE102 and IDE105 commercially available from Idemitsu Inc., and as a phosphorescent dopant, it is possible to use tris(2-phenylpyridine)iridium (III)(Ir(ppy)3), iridium (III)bis[(4,6-difluorophenyl)pyridinato-N,C-2']pi-colinate (FIrpic) (reference literature [Chihaya Adachi et al., Appl. Phys. Lett., 2001, 79, 3082-3084]), platinum (II) octaethylporphyrin (PtOEP), TBE002 (Corbion), and the like.

An electron transport layer (ETL) material is thermally vacuum-deposited onto the surface of the light emitting layer or the surface of the light emitting layer is spin-coated with the electron transport layer (ETL) material, by a typical method, thereby forming an electron transport layer. In this case, the electron transport layer material used is not particularly limited, and preferably, tris(8-hydroxyquinolinolato)aluminum (Alq$_3$) may be used.

Selectively, by additionally forming a hole blocking layer (HBL) between the light emitting layer and the electron transport layer and using a phosphorescent dopant together in the light emitting layer, it is possible to prevent triplet excitons or holes from diffusing into the electron transport layer.

The hole blocking layer may be formed by the thermal vacuum deposition and spin-coating of the hole blocking layer material by a typical method, and the hole blocking layer material is not particularly limited, but preferably, (8-hydroxyquinolinolato)lithium (Liq), bis(8-hydroxy-2-methylquinolinolato)-aluminumbiphenoxide (BAlq), bathocuproine (BCP), LiF, and the like may be used.

An electron injection layer (EIL) material is thermally vacuum-deposited onto the surface of the electron transport layer or the surface of the electron transport layer is spin-coated with the electron injection layer (EIL) material, by a typical method, thereby forming an electron injection layer. In this case, as the electron injection layer material used, a material such as LiF, Liq, Li$_2$O, BaO, NaCl, and CsF may be used.

A material for a negative electrode is thermally vacuum-deposited onto the surface of the electron injection layer by a typical method, thereby forming a negative electrode.

In this case, as the material for a negative electrode used, lithium (Li), aluminum (Al), aluminum-lithium (Al—Li), calcium (Ca), magnesium (Mg), magnesium-indium (Mg—In), magnesium-silver (Mg—Ag), and the like may be used. In addition, in the case of a top-emission electroluminescent device, a transparent negative electrode through which light may pass may also be formed using indium tin oxide (ITO) or indium zinc oxide (IZO).

A capping layer (CPL) may be formed on the surface of the negative electrode by a composition for forming a capping layer.

Hereinafter, a method for synthesizing the compounds will be described below with reference to representative examples. However, the method for synthesizing the compounds of the present invention is not limited to the methods exemplified below, and the compounds of the present invention may be prepared by the methods exemplified below and methods publicly known in the art.

Synthesis Example 1—Preparation of Compound 1

1-A) Preparation of Intermediate 1-A

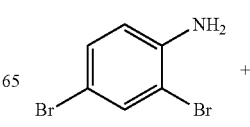

-continued

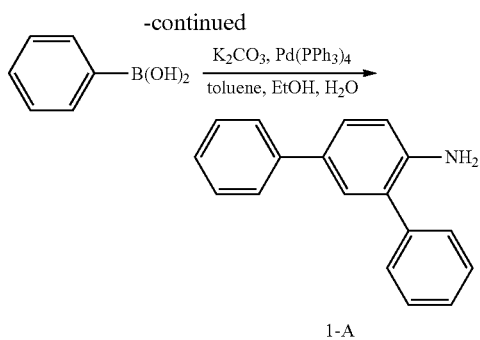

1-A 2,4-Dibromoaniline (20.0 g, 79.71 mmol), phenylboronic acid (23.32 g, 191.30 mmol), potassium carbonate (44.07 g, 318.83 mmol), tetrakis(triphenylphosphine)palladium(0) (5.53 g, 4.78 mmol), toluene (300 mL), EtOH (75 mL), and H$_2$O (75 mL) were put into a 1,000 mL flask under nitrogen flow, and the resulting mixture was stirred and refluxed. After the reaction was terminated, a toluene layer was extracted using toluene and water. The extracted solution was treated with MgSO$_4$ to remove the remaining moisture, concentrated under reduced pressure, and then purified by a column chromatography method to obtain 14.78 g of Compound 1-A at a yield of 75.6%.

1-B) Preparation of Compound 1

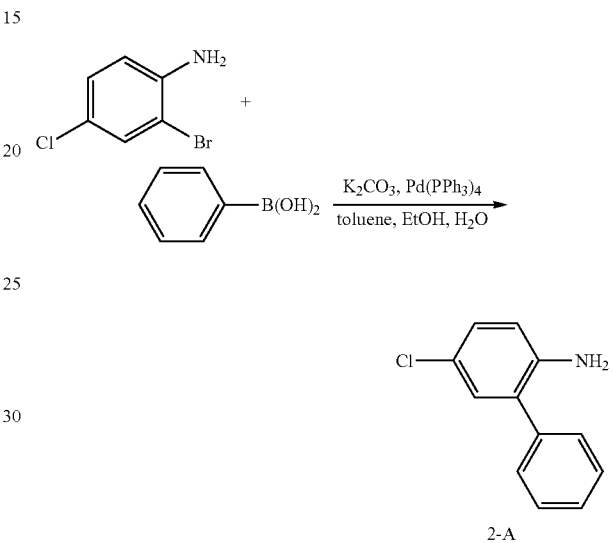

Compound 1-A (7.0 g, 28.53 mmol), 2-bromo-9,9-dimethyl-9H-fluorene (18.71 g. 68.48 mmol), sodium tert-butoxide (13.71 g, 142.66 mmol) tris(dibenzylideneacetone) dipalladium(0) (1.05 g, 1.14 mmol), a 50% tri-tert-butylphosphine solution (1.07 mL, 4.57 mmol), and 200 mL of toluene were put into a 500 mL flask under nitrogen flow, and the resulting mixture was stirred and refluxed. After the reaction was terminated, a toluene layer was extracted using 100 mL of water. The extracted solution was treated with MgSO$_4$ to remove the remaining moisture, concentrated under reduced pressure, and then purified using a column chromatography method, and recrystallized with dichloromethane/heptane to obtain 9.02 g of Compound 1 at a yield of 50.2%.

Synthesis Example 2—Preparation of Compound 2

2-A) Preparation of Intermediate 2-A

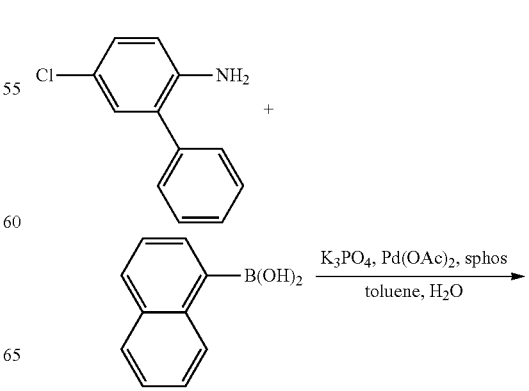

2-A 2-bromo-4-chloroaniline (25.0 g, 121.08 mmol), phenylboronic acid (17.72 g, 145.30 mmol), potassium carbonate (33.47 g, 242.17 mmol), tetrakis(triphenylphosphine)palladium(0) (4.20 g, 3.63 mmol), toluene (300 mL), EtOH (80 mL), and H$_2$O (80 mL) were put into a 500 mL flask under nitrogen flow, and the resulting mixture was stirred and refluxed. After the reaction was terminated, a toluene layer was extracted using toluene and water. The extracted solution was treated with MgSO$_4$ to remove the remaining moisture, concentrated under reduced pressure, and then purified by a column chromatography method to obtain 17.78 g of Compound 2-A at a yield of 72.1%.

2-B) Preparation of Intermediate 2-B

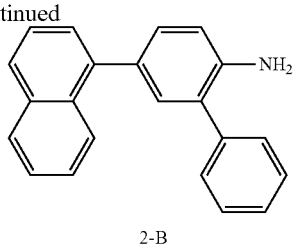

2-B

Compound 2-A (6.0 g, 29.46 mmol), 1-napthalene boronic acid (6.08 g, 35.35 mmol), potassium phosphate tribasic (15.63 g, 73.65 mmol), palladium(II) acetate (0.198 g, 0.884 mmol), 2-dicyclohexylphosphino-2',6'-dimethoxybiphenyl (0.726 g, 1.767 mmol), toluene (100 mL), and H2O (10 mL) were put into a 250 mL flask under nitrogen flow, and the resulting mixture was stirred and refluxed. After the reaction was terminated, a toluene layer was extracted using toluene and water. The extracted solution was treated with MgSO$_4$ to remove the remaining moisture, concentrated under reduced pressure, and then purified by a column chromatography method to obtain 6.16 g of Compound 2-B at a yield of 70.8%.

2-C) Preparation of Compound 2

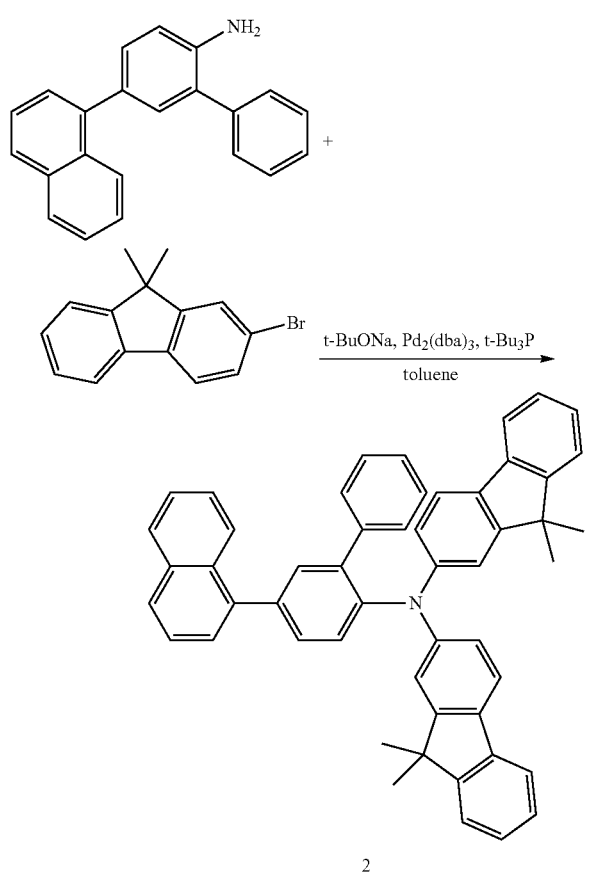

2

6.60 g of Compound 2 was obtained at a yield of 47.8% by performing the synthesis and purification in the same manner as in the preparation of Compound 1, except that Compound 2-B (6.0 g, 20.31 mmol) was used instead of Compound 1-A.

Synthesis Example 3—Preparation of Compound 3

3-A) Preparation of Intermediate 3-A

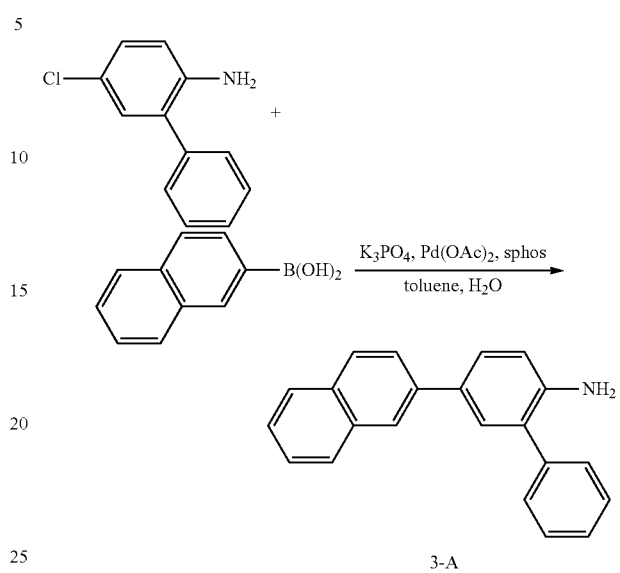

3-A 6.22 g of Compound 3-A was obtained at a yield of 71.5% by performing the synthesis and purification in the same manner as in the preparation of Compound 2-B, except that 2-naphthalene boronic acid (6.08 g, 35.35 mmol) was used instead of naphthalene boronic acid.

3-B) Preparation of Compound 3

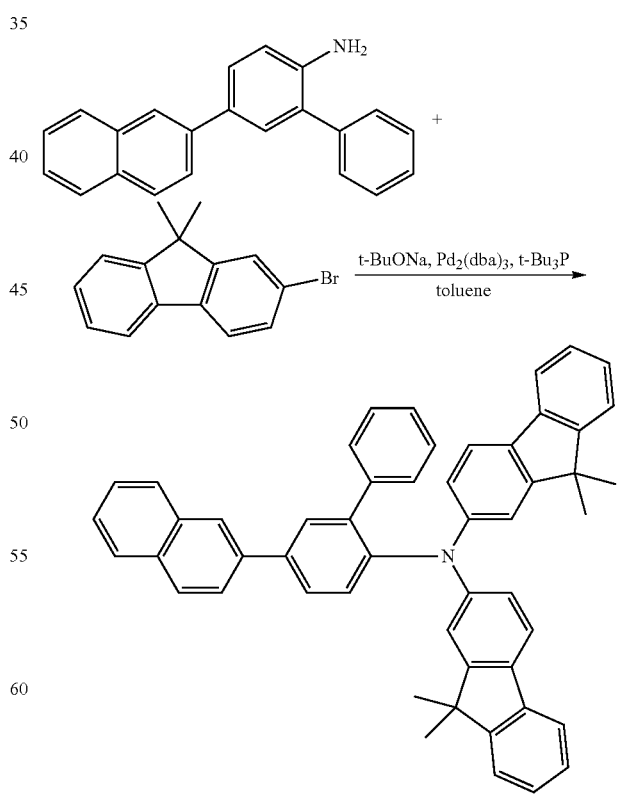

3

6.70 g of Compound 3 was obtained at a yield of 48.5% by performing the synthesis and purification in the same manner as in the preparation of Compound 1, except that Compound 3-A (6.0 g, 20.31 mmol) was used instead of Compound 1-A.

Synthesis Example 4—Preparation of Compound 4

4-A) Preparation of Intermediate 4-A

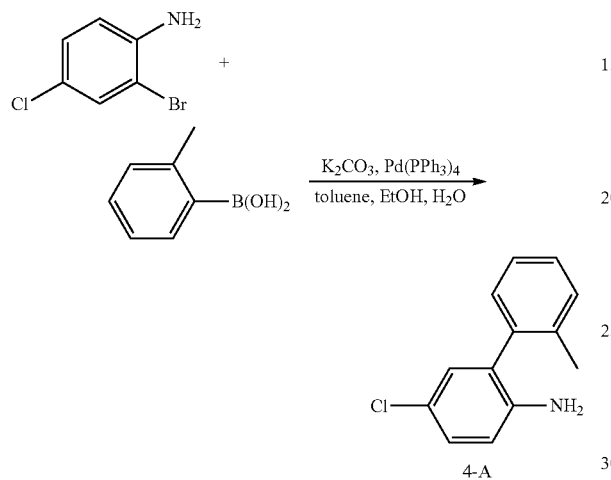

16.45 g of Compound 4-A was obtained at a yield of 62.4% by performing the synthesis an purification in the same manner as in the preparation of Compound 2-A, except that o-tolylboronic acid (19.75 g, 145.30 mmol) was used instead of phenylboronic acid.

4-B) Preparation of Intermediate 4-B

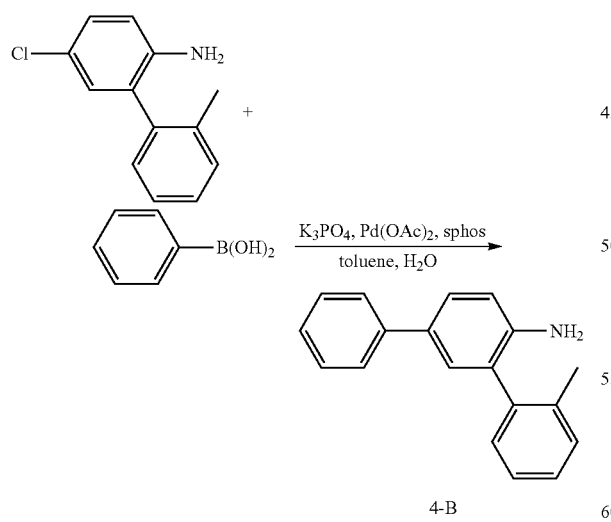

7.78 g of Compound 4-B was obtained at a yield of 65.3% by performing the synthesis and purification in the same manner as in the preparation of Compound 2-B, except that Compound 4-A (10.0 g, 45.93 mmol) and phenylboronic acid (6.72 g, 55.12 mmol) were used.

4-C) Preparation of Compound 4

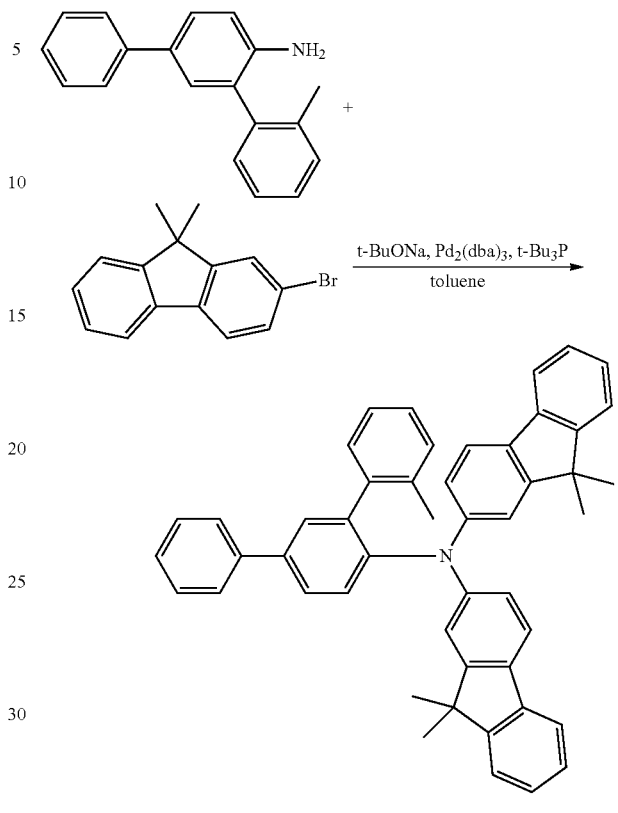

7.61 g of Compound 4 was obtained at a yield of 43.8% by performing the synthesis and purification in the same manner as in the preparation of Compound 1, except that Compound 4-B (7.0 g, 26.99 mmol) was used instead of Compound 1-A.

Synthesis Example 5—Preparation of Compound 5

5-A) Preparation of Intermediate 5-A

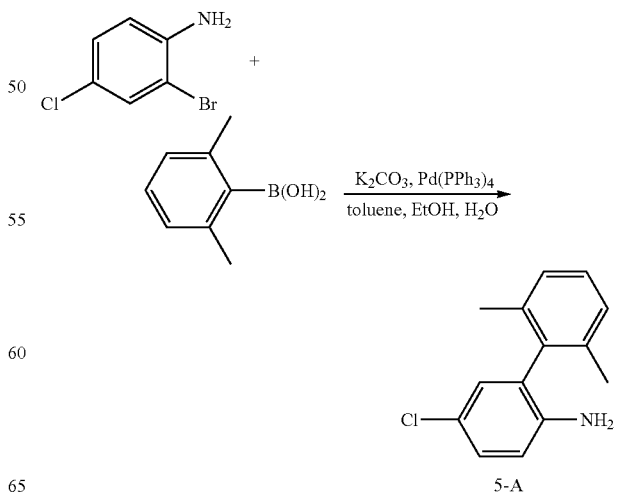

16.92 g of Compound 5-A was obtained at a yield of 60.3% by performing the synthesis and purification in the same manner as in the preparation of Compound 2-A, except that (2,6-dimethylphenyl)boronic acid (21.79 g, 145.30 mmol) was used instead of phenylboronic acid.

5-B) Preparation of Intermediate 5-B

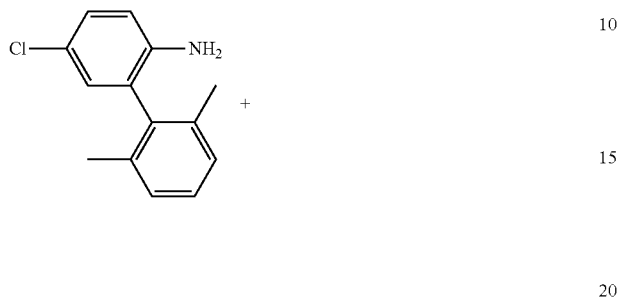

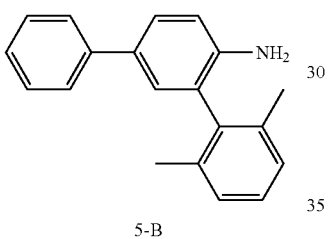

5-B 7.12 g of Compound 5-B was obtained at a yield of 63.6% by performing the synthesis and purification in the same manner as in the preparation of Compound 2-B, except that Compound 5-A (10.0 g, 43.16 mmol) and phenylboronic acid (6.31 g, 51.79 mmol) were used.

5-C) Preparation of Compound 5

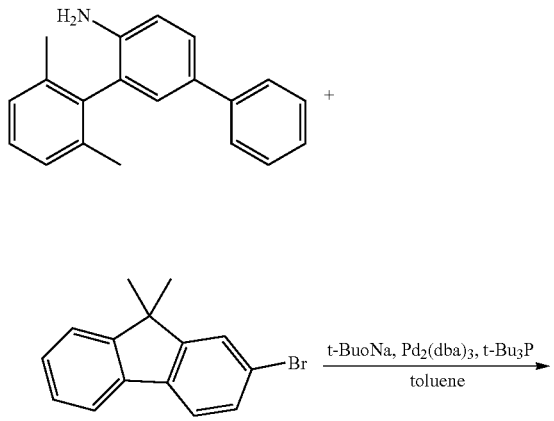

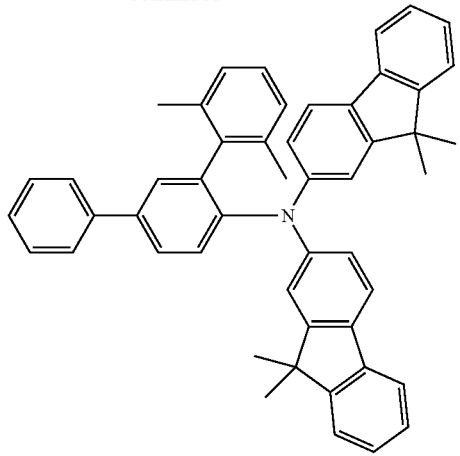

5

7.18 g of Compound 5 was obtained at a yield of 42.6% by performing the synthesis and purification in the same manner as in the preparation of Compound 1, except that Compound 5-B (7.0 g, 25.61 mmol) was used instead of Compound 1-A.

Synthesis Example 6—Preparation of Compound 6

6-A) Preparation of Intermediate 6-A

6-A 14.32 g of Compound 6-A was obtained at a yield of 60.9% by performing the synthesis and purification in the same manner as in the preparation of Compound 2-B, except that 2-bromo-4-chloroaniline (20.0 g, 90.71 mmol) and phenylboronic acid (26.54 g, 217.70 mmol) were used.

6-B) Preparation of Compound-6

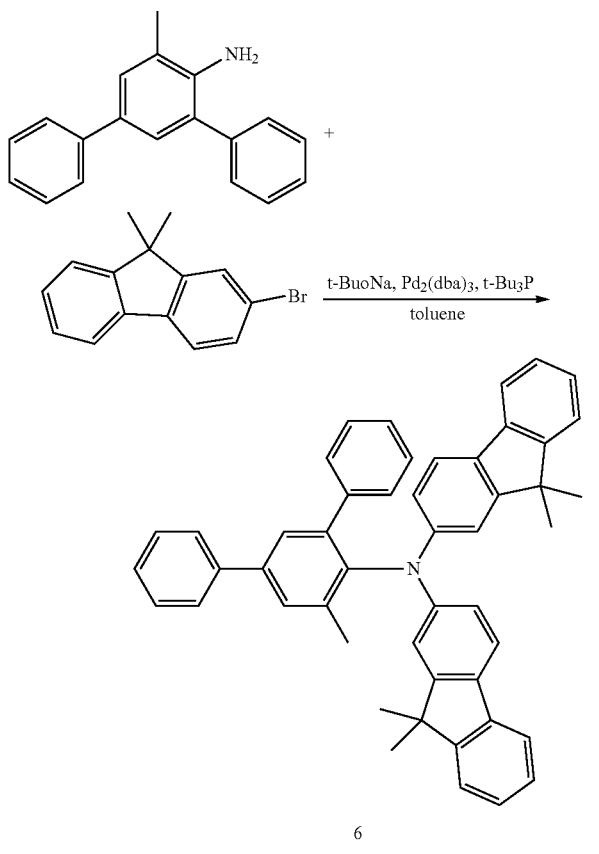

6

7.61 g of Compound 6 was obtained at a yield of 43.8% by performing the synthesis and purification in the same manner as in the preparation of Compound 1, except that Compound 6-A (7.0 g, 26.99 mmol) was used instead of Compound 1-A.

Synthesis Example 7—Preparation of Compound 7

7-A) Preparation of Intermediate 7-A

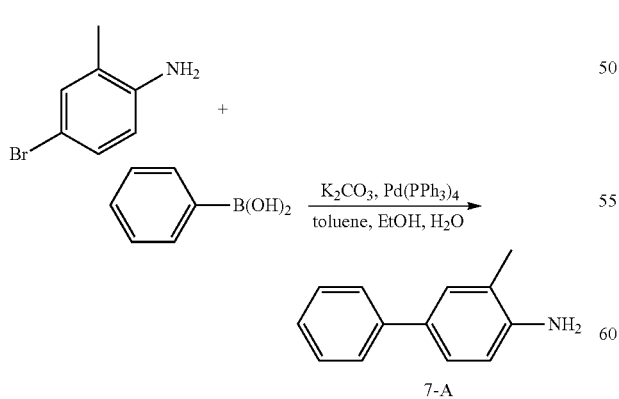

7-A 13.22 g of Compound 7-A was obtained at a yield of 67.1% by performing the synthesis and purification in the same manner as in the preparation of Compound 2-A, except that 4-bromo-2-methylaniline (20.0 g, 107.50 mmol) was used instead of 2-bromo-4-chloroaniline.

7-B) Preparation of Compound 7

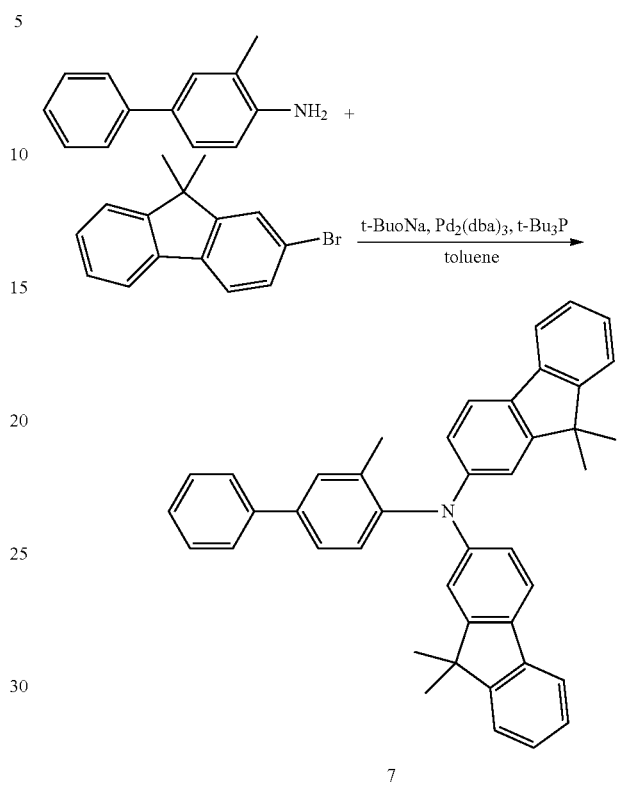

7

8.64 g of Compound 7 was obtained at a yield of 46.5% by performing the synthesis and purification in the same manner as in the preparation of Compound 1, except that Compound 7-A (6.0 g, 32.74 mmol) was used instead of Compound 1-A.

Synthesis Example 8—Preparation of Compound 8

8-A) Preparation of Intermediate 8-A

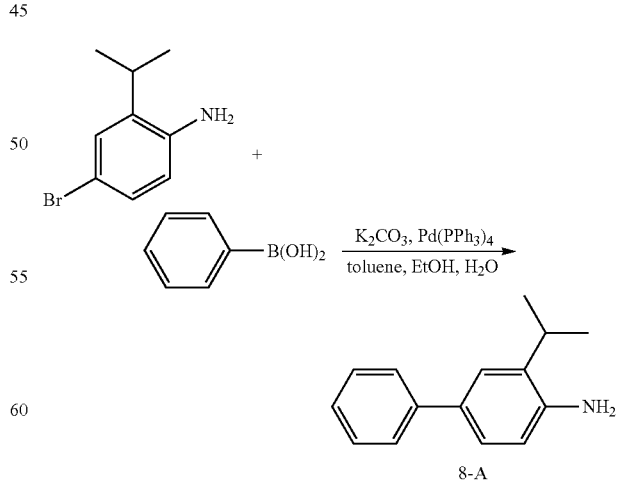

8-A 12.08 g of Compound 8-A was obtained at a yield of 61.2% by performing the synthesis and purification in the same manner as in the preparation of Compound 2-A, except that 4-bromo-2-isopropylaniline (20.0 g, 93.41 mmol) was used instead of 2-bromo-4-chloroaniline.

8-B) Preparation of Compound 8

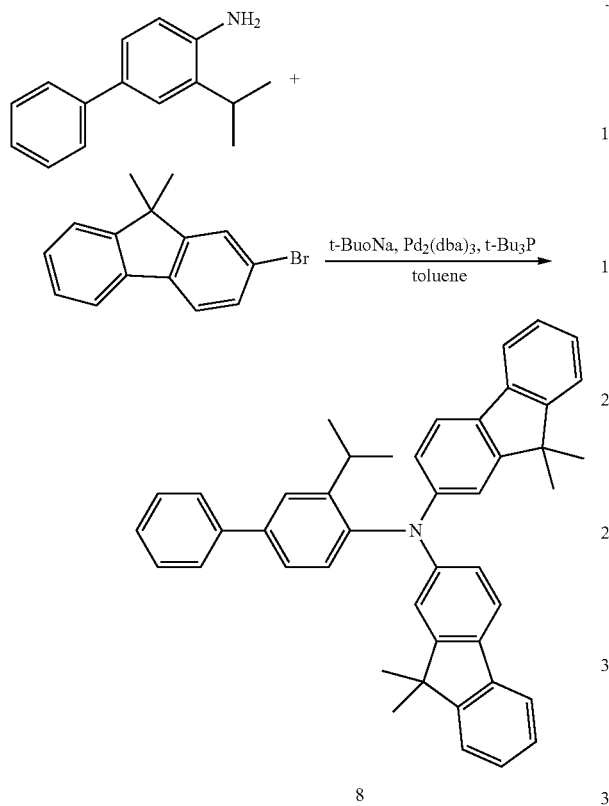

7.24 g of Compound 8 was obtained at a yield of 42.8% by performing the synthesis and purification in the same manner as in the preparation of Compound 1, except that Compound 8-A (6.0 g, 28.39 mmol) was used instead of Compound 1-A.

Synthesis Example 9—Preparation of Compound 9

9-A) Preparation of Intermediate 9-A 19.26 g of Compound 9-A was obtained at a yield of 62.7% by performing the synthesis and purification in the same manner as in the preparation of Compound 2-A, except that 1-naphthalene boronic acid (24.99 g, 145.30 mmol) was used instead of phenylboronic acid.

9-B) Preparation of Intermediate 9-B

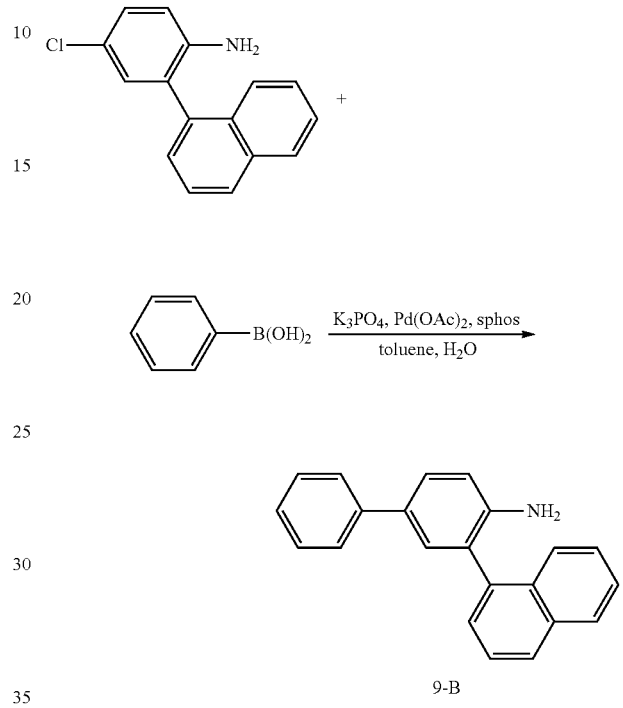

7.82 g of Compound 9-B was obtained at a yield of 67.2% by performing the synthesis and purification in the same manner as in the preparation of Compound 2-B, except that Compound 9-A (10.0 g, 39.41 mmol) and phenylboronic acid (5.77 g, 47.29 mmol) were used.

9-C) Preparation of Compound 9

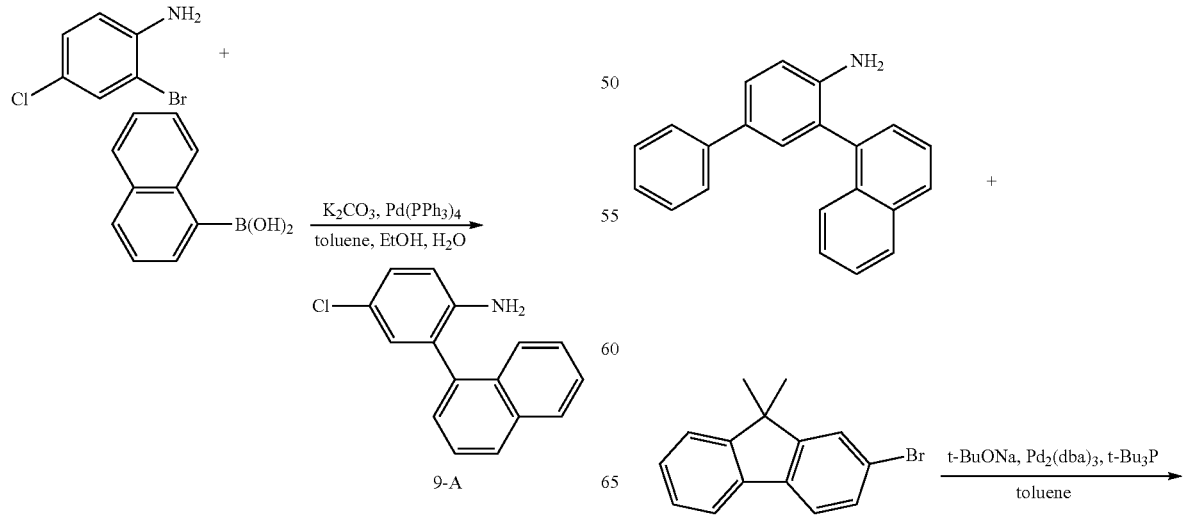

-continued

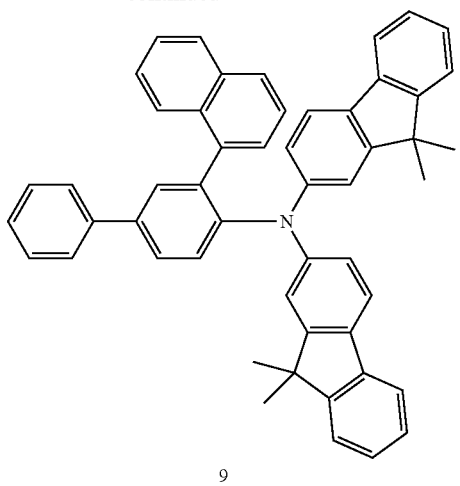

9

7.39 g of Compound 9 was obtained at a yield of 45.9% by performing the synthesis and purification in the same manner as in the preparation of Compound 1, except that Compound 9-B (7.0 g, 23.70 mmol) was used instead of Compound 1-A.

Synthesis Example 10—Preparation of Compound 10

10-A) Preparation of Intermediate 10-A 19.69 g of Compound 10-A was obtained at a yield of 64.1% by performing the synthesis and purification in the same manner as in the preparation of Compound 2-A, except that 2-naphthalene boronic acid (24.99 g, 145.30 mmol) was used instead of phenylboronic acid.

10-B) Preparation of Intermediate 10-B

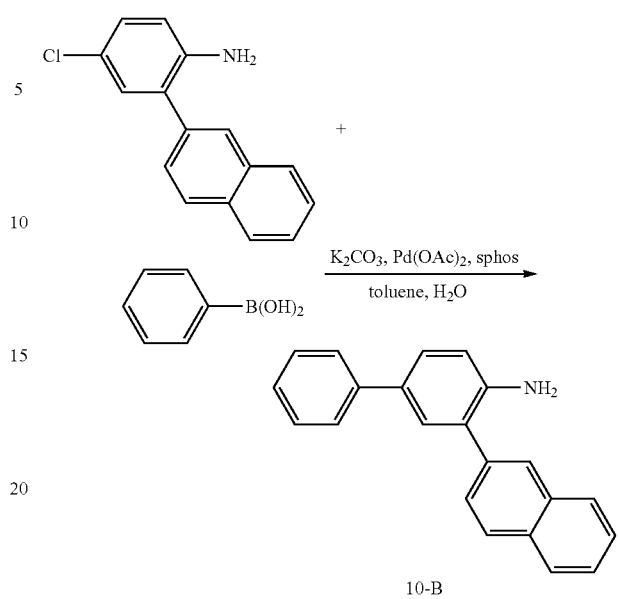

8.07 g of Compound 10-B was obtained at a yield of 69.3% by performing the synthesis and purification in the same manner as in the preparation of Compound 2-B, except that Compound 10-A (10.0 g, 39.41 mmol) and phenylboronic acid (5.77 g, 47.29 mmol) were used.

10-C) Preparation of Compound 10

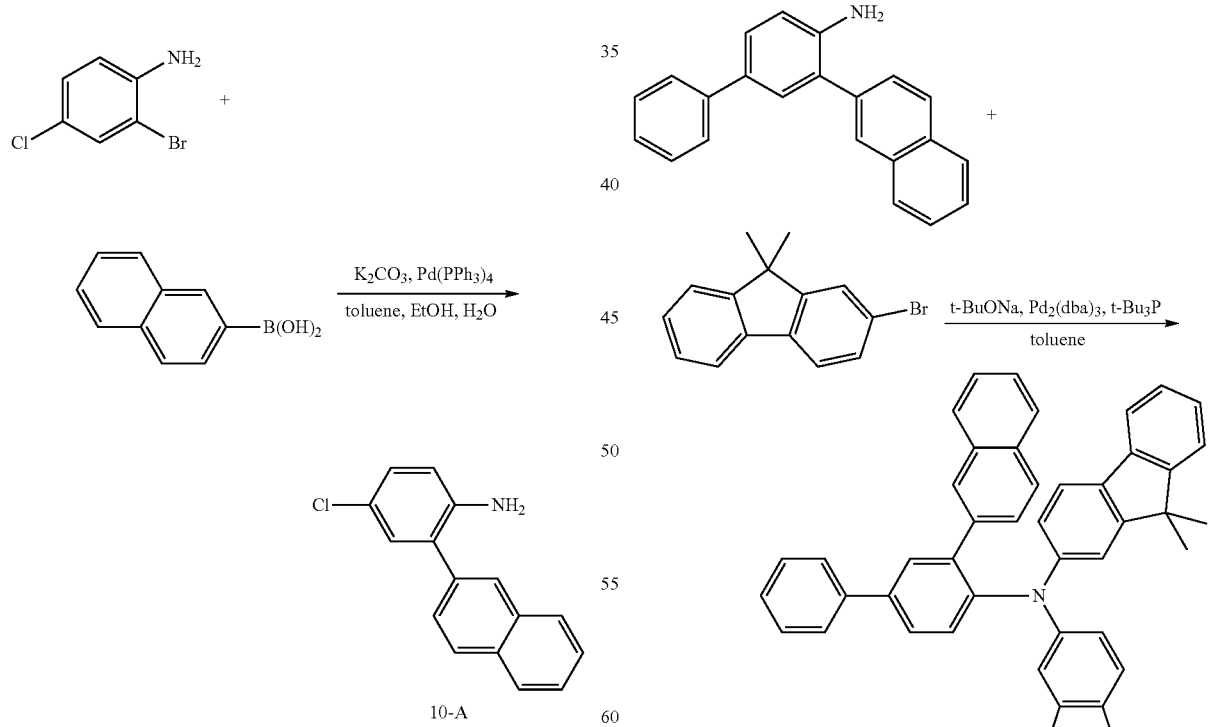

10

7.75 g of Compound 10 was obtained at a yield of 48.1% by performing the synthesis and purification in the same manner as in the preparation of Compound 1, except that Compound 10-B (7.0 g, 23.70 mmol) was used instead of Compound 1-A.

Synthesis Example 11—Preparation of Compound 11

11-A) Preparation of Intermediate 11-A

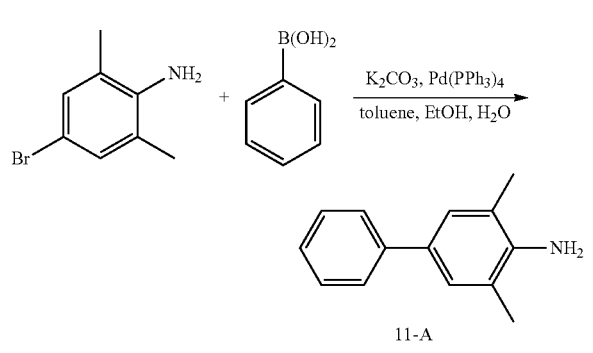

12.84 g of Compound 11-A was obtained at a yield of 65.1% by performing the synthesis and purification in the same manner as in the preparation of Compound 2-A, except that 4-bromo-2,6-dimethylaniline (20.0 g, 99.96 mmol) was used instead of 2-bromo-4-chloroaniline.

11-B) Preparation of Compound 11

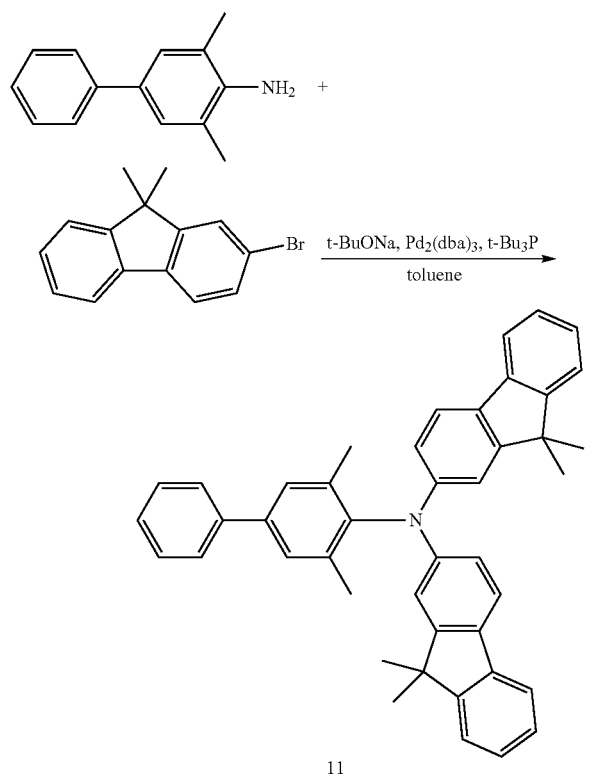

7.84 g of Compound 11 was obtained at a yield of 44.3% by performing the synthesis and purification in the same manner as in the preparation of Compound 1, except that Compound 11-A (6.0 g, 30.41 mmol) was used instead of Compound 1-A.

Synthesis Example 12—Preparation of Compound 12

12-A) Preparation of Intermediate 12-A

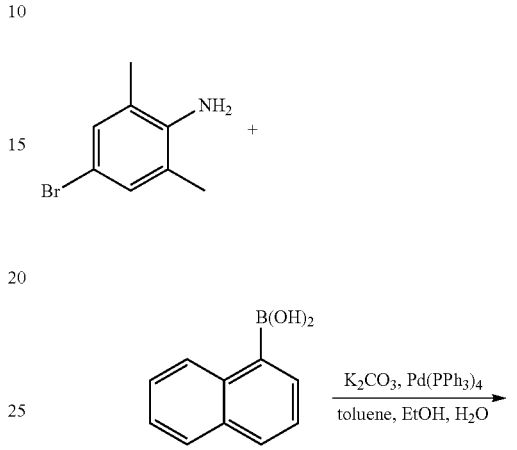

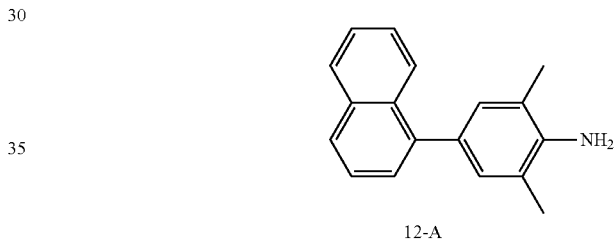

7.87 g of Compound 12-A was obtained at a yield of 63.7% by performing the synthesis and purification in the same manner as in the preparation of Compound 2-A, except that 4-bromo-2,6-dimethylaniline (10.0 g, 49.98 mmol) and 1-naphthalene boronic acid (10.32 g, 59.98 mmol) were used.

12-B) Preparation of Compound 12

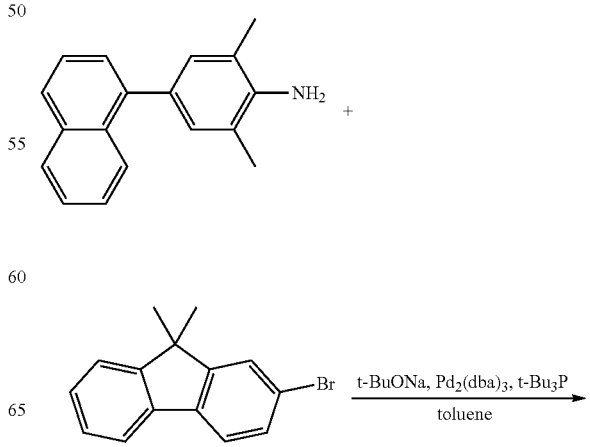

-continued

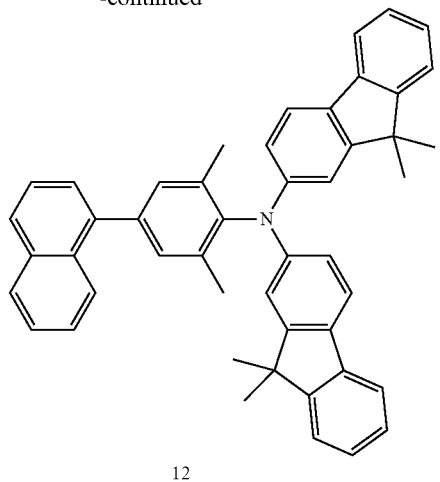

12

8.06 g of Compound 12 was obtained at a yield of 45.1% by performing the synthesis and purification in the same manner as in the preparation of Compound 1, except that Compound 12-A (7.0 g, 28.30 mmol) was used instead of Compound 1-A.

Synthesis Example 13—Preparation of Compound 13

13-A) Preparation of Intermediate 13-A

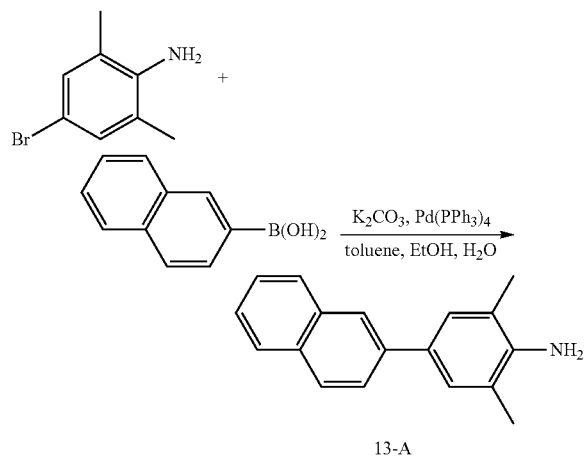

13-A 8.13 g of Compound 13-A was obtained at a yield of 65.8% by performing the synthesis and purification in the same manner as in the preparation of Compound 2-A, except that 4-bromo-2,6-dimethylaniline (10.0 g, 49.98 mmol) and 2-naphthalene boronic acid (10.32 g, 59.98 mmol) were used.

13-B) Preparation of Compound 13

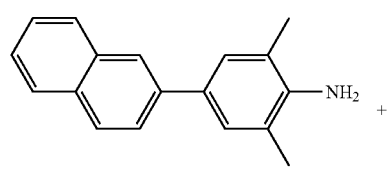

-continued

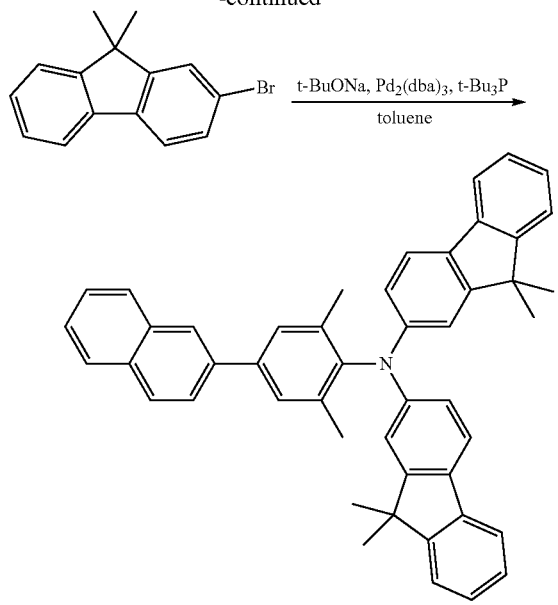

13

7.62 g of Compound 13 was obtained at a yield of 42.6% by performing the synthesis and purification in the same manner as in the preparation of Compound 1, except that Compound 13-A (7.0 g, 28.30 mmol) was used instead of Compound 1-A.

Synthesis Example 14—Preparation of Compound 14

14-A) Preparation of Intermediate 14-A

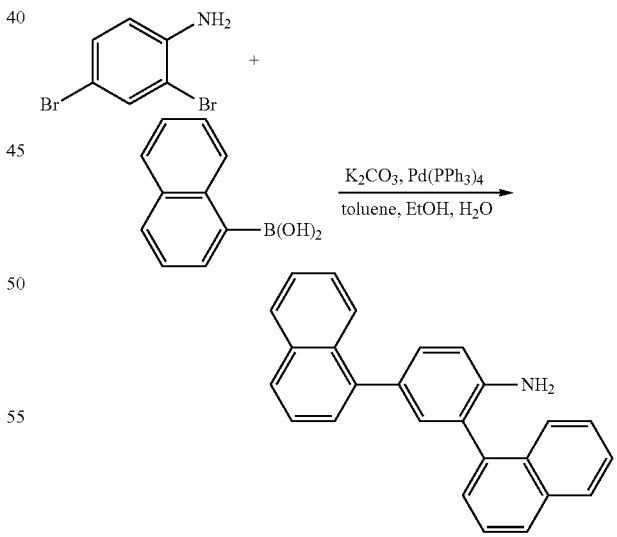

14-A 19.35 g of Compound 14-A was obtained at a yield of 70.3% by performing the synthesis and purification in the same manner as in the preparation of Compound 1-A, except that 1-naphthalene boronic acid (32.90 g, 191.30 mmol) was used instead of phenylboronic acid.

14-B) Preparation of Compound 14

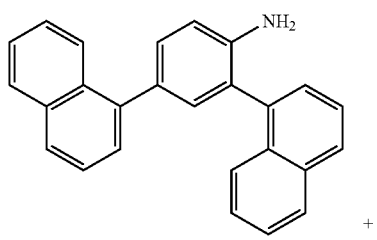

+

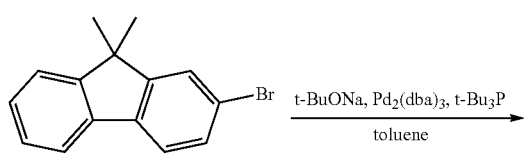

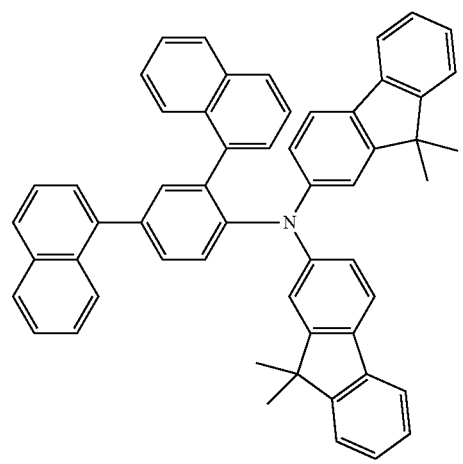

14

7.74 g of Compound 14 was obtained at a yield of 45.8% by performing the synthesis and purification in the same manner as in the preparation of Compound 1, except that Compound 14-A (8.0 g, 23.16 mmol) was used instead of Compound 1-A.

Synthesis Example 15—Preparation of Compound 15

15-A) Preparation of Intermediate 15-A

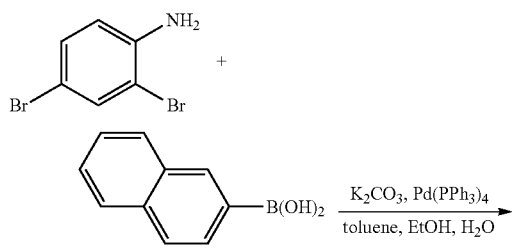

-continued

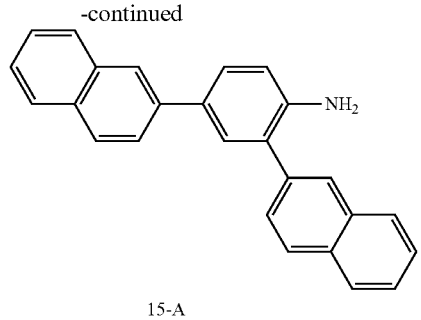

15-A 19.99 g of Compound 15-A was obtained at a yield of 72.6% by performing the synthesis and purification in the same manner as in the preparation of Compound 1-A, except that 2-naphthalene boronic acid (32.90 g, 191.30 mmol) was used instead of phenylboronic acid.

15-B) Preparation of Compound 15

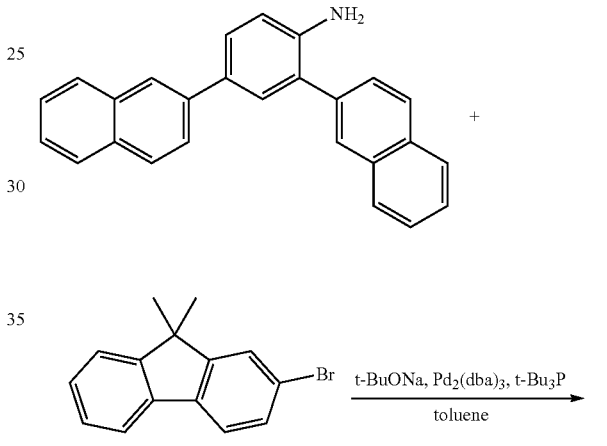

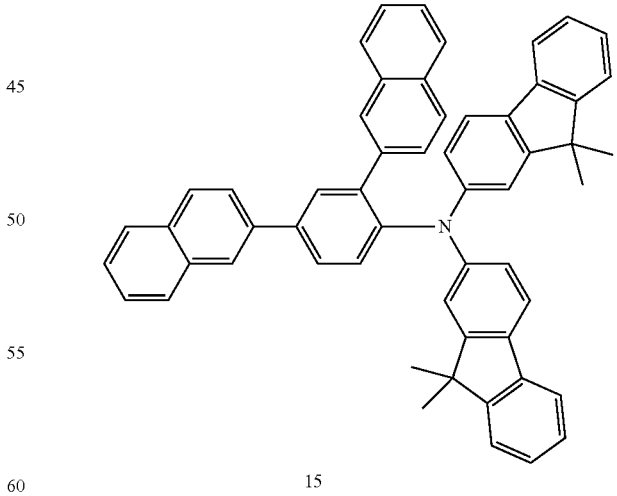

15

7.27 g of Compound 15 was obtained at a yield of 43.0% by performing the synthesis and purification in the same manner as in the preparation of Compound 1, except that Compound 15-A (8.0 g, 23.16 mmol) was used instead of Compound 1-A.

Synthesis Example 16—Preparation of Compound 16

16-A) Preparation of Intermediate 16-A

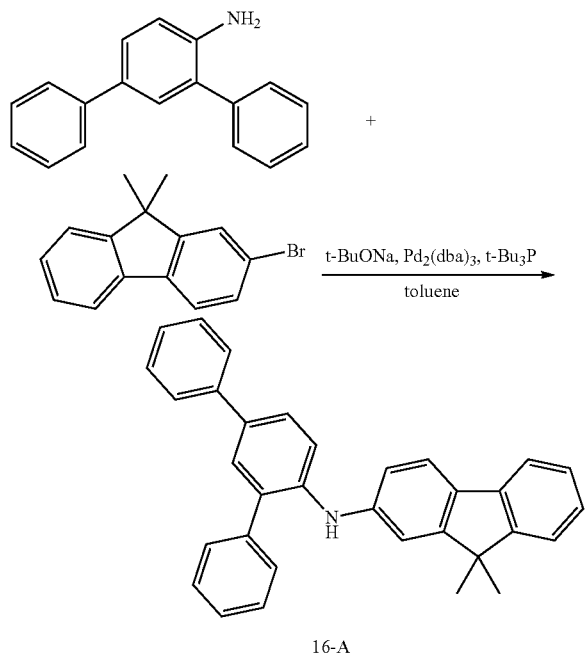

Compound 1-A (7.0 g, 28.53 mmol), 2-bromo-9,9-dimethyl-9H-fluorene (7.79 g. 28.53 mmol), sodium tert-butoxide (6.86 g, 71.33 mmol) tris(dibenzylideneacetone)dipalladium(0) (0.523 g, 0.571 mmol), a 50% tri-tert-butylphosphine solution (0.54 mL, 2.28 mmol), and 100 mL of toluene were put into a 250 mL flask under nitrogen flow, and the resulting mixture was stirred and refluxed. After the reaction was terminated, a toluene layer was extracted using 50 mL of water. The extracted solution was treated with $MgSO_4$ to remove the remaining moisture, concentrated under reduced pressure, and then purified using a column chromatography method, and recrystallized with dichloromethane/heptane to obtain 9.27 g of Compound 16-A at a yield of 74.2%.

16-B) Preparation of Compound 16

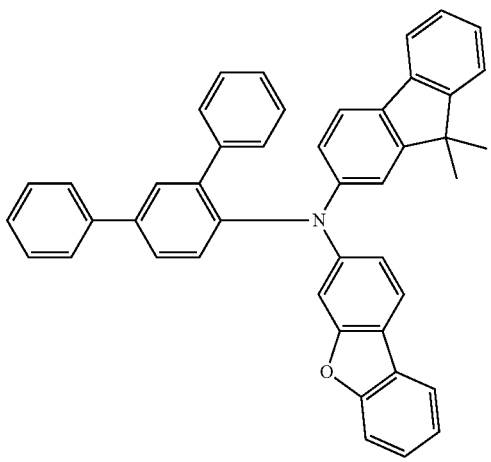

6.06 g of Compound 16 was obtained at a yield of 48.8% by performing the synthesis and purification in the same manner as in the preparation of Compound 16-A, except that Compound 16-A (9.0 g, 20.57 mmol) and 3-bromodibenzofuran (6.10 g, 24.68 mmol) were used.

Synthesis Example 17—Preparation of Compound 17

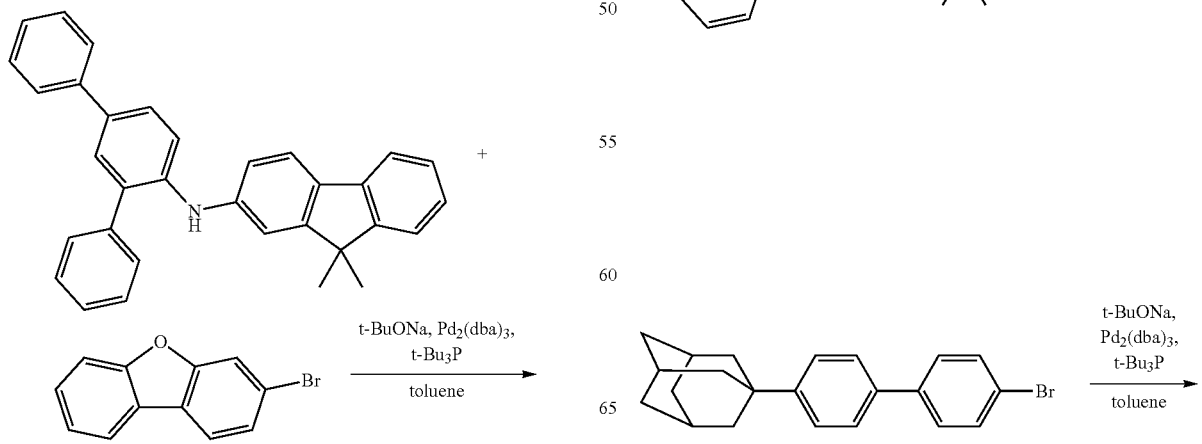

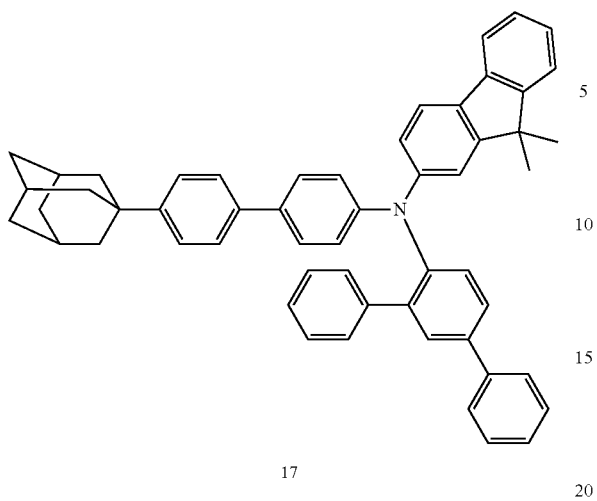

17

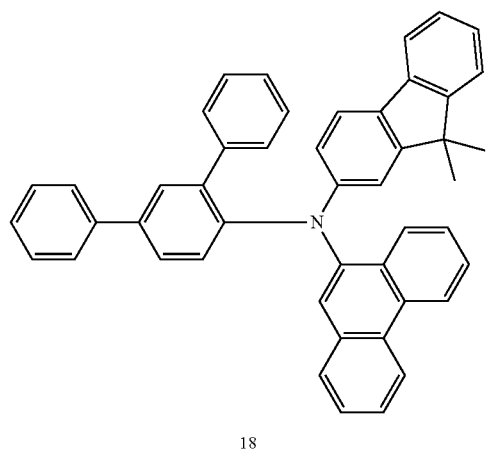

18

7.47 g of Compound 17 was obtained at a yield of 50.2% by performing the synthesis and purification in the same manner as in the preparation of Compound 16-A, except that Compound 16-A (9.0 g, 20.57 mmol) and 1-(4-bromo-[1,1'-biphenyl]-4-y)adamantane (9.07 g, 24.68 mmol) were used.

5.96 g of Compound 18 was obtained at a yield of 47.2% by performing the synthesis and purification in the same manner as in the preparation of Compound 16-A, except that Compound 16-A (9.0 g, 20.57 mmol) and 9-bromophenanthrene (6.35 g, 24.68 mmol) were used.

Synthesis Example 18—Preparation of Compound 18

Synthesis Example 19—Preparation of Compound 19

19-A) Preparation of Intermediate 19-A

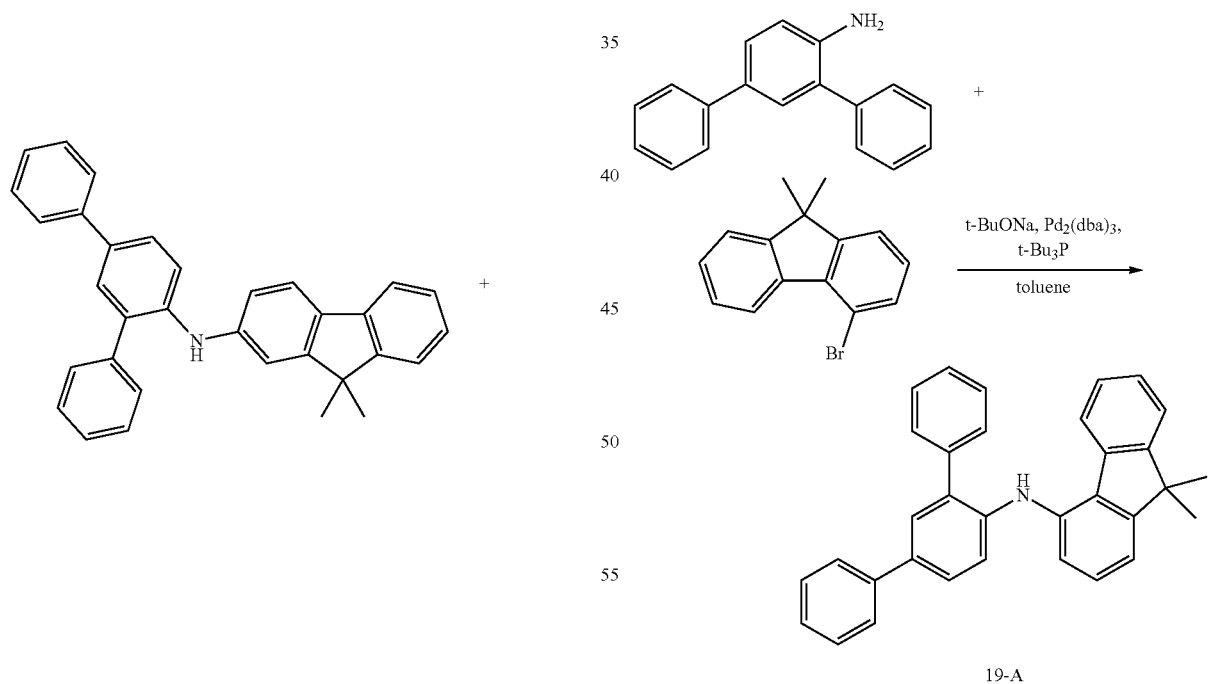

19-A

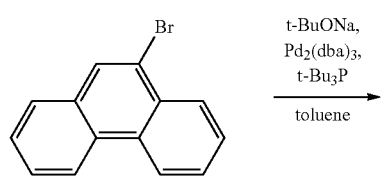

9.03 g of Compound 19-A was obtained at a yield of 72.3% by performing the synthesis and purification in the same manner as in the preparation of Compound 16-A, except that 4-bromo-9,9-dimethyl-9H-fluorene (7.34 g, 28.53 mmol) was used instead of 2-bromo-9,9-dimethyl-9H-fluorene.

19-B) Preparation of Compound 19

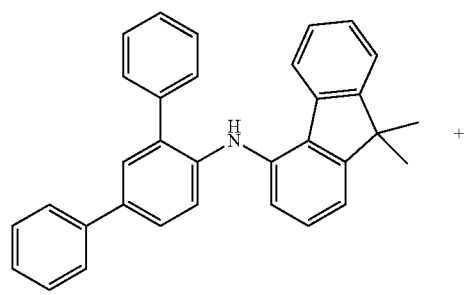

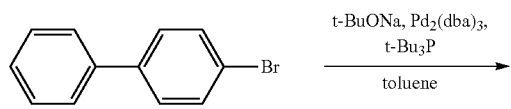

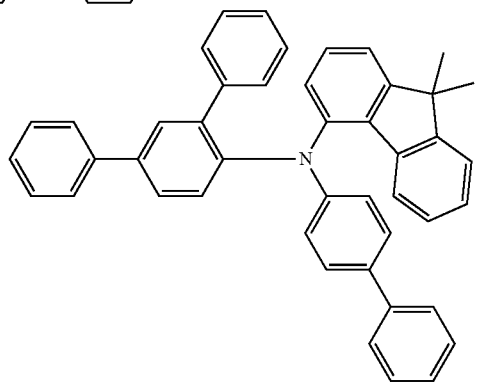

19

5.52 g of Compound 19 was obtained at a yield of 45.5% by performing the synthesis and purification in the same manner as in the preparation of Compound 16-A, except that Compound 19-A (9.0 g, 20.57 mmol) and 4-bromobiphenyl (5.75 g, 24.68 mmol) were used.

Synthesis Example 20—Preparation of Compound 20

20-A) Preparation of Intermediate 20-A

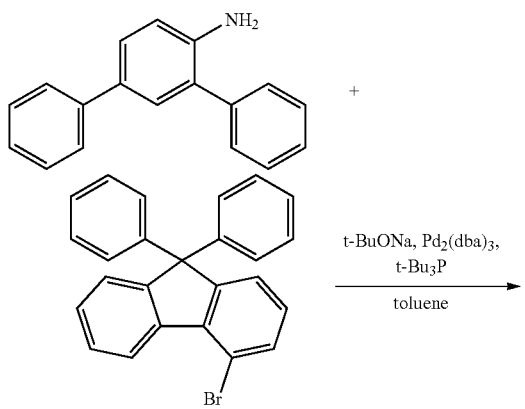

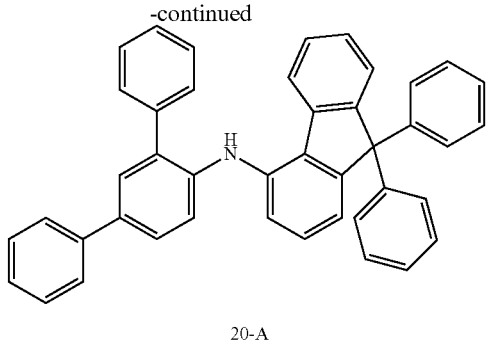

20-A 10.90 g of Compound 20-A was obtained at a yield of 68.0% by performing the synthesis and purification in the same manner as in the preparation of Compound 16-A, except that 4-bromo-9,9-diphenyl-9H-fluorene (11.34 g, 28.53 mmol) was used instead of 2-bromo-9,9-dimethyl-9H-fluorene.

20-B) Preparation of Compound 20

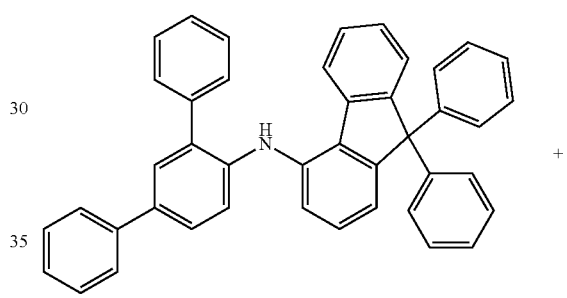

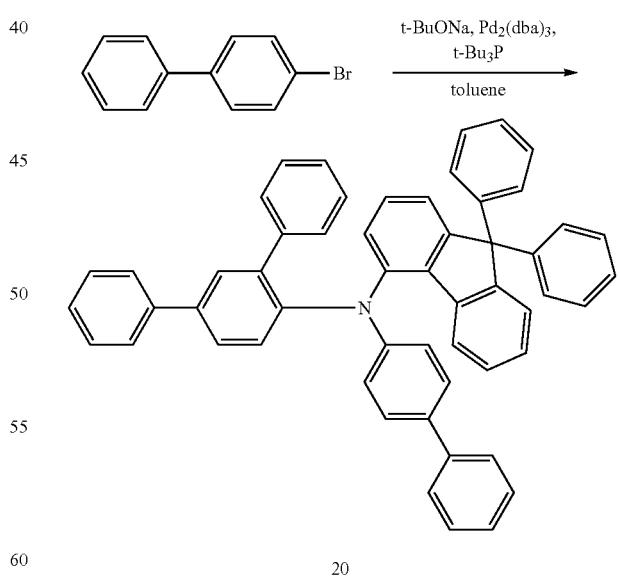

20

5.70 g of Compound 20 was obtained at a yield of 42.7% by performing the synthesis and purification in the same manner as in the preparation of Compound 16-A, except that Compound 20-A (10.5 g, 18.69 mmol) and 4-bromobiphenyl (5.23 g, 22.43 mmol) were used.

Synthesis Example 21—Preparation of Compound 21

21-A) Preparation of Intermediate 21-A

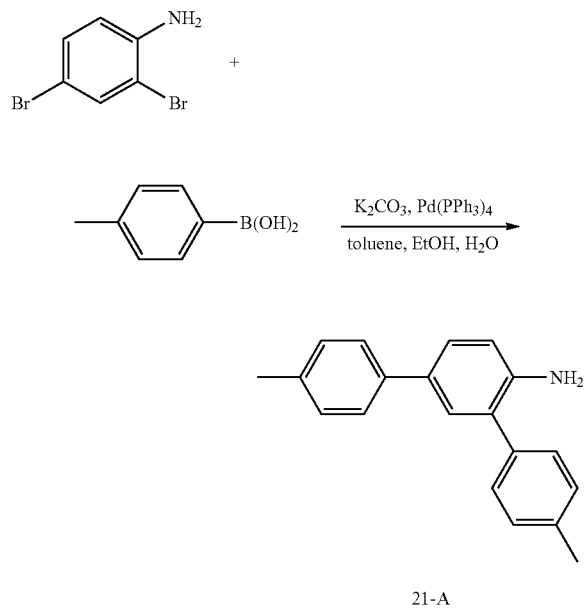

2,4-dibromoaniline (15.0 g, 59.78 mmol), 4-methylphenylboronic acid (19.51 g, 143.5 mmol), potassium carbonate (41.31 g, 298.9 mmol), tetrakis(triphenylphosphine)palladium(0) (2.76 g, 2.39 mmol), toluene (200 mL), EtOH (75 mL), and H₂O (75 mL) were put into a 1,000 mL flask under nitrogen flow, and the resulting mixture was stirred and refluxed. After the reaction was terminated, a toluene layer was extracted using toluene and water. The extracted solution was treated with MgSO₄ to remove the remaining moisture, concentrated under reduced pressure, and then purified by a column chromatography method to obtain 13.98 g of Compound 21-A at a yield of 85.6%.

21-B) Preparation of Compound 21

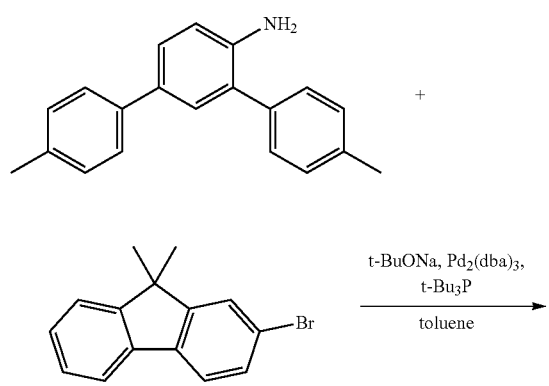

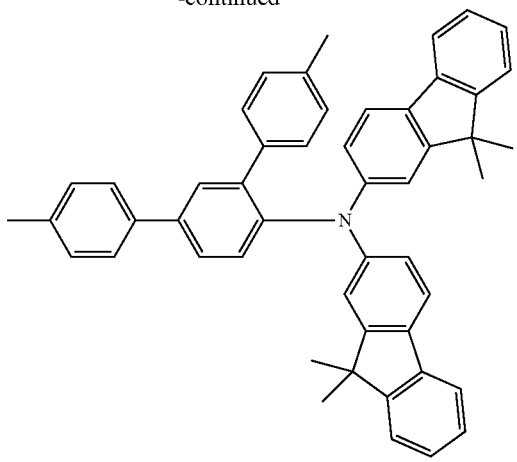

21

Compound 21-A (13.8 g, 50.05 mmol), 2-bromo-9,9-dimethyl-9H-fluorene (31.72 g, 116.1 mmol), sodium tert-butoxide (24.26 g, 252.4 mmol) tris(dibenzylideneacetone)dipalladium(0) (1.85 g, 2.02 mmol), a 50% tri-tert-butylphosphine solution (1.9 mL, 8.08 mmol), and 300 mL of toluene were put into a 500 mL flask under nitrogen flow, and the resulting mixture was stirred and refluxed. After the reaction was terminated, a toluene layer was extracted using toluene and water. The extracted solution was treated with MgSO₄ to remove the remaining moisture, concentrated under reduced pressure, and then purified using a column chromatography method, and recrystallized with dichloromethane/heptane to obtain 17.7 g of Compound 21 at a yield of 53.4%.

Synthesis Example 22—Preparation of Compound 22

22-A) Preparation of Intermediate 22-A

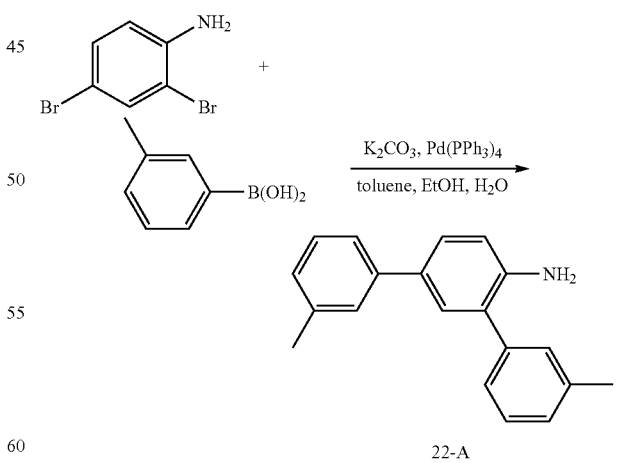

13.77 g of Compound 22-A was obtained at a yield of 84.3% by performing the synthesis and purification in the same manner as in the preparation of Compound 21-A, except that 3-methylphenylboronic acid (19.51 g, 143.5 mmol) was used instead of 4-methylphenylboronic acid.

22-B) Preparation of Compound 22

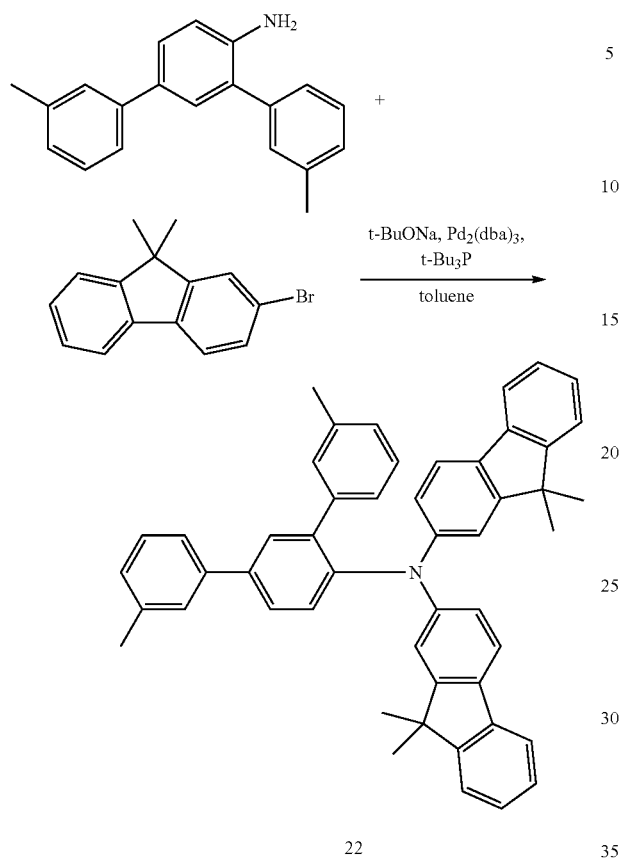

16.3 g of Compound 22 was obtained at a yield of 49.8% by performing the synthesis and purification in the same manner as in the preparation of Compound 21, except that Compound 22-A (13.6 g, 49.75 mmol) was used instead of Compound 21-A.

Synthesis Example 23—Preparation of Compound 23

3-A) Preparation of Intermediate 23-A

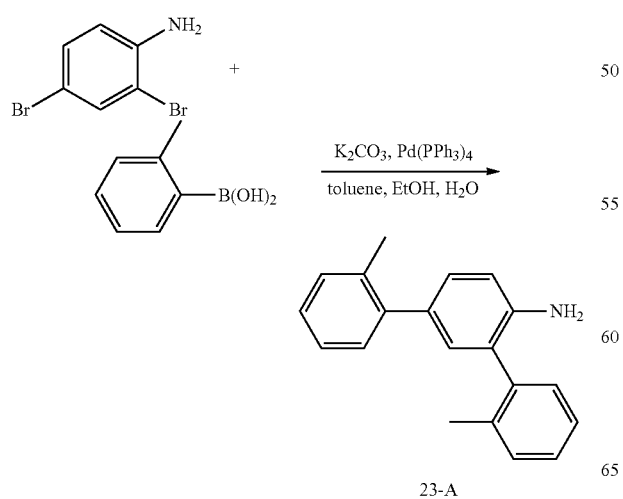

14.0 g of Compound 23-A was obtained at a yield of 85.7% by performing the synthesis and purification in the same manner as in the preparation of Compound 21-A, except that 2-methylphenylboronic acid (19.51 g, 143.5 mmol) was used instead of 4-methylphenylboronic acid.

23-B) Preparation of Compound 3

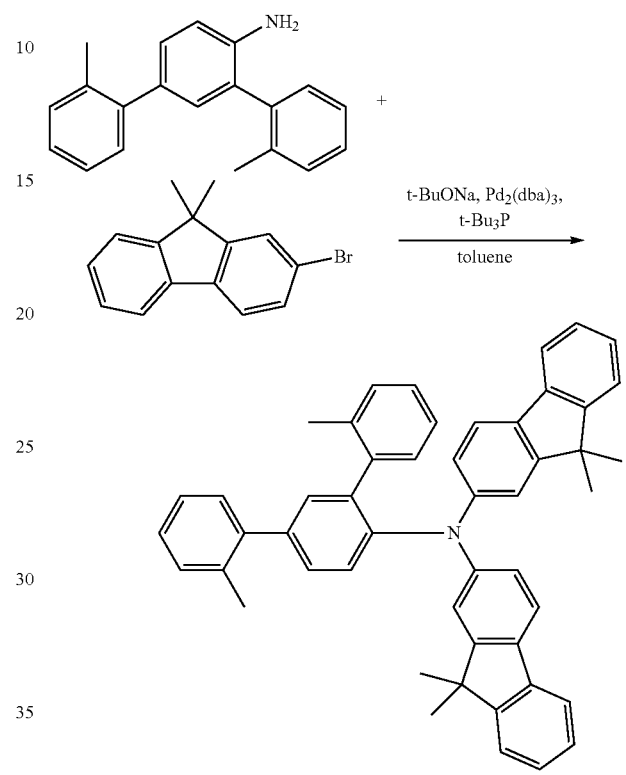

17.25 g of Compound 23 was obtained at a yield of 51.2% by performing the synthesis and purification in the same manner as in the preparation of Compound 21, except that Compound 23-A (14.0 g, 51.21 mmol) was used instead of Compound 21-A.

Synthesis Example 24—Preparation of Compound 25

24-A) Preparation of Intermediate 25-A

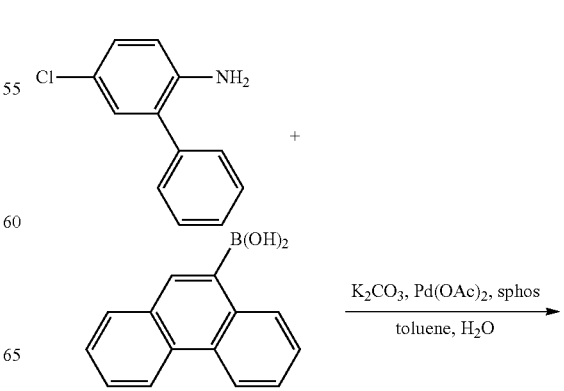

-continued

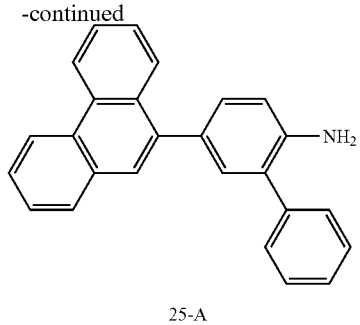

25-A 7.33 g of Compound 25-A was obtained at a yield of 72.1% by performing the synthesis and purification in the same manner as in the preparation of Compound 2-B, except that 9-phenanthreneboronic acid (7.85 g, 35.35 mmol) was used instead of 1-naphthaleneboronic acid.

24-B) Preparation of Compound 25

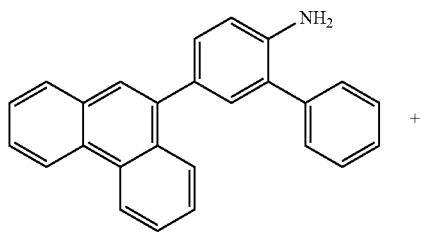 +

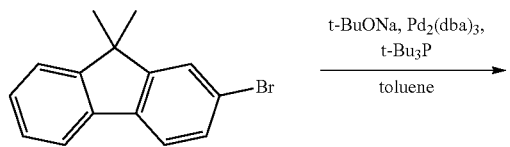

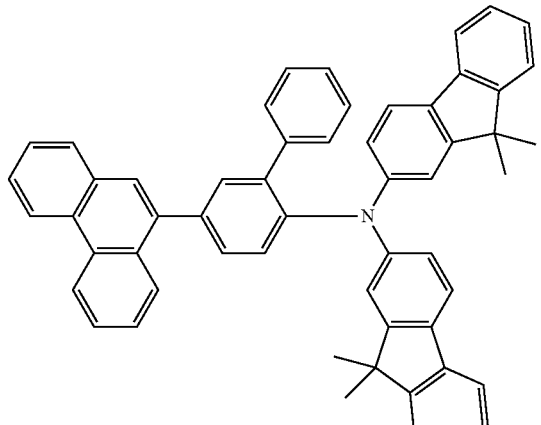

25

7.19 g of Compound 25 was obtained at a yield of 48.5% by performing the synthesis and purification in the same manner as in the preparation of Compound 21, except that Compound 25-A (7.02 g, 20.31 mmol) was used instead of Compound 21-A.

Synthesis Example 25—Preparation of Compound 26

25-A) Preparation of Intermediate 26-A

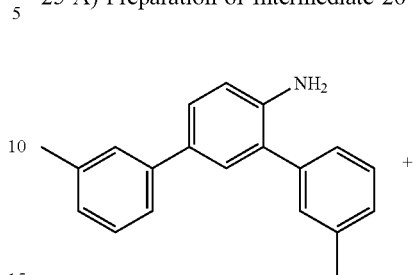 +

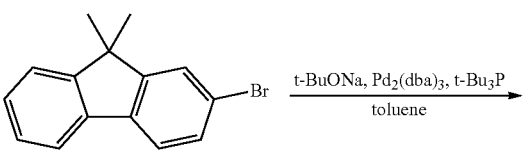

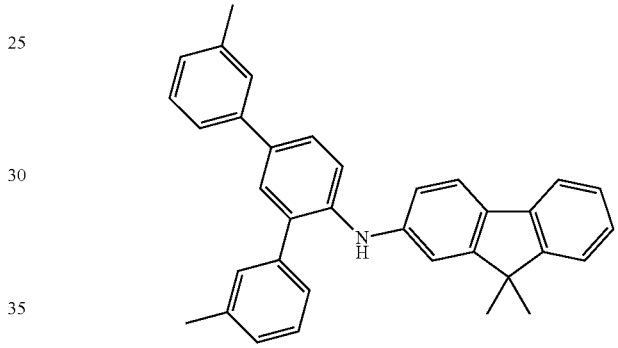

26-A 38.43 g of Compound 26-A was obtained at a yield of 75.2% by performing the synthesis and purification in the same manner as in the preparation of Compound 1-B, except that Compound 22-A (30.0 g, 109.7 mmol) was used instead of Compound 1-A.

25-B) Preparation of Compound 26

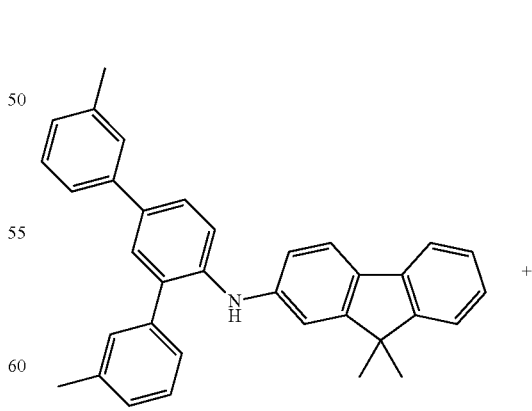 +

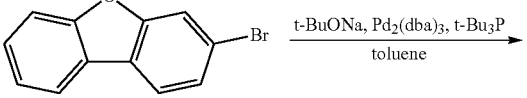

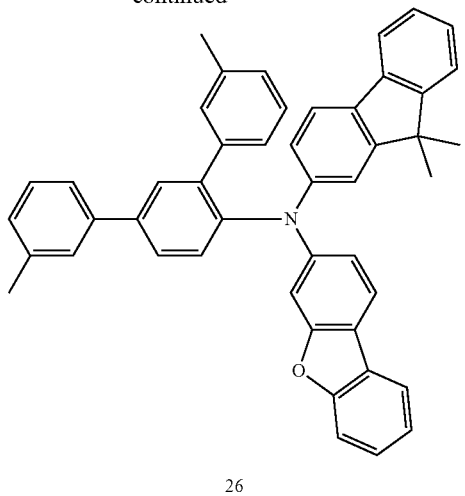

26

5.96 g of Compound 26 was obtained at a yield of 48.8% by performing the synthesis and purification in the same manner as in the preparation of Compound 1-B, except that Compound 26-A (9.0 g, 19.33 mmol) and 3-bromodibenzofuran (5.73 g, 23.19 mmol) were used.

Synthesis Example 26—Preparation of Compound 27

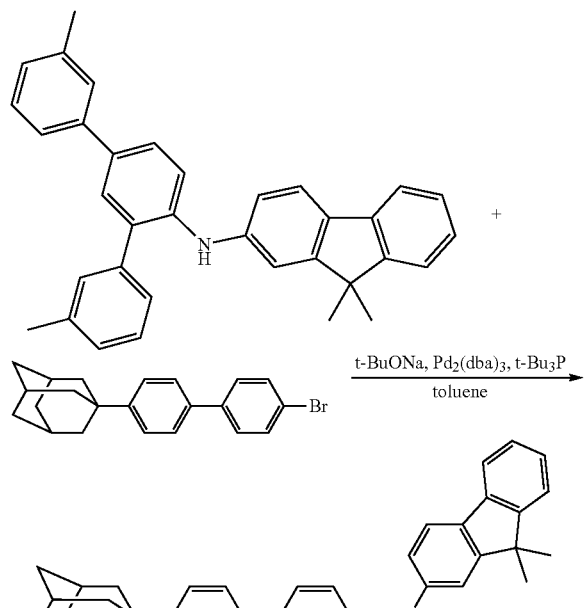

27

7.30 g of Compound 27 was obtained at a yield of 50.2% by performing the synthesis and purification in the same manner as in the preparation of Compound 15-B, except that Compound 26-A (9.0 g, 19.33 mmol) and 1-(4-bromo-[1,1'-biphenyl]-4-y)adamantane (8.52 g, 23.19 mmol) were used.

Synthesis Example 27—Preparation of Compound 28

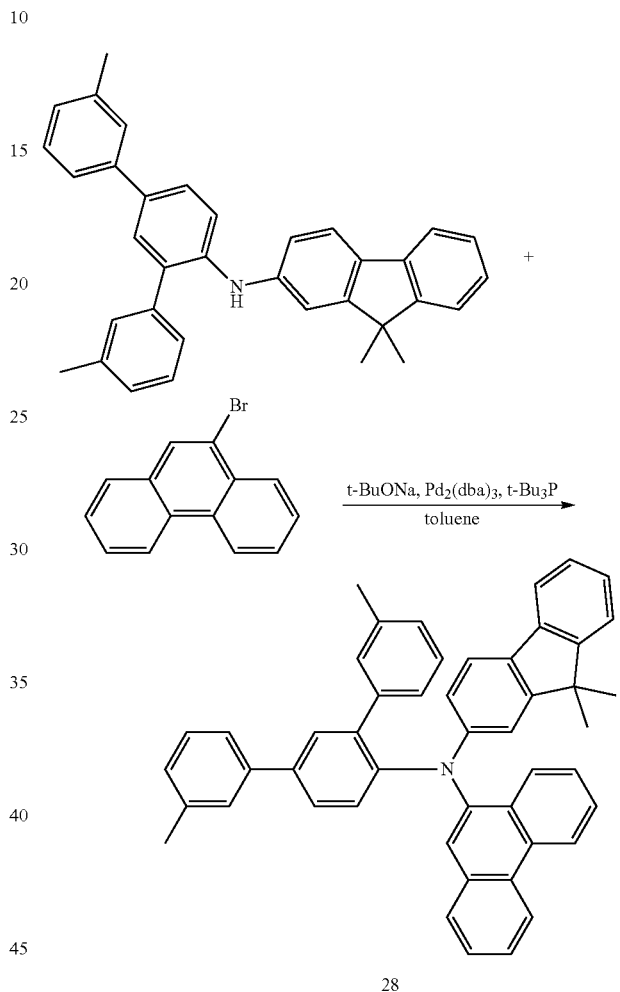

28

5.86 g of Compound 28 was obtained at a yield of 47.2% by performing the synthesis and purification in the same manner as in the preparation of Compound 1-B, except that Compound 26-A (9.0 g, 19.33 mmol) and 9-bromophenanthrene (5.96 g, 23.19 mmol) were used.

Synthesis Example 28—Preparation of Compound 29

28-A) Preparation of Intermediate 29-A

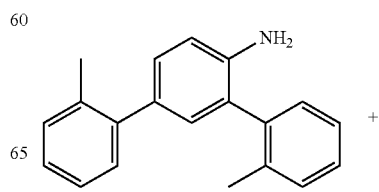

-continued

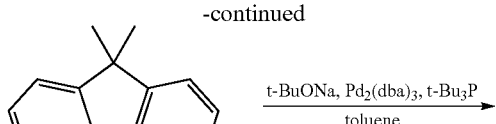

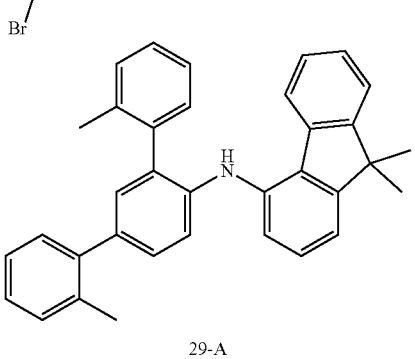

29-A 9.60 g of Compound 29-A was obtained at a yield of 72.3% by performing the synthesis and purification in the same manner as in the preparation of Compound 1-B, except that Compound 23-A (7.80 g, 28.53 mmol) and 4-bromo-9,9-dimethyl-9H-fluorene (7.79 g, 28.53 mmol) were used.

28-B) Preparation of Compound 29

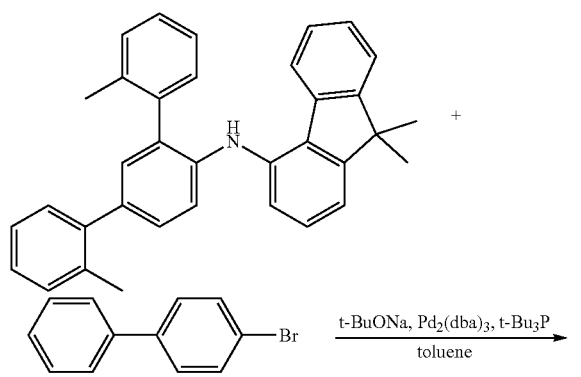

29

5.43 g of Compound 29 was obtained at a yield of 45.5% by performing the synthesis and purification in the same manner as in the preparation of Compound 1-B, except that Compound 29-A (9.0 g, 19.33 mmol) and 4-bromobiphenyl (5.41 g, 23.19 mmol) were used.

Synthesis Example 29—Preparation of Compound 30

29-A) Preparation of Intermediate 30-A

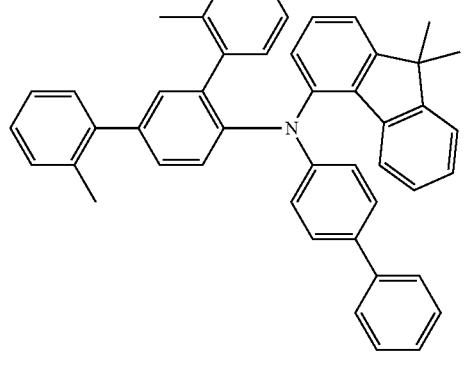

30-A 11.44 g of Compound 30-A was obtained at a yield of 68.0% by performing the synthesis and purification in the same manner as in the preparation of Compound 1-B, except that Compound 23-A (7.80 g, 28.53 mmol) and 4-bromo-9,9-diphenyl-9H-fluorene (11.34 g, 28.53 mmol) were used.

29-B) Preparation of Compound 30

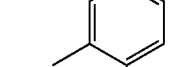
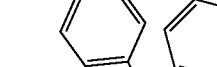
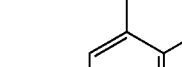

-continued

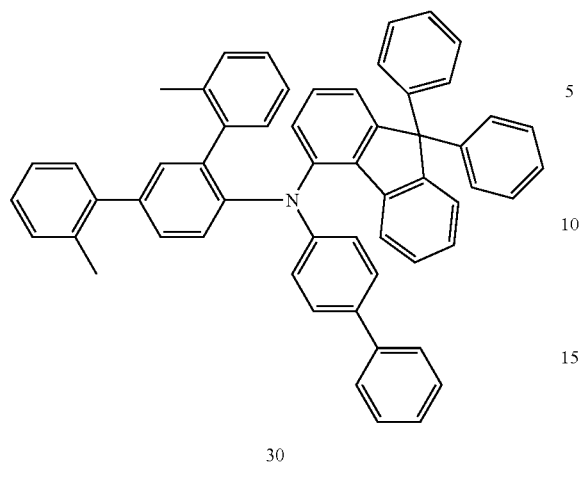

30

6.12 g of Compound 30 was obtained at a yield of 42.7% by performing the synthesis and purification in the same manner as in the preparation of Compound 1-B, except that Compound 30-A (11.4 g, 19.33 mmol) and 4-bromobiphenyl (5.41 g, 23.19 mmol) were used.

Synthesis Example 30—Preparation of Compound 31

-continued

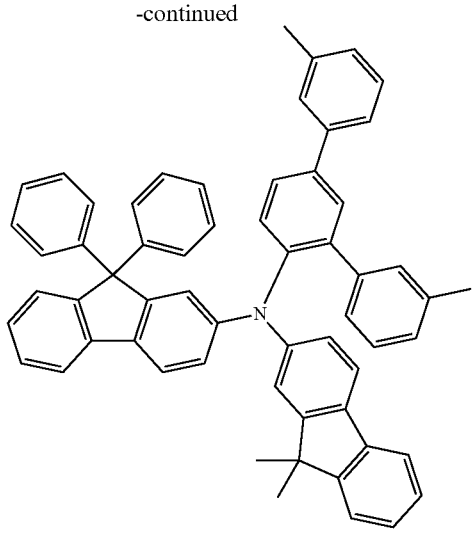

31

6.59 g of Compound 31 was obtained at a yield of 43.6% by performing the synthesis and purification in the same manner as in the preparation of Compound 1-B, except that Compound 26-A (9.0 g, 19.33 mmol) and 2-bromo-9,9-diphenyl-9H-fluorene (9.21 g, 23.19 mmol) were used.

Synthesis Example 31—Preparation of Compound 32

31-A) Preparation of Intermediate 32-A

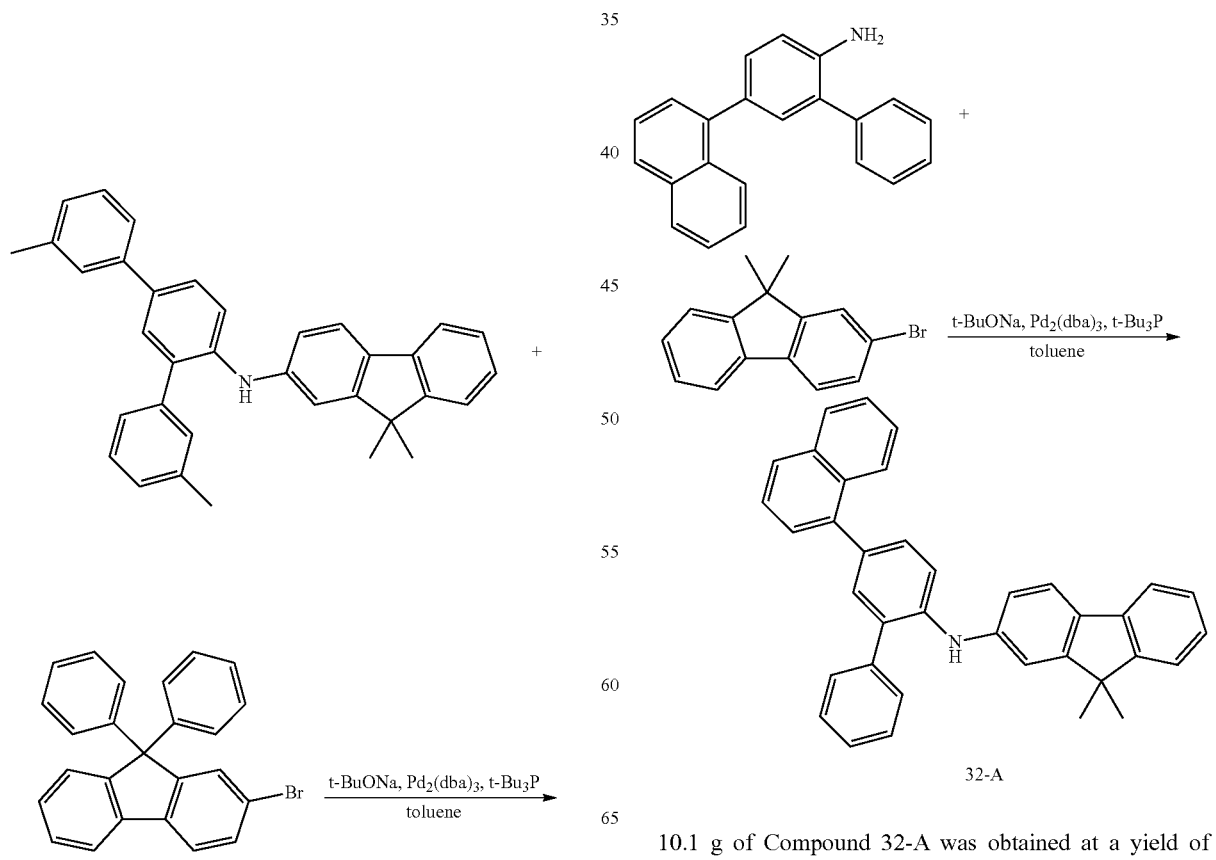

32-A 10.1 g of Compound 32-A was obtained at a yield of 76.5% by performing the synthesis and purification in the same manner as in the preparation of Compound 1-B, except that Compound 2-B (8.0 g, 27.08 mmol) was used instead of Compound 1-A.

31-B) Preparation of Compound 32

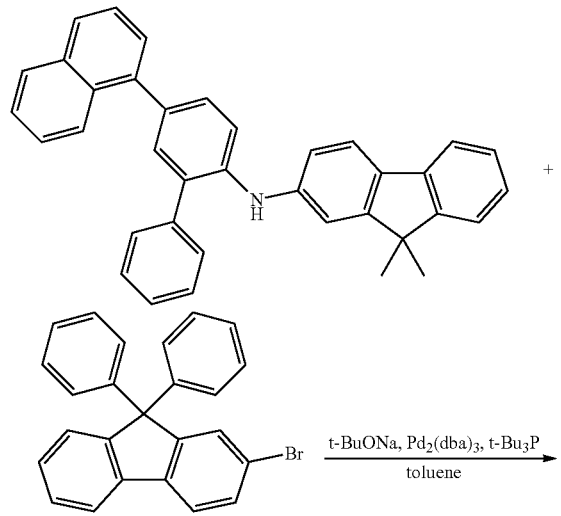

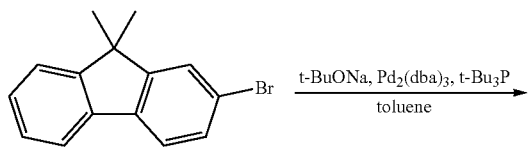

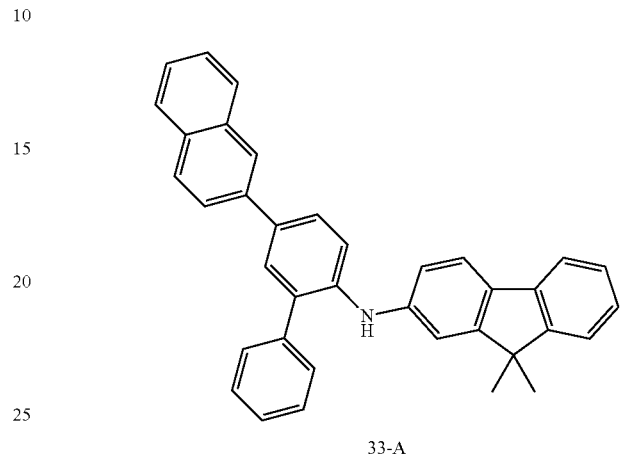

9.73 g of Compound 33-A was obtained at a yield of 73.7% by performing the synthesis and purification in the same manner as in the preparation of Compound 1-B, except that Compound 3-A (8.0 g, 27.08 mmol) was used instead of Compound 1-A.

32-B) Preparation of Compound 33

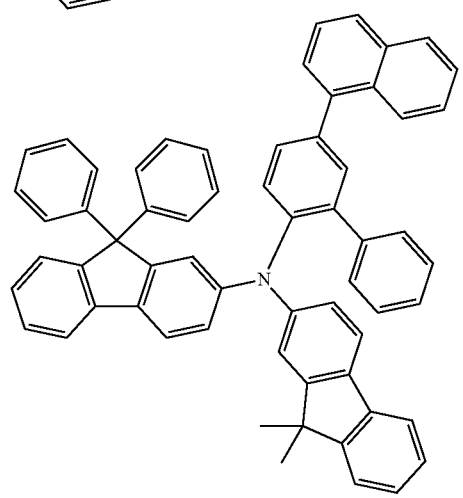

6.35 g of Compound 34 was obtained at a yield of 42.8% by performing the synthesis and purification in the same manner as in the preparation of Compound 32-B, except that Compound 32-A (9.0 g, 18.46 mmol) and 2-bromo-9,9-diphenyl-9H-fluorene (8.80 g, 22.15 mmol) were used.

Synthesis Example 32—Preparation of Compound 33

32-A) Preparation of Intermediate 33-A

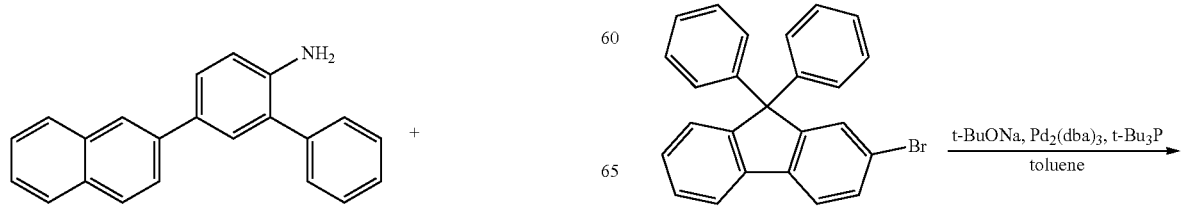

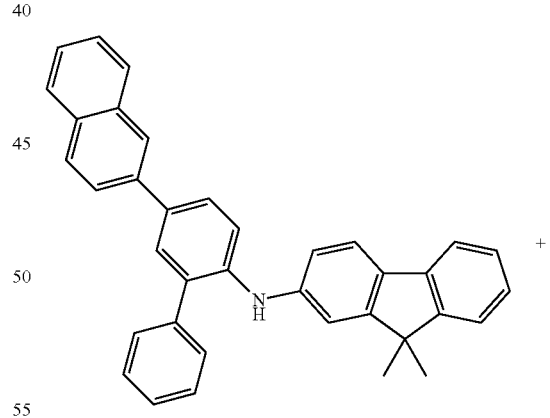

-continued

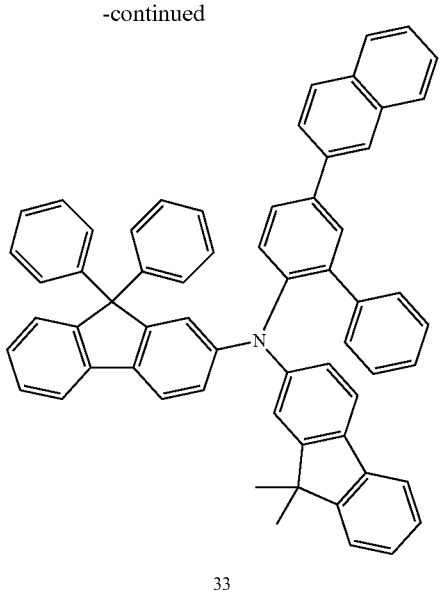

33

6.55 g of Compound 33 was obtained at a yield of 44.1% by performing the synthesis and purification in the same manner as in the preparation of Compound 1-B, except that Compound 33-A (9.0 g, 18.46 mmol) and 2-bromo-9,9-diphenyl-9H-fluorene (8.80 g, 22.15 mmol) were used.

Synthesis Example 33—Preparation of Compound 34

33-A) Preparation of Intermediate 34-A

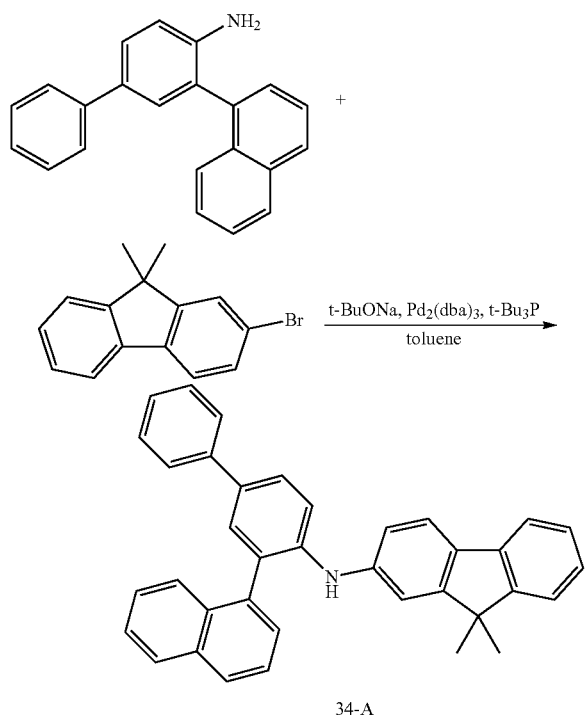

34-A 9.94 g of Compound 34-A was obtained at a yield of 75.3% by performing the synthesis and purification in the same manner as in the preparation of Compound 1-B, except that Compound 9-B (8.0 g, 27.08 mmol) was used instead of Compound 1-A.

33-B) Preparation of Compound 34

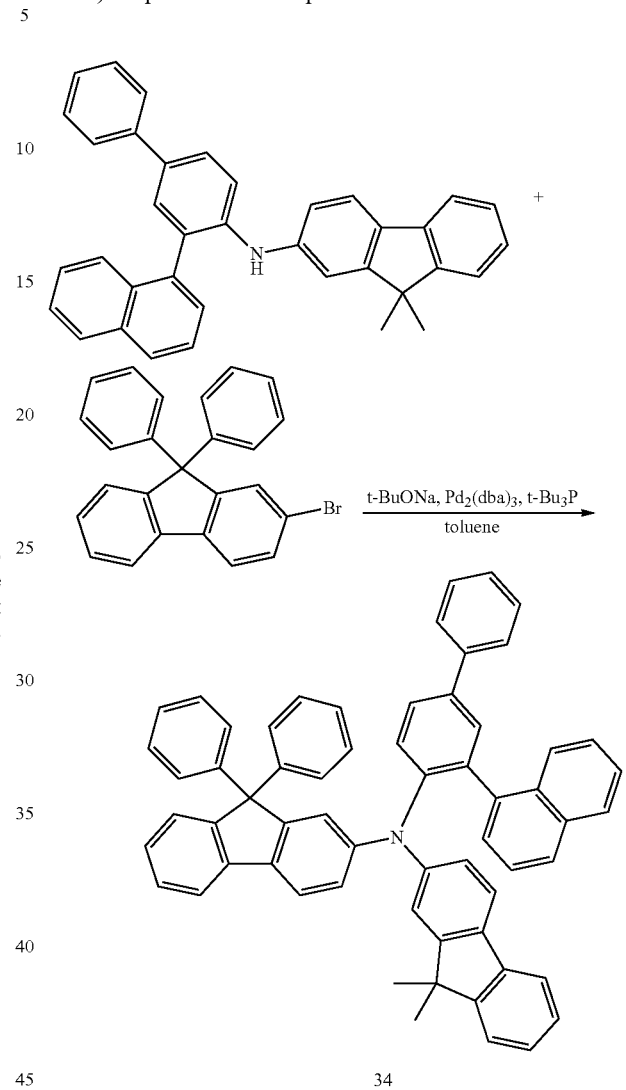

34

6.22 g of Compound 34 was obtained at a yield of 41.9% by performing the synthesis and purification in the same manner as in the preparation of Compound 1-B, except that Compound 34-A (9.0 g, 18.46 mmol) and 2-bromo-9,9-diphenyl-9H-fluorene (8.80 g, 22.15 mmol) were used.

Example 1-1: Manufacture of Organic Electroluminescent Device

A positive electrode was formed with ITO on a substrate on which a reflective layer was formed, and the positive electrode was surface-treated with $N_2$ plasma or UV-ozone. HAT-CN was deposited to have a thickness of 10 nm thereon as a hole injection layer (HIL). Subsequently, N4,N4,N4', N4'-tetra([1,1'-biphenyl]-4-yl)-[1,1'-biphenyl]-4,4'-diamine was deposited to have a thickness of 100 nm, thereby forming a hole transport layer (HTL).

A hole transport auxiliary layer was formed by vacuum-depositing Compound 1 of the present invention to have a thickness of 85 nm on the top of the hole transport layer, and while 4,4-N,N'-dicarbazole-biphenyl (CBP) was deposited to have a thickness of 35 nm as a light emitting layer (EML) on the top of the hole transport auxiliary layer, the light emitting layer was doped with about 3% of (piq)2Ir(acac) [bis-(1-phenylisoquinolyl)iridium(III)acetylacetonate] as a dopant.

An electron transport layer (ETL) was deposited to have a thickness of 30 nm thereon by mixing an anthracene derivative and LiQ at 1:1, and LiQ was deposited to have a thickness of 1 nm as an electron injection layer (EIL) thereon. Thereafter, a mixture in which magnesium and silver (Ag) were mixed at 1:4 was deposited to have a thickness of 16 nm as a negative electrode, and N4,N4'-bis [4-[bis(3-methylphenyl)amino]phenyl]-N4,N4'-diphenyl-[1,1'-biphenyl]-4,4'-diamine (DNTPD) was deposited to have a thickness of 60 nm as a capping layer on the negative electrode. An organic electroluminescent device was manufactured by laminating a seal cap containing a moisture absorbent as a UV curable adhesive thereon to protect the organic electroluminescent device from $O_2$ or moisture in the atmosphere.

Examples 1-2 to 1-19

Organic electroluminescent devices were manufactured in the same manner as in Example 1, except that in Example 1-1, Compound 2 to Compound 19 were used instead of Compound 1 as a material for a hole transport auxiliary layer.

Comparative Examples 1-1 to 1-4

Organic electroluminescent devices were manufactured in the same manner as in Example 1, except that in Example 1-1, NPB and Compound A to Compound C were used instead of Compound 1 as a material for a hole transport auxiliary layer.

[Compound A]

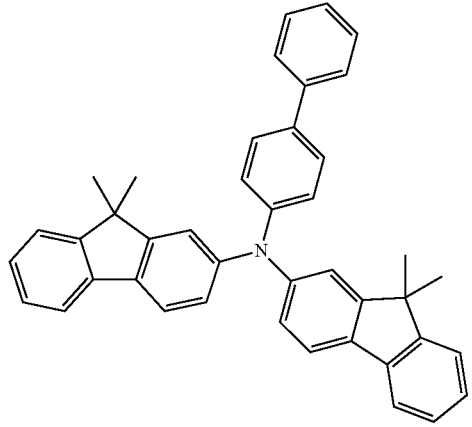

[Compound B]

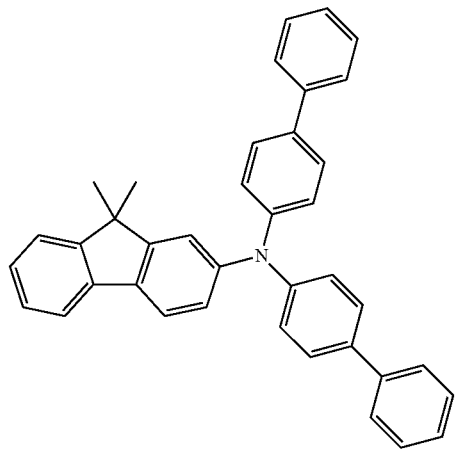

[Compound C]

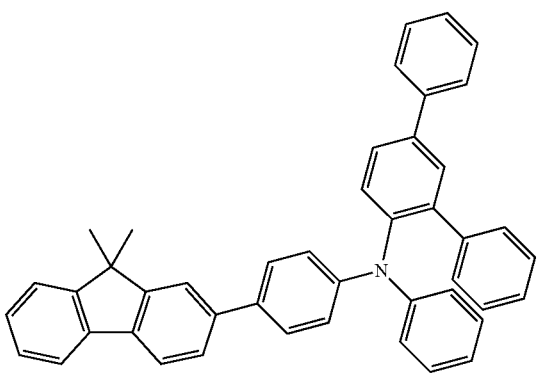

Experimental Example 1-1: Device Performance Analysis

For the organic electroluminescent devices manufactured in the Examples and the Comparative Examples, electrical optical characteristics were measured when the devices were driven at a current of 10 mA/cm$^2$ and the 95% reduced service lives were measured when the devices were driven at a constant current of 20 mA/cm$^2$, and the results there are shown in Table 1.

TABLE 1

| | Hole transport auxiliary layer | Driving voltage (V) | Efficiency | | | Color | | Service life |
| | | | Cd/A | lm/W | EQE | CIEx | CIEy | T95 (hrs) |
|---|---|---|---|---|---|---|---|---|
| Example 1-1 | Compound 1 | 4.43 | 37.4 | 26.5 | 37.1 | 0.695 | 0.305 | 205 |
| Example 1-2 | Compound 2 | 4.60 | 35.4 | 24.2 | 23.4 | 0.675 | 0.325 | 195 |
| Example 1-3 | Compound 3 | 4.35 | 35.5 | 25.6 | 23.3 | 0.673 | 0.327 | 180 |
| Example 1-4 | Compound 4 | 4.70 | 36.0 | 24.1 | 20.9 | 0.659 | 0.341 | 210 |

TABLE 1-continued

|  | Hole transport auxiliary layer | Driving voltage (V) | Efficiency | | | Color | | Service life T95 (hrs) |
| --- | --- | --- | --- | --- | --- | --- | --- | --- |
|  |  |  | Cd/A | lm/W | EQE | CIEx | CIEy |  |
| Example 1-5 | Compound 5 | 4.31 | 36.3 | 26.5 | 23.7 | 0.673 | 0.327 | 230 |
| Example 1-6 | Compound 6 | 4.27 | 38.2 | 28.1 | 25.0 | 0.673 | 0.327 | 230 |
| Example 1-7 | Compound 7 | 4.45 | 39.7 | 28.0 | 24.3 | 0.669 | 0.331 | 210 |
| Example 1-8 | Compound 8 | 4.48 | 38.2 | 26.8 | 23.2 | 0.664 | 0.336 | 240 |
| Example 1-9 | Compound 9 | 4.55 | 37.9 | 26.2 | 23.7 | 0.670 | 0.330 | 180 |
| Example 1-10 | Compound 10 | 4.51 | 35.2 | 24.5 | 21.0 | 0.666 | 0.333 | 185 |
| Example 1-11 | Compound 11 | 4.60 | 35.5 | 24.2 | 23.3 | 0.673 | 0.327 | 250 |
| Example 1-12 | Compound 12 | 4.62 | 35.7 | 24.3 | 20.9 | 0.665 | 0.335 | 260 |
| Example 1-13 | Compound 13 | 4.50 | 35.0 | 24.4 | 20.8 | 0.666 | 0.333 | 230 |
| Example 1-14 | Compound 14 | 4.73 | 31.8 | 21.1 | 25.0 | 0.670 | 0.328 | 205 |
| Example 1-15 | Compound 15 | 4.70 | 31.5 | 21.1 | 18.3 | 0.661 | 0.339 | 190 |
| Example 1-16 | Compound 16 | 4.80 | 31.9 | 20.9 | 26.0 | 0.674 | 0.325 | 170 |
| Example 1-17 | Compound 17 | 4.95 | 39.7 | 25.2 | 24.3 | 0.669 | 0.331 | 185 |
| Example 1-18 | Compound 18 | 4.70 | 34.2 | 22.9 | 19.5 | 0.661 | 0.338 | 200 |
| Example 1-19 | Compound 19 | 4.55 | 38.2 | 26.4 | 25.0 | 0.673 | 0.327 | 210 |
| Comparative Example 1-1 | NPB | 5.15 | 25.0 | 15.3 | 26.4 | 0.682 | 0.316 | 110 |
| Comparative Example 1-2 | Compound A | 4.50 | 29.9 | 20.9 | 27.2 | 0.677 | 0.321 | 130 |
| Comparative Example 1-3 | Compound B | 4.30 | 28.9 | 21.1 | 26.8 | 0.678 | 0.320 | 140 |
| Comparative Example 1-4 | Compound C | 4.35 | 27.0 | 19.5 | 18.6 | 0.663 | 0.336 | 125 |

Through Table 1, it was confirmed that when the compound according to the present invention was used as a material for a hole transport auxiliary layer, high efficiency and increases in service life were exhibited as compared to the Comparative Examples.

In particular, it was confirmed that when the Comparative Examples were compared to the Examples of the present invention, the light emitting efficiency was improved by about 8% to 47%, and the service lives were increased up to 2.3 folds.

Example 2-1: Manufacture of Organic Electroluminescent Device

A positive electrode was formed with ITO on a substrate on which a reflective layer was formed, and the positive electrode was surface-treated with $N_2$ plasma or UV-ozone. HAT-CN was deposited to have a thickness of 10 nm thereon as a hole injection layer (HIL). Subsequently, N4,N4,N4', N4'-tetra([1,1'-biphenyl]-4-yl)-[1,1'-biphenyl]-4,4'-diamine was deposited to have a thickness of 110 nm, thereby forming a hole transport layer (HTL).

A hole transport auxiliary layer was formed by vacuum-depositing Compound 1 of the present invention to have a thickness of 40 nm on the top of the hole transport layer, and while 4,4'-N,N'-dicarbazole-biphenyl (CBP) was deposited to have a thickness of 35 nm as a light emitting layer (EML) on the top of the hole transport auxiliary layer, the light emitting layer was doped with about 5% of Ir(ppy)3 [tris (2-phenylpyridine)-iridium] as a dopant.

An electron transport layer (ETL) was deposited to have a thickness of 30 nm thereon by mixing an anthracene derivative and LiQ at 1:1, and LiQ was deposited to have a thickness of 1 nm as an electron injection layer (EIL) thereon. Thereafter, a mixture in which magnesium and silver (Ag) were mixed at 1:4 was deposited to have a thickness of 16 nm as a negative electrode, and N4,N4'-bis [4-[bis(3-methylphenyl)amino]phenyl]-N4,N4'-diphenyl-[1,1'-biphenyl]-4,4'-diamine (DNTPD) was deposited to have a thickness of 60 nm as a capping layer on the negative electrode. An organic electroluminescent device was manufactured by laminating a seal cap containing a moisture absorbent as a UV curable adhesive thereon to protect the organic electroluminescent device from $O_2$ or moisture in the atmosphere.

Examples 2-2 to 2-5

Organic electroluminescent devices were manufactured in the same manner as in Example 2-1, except that in Example 2-1, Compound 3, Compound 10, Compound 16, and Compound 17 were used instead of Compound 1 as a material for a hole transport auxiliary layer.

Comparative Examples 2-1 to 2-3

Organic electroluminescent devices were manufactured in the same manner as in Example 1, except that in Example 2-1, NPB, Compound A, and Compound B were used instead of Compound 1 as a material for a hole transport auxiliary layer.

Experimental Example 2-1: Device Performance Analysis

For the organic electroluminescent devices manufactured in the Examples and the Comparative Examples, electrical optical characteristics were measured when the devices were driven at a current of 10 mA/cm$^2$, the 95% reduced service lives were measured when the devices were driven at a constant current of 20 mA/cm$^2$, and the results are shown in Table 2.

TABLE 2

| | Hole transport auxiliary layer | Driving voltage (V) | Efficiency | | | Color | | Service life |
|---|---|---|---|---|---|---|---|---|
| | | | Cd/A | lm/W | EQE | CIEx | CIEy | T95 (hrs) |
| Example 2-1 | Compound 1 | 4.04 | 100.5 | 78.2 | 25.5 | 0.209 | 0.725 | 180 |
| Example 2-2 | Compound 3 | 3.95 | 98.1 | 78.0 | 25.2 | 0.206 | 0.725 | 150 |
| Example 2-3 | Compound 10 | 4.10 | 98.2 | 75.3 | 25.0 | 0.209 | 0.724 | 100 |
| Example 2-4 | Compound 16 | 4.17 | 89.4 | 67.4 | 21.8 | 0.218 | 0.730 | 160 |
| Example 2-5 | Compound 17 | 4.24 | 93.6 | 69.4 | 22.9 | 0.218 | 0.730 | 140 |
| Comparative Example 2-1 | NPB | 4.50 | 71.2 | 49.7 | 19.7 | 0.201 | 0.738 | 55 |
| Comparative Example 2-2 | Compound A | 3.95 | 78.8 | 62.7 | 20.7 | 0.223 | 0.727 | 70 |
| Comparative Example 2-3 | Compound B | 4.04 | 80.6 | 62.7 | 21.3 | 0.227 | 0.724 | 80 |

Through Table 2, it was confirmed that when the compound according to the present invention was used as a material for a hole transport auxiliary layer, high efficiency and increases in service life were exhibited as compared to the Comparative Examples.

In particular, it was confirmed that when the Comparative Examples were compared to the Examples of the present invention, the light emitting efficiency was improved by about 11% to 41%, and the service lives were increased up to 2.3 folds.

Example 3-1: Manufacture of Organic Electroluminescent Device

A positive electrode was formed with ITO on a substrate on which a reflective layer was formed, and the positive electrode was surface-treated with $N_2$ plasma or UV-ozone. HAT-CN was deposited to have a thickness of 10 nm thereon as a hole injection layer (HIL). Subsequently, N4,N4,N4',N4'-tetra([1,1'-biphenyl]-4-yl)-[1,1'-biphenyl]-4,4'-diamine was deposited to have a thickness of 110 nm, thereby forming a hole transport layer (HTL).

A hole transport auxiliary layer was formed by vacuum-depositing Compound 16 to have a thickness of 15 nm on the top of the hole transport layer, and while 9,10-bis(2-naphthyl)anthraces (ADN) capable of forming a blue EML was deposited to have a thickness of 25 nm as a light emitting layer (EML) on the top of the hole transport auxiliary layer, the light emitting layer was doped with about 3 wt % of 2,5,8,11-tetra-butyl-perylene (t-Bu-Perylene) as a dopant.

An electron transport layer (ETL) was deposited to have a thickness of 30 nm thereon by mixing an anthracene derivative and LiQ at 1:1, and LiQ was deposited to have a thickness of 1 nm as an electron injection layer (EIL) thereon. Thereafter, a mixture in which magnesium and silver (Ag) were mixed at 9:1 was deposited to have a thickness of 15 nm as a negative electrode, and N4,N4'-bis[4-[bis(3-methylphenyl)amino]phenyl]-N4,N4'-diphenyl-[1,1'-biphenyl]-4,4'-diamine (DNTPD) was deposited to have a thickness of 60 nm as a capping layer on the negative electrode. An organic electroluminescent device was manufactured by laminating a seal cap containing a moisture absorbent as a UV curable adhesive thereon to protect the organic electroluminescent device from $O_2$ or moisture in the atmosphere.

Examples 3-2 to 3-5

Organic electroluminescent devices were manufactured in the same manner as in Example 1, except that in Example 3-1, Compound 17 to Compound 20 were used instead of Compound 1 as a material for a hole transport auxiliary layer.

Comparative Examples 2-1 to 2-3

Organic electroluminescent devices were manufactured in the same manner as in Example 3-1, except that in Example 1, NPB, Compound B, and Compound C were used instead of Compound 1 as a material for a hole transport auxiliary layer.

Experimental Example 3-1: Device Performance Analysis

For the organic electroluminescent devices manufactured in the Examples and the Comparative Examples, electrical optical characteristics were analyzed under the condition of a constant current of 10 mA/cm², the service lives were measured under a driving condition of 20 mA/cm², and the results thereof are shown in the following Table 3.

TABLE 3

| | Hole transport auxiliary layer | Driving voltage (V) | Efficiency | | | Color | | Service life |
|---|---|---|---|---|---|---|---|---|
| | | | Cd/A | lm/AV | EQE | CIEx | CIEy | T95 (hrs) |
| Example 3-1 | Compound 16 | 3.94 | 5.0 | 4.0 | 10.0 | 0.138 | 0.049 | 160 |
| Example 3-2 | Compound 17 | 4.00 | 5.3 | 4.2 | 10.7 | 0.138 | 0.049 | 145 |
| Example 3-3 | Compound 18 | 3.96 | 5.2 | 4.1 | 10.1 | 0.137 | 0.051 | 170 |
| Example 3-4 | Compound 19 | 3.96 | 5.5 | 4.4 | 10.7 | 0.137 | 0.050 | 150 |
| Example 3-5 | Compound 20 | 3.80 | 5.0 | 1.6 | 10.0 | 0.138 | 0.049 | 180 |
| Comparative Example 3-1 | NPB | 4.60 | 4.0 | 2.7 | 6.4 | 0.132 | 0.061 | 90 |

TABLE 3-continued

|  | Hole transport auxiliary layer | Driving voltage (V) | Efficiency | | | Color | | Service life |
| --- | --- | --- | --- | --- | --- | --- | --- | --- |
|  |  |  | Cd/A | lm/AV | EQE | CIEx | CIEy | T95 (hrs) |
| Comparative Example 3-2 | Compound B | 4.46 | 4.1 | 2.9 | 8.3 | 0.138 | 0.048 | 110 |
| Comparative Example 3-3 | Compound C | 4.30 | 4.3 | 3.1 | 8.4 | 0.137 | 0.051 | 105 |

Through Table 3, it was confirmed that when the compound according to the present invention was used as a material for a hole transport auxiliary layer, decreases in driving voltage, high efficiency, and increases in service life were exhibited as compared to the Comparative Examples.

In particular, it was confirmed that when the Comparative Examples were compared to the Examples of the present invention, the driving voltage was decreased by 0.3 to 0.8 eV, the light emitting efficiency was improved by about 16% to 38%, and the service lives were increased up to 2 folds.

Example 4-1: Manufacture of Organic Electroluminescent Device

A positive electrode was formed with ITO on a substrate on which a reflective layer was formed, and the positive electrode was surface-treated with $N_2$ plasma or UV-ozone. HAT-CN was deposited to have a thickness of 10 nm thereon as a hole injection layer (HIL). Subsequently, Compound 2 was deposited to have a thickness of 110 nm, thereby forming a hole transport layer (HTL).

A hole transport auxiliary layer was formed by vacuum-depositing Compound D to have a thickness of 40 nm on the top of the hole transport layer, and while 4,4'-N,N'-dicarbazole-biphenyl (CBP) was deposited to have a thickness of 35 nm as a light emitting layer (EML) on the top of the hole transport auxiliary layer, the light emitting layer was doped with about 5% of Ir(ppy)3 [tris(2-phenylpyridine)-iridium] as a dopant.

An electron transport layer (ETL) was deposited to have a thickness of 30 nm thereon by mixing an anthracene derivative and LiQ at 1:1, and LiQ was deposited to have a thickness of 1 nm as an electron injection layer (EIL) thereon. Thereafter, a mixture obtained by mixing magnesium and silver (Ag) at 1:4 was deposited to have a thickness of 16 nm as a negative electrode, and N4,N4'-bis[4-[bis(3-methylphenyl)amino]phenyl]-N4,N4'-diphenyl-[1,1'-biphenyl]-4,4'-diamine (DNTPD) was deposited to have a thickness of 60 nm as a capping layer on the negative electrode. An organic electroluminescent device was manufactured by laminating a seal cap containing a moisture absorbent as a UV curable adhesive thereon to protect the organic electroluminescent device from $O_2$ or moisture in the atmosphere.

[Compound D]

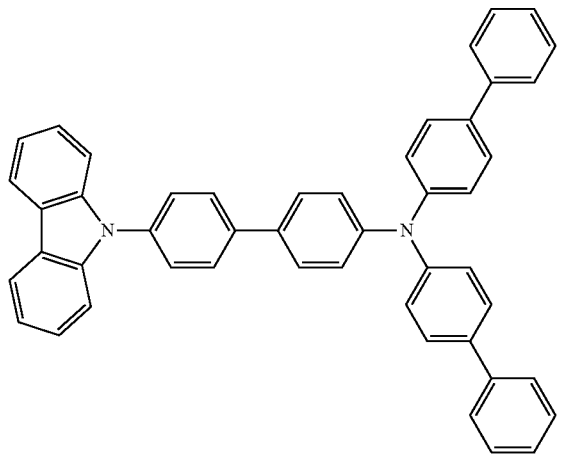

Examples 4-2 to 4-4

Organic electroluminescent devices were manufactured in the same manner as in Example 1, except that as the hole transport layer, Compounds 2 to 5, Compound 9, Compound 10, Compounds 12 to 14, Compounds 21 to 23, Compounds 25 to 28, and Compounds 31 to 34 were used instead of Compound 2 in Example 4-1.

TABLE 4

|  | Hole transport layer | Driving voltage (V) | Efficiency | | | Color | | Service life |
| --- | --- | --- | --- | --- | --- | --- | --- | --- |
|  |  |  | Cd/A | lm/W | EQE | CIEx | CIEy | T95(hrs) |
| Example 4-1 | Compound 2 | 3.87 | 5.8 | 7.1 | 13.6 | 0.137 | 0.052 | 160 |
| Example 4-2 | Compound 3 | 3.82 | 5.1 | 6.3 | 12.2 | 0.138 | 0.051 | 235 |
| Example 4-3 | Compound 4 | 3.75 | 5.8 | 4.9 | 11.6 | 0.14 | 0.049 | 146 |
| Example 4-4 | Compound 5 | 3.98 | 5.0 | 6.3 | 13 | 0.14 | 0.047 | 360 |
| Example 4-5 | Compound 9 | 3.9 | 6.2 | 7.6 | 13.8 | 0.135 | 0.057 | 150 |
| Example 4-6 | Compound 10 | 3.94 | 5.4 | 6.7 | 12.6 | 0.136 | 0.054 | 250 |
| Example 4-7 | Compound 12 | 3.78 | 5.8 | 4.8 | 11.6 | 0.141 | 0.049 | 166 |
| Example 4-8 | Compound 13 | 3.77 | 7.5 | 6.2 | 14.1 | 0.136 | 0.053 | 200 |
| Example 4-9 | Compound 14 | 4.17 | 4.3 | 5.7 | 12.8 | 0.143 | 0.041 | 180 |
| Example 4-10 | Compound 21 | 4.19 | 5.4 | 7.2 | 13.9 | 0.138 | 0.047 | 130 |
| Example 4-11 | Compound 22 | 3.85 | 5.9 | 7.3 | 14.3 | 0.138 | 0.05 | 300 |
| Example 4-12 | Compound 23 | 3.95 | 6.0 | 7.5 | 14 | 0.136 | 0.054 | 250 |
| Example 4-13 | Compound 25 | 3.75 | 5.6 | 6.7 | 12.1 | 0.135 | 0.057 | 180 |
| Example 4-14 | Compound 26 | 3.8 | 4.4 | 5.4 | 11.8 | 0.142 | 0.042 | 160 |

TABLE 4-continued

| | Hole transport layer | Driving voltage (V) | Efficiency | | | Color | | Service life |
| --- | --- | --- | --- | --- | --- | --- | --- | --- |
| | | | Cd/A | lm/W | EQE | CIEx | CIEy | T95(hrs) |
| Example 4-15 | Compound 27 | 4.11 | 5.4 | 7.1 | 13 | 0.135 | 0.056 | 200 |
| Example 4-16 | Compound 28 | 3.78 | 5.8 | 4.8 | 11.9 | 0.142 | 0.047 | 220 |
| Example 4-17 | Compound 31 | 4.29 | 4.9 | 6.7 | 13.34 | 0.139 | 0.049 | 160 |
| Example 4-18 | Compound 32 | 3.95 | 6 | 7.5 | 14 | 0.136 | 0.054 | 150 |
| Example 4-19 | Compound 33 | 3.88 | 5.9 | 7.2 | 14 | 0.137 | 0.051 | 210 |
| Example 4-20 | Compound 34 | 4.28 | 4.73 | 6.44 | 13.09 | 0.139 | 0.048 | 180 |
| Comparative Example 1-2 | Compound A | 4.04 | 3.5 | 4.5 | 451 | 0.136 | 0.051 | 60 |
| Comparative Example 1-3 | Compound B | 4.23 | 3.4 | 4.5 | 452 | 0.139 | 0.046 | 80 |
| Comparative Example 1-4 | Compound C | 4.26 | 3 | 4.1 | 413 | 0.137 | 0.05 | 75 |

Through Table 4, it was confirmed that when the compound according to the present invention was used as a material for a hole transport layer, decreases in driving voltage, high efficiency, and increases in service life were exhibited as compared to the Comparative Examples.

While preferred embodiments of the present invention have been described in detail hereinabove, it is to be understood that the scope of the present invention is not limited thereto, and various modifications and improvements made by those skilled in the art using basic concepts of the present invention, which are defined in the following claims also fall within the scope of the present invention.

What is claimed is:

1. A compound selected from any one of the following compounds:

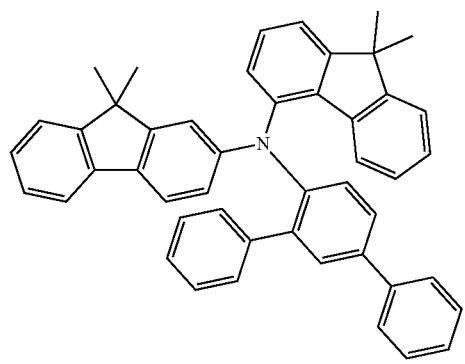

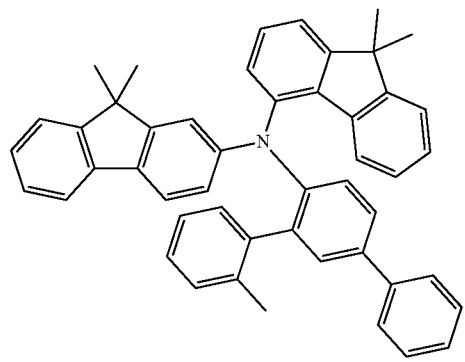

-continued

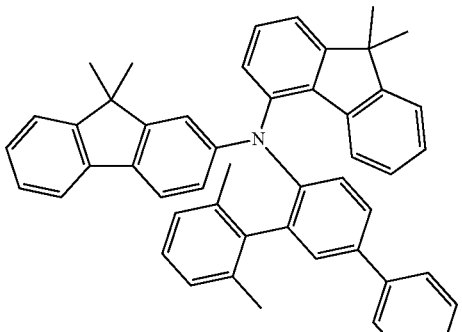

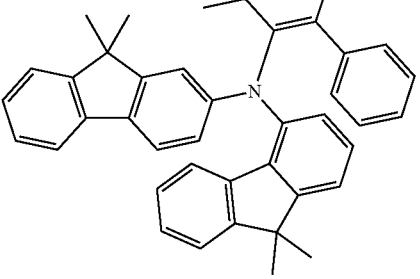

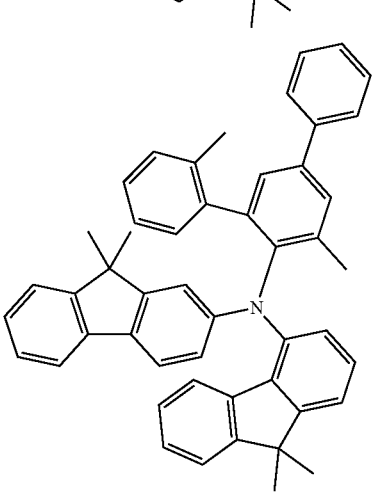

183
-continued
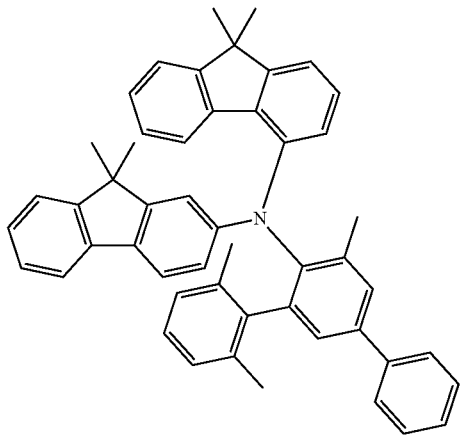
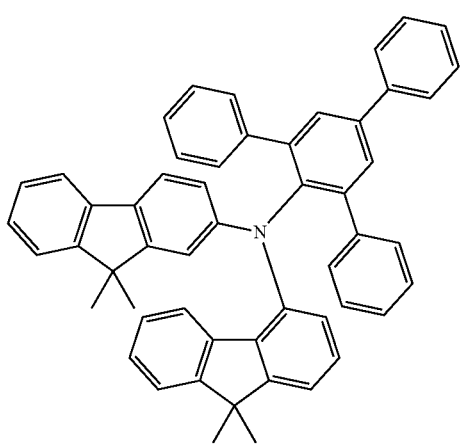
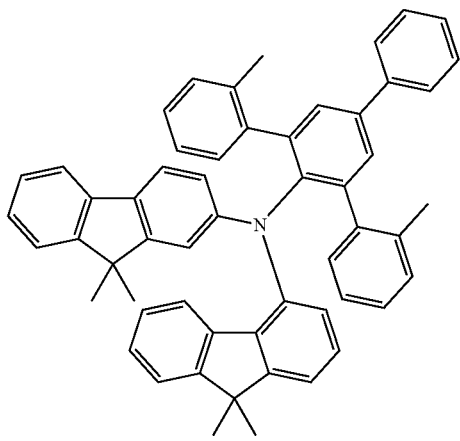
184
-continued
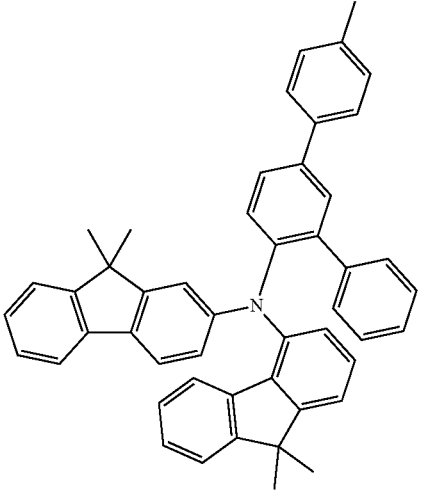
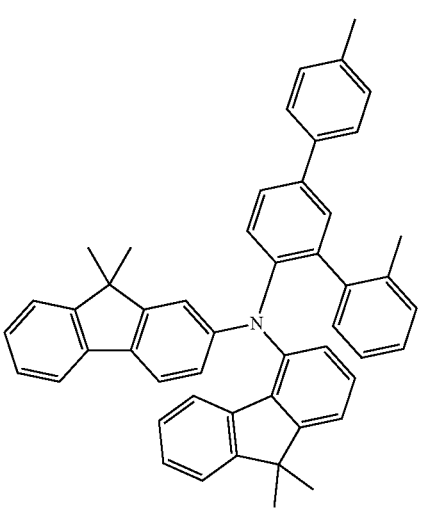
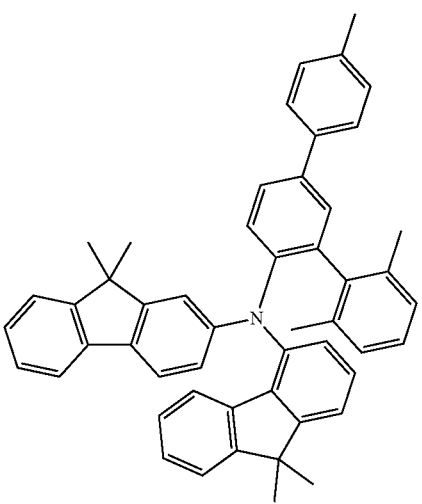

185
-continued
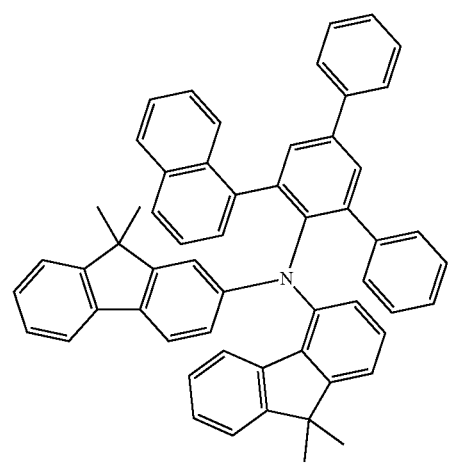
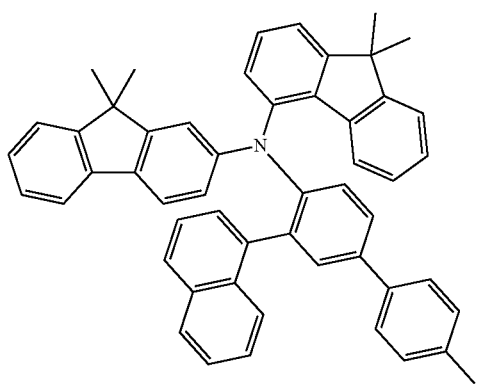
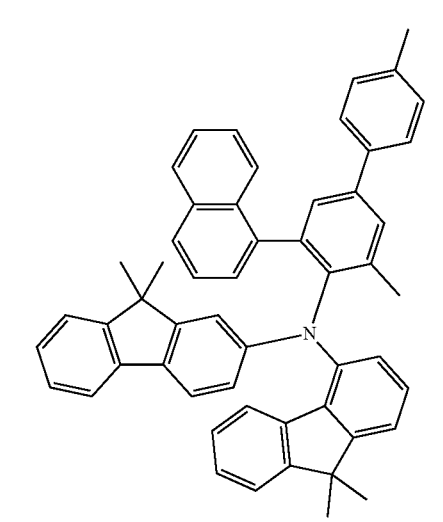
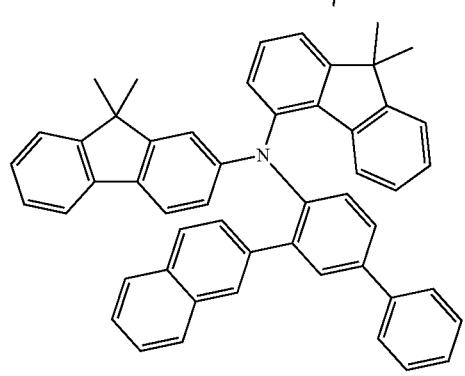
186
-continued
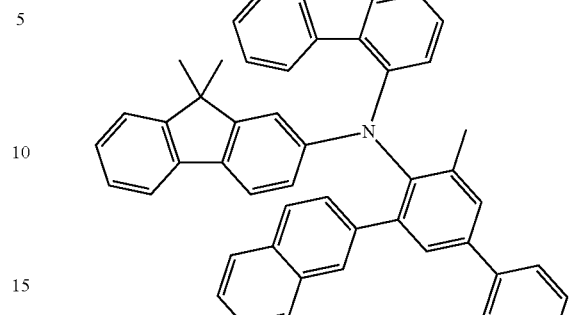
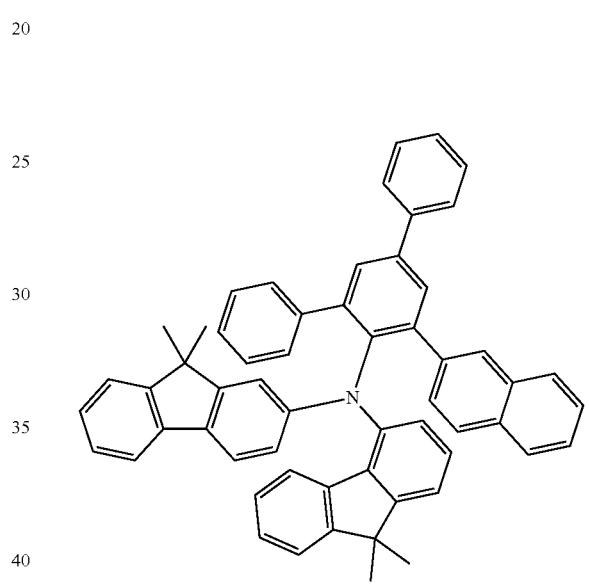
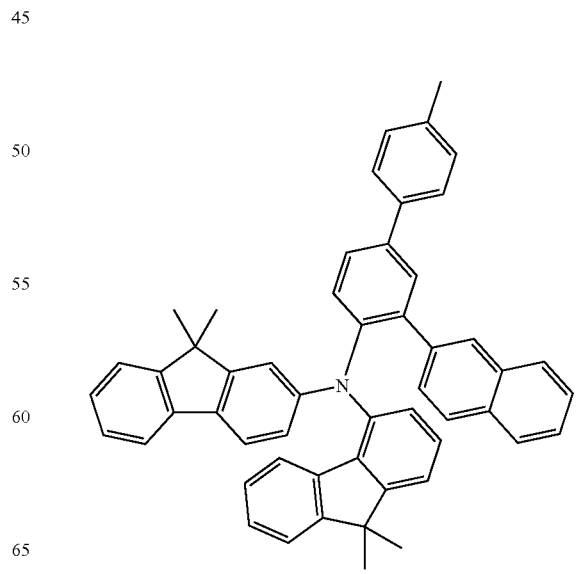

187
-continued
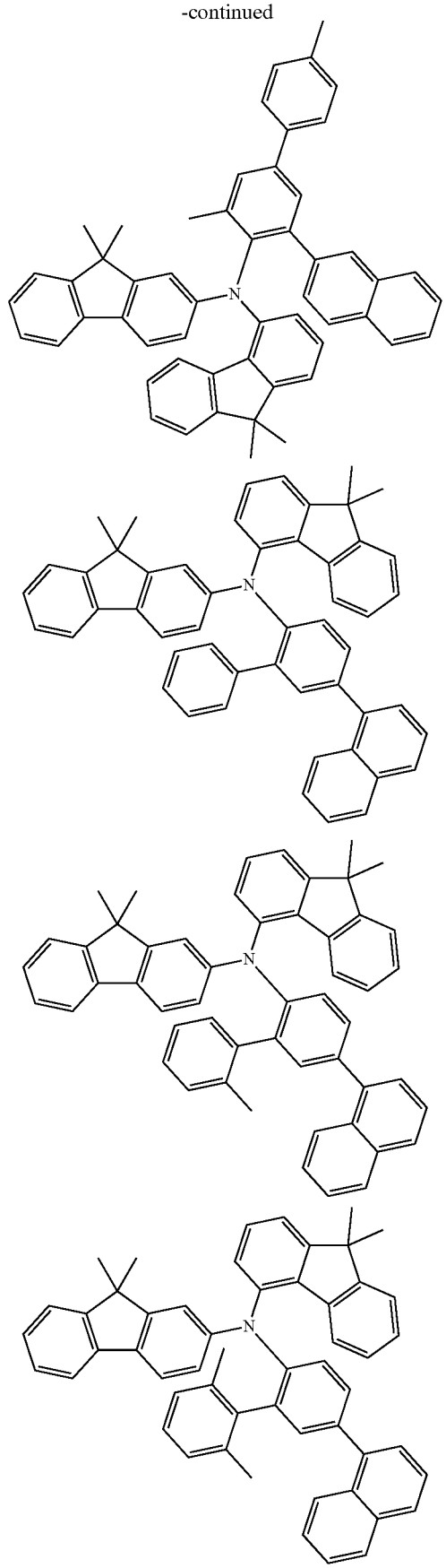
188
-continued
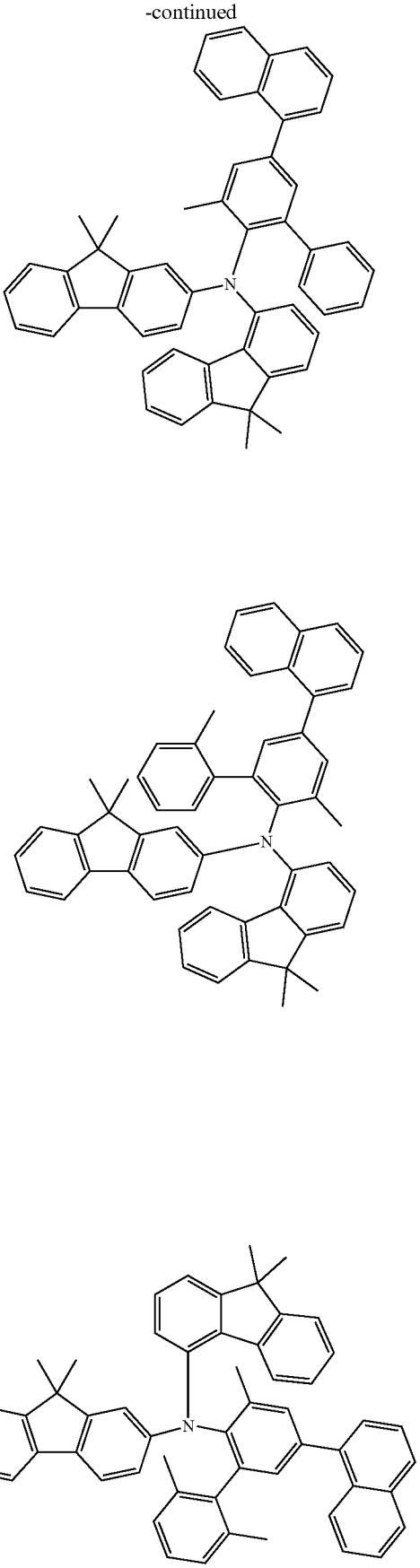

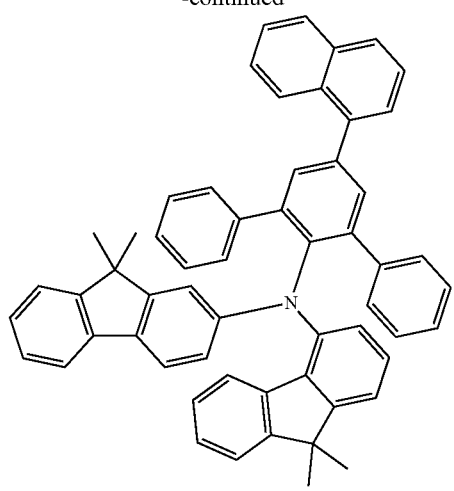
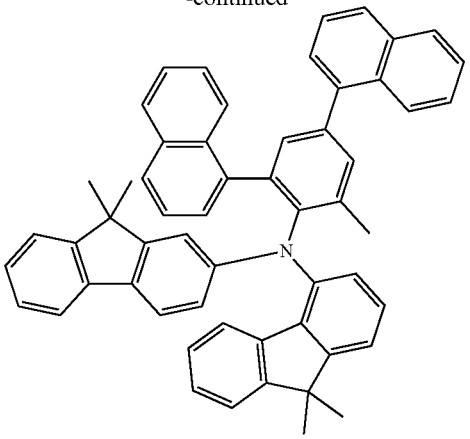
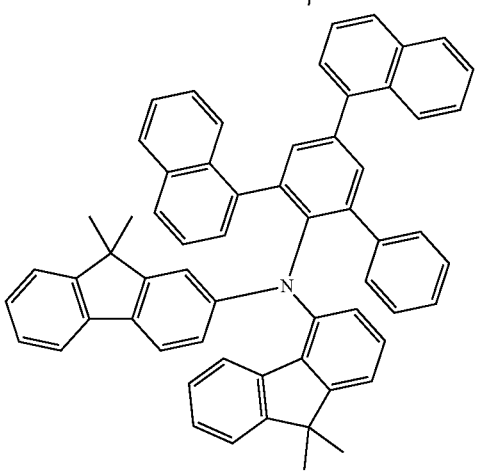
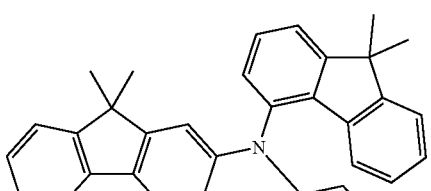
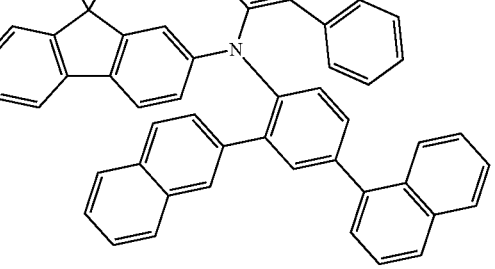
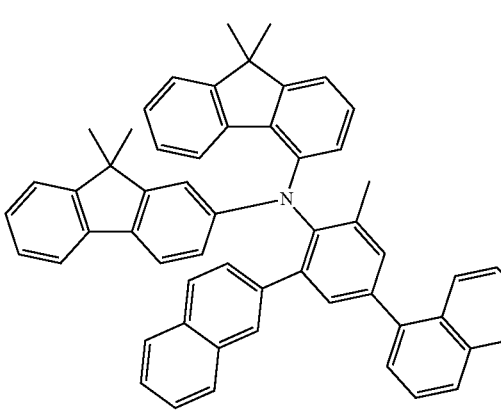

| 191 -continued | 192 -continued |
|---|---|
| 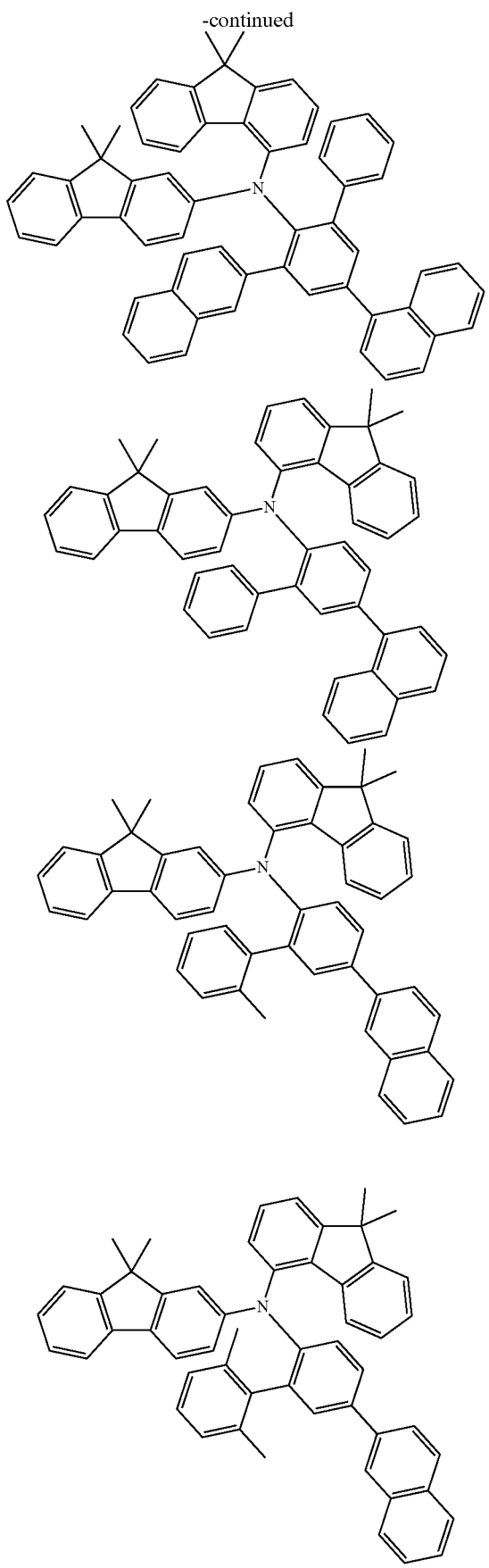 | 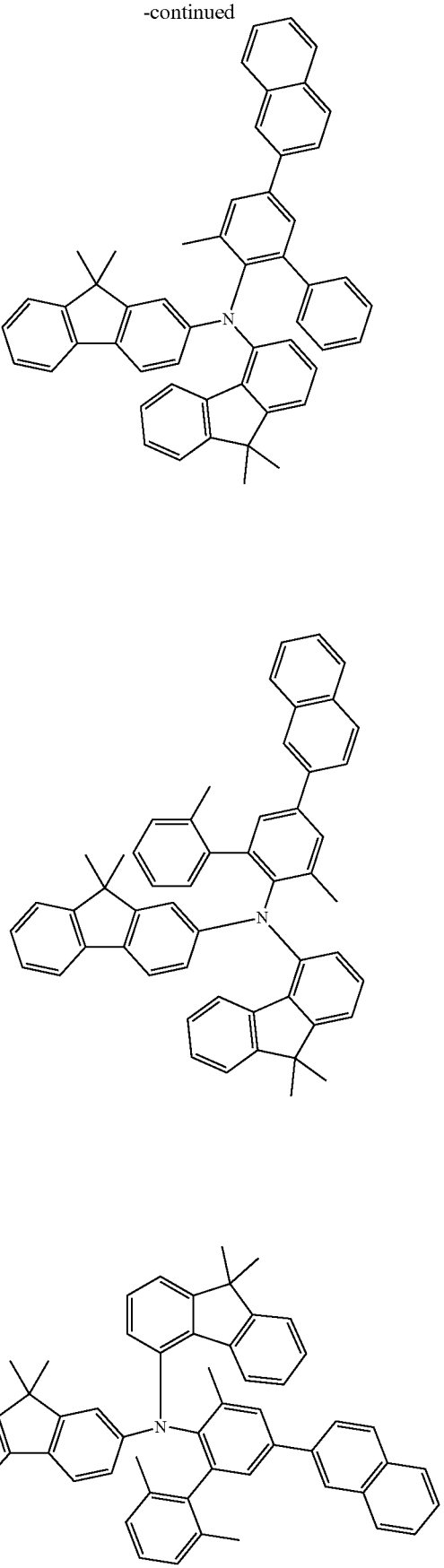 |

193
-continued
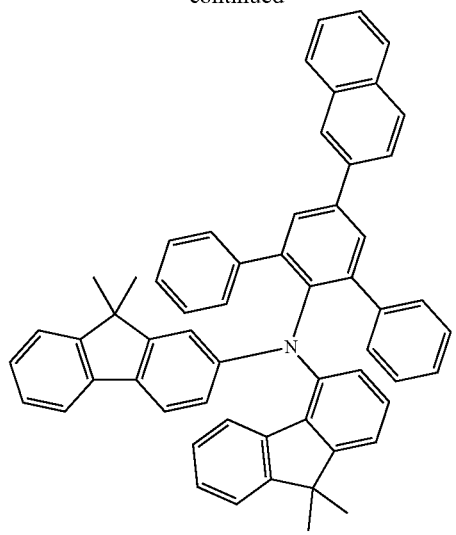
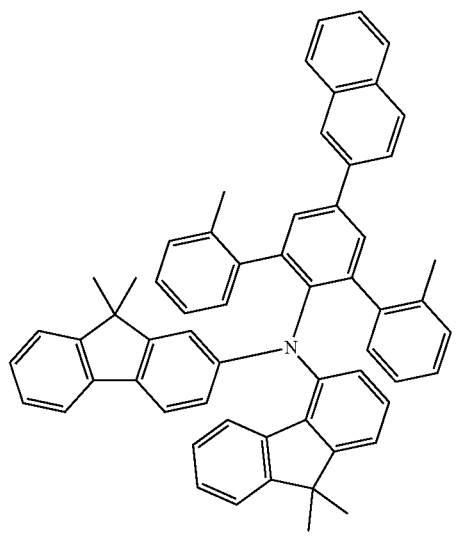
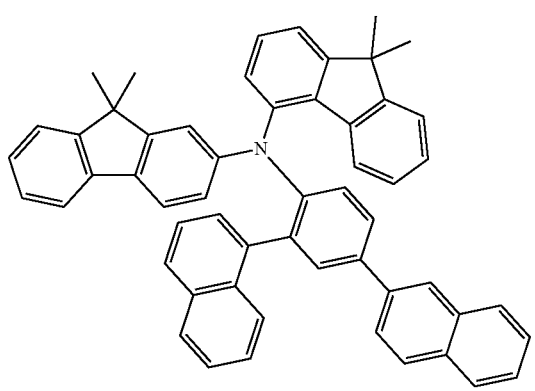
194
-continued
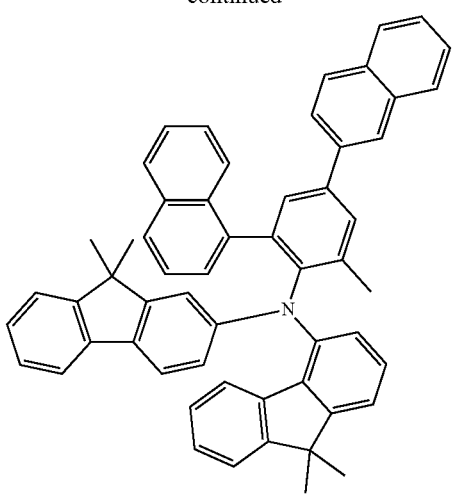
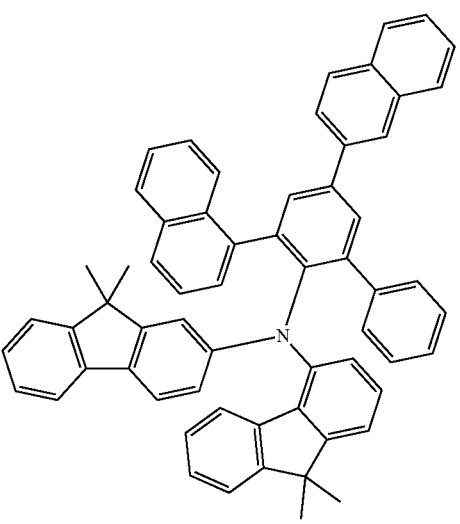
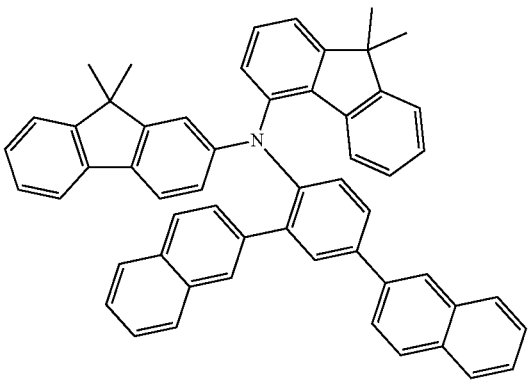

-continued
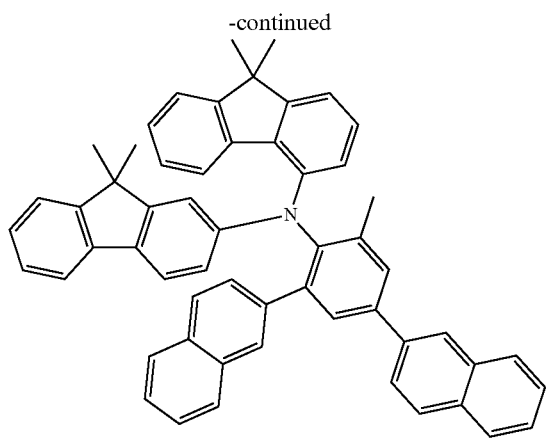
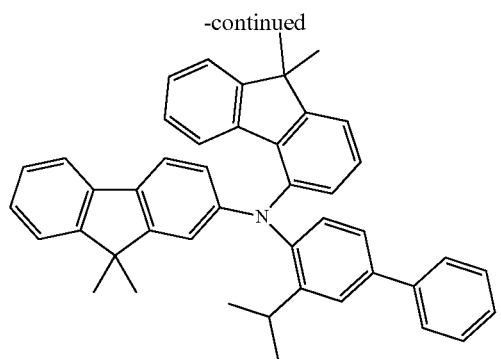
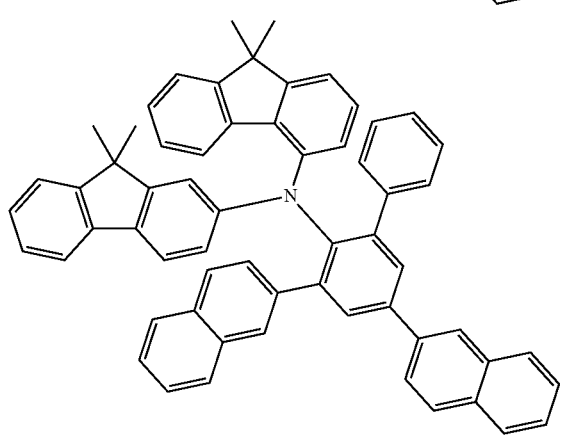
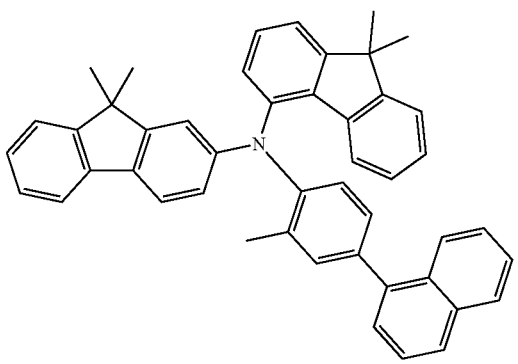
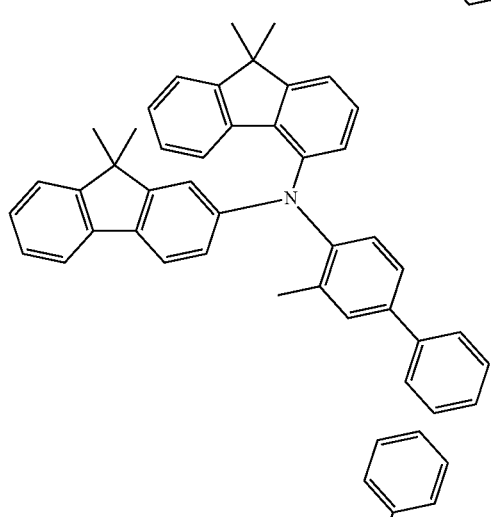
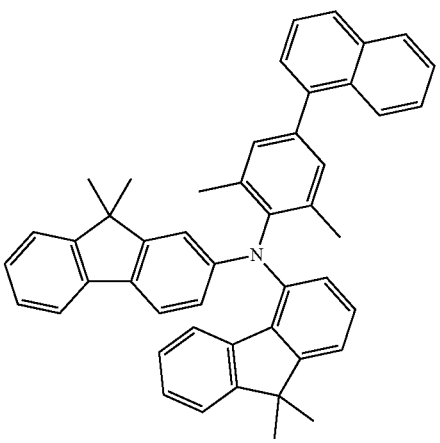
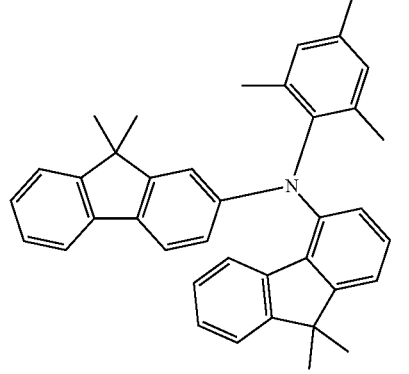
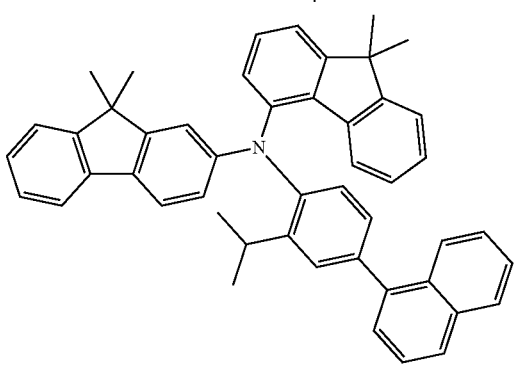

197
-continued
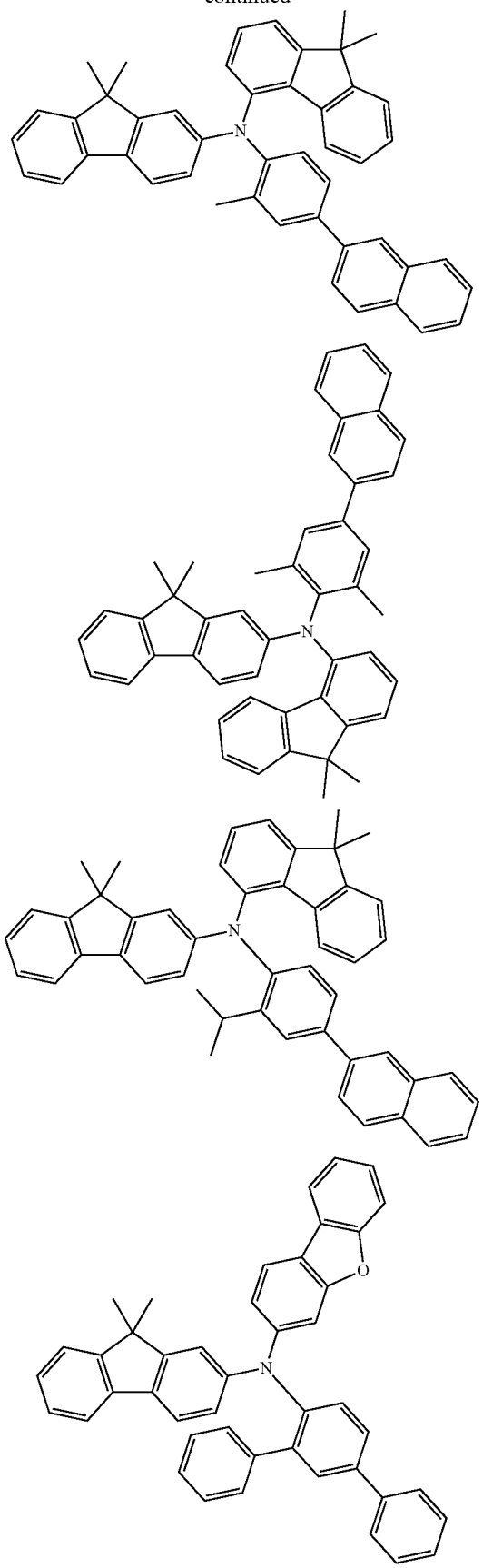
198
-continued
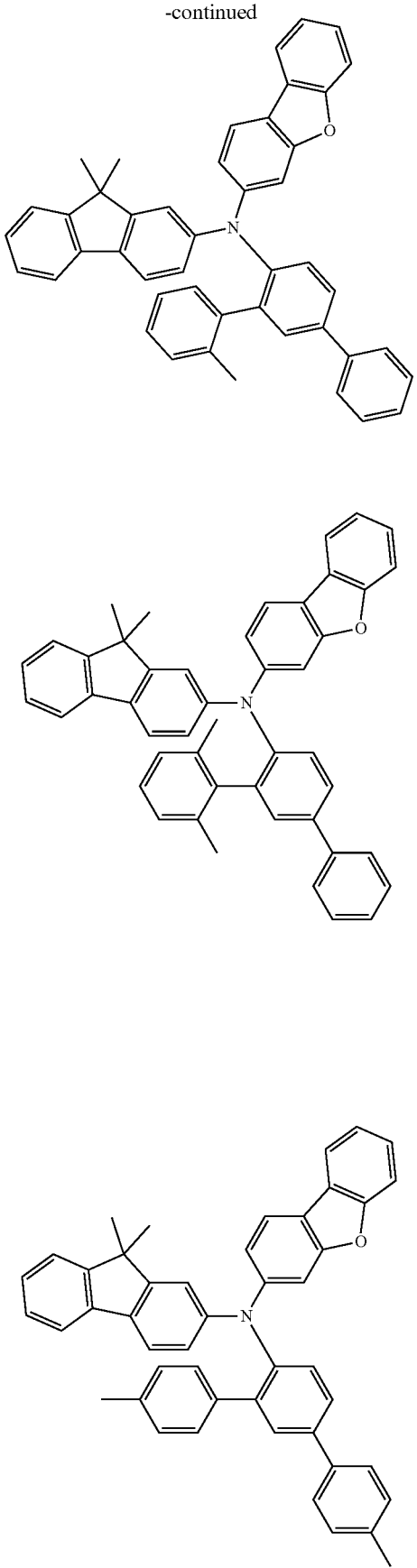

199
-continued
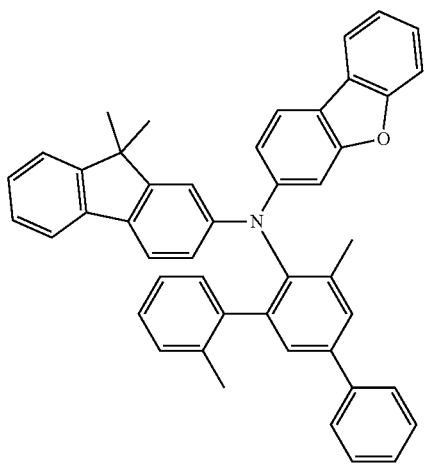
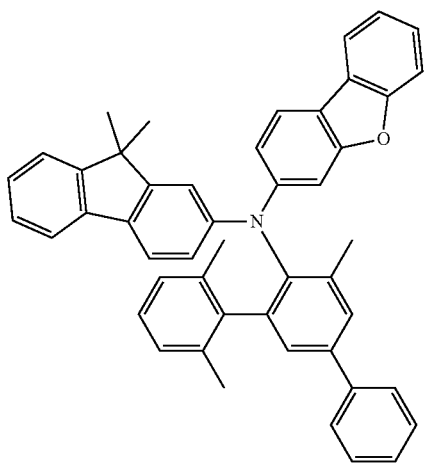
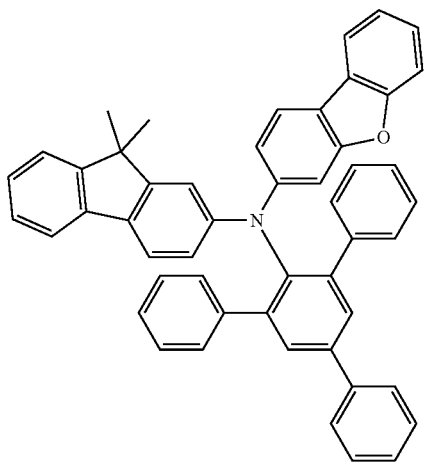
200
-continued
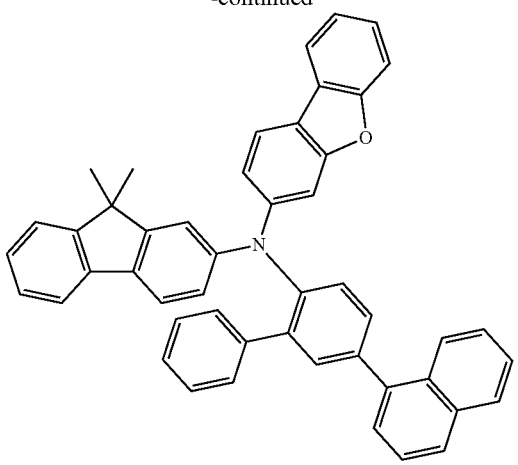
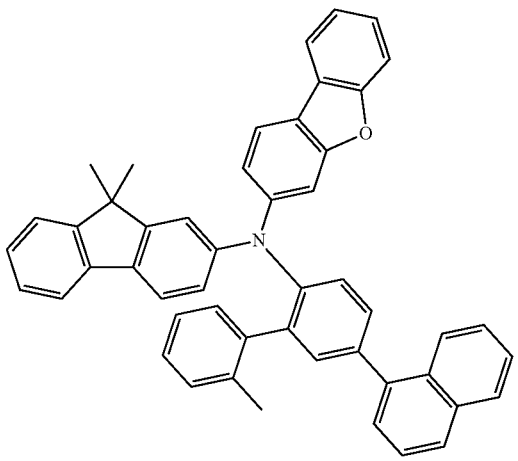
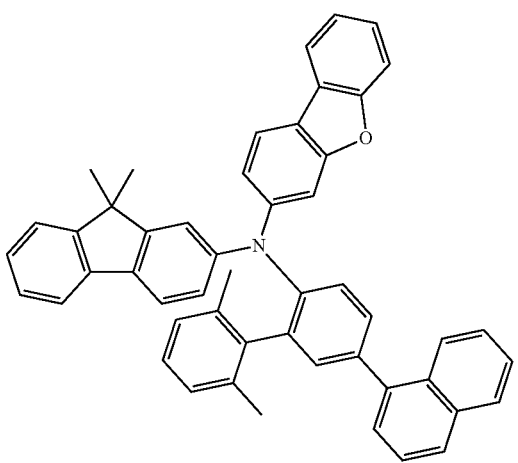

201
-continued
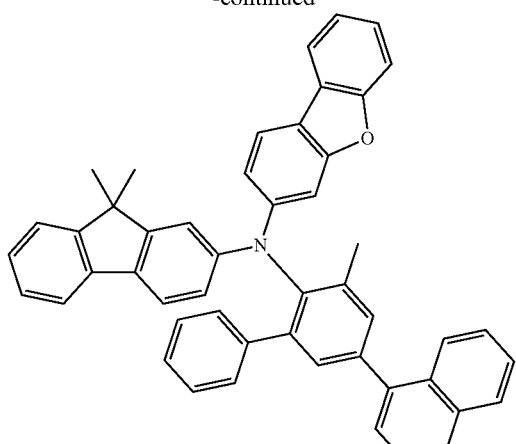
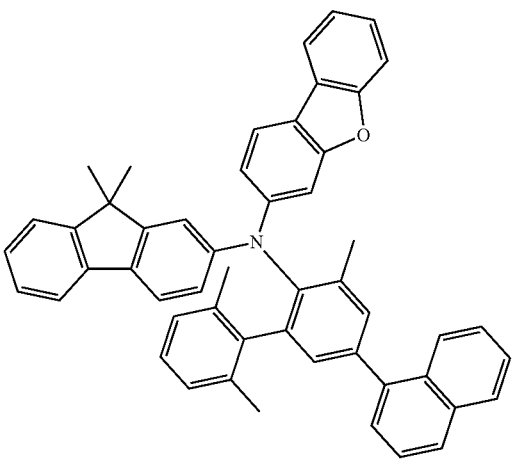
202
-continued
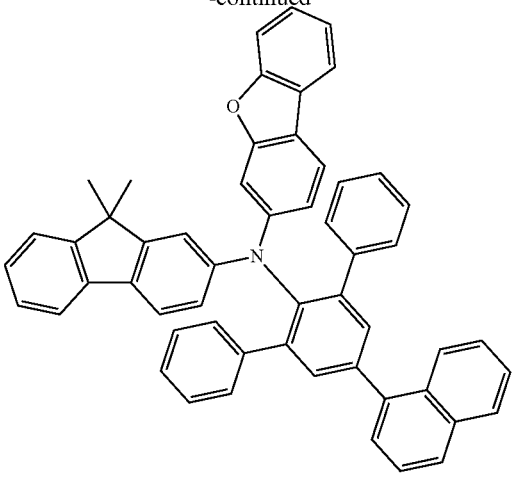
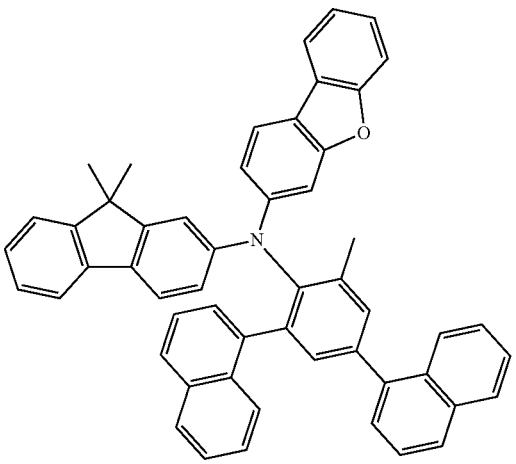

203
-continued
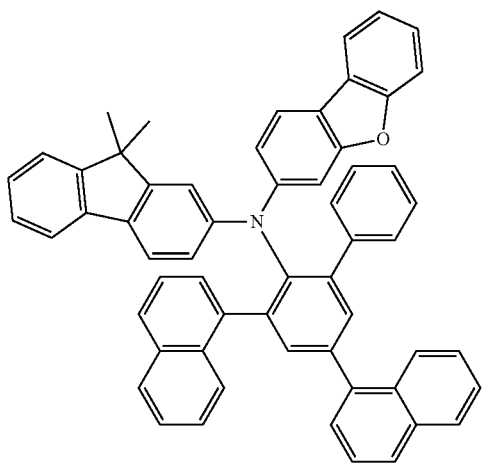
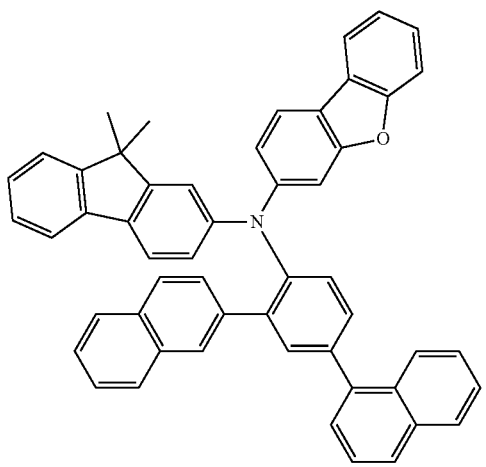
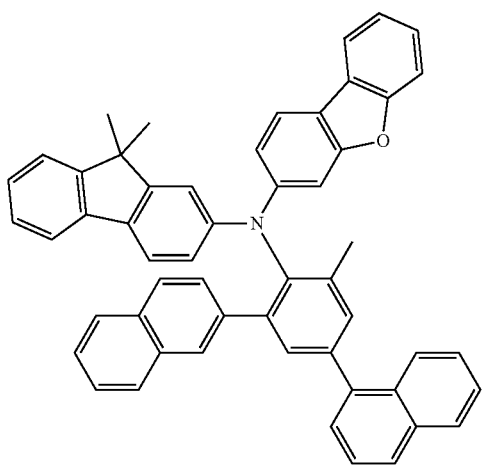
204
-continued
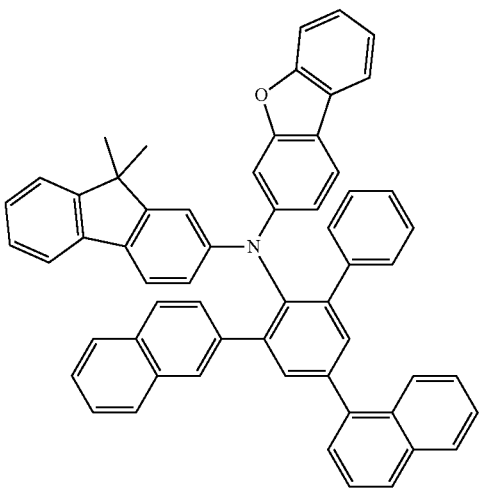
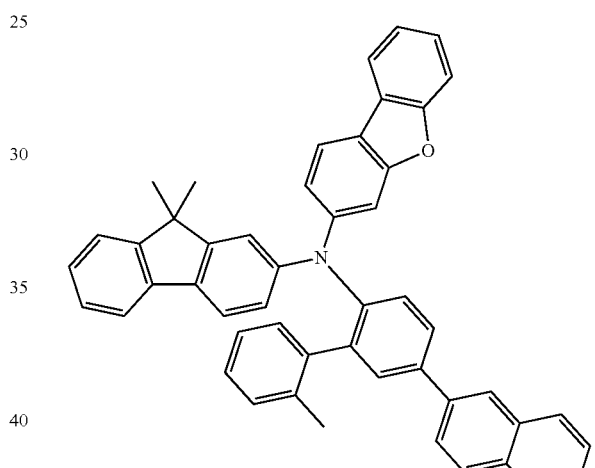
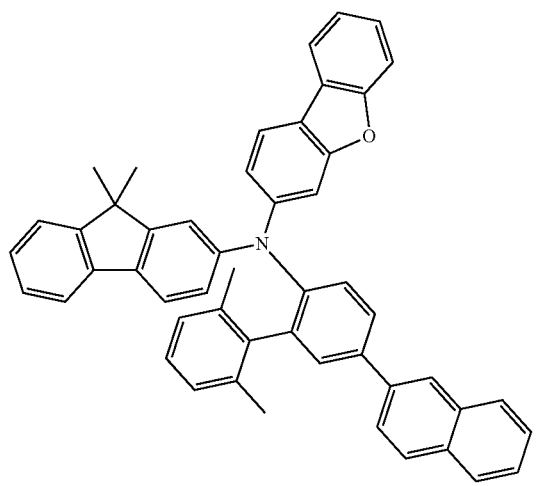

205
-continued
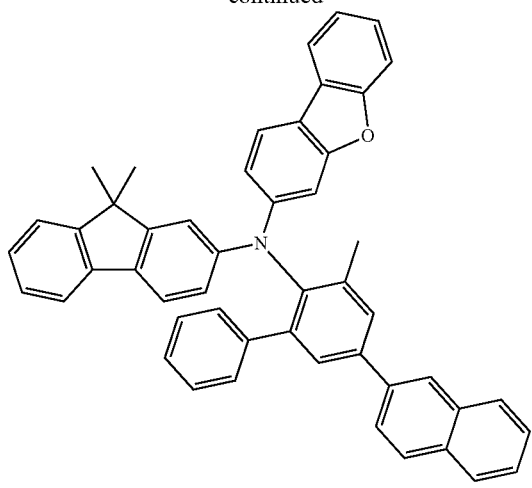
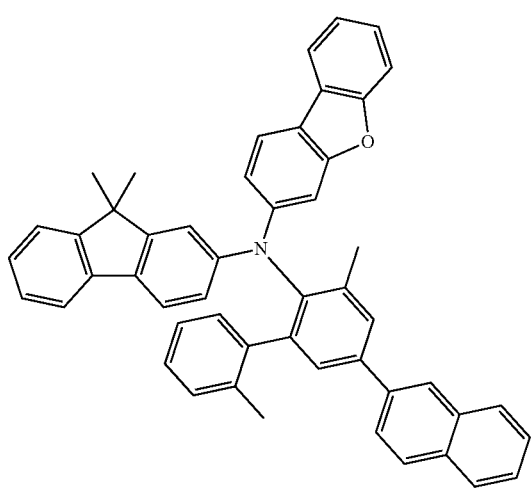
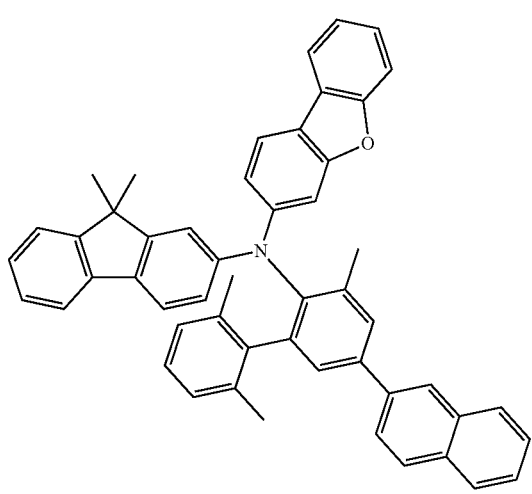
206
-continued
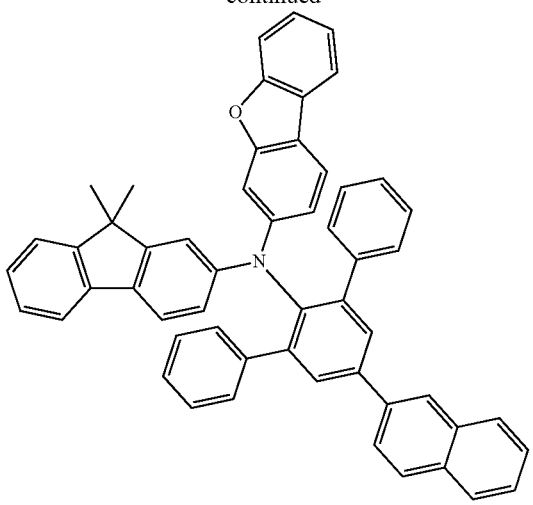
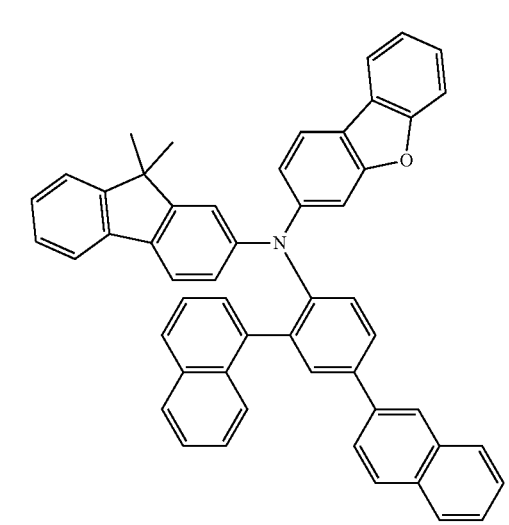
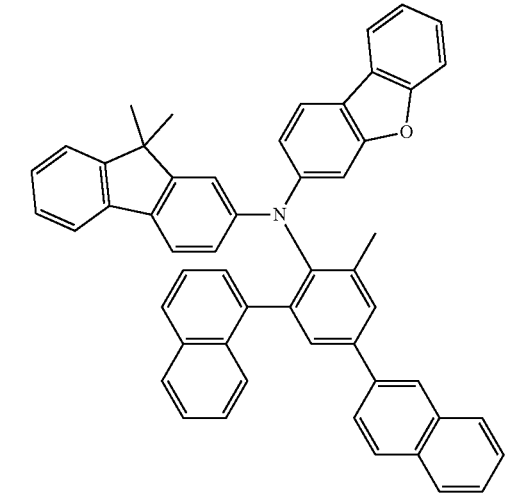

207
-continued
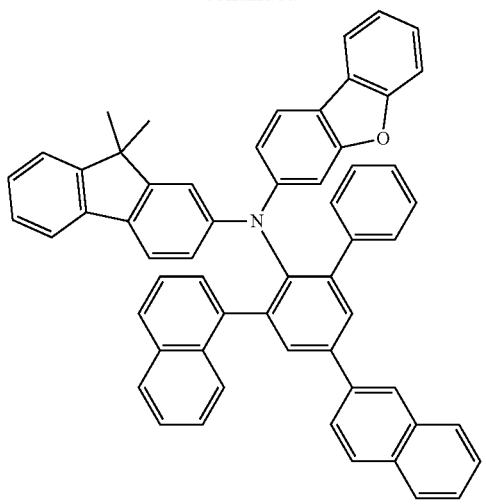
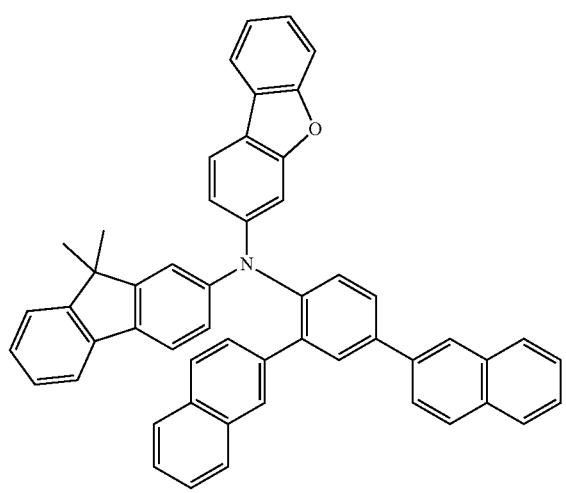
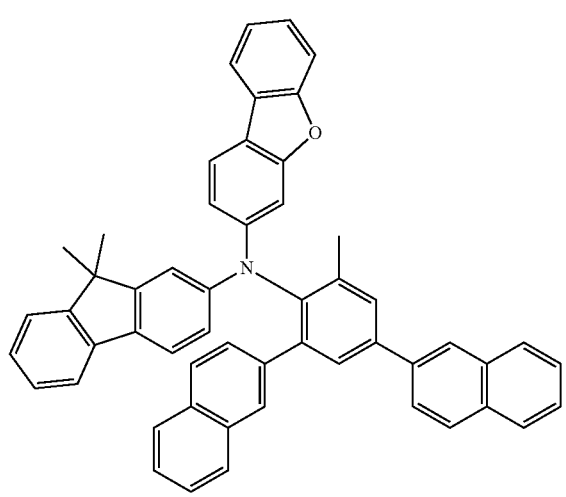
208
-continued
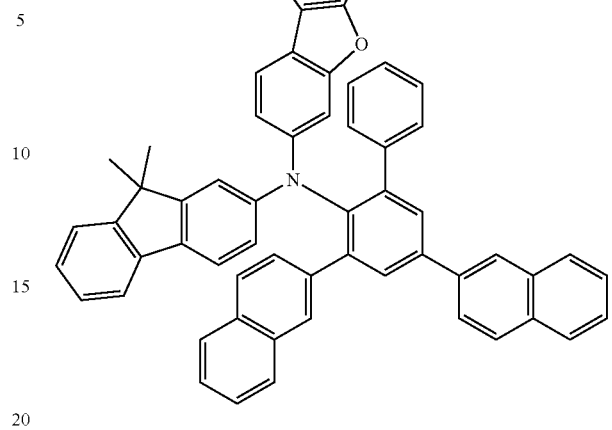
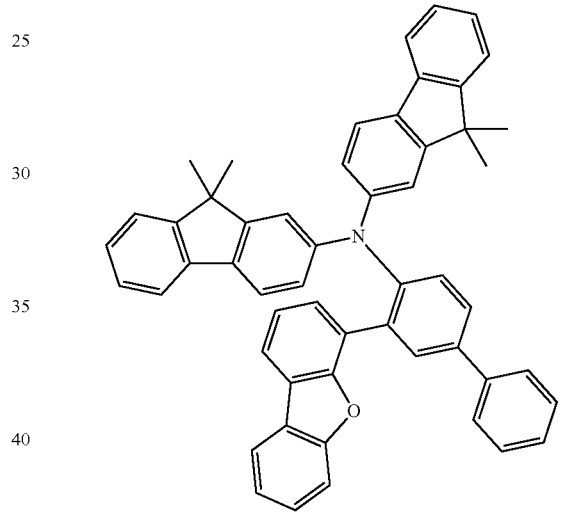
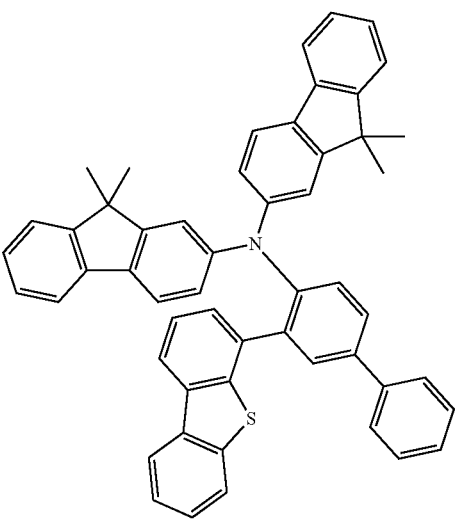

209
-continued
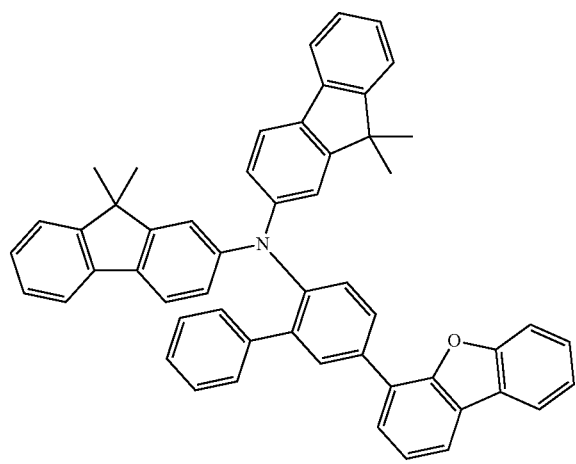
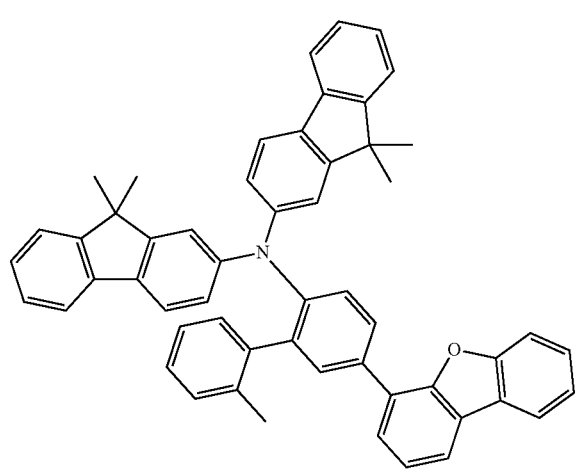
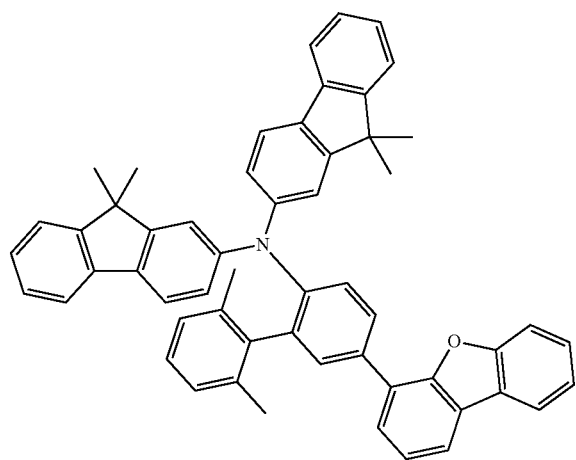
210
-continued
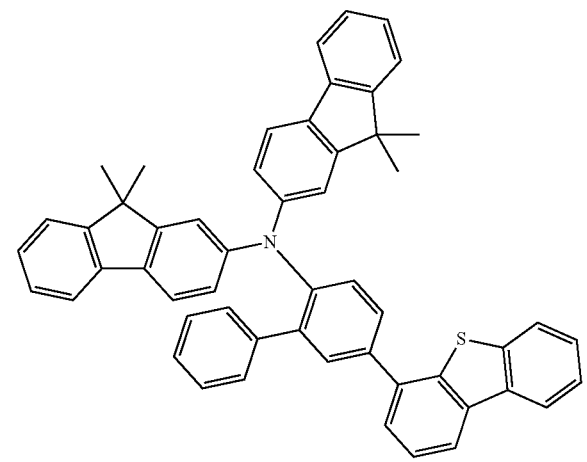
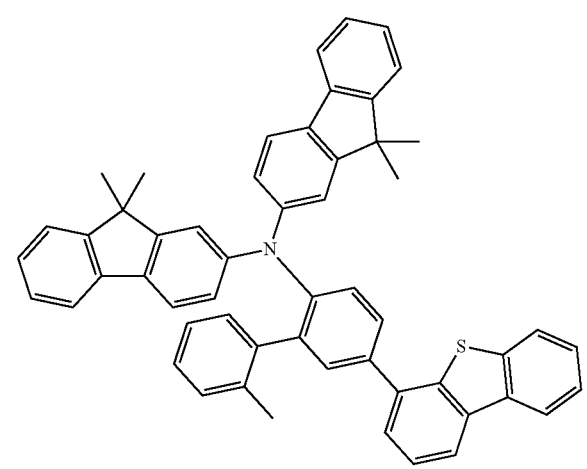

211
-continued
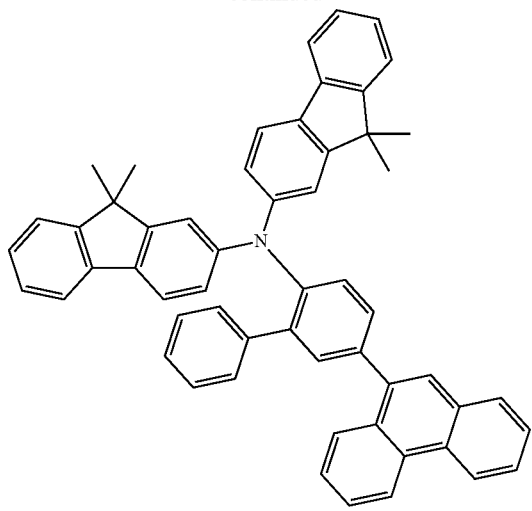
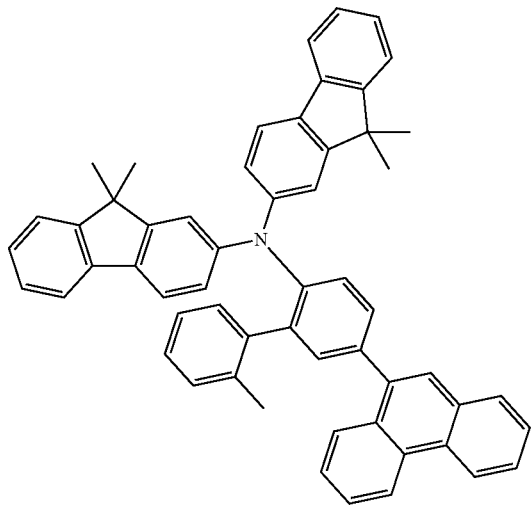
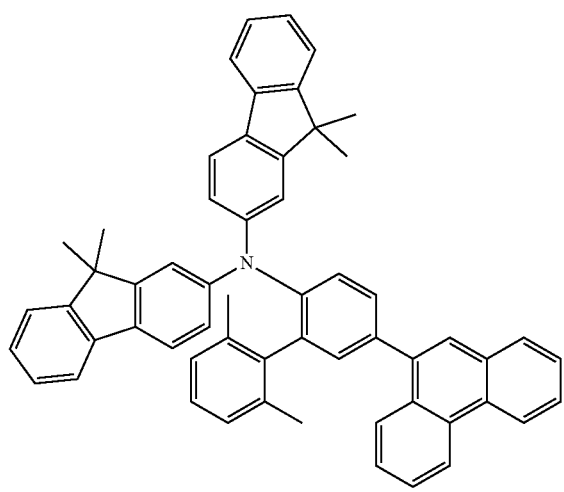
212
-continued
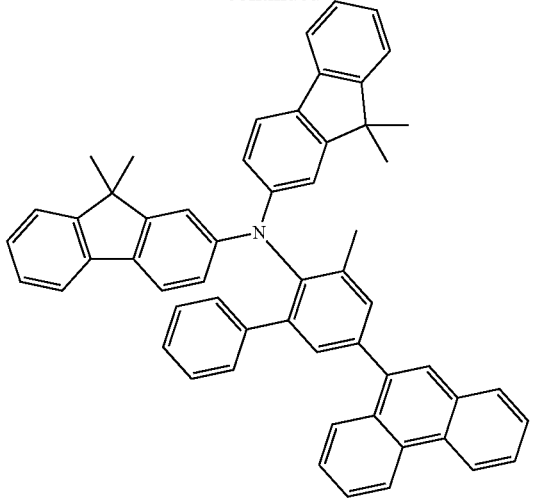
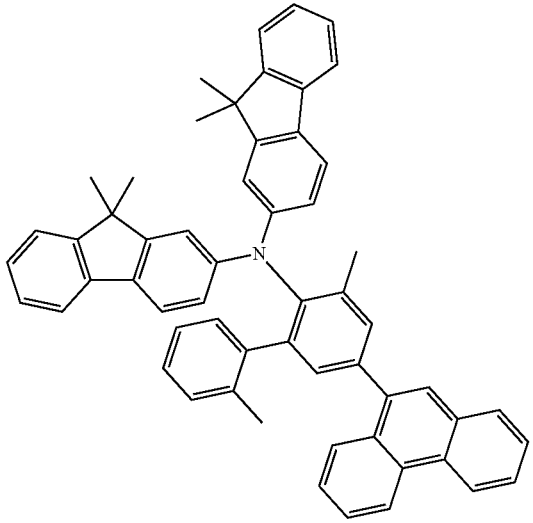
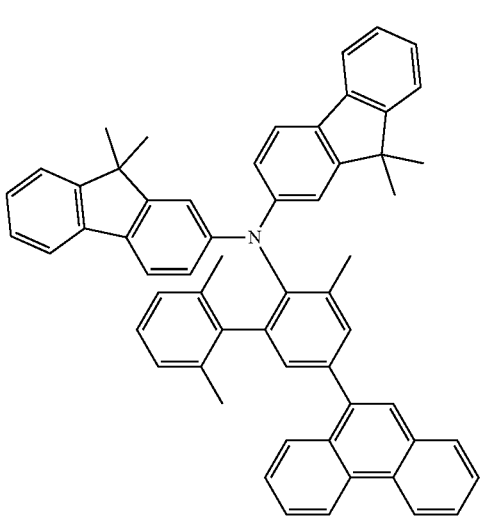

213
-continued
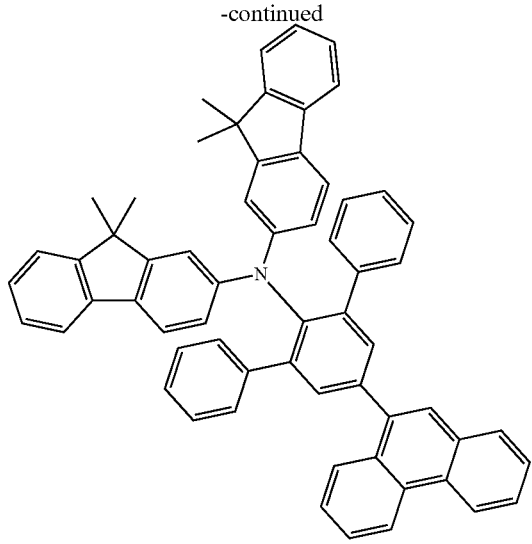
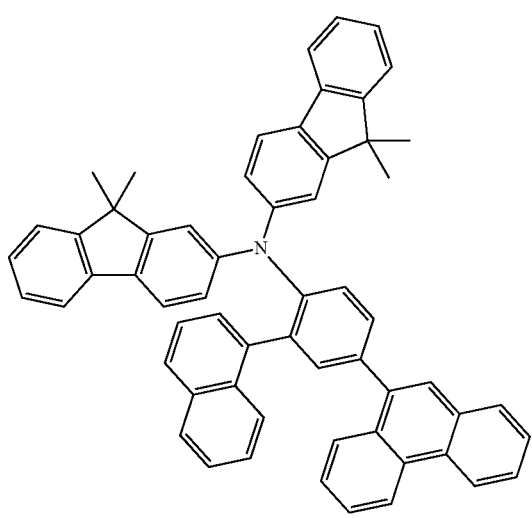
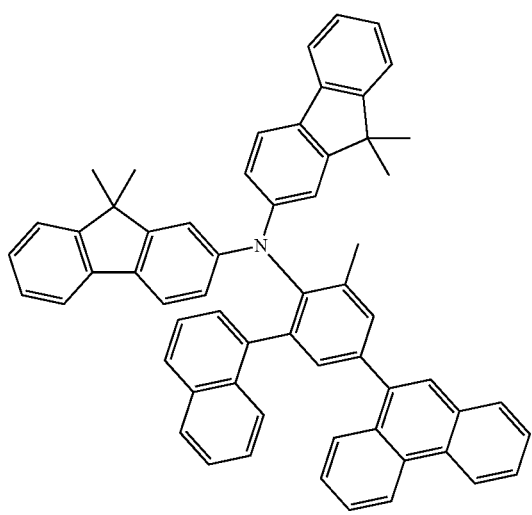
214
-continued
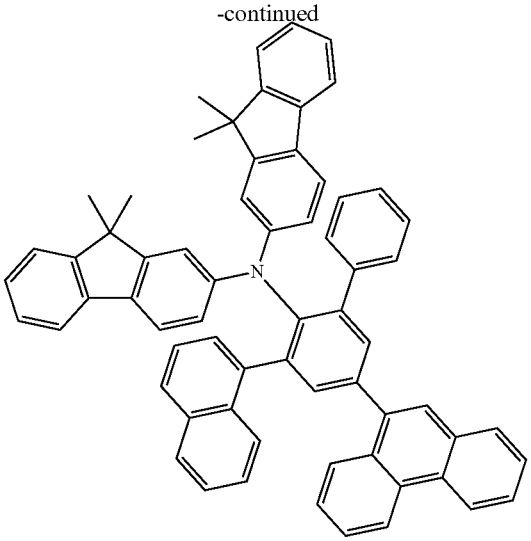
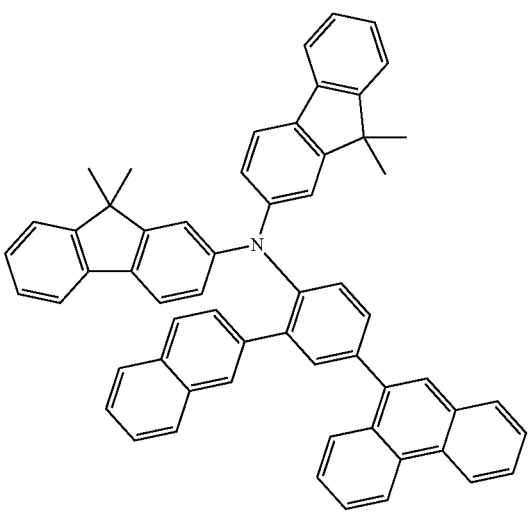
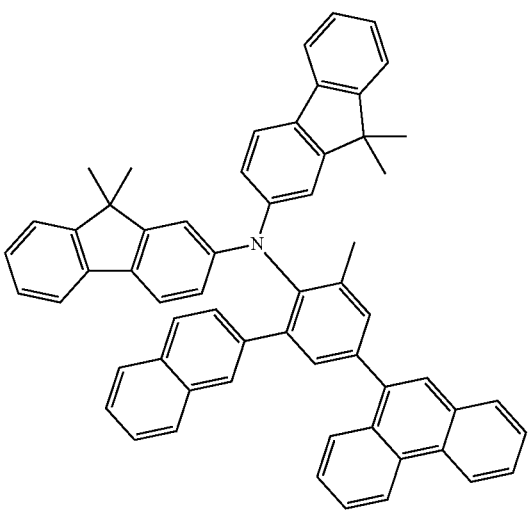

215
-continued
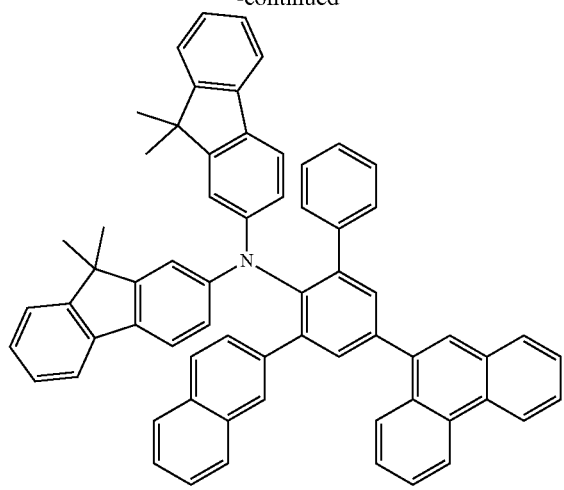
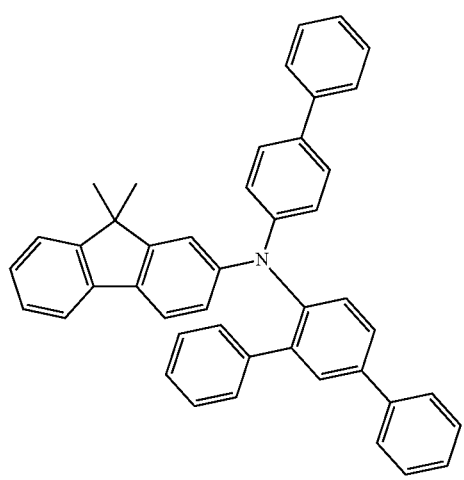
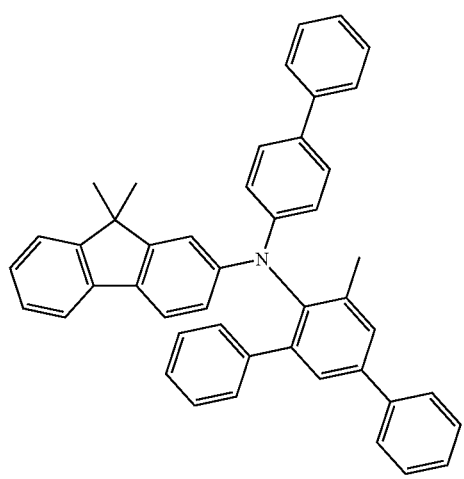
216
-continued
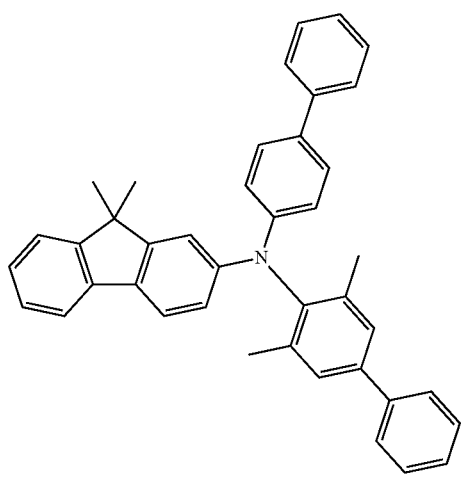
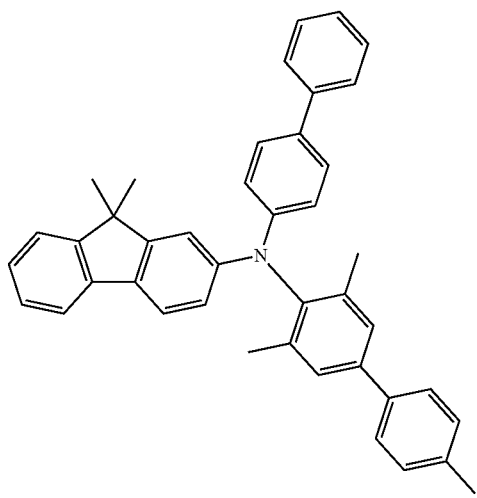
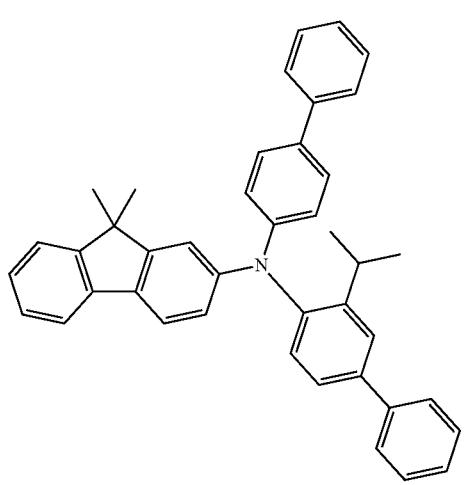

217
-continued
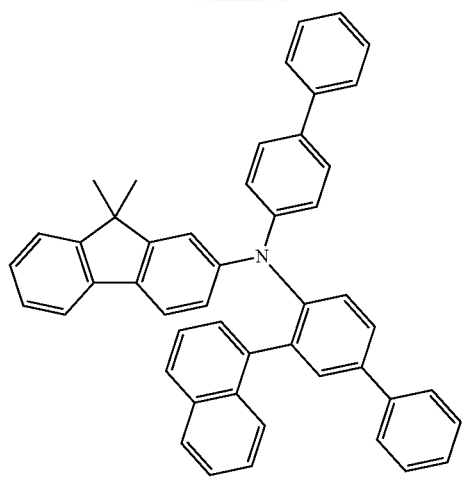
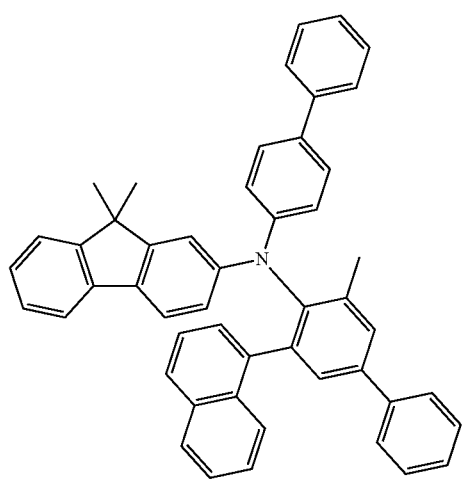
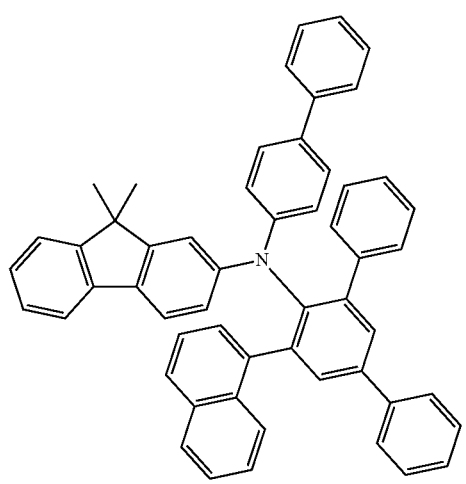
218
-continued
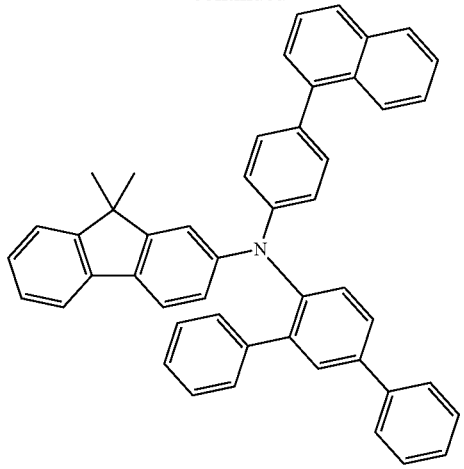
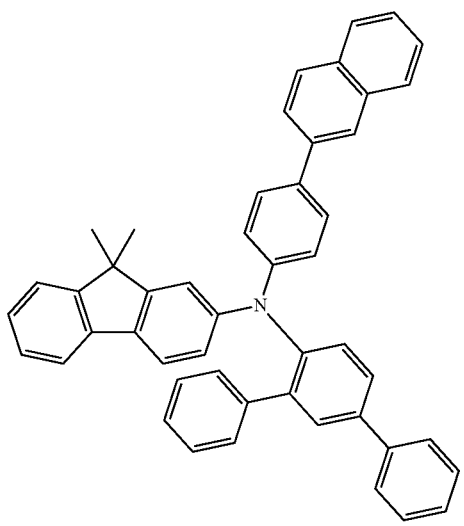
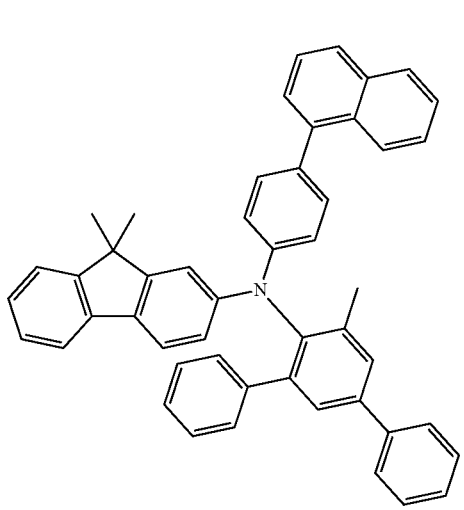

219
-continued
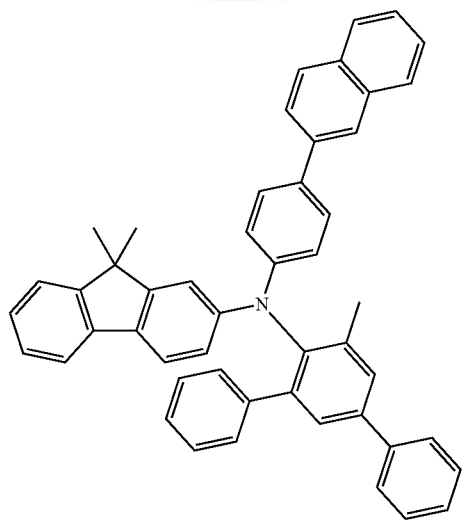
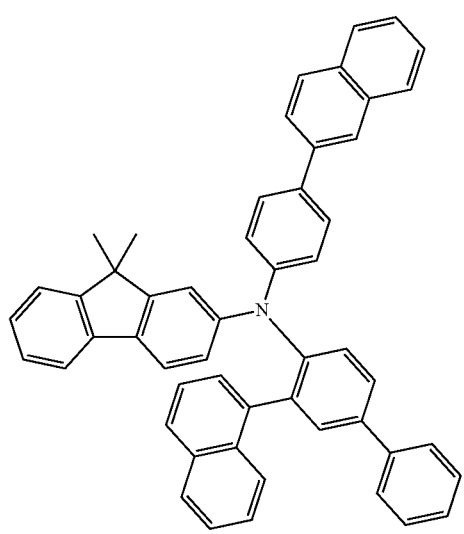
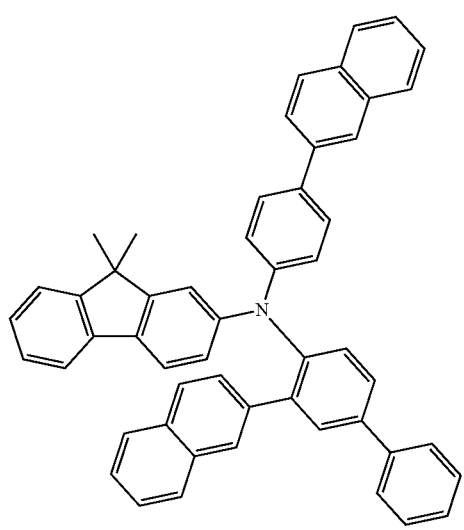
220
-continued
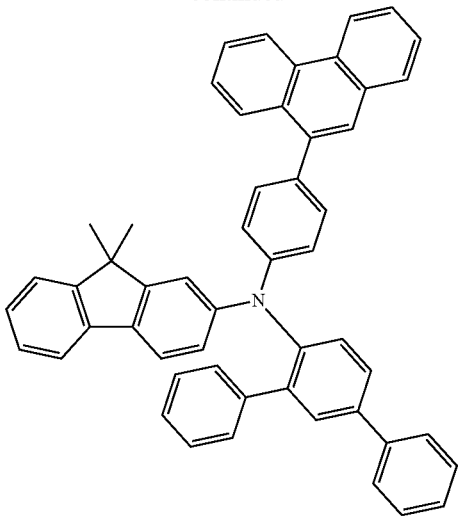
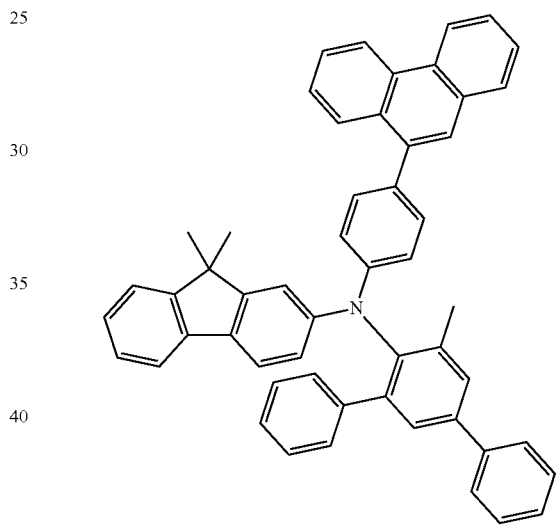
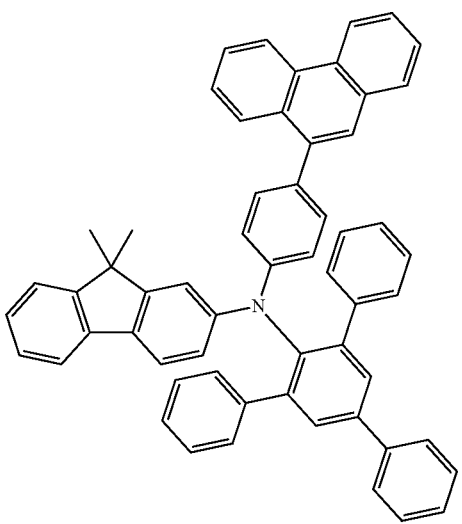

221
-continued
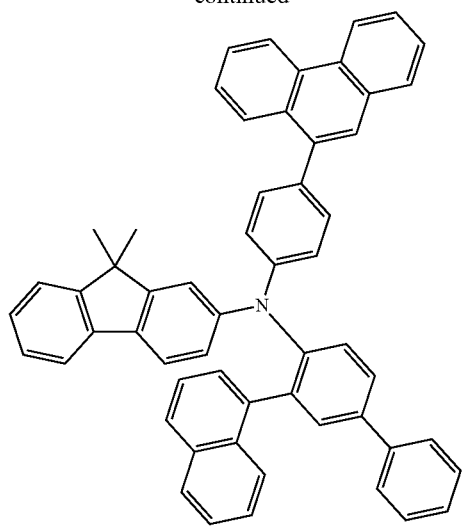
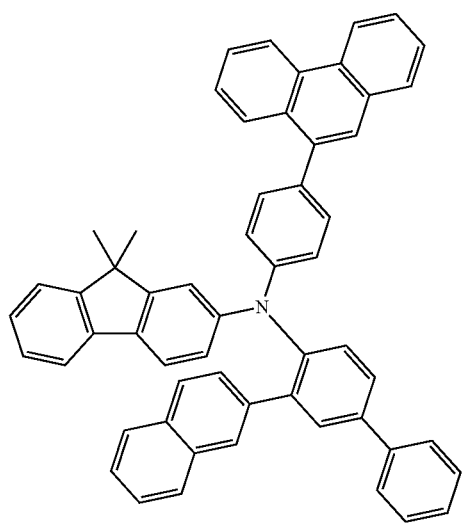
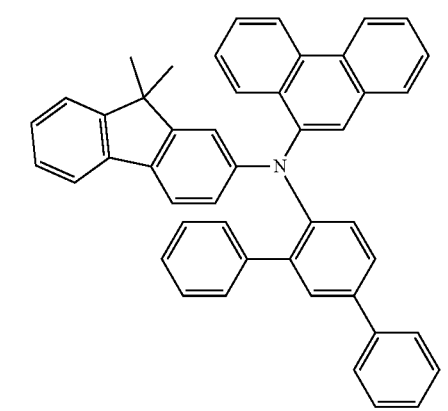
222
-continued
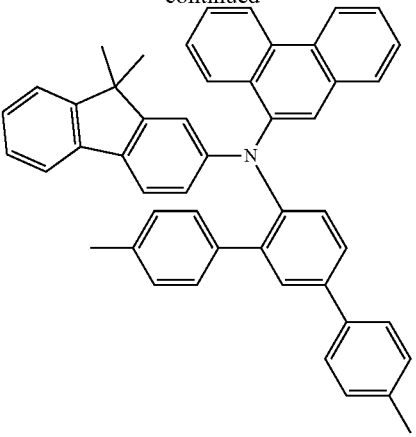
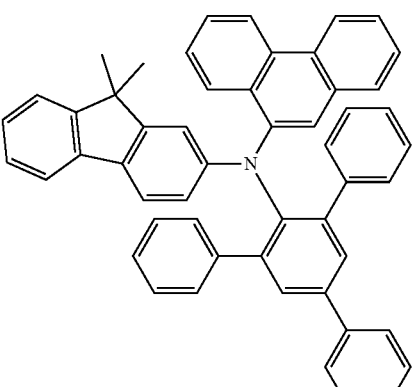
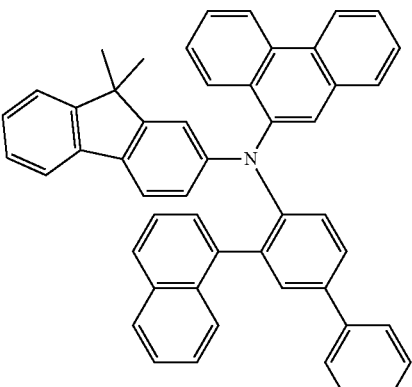
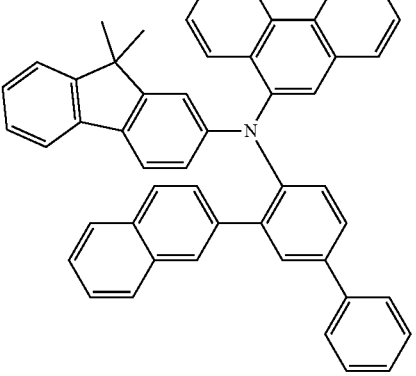

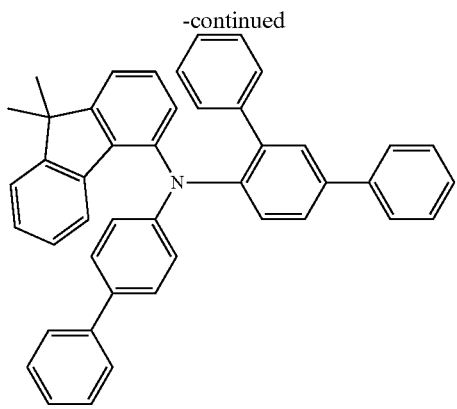
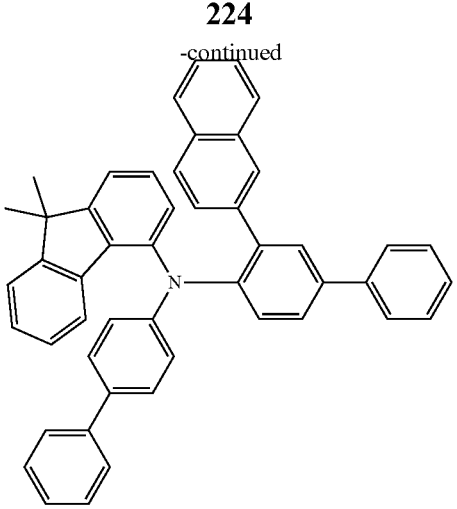
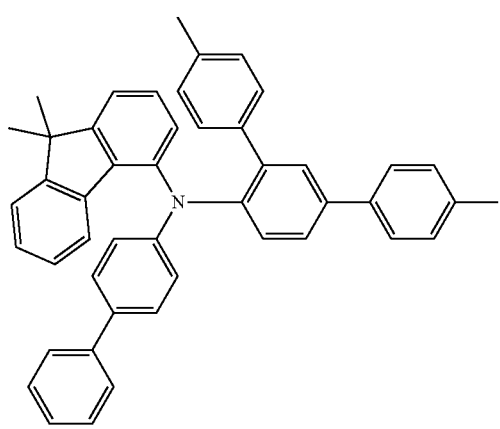
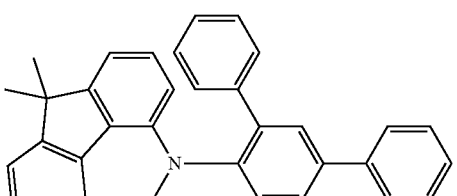
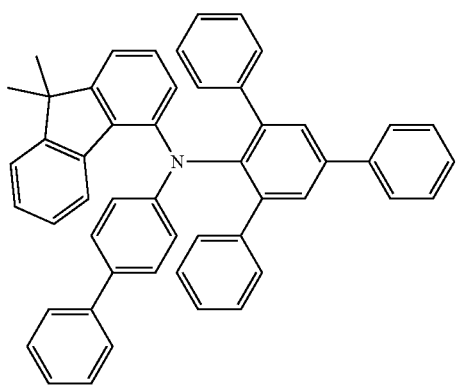
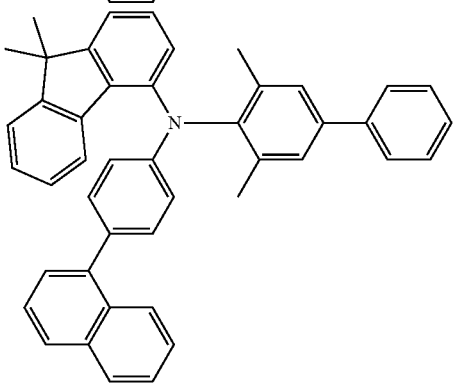
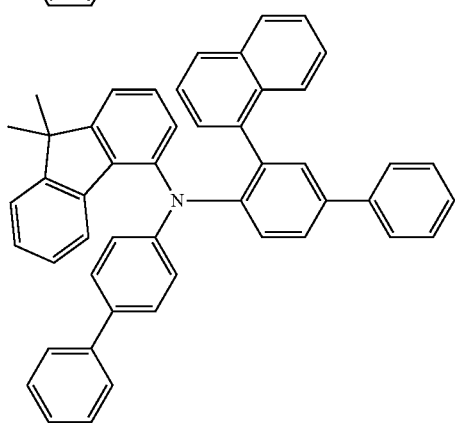
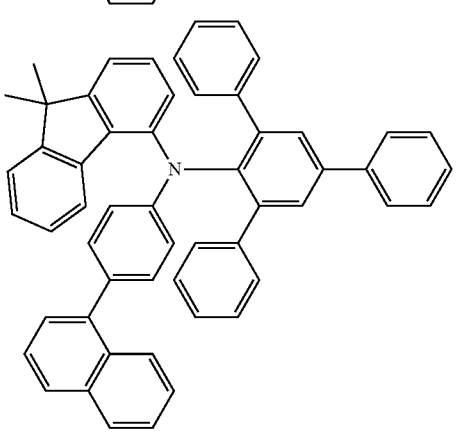

225
-continued
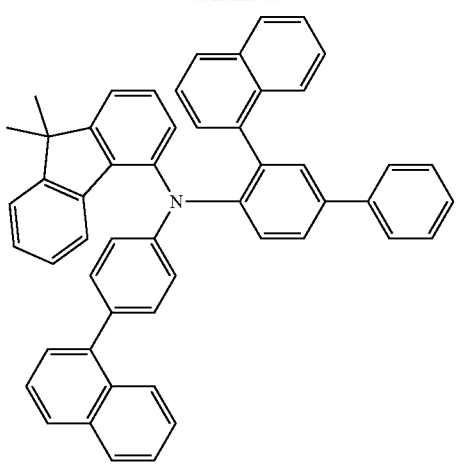
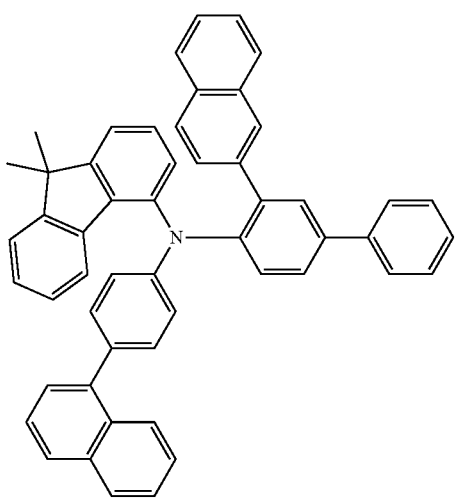
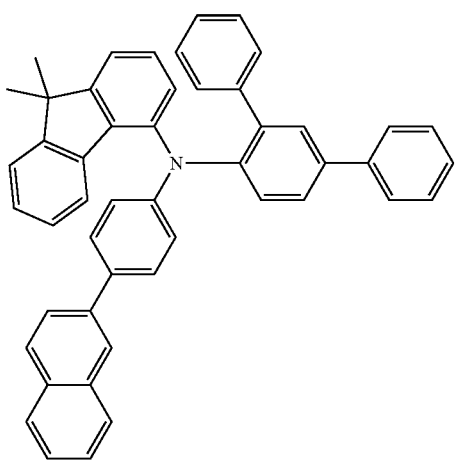
226
-continued
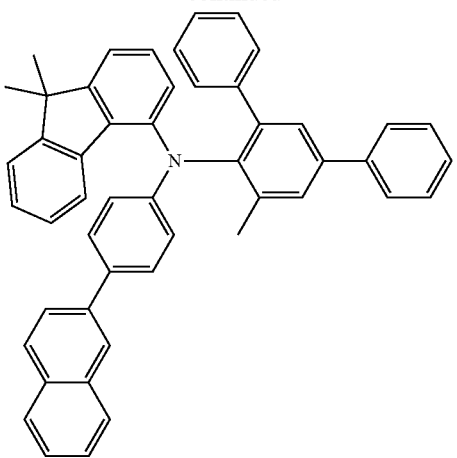
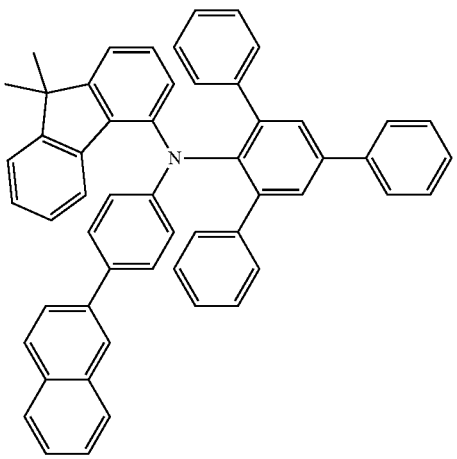
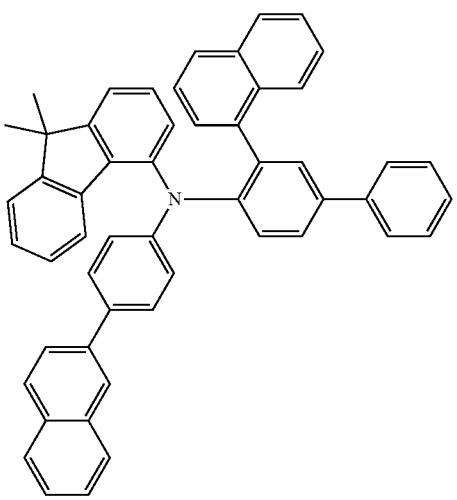

227
-continued
228
-continued
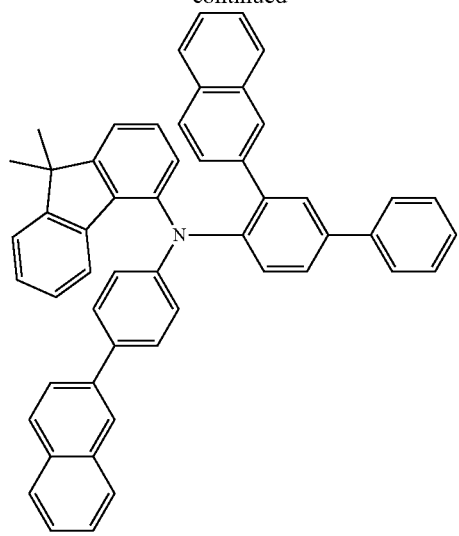
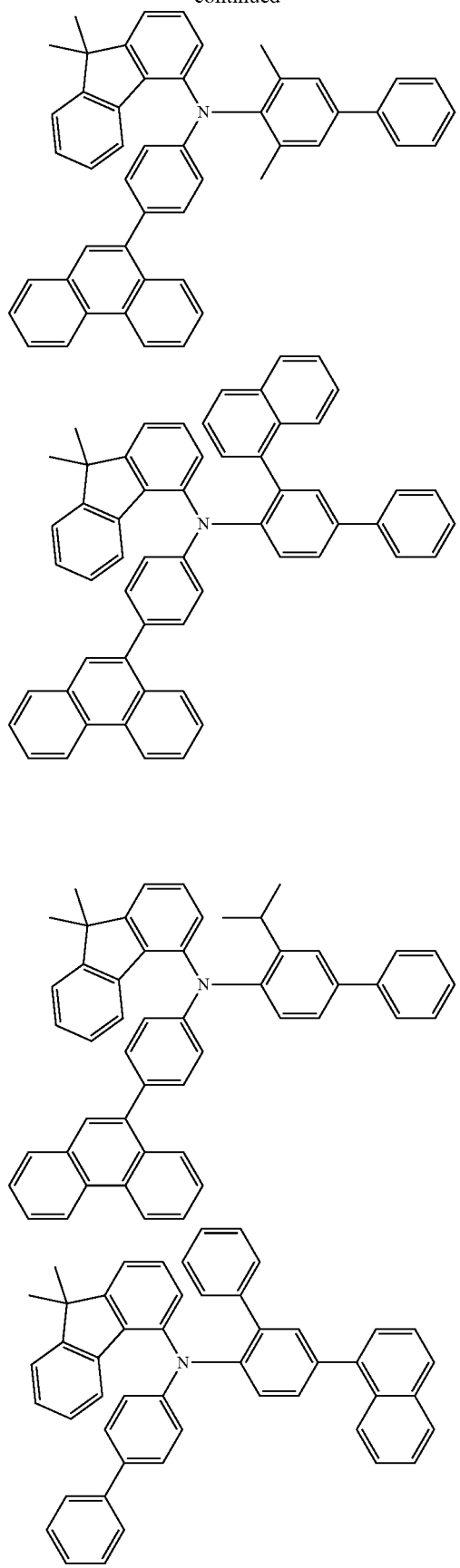

-continued
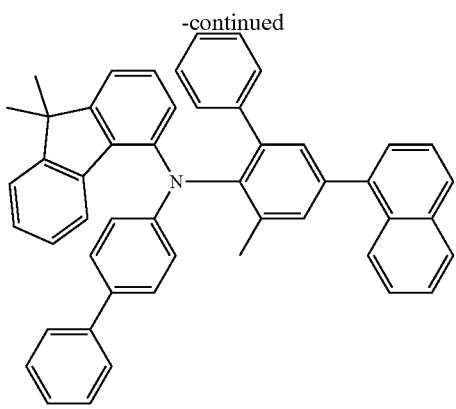
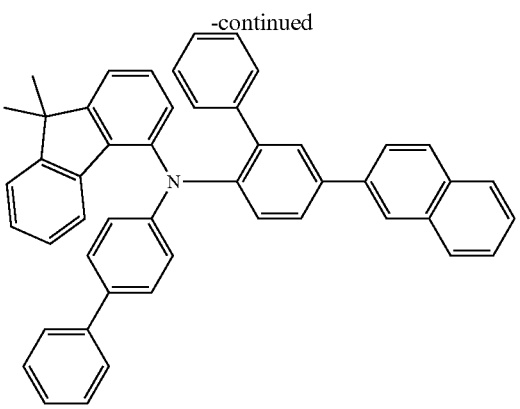
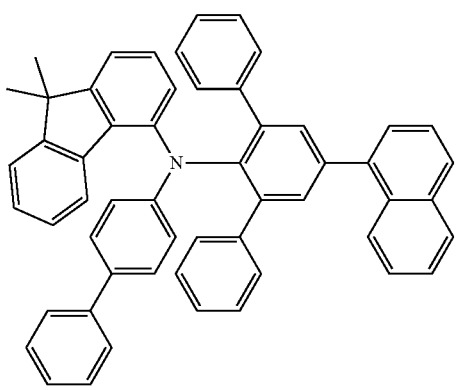
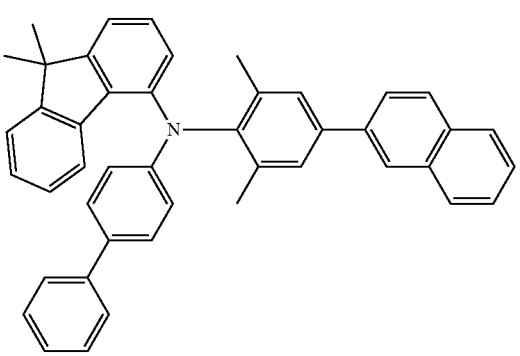
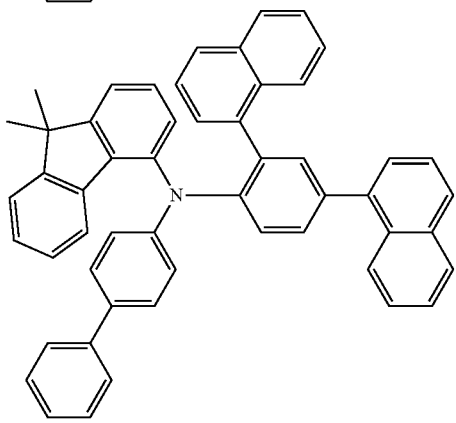
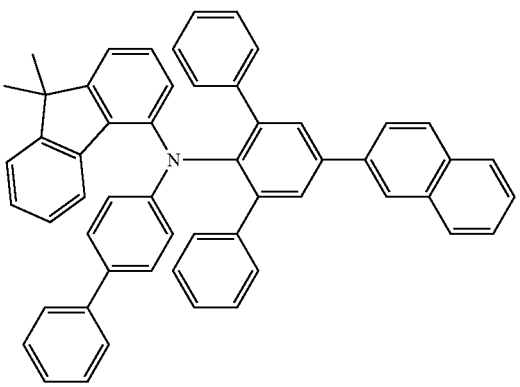
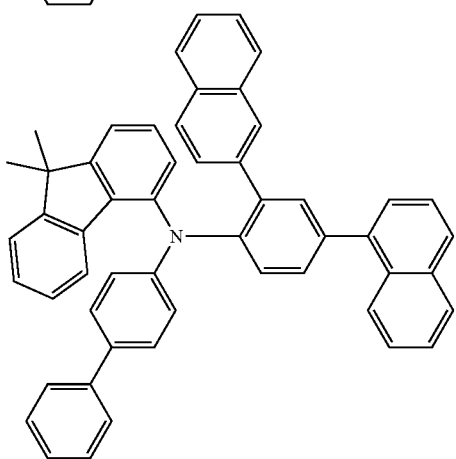
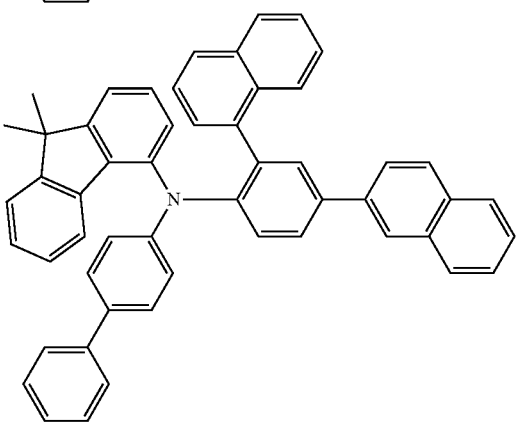

231
-continued

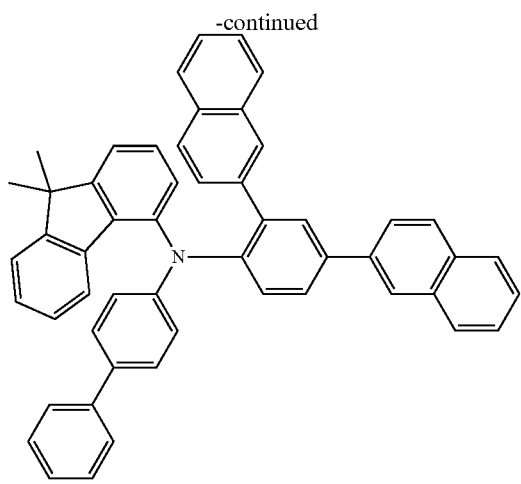

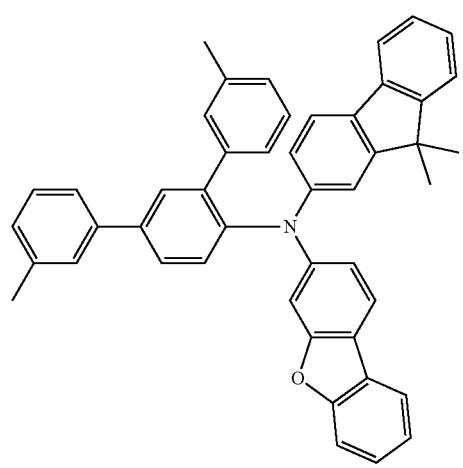

232
-continued

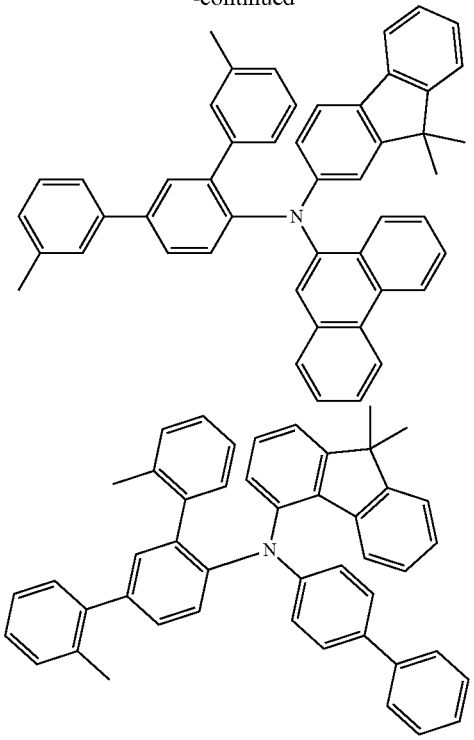

2. An organic electroluminescent device comprising:
  a first electrode:
  a second electrode provided to face the first electrode; and
  one or more organic material layers interposed between the first electrode and the second electrode,
  wherein the organic material layers comprise a hole transport layer or a hole transport auxiliary layer,
  wherein the hole transport layer or the hole transport auxiliary layer comprise the compound of the claim 1.

* * * * *